(12) United States Patent
Kawashima et al.

(10) Patent No.: US 9,919,300 B2
(45) Date of Patent: *Mar. 20, 2018

(54) 1-HEXENE PRODUCTION PROCESS

(71) Applicant: Sumitomo Chemical Company, Limited, Tokyo (JP)

(72) Inventors: Yasutoyo Kawashima, Pasadena, CA (US); Takahiro Hino, Chiba (JP); Taichi Senda, Chiba (JP); Masaya Tanimoto, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/331,104

(22) Filed: Oct. 21, 2016

(65) Prior Publication Data

US 2017/0036200 A1 Feb. 9, 2017

Related U.S. Application Data

(62) Division of application No. 14/575,250, filed on Dec. 18, 2014, now abandoned, which is a division of application No. 13/498,980, filed as application No. PCT/JP2010/067127 on Sep. 30, 2010, now abandoned.

(30) Foreign Application Priority Data

Sep. 30, 2009 (JP) ................................. 2009-226685
Oct. 6, 2009 (JP) ................................. 2009-232247

(51) Int. Cl.
| | | |
|---|---|---|
| *B01J 31/22* | (2006.01) |
| *C07C 2/34* | (2006.01) |
| *C07F 17/00* | (2006.01) |
| *C08F 10/00* | (2006.01) |
| *C07F 19/00* | (2006.01) |
| *C07F 7/28* | (2006.01) |
| *B01J 31/14* | (2006.01) |

(52) U.S. Cl.
CPC ......... *B01J 31/2295* (2013.01); *B01J 31/143* (2013.01); *C07C 2/34* (2013.01); *C07F 7/28* (2013.01); *C07F 17/00* (2013.01); *C07F 19/00* (2013.01); *C08F 10/00* (2013.01); *B01J 2231/20* (2013.01); *B01J 2231/32* (2013.01); *B01J 2531/46* (2013.01); *B01J 2531/48* (2013.01); *B01J 2531/49* (2013.01); *C07C 2531/14* (2013.01); *C07C 2531/22* (2013.01); *Y02P 20/52* (2015.11)

(58) Field of Classification Search
None
See application file for complete search history.

(56) References Cited

U.S. PATENT DOCUMENTS

| | | |
|---|---|---|
| 5,712,354 A | 1/1998 | Boncella et al. |
| 6,121,402 A | 9/2000 | Machida et al. |
| 6,329,478 B1 | 12/2001 | Katayama et al. |
| 7,115,539 B2 | 10/2006 | Takaoki et al. |
| 7,163,907 B1 | 1/2007 | Canich et al. |
| 2004/0030082 A1 | 2/2004 | Iseki |
| 2004/0097772 A1 | 5/2004 | Deckers et al. |
| 2006/0089417 A1 | 4/2006 | Hisayama et al. |
| 2007/0244286 A1 | 10/2007 | Okamoto et al. |
| 2012/0184431 A1 | 7/2012 | Kawashima et al. |
| 2012/0184693 A1 | 7/2012 | Kawashima et al. |
| 2013/0005931 A1 | 1/2013 | Kawashima et al. |
| 2014/0012056 A1 | 1/2014 | Hishiya et al. |
| 2014/0018564 A1 | 1/2014 | Senda et al. |

FOREIGN PATENT DOCUMENTS

| | | |
|---|---|---|
| CN | 1193323 A | 9/1998 |
| CN | 1433433 A | 7/2003 |
| CN | 1448416 A | 10/2003 |

(Continued)

OTHER PUBLICATIONS

Nabika et al. Kobunshi Ronbusnhu, 59 (6), 382-387, 2002.*
Deckers et al, "Catalytic Trimerization of Ethene with Highly Active Cyclopentadienyl-Arene Titanium Catalysts," Organometallics, vol. 21, pp. 5122-5135 (2002).
Wang et al, "Catalytic Trimerization of Ethylene with Highly Active Half-sandwich Titanium Complexes Bearing Pendant p-Fluorophenyl Groups," Chinese Journal of Chemistry, vol. 24, pp. 1397-1401 (2006).
Ye et al, "A Tandem Catalytic System for the Synthesis of Ethylene-Hex-1-ene Copolymers from Ethylene Stock," Macromolecular Rapid Communications, vol. 25, pp. 647-652 (2004).

(Continued)

*Primary Examiner* — Yun Qian
(74) *Attorney, Agent, or Firm* — Panitch Schwarze Belisario & Nadel LLP

(57) ABSTRACT

Disclosed is transition metal complex that serves as a catalytic component with which 1-hexene can be produced efficiently with excellent selectivity, even under high temperature conditions, by means of an ethylene trimerization reaction. Said transition metal complex is represented by the following general formula (1), wherein $M^1$ represents a Group 4 transition metal atom, and $R^1$ through $R^{11}$ and $X^1$ through $X^3$ each independently represent a hydrogen atom, a halogen atom, or a specific organic group.

(1)

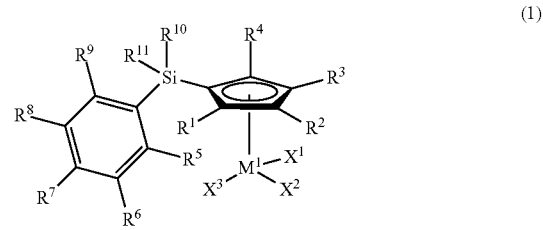

6 Claims, 2 Drawing Sheets

(56) References Cited

FOREIGN PATENT DOCUMENTS

| | | |
|---|---|---|
| CN | 1492847 A | 4/2004 |
| CN | 101050216 A | 10/2007 |
| EP | 0617044 A2 | 9/1994 |
| EP | 2045254 A1 | 4/2009 |
| EP | 2484685 A1 | 8/2012 |
| JP | H07-082322 A | 3/1995 |
| JP | 09-087313 A | 3/1997 |
| JP | 2004-524959 A | 8/2004 |
| JP | 2005-248013 A | 9/2005 |
| JP | 2006-002057 A | 1/2006 |
| JP | 2006-504858 A | 2/2006 |
| JP | 2006-083370 A | 3/2006 |
| JP | 2006-152271 A | 6/2006 |
| JP | 2006-347899 A | 12/2006 |
| JP | 2008-546891 A | 12/2008 |
| WO | 9703992 A1 | 2/1997 |
| WO | 0148028 A1 | 7/2001 |
| WO | 02066404 A1 | 8/2002 |
| WO | 02066405 A1 | 8/2002 |
| WO | 2004046214 A2 | 6/2004 |
| WO | 2007002435 A1 | 1/2007 |
| WO | 2011040555 A1 | 4/2011 |
| WO | 2012/133924 A1 | 10/2012 |
| WO | 2012/133937 A1 | 10/2012 |

OTHER PUBLICATIONS

Alobaidi et al, "Direct Synthesis of Linear Low-Density Polyethylene of Ethylene/1-Hexene from Ethylene with a Tandem Catalytic System in a Single Reactor," Journal of Polymer Science Part A: Polymer Chemistry, vol. 42, pp. 4327-4336 (2004).

Int'l Search Report dated Oct. 26, 2010 in Int'l Application No. PCT/JP2010/067127.

Hanaoka et al, "Synthesis and characterization of titanuim and zirconium complexes with silicone-bridged phenoxycyclopentadienyl ligands," Journal of Organometallic Chemistry, vol. 692, pp. 4059-4066 (2007).

Chen et al, "Reactions of SiH-Functionalized Cyclopentadienes with Metal Carbonyls," Organometallics, vol. 26, pp. 4212-4219 (2007).

Lukesova et al, "Synthesis and crystal structures of thermally stable titanocenes," Journal of Organometallic Chemistry, vol. 663, pp. 134-144 (2002).

Search Report dated Jul. 3, 2013 in CN Application No. 2010800541680.

Int'l Search Report dated Jun. 26, 2012 in Int'l Application No. PCT/JP2012/059282.

Saβmannshausen et al, "Half-sandwich complexes of titanium and zirconium with pendant phenyl substituents. The influence of ansa-aryl coordination on the polymerisation activity of half-sandwich catalysts," Journal of Organometallic Chemistry, vol. 592, pp. 84-94 (1999).

Int'l Search Report dated Jun. 26, 2012 in Int'l Application No. PCT/JP2012/059283.

Int'l Search Report dated Jul. 10, 2012 in Int'l Applicaiton No. PCT/JP2012/059296.

Nabika et al, "Olefin Polymerization Catalyzed by Low Valent Half-Titanocene Complex," Kobunshi Ronbunshu, vol. 59, No. 6, pp. 382-387 (Jun. 2002).

Otten et al, "Versatile Coordination of Cyclopentadienyl-Arene Ligands and Its Role in Titanium-Catalyzed Ethylene Trimerization," Journal of the American Chemical Society, vol. 131, pp. 5298-5312 (2009).

Hagen et al, "Selective ethylene trimerization: A study into the mechanism and the reduction of PE formation," Journal of Molecular Catalysis A: Chemical 248, pp. 237-247 (2006).

Extended European Search Report dated Oct. 14, 2013 in EP Application No. 10820670.7.

Hitzbleck et al, "Half-sandwich dibenzyl complexes of scandium: Synthesis, structure, and styrene polymerization activity," Journal of Organometallic Chemistry, vol. 692, No. 21, pp. 4702-4207 (Sep. 14, 2007).

Sassmannshausen et al, "Models for Solvation of Zirconocene Cations: Synthesis, Reactivity, and Computational Studies of Phenylsilyl-Substituted Cationic and Dicationic Zirconocene Compounds," Organometallics, vol. 25, No. 11, pp. 2796-2805 (Apr. 22, 2006).

Office Action dated Jan. 22, 2014 in CN Application No. 201080054170.8.

Office Action dated Nov. 20, 2013 in U.S. Appl. No. 13/498,980.

Office Action dated May 21, 2014 in U.S. Appl. No. 13/498,980.

Office Action dated Jun. 6, 2014 in U.S. Appl. No. 14/007,218.

Office Action dated Sep. 3, 2014 in CN Application No. 201280016301.2.

Office Action dated Sep. 26, 2014 in U.S. Appl. No. 13/498,980.

Office Action dated Sep. 4, 2014 in CN Application No. 201080054170.8.

Office Action dated Aug. 14, 2014 in U.S. Appl. No. 14/007,692.

Office Action dated Nov. 3, 2014 in CN Application No. 201280015878.1.

Office Action dated Dec. 5, 2014 in U.S. Appl. No. 14/007,692.

Extended European Search Report dated Nov. 25, 2014 in EP Application No. 12763507.6.

Bowen et al, "One electron oxidation of chromium N,N-bis(diarylphosphino)amine and bis(diarylphosphino)methane complexes relevant to ethene trimerisation and tetramerisation," Dalton Transactions, vol. 11, pp. 1160-1168 (2007).

Zaeni et al, Unsolved [KFl(SiPh3)]n (Fl=fluorenyl): A supramolecular chain structure assembled exclusively through K . . . C—Pi-bonding. Journal of Organometallic Chemistry 696 (2011) 1935-1938.

Extended European Search Report dated Jan. 15, 2015 in EP Application No. 12764484.7.

English translation of an Office Action dated Feb. 15, 2015 in CN Application No. 201080054170.8.

Office Action dated Apr. 23, 2015 in CN Application No. 201280016301.2.

Office Action dated Jun. 24, 2015 in U.S. Appl. No. 14/007,715, by Hishiya.

Office Action dated Jul. 28, 2015 in JP Application No. 2012-071307.

Office Action dated Dec. 8, 2015 in U.S. Appl. No. 14/575,188 by Kawashima.

Office Action dated Dec. 9, 2015 in U.S. Appl. No. 14/575,250 by Kawashima.

Office Action dated May 18, 2016 in U.S. Appl. No. 14/575,188 by Kawashima.

Office Action dated May 25, 2016 in U.S. Appl. No. 14/575,250 by Kawashima.

Office Action dated Oct. 16, 2015 in U.S. Appl. No. 14/007,715, by Hishiya.

\* cited by examiner

1-HEXENE PRODUCTION PROCESS

CROSS-REFERENCE TO RELATED APPLICATIONS

This application is a divisional of co-pending U.S. patent application Ser. No. 14/575,250, filed Dec. 18, 2014, which is a divisional of U.S. patent application Ser. No. 13/498,980, filed Mar. 29, 2012, now abandoned, which was a Section 371 of International Application No. PCT/JP2010/067127, filed Sep. 30, 2010, which was published in the Japanese language on Apr. 7, 2011, under International Publication No. WO 2011/040555 A1, the disclosures of which are all incorporated herein by reference.

TECHNICAL FIELD

The present invention relates to a transition metal complex, a process for producing the transition metal complex, a trimerization catalyst, a process for producing 1-hexene, a process for producing an ethylenic polymer, a substituted cyclopentadiene compound and a process for producing the substituted cyclopentadiene compound.

BACKGROUND ART

An α-olefin is an industrially important raw material monomer that is produced by the oligomerization of ethylene using a metal catalyst. However, the oligomerization of ethylene usually gives α-olefin mixtures according to Shultz-Flory distribution. Therefore, the development of a catalyst system capable of selectively producing α-olefin is very important industrially.

For example, PATENT DOCUMENT 1 has reported that a half-metallocene titanium complex represented by the formula $(Cp-B(R)_nAr)TiR^1_3$ works as a catalytic component for selective trimerization of ethylene in the presence of an activating co-catalytic component.

Among these catalysts for selective ethylene trimerization, a half-metallocene titanium complex comprising cyclopentadiene bonded to a substituted aryl group via a carbon atom, such as [1-(1-methyl-1-(3,5-dimethylphenyl)ethyl)-3-trimethylsilylcyclopentadienyl]titanium trichloride, has been reported to work as an efficient ethylene trimerization catalyst under condition of 30° C. with MAO (methylaluminoxane) as an activating co-catalytic component (see e.g., NON-PATENT DOCUMENT 1). On the other hand, [dimethylphenylsilylcyclopentadienyl]titanium trichloride comprising cyclopentadiene bonded to a phenyl group via a silicon atom has been reported to have low catalytic activity in ethylene trimerization reaction under the same condition as above and to produce a large amount of polyethylene as a by-product (see NON-PATENT DOCUMENT 1).

Moreover, it has been reported that a catalyst system for ethylene trimerization using a similar half-metallocene titanium complex comprising cyclopentadiene bonded to a substituted aryl group via a carbon atom exhibits much lower catalytic activity in 1-hexene production and 1-hexene production selectivity under high temperature conditions of 80° C. than at 30° C. (see NON-PATENT DOCUMENT 2).

An ethylenic copolymer having a main chain with ethylene units and an alkyl side chain (e.g., an ethyl or butyl branch), for example, linear low-density polyethylene, has conventionally been produced by copolymerizing ethylene and α-olefin (e.g., 1-butene or 1-hexene) in the presence of an olefin polymerization catalyst.

However, the conventional process for producing an ethylenic copolymer requires using ethylene and expensive α-olefin as raw material monomers and was thus a less-than-sufficient process economically. Thus, a process for producing an ethylenic polymer having an alkyl side chain has been studied in recent years, which utilizes a tandem polymerization process in which only ethylene is used as the raw material monomer and an ethylene oligomerization catalyst and an olefin copolymerization catalyst are used in one reactor.

For example, a process for producing an ethylenic polymer having a butyl branch has been proposed, which comprises polymerizing ethylene in the presence of an olefin polymerization catalyst obtainable by bringing dimethylsilylene(tert-butylamido)(tetramethylcyclopentadienyl)titanium dichloride as an olefin copolymerization catalyst, [1-(1-methyl-1-phenylethyl)-cyclopentadienyl]titanium trichloride as an ethylene trimerization catalyst, and MMAO as an activating co-catalytic component into contact with each other (see NON-PATENT DOCUMENTS 3 and 4). It has been reported therein that an ethylenic polymer having a wide range of melting points and crystallinity is obtained by changing the mixing ratio of the olefin copolymerization catalyst and the ethylene trimerization catalyst and that the ethylenic polymer obtained at 45 to 50° C. however has a much lower 1-hexene content than that obtained at 25 to 30° C. (see NON-PATENT DOCUMENT 3). It has also been reported that particularly at 70° C., the incorporation of 1-hexene is not observed and an ethylene copolymer having a melting point as very high as 133.6° C. is obtained (see NON-PATENT DOCUMENT 4).

NON-PATENT DOCUMENT 4 discloses that an ethylenic polymer having a low melting point is obtained by polymerizing ethylene in the presence of an olefin polymerization catalyst obtainable by bringing rac-dimethylsilylenebis(2-methylbenz[e]indenyl)zirconium dichloride as an olefin copolymerization catalyst, [1-(1-methyl-1-phenylethyl)-cyclopentadienyl]titanium trichloride as an ethylene trimerization catalyst, and MMAO as an activating co-catalytic component into contact with each other. However, no case has reported polymerization at a temperature exceeding 25° C.

CITATION LIST

PATENT DOCUMENT 1: JP-2004-524959 A
NON-PATENT DOCUMENT 1: Organometallics 2002, 21, pp 5122-5135.
NON-PATENT DOCUMENT 2: Chinese Journal of Chemistry 2006, 24, pp 1397-1401.
NON-PATENT DOCUMENT 3: Macromolecular Rapid Communications 2004, 25, pp 647-652.
NON-PATENT DOCUMENT 4: Journal of Polymer Science: Part A: Polymer Chemistry 2004, 42, pp 4327-4336.

SUMMARY OF THE INVENTION

Problems to be Solved by the Invention

Under such circumstances, an object of the present invention is to provide a transition metal complex that serves as a catalytic component capable of efficiently and highly selectively producing 1-hexene through the trimerization reaction of ethylene even under high temperature conditions. Another object of the present invention is to provide a process for economically producing an ethylenic polymer having a butyl branch even under high temperature conditions, comprising polymerizing ethylene in the presence of an olefin polymerization catalyst obtainable by bringing the transition metal complex used as an ethylene trimerization catalyst, an olefin copolymerization catalyst and an activating co-catalytic component into contact with each other.

Means for Solving the Problems

Specifically, a 1st aspect of the present invention relates to a transition metal complex represented by general formula (1):

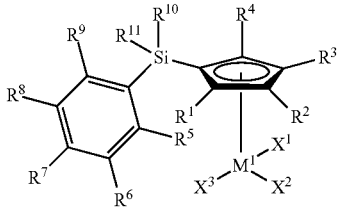

wherein
$M^1$ represents a transition metal atom of Group 4 of the Periodic Table of the Elements; $R^1$, $R^2$, $R^3$ and $R^4$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by $-Si(R^{12})_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by $-N(R^{13})_2$, wherein the two $R^{13}$ groups each independently represent a hydrocarbyl group or a halogenated hydrocarbyl group, and the total number of the carbon atoms in the two $R^{13}$ groups is 2 to 20, and
at least one of $R^1$, $R^2$, $R^3$ and $R^4$ is a halogen atom, the alkyl group, the alkoxy group, the aryl group,
the aryloxy group, the aralkyl group, the aralkyloxy group, the substituted silyl group or the disubstituted amino group;
$R^5$ and $R^9$ each independently represent
a hydrogen atom, a halogen atom,
an alkyl group having 1 to 20 carbon atoms which may have a halogen atom as a substituent,
an alkoxy group having 2 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by $-Si(R^{12})_3$, wherein the three $R^{12}$s each independently represent a hydrogen atom, a hydrocarbyl group or a halogenated hydrocarbyl group, and the total number of the carbon atoms in the three $R^{12}$ groups is 1 to 20, or
a disubstituted amino group represented by $-N(R^{13})_2$, wherein the two $R^{13}$ groups each independently represent a hydrocarbyl group or a halogenated hydrocarbyl group, and the total number of the carbon atoms in the two $R^{13}$ groups is 2 to 20;
$R^6$, $R^7$ and $R^8$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by $-Si(R^{12})_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by $-N(R^{13})_2$, wherein the two $R^{13}$ groups each independently represent a hydrocarbyl group or a halogenated hydrocarbyl group, and the total number of the carbon atoms in the two $R^{13}$ groups is 2 to 20;
$R^{10}$ and $R^{11}$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by $-Si(R^{12})_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by $-N(R^{13})_2$, wherein the two $R^{13}$ groups each independently represent a hydrocarbyl group or a halogenated hydrocarbyl group, and the total number of the carbon atoms in the two $R^{13}$ groups is 2 to 20;
$X^1$, $X^2$ and $X^3$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent, an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20;
of $R^1$, $R^2$, $R^3$ and $R^4$, two groups bonded to two adjacent carbon atoms may be bonded to each other to form a ring together with the two carbon atoms to which the two groups are bonded;
of $R^5$, $R^6$, $R^7$, $R^8$ and $R^9$, two groups bonded to two adjacent carbon atoms may be bonded to each other to form a ring together with the two carbon atoms to which the two groups are bonded; and $R^{10}$ and $R^{11}$ may be bonded to each other to form a ring together with the silicon atom to which $R^{10}$ and $R^{11}$ are bonded.

Moreover, a 2nd aspect of the present invention relates to a trimerization catalyst which is obtainable by contacting the above-mentioned transition metal complex with an activating co-catalytic component.

Furthermore, a 3rd aspect of the present invention relates to a process for producing 1-hexene using the trimerization catalyst.

Moreover, a 4th aspect of the present invention relates to a process for producing an ethylenic polymer, comprising polymerizing ethylene in the presence of an olefin polymerization catalyst obtainable by contacting
a catalytic component for olefin polymerization,
a catalytic component for trimerization comprising a transition metal complex represented by the following general formula (1), and
an activating co-catalytic component:

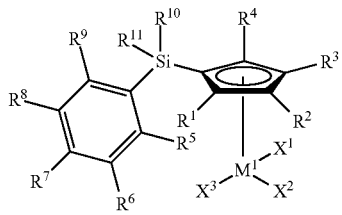

(1)

wherein
$M^1$ represents a transition metal atom of Group 4 of the Periodic Table of the Elements; $R^1$, $R^2$, $R^3$ and $R^4$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$s each independently represent a hydrogen atom, a hydrocarbyl group or a halogenated hydrocarbyl group, and the total number of the carbon atoms in the three $R^{12}$ groups is 1 to 20, or
a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20, and
at least one of $R^1$, $R^2$, $R^3$ and $R^4$ is a halogen atom, the alkyl group, the alkoxy group, the aryl group, the aryloxy group, the aralkyl group, the aralkyloxy group, the substituted silyl group or the disubstituted amino group;
$R^5$ and $R^9$ each independently represent
a hydrogen atom, a halogen atom,
an alkyl group having 1 to 20 carbon atoms which may have a halogen atom as a substituent,
an alkoxy group having 2 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20;
$R^6$, $R^7$ and $R^8$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20;

$R^{10}$ and $R^{11}$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by $-Si(R^{12})_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by $-N(R^{13})_2$, wherein the two $R^{13}$ groups each independently represent a hydrocarbyl group or a halogenated hydrocarbyl group, and the total number of the carbon atoms in the two $R^{13}$ groups is 2 to 20;

$X^1$, $X^2$ and $X^3$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by $-Si(R^{12})_3$, wherein the three $R^{12}$s each independently represent a hydrogen atom, a hydrocarbyl group or a halogenated hydrocarbyl group, and the total number of the carbon atoms in the three $R^{12}$ groups is 1 to 20, or
a disubstituted amino group represented by $-N(R^{13})_2$, wherein the two $R^{13}$ groups each independently represent a hydrocarbyl group or a halogenated hydrocarbyl group, and the total number of the carbon atoms in the two $R^{13}$ groups is 2 to 20;

of $R^1$, $R^2$, $R^3$ and $R^4$, two groups bonded to two adjacent carbon atoms may be bonded to each other to form a ring together with the two carbon atoms to which the two groups are bonded;

of $R^5$, $R^6$, $R^7$, $R^8$ and $R^9$, two groups bonded to two adjacent carbon atoms may be bonded to each other to form a ring together with the two carbon atoms to which the two groups are bonded; and $R^{10}$ and $R^{11}$ may be bonded to each other to form a ring together with the silicon atom to which $R^{10}$ and $R^{11}$ are bonded.

Furthermore, a 5th aspect of the present invention relates to a process for producing the transition metal complex represented by the general formula (1) or a transition metal complex represented by the following general formula (1-2) or (1-3):

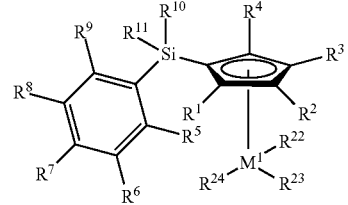
(1-2)

wherein $M^1$, $R^1$, $R^2$, $R^3$, $R^4$, $R^5$, $R^6$, $R^7$, $R^8$, $R^9$, $R^{10}$ and $R^{11}$ are as defined above,
$R^{22}$, $R^{23}$ and $R^{24}$ each independently represent
a halogen atom,
an alkyl group having 1 to 20 carbon atoms which may have a halogen atom as a substituent,
an aryl group having 6 to 20 carbon atoms which may have a halogen atom as a substituent, or
an aralkyl group having 7 to 20 carbon atoms which may have a halogen atom as a substituent, and
at least one of $R^{22}$, $R^{23}$ and $R^{24}$ is the alkyl group, the aryl group or the aralkyl group; and

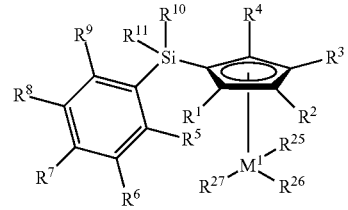
(1-3)

wherein $M^1$, $R^1$, $R^2$, $R^3$, $R^4$, $R^5$, $R^6$, $R^7$, $R^8$, $R^9$, $R^{10}$ and $R^{11}$ are as defined above,
$R^{25}$, $R^{26}$ and $R^{27}$ each independently represent
a halogen atom,
an alkoxy group having 1 to 20 carbon atoms which may have a halogen atom as a substituent,
an aryloxy group having 6 to 20 carbon atoms which may have a halogen atom as a substituent, or
an aralkyloxy group having 7 to 20 carbon atoms which may have a halogen atom as a substituent, and
at least one of $R^{25}$, $R^{26}$ and $R^{27}$ is the alkoxy group, the aryloxy group or the aralkyloxy group.

Moreover, a 6th aspect of the present invention relates to a substituted cyclopentadiene compound represented by general formula (6-1):

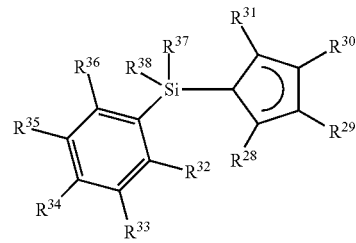
(6-1)

wherein $R^{28}$, $R^{29}$, $R^{30}$ and $R^{31}$ each independently represent
a hydrogen atom, a halogen atom,
an alkyl group having 1 to 20 carbon atoms which may have a halogen atom as a substituent, an alkoxy group having 1 to 20 carbon atoms which may have a halogen atom as a substituent, an aryl group having 6 to 20 carbon atoms which may have a halogen atom as a substituent, an aryloxy group having 6 to 20 carbon atoms which may have a halogen atom as a substituent, an aralkyl group having 7 to 20 carbon atoms which may have a halogen atom as a substituent, an aralkyloxy group having 7 to 20 carbon atoms which may have a halogen atom as a substituent, a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20, and at least one of $R^{28}$, $R^{29}$, $R^{30}$ and $R^{31}$ is a halogen atom, the alkyl group, the alkoxy group, the aryl group, the aryloxy group, the aralkyl group, the aralkyloxy group, the substituted silyl group or the disubstituted amino group;

$R^{32}$ and $R^{36}$ each independently represent a hydrogen atom, a halogen atom, an alkyl group having 1 to 20 carbon atoms which may have a halogen atom as a substituent, an aryl group having 6 to 20 carbon atoms which may have a halogen atom as a substituent, an aralkyl group having 7 to 20 carbon atoms which may have a halogen atom as a substituent, a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20;

$R^{33}$, $R^{34}$ and $R^{35}$ each independently represent a hydrogen atom, a halogen atom, an alkyl group having 1 to 20 carbon atoms which may have a halogen atom as a substituent, an alkoxy group having 1 to 20 carbon atoms which may have a halogen atom as a substituent, an aryl group having 6 to 20 carbon atoms which may have a halogen atom as a substituent, an aryloxy group having 6 to 20 carbon atoms which may have a halogen atom as a substituent, an aralkyl group having 7 to 20 carbon atoms which may have a halogen atom as a substituent, an aralkyloxy group having 7 to 20 carbon atoms which may have a halogen atom as a substituent, a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20;

$R^{37}$ represents an alkyl group having 1 to 20 carbon atoms which may have a halogen atom as a substituent, an aryl group having 6 to 20 carbon atoms which may have a halogen atom as a substituent, an aralkyl group having 7 to 20 carbon atoms which may have a halogen atom as a substituent, or a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20;

$R^{38}$ represents an alkyl group having 2 to 20 carbon atoms which may have a halogen atom as a substituent, an aralkyl group having 7 to 20 carbon atoms which may have a halogen atom as a substituent, or a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20;

of $R^{32}$, $R^{33}$, $R^{34}$, $R^{35}$ and $R^{36}$, two groups bonded to two adjacent carbon atoms may be bonded to each other to form a ring together with the two carbon atoms to which the two groups are bonded;

$R^{37}$ and $R^{38}$ may be bonded to each other to form a ring together with the silicon atom to which $R^{37}$ and $R^{38}$ are bonded; and the moiety

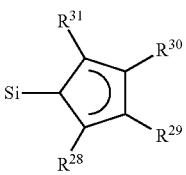

represents

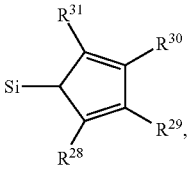

a substituted cyclopentadiene compound represented by general formula (6-2):

(6-2)

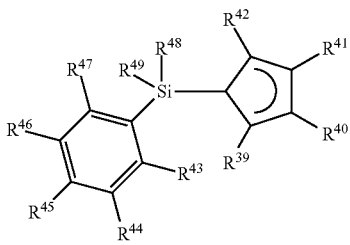

wherein $R^{39}$, $R^{40}$, $R^{41}$ and $R^{42}$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20, and
at least one of $R^{39}$, $R^{40}$, $R^{41}$ and $R^{42}$ is a halogen atom, the alkyl group, the alkoxy group, the aryl group, the aryloxy group, the aralkyl group, the aralkyloxy group, the substituted silyl group or the disubstituted amino group;
$R^{43}$ and $R^{47}$ each independently represent
a hydrogen atom, a halogen atom,
an alkyl group having 1 to 20 carbon atoms which may have a halogen atom as a substituent,
an aryl group having 6 to 20 carbon atoms which may have a halogen atom as a substituent,
an aralkyl group having 7 to 20 carbon atoms which may have a halogen atom as a substituent,
a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20;
$R^{44}$, $R^{45}$ and $R^{46}$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20;
$R^{48}$ and $R^{49}$ each independently represent
an aryl group having 6 to 20 carbon atoms which may have a halogen atom as a substituent;
of $R^{43}$, $R^{44}$, $R^{45}$, $R^{46}$ and $R^{47}$, two groups bonded to two adjacent carbon atoms may be bonded to each other to form a ring together with the two carbon atoms to which the two groups are bonded;
$R^{48}$ and $R^{49}$ may be bonded to each other to form a ring together with the silicon atom to which $R^{48}$ and $R^{49}$ are bonded; and
the moiety

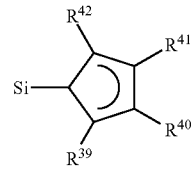

represents

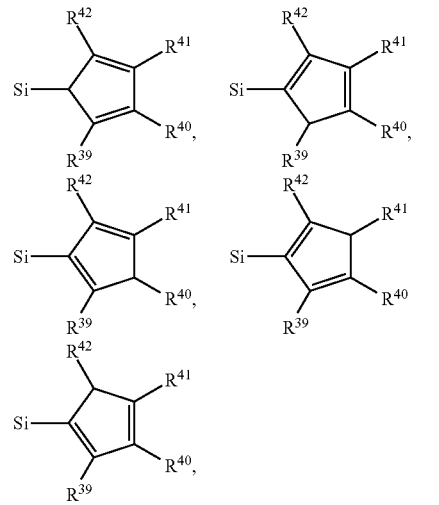

a substituted cyclopentadiene compound represented by general formula (6-3):

(6-3)

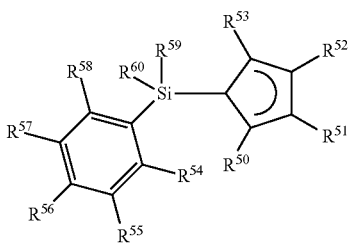

wherein $R^5$, $R^{51}$, $R^{52}$ and $R^{53}$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$s each independently represent a hydrogen atom, a hydrocarbyl group or a halogenated hydrocarbyl group, and the total number of the carbon atoms in the three $R^{12}$ groups is 1 to 20, or
a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20, and
at least two of $R^{50}$, $R^{51}$, $R^{52}$ and $R^{53}$ are the alkyl group;
$R^{54}$ and $R^{58}$ each independently represent
a hydrogen atom, a halogen atom,
an alkyl group having 1 to 20 carbon atoms which may have a halogen atom as a substituent,
an aryl group having 6 to 20 carbon atoms which may have a halogen atom as a substituent,
an aralkyl group having 7 to 20 carbon atoms which may have a halogen atom as a substituent,
a substituted silyl group represented by —Si($R^{12}$)$_3$, wherein the three $R^{12}$ groups each independently represent a hydrogen atom, a hydrocarbyl group or a halogenated hydrocarbyl group, and the total number of carbon atoms in the three $R^{12}$ groups is 1 to 20, or
a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20;
$R^{55}$, $R^{56}$ and $R^{57}$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20;
$R^{59}$ and $R^{60}$ each independently represent
an alkyl group having 1 to 20 carbon atoms which may have a halogen atom as a substituent,
an aryl group having 6 to 20 carbon atoms which may have a halogen atom as a substituent,
an aralkyl group having 7 to 20 carbon atoms which may have a halogen atom as a substituent, or
a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20;
of $R^{50}$, $R^{51}$, $R^{52}$, and $R^{53}$, two of the alkyl groups bonded to two adjacent carbon atoms are bonded to each other to form a cyclohexene ring together with the two carbon atoms to which the two alkyl groups are bonded;
of $R^{54}$, $R^{55}$, $R^{56}$, $R^{57}$ and $R^{58}$, two groups bonded to two adjacent carbon atoms may be bonded to each other to form a ring together with the two carbon atoms to which the two groups are bonded;
$R^{59}$ and $R^{60}$ may be bonded to each other to form a ring together with the silicon atom to which $R^{59}$ and $R^{60}$ are bonded; and
the moiety

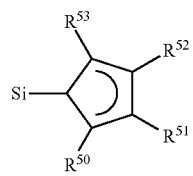

represents

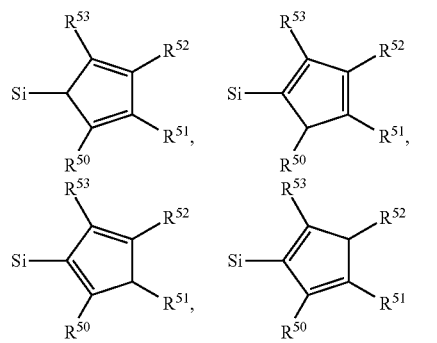

or

-continued

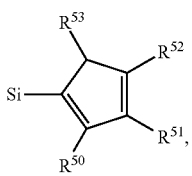

a substituted cyclopentadiene compound represented by general formula (6-4):

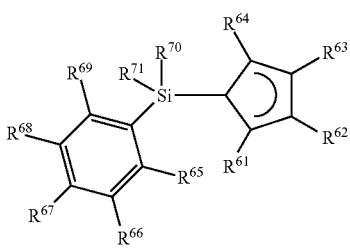
(6-4)

wherein $R^{61}$, $R^{62}$, $R^{63}$ and $R^{64}$ each independently represent a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20, and
at least one of $R^{61}$, $R^{62}$, $R^{63}$ and $R^{64}$ is a halogen atom, the alkyl group, the alkoxy group, the aryl group, the aryloxy group, the aralkyl group, the aralkyloxy group, the substituted silyl group or the disubstituted amino group;
a substructural formula (14)

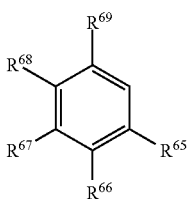
(14)

formed with $R^{65}$, $R^{66}$, $R^{67}$, $R^{68}$ and $R^{69}$ is methylphenyl, dimethylphenyl, trimethylphenyl, tetramethylphenyl, pentamethylphenyl, tert-butylphenyl, di-tert-butylphenyl, tert-butylmethylphenyl, di(tert-butyl)methylphenyl, anthracene, chlorophenyl, dichlorophenyl, fluorophenyl or bis(trifluoromethyl)phenyl;
each of $R^{70}$ and $R^{71}$ is a methyl group; and
the moiety

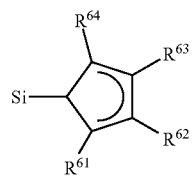

represents

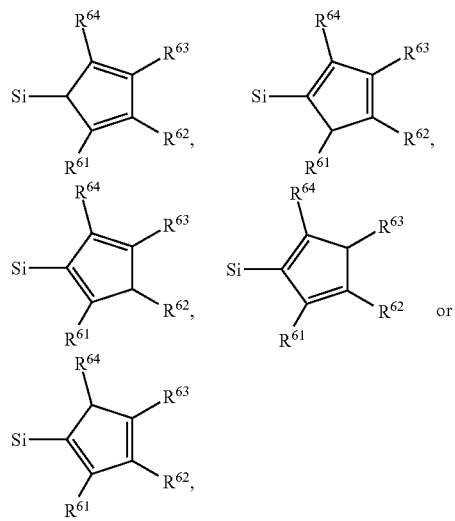

a substituted cyclopentadiene compound represented by general formula (6-5):

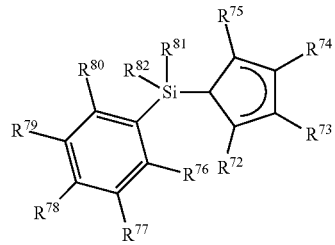
(6-5)

wherein $R^{72}$, $R^{73}$, $R^{74}$ and $R^{75}$ each independently represent a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent, an aralkyloxy group having 7 to 20 carbon atoms which may have a halogen atom as a substituent,
a substituted silyl group represented by —Si(R$^{12}$)$_3$, wherein the three R$^{12}$ groups each independently represent a hydrogen atom, a hydrocarbyl group or a halogenated hydrocarbyl group, and the total number of the carbon atoms in the three R$^{12}$ groups is 1 to 20, or
a disubstituted amino group represented by —N(R$^{13}$)$_2$, wherein the two R$^{13}$ groups each independently represent a hydrocarbyl group or a halogenated hydrocarbyl group, and the total number of the carbon atoms in the two R$^{13}$ groups is 2 to 20, and
at least one of R$^{72}$, R$^{73}$, R$^{74}$ and R$^{75}$ is a halogen atom, the alkyl group, the alkoxy group, the aryl group, the aryloxy group, the aralkyl group, the aralkyloxy group, the substituted silyl group or the disubstituted amino group;
R$^{76}$ and R$^{80}$ each independently represent
a hydrogen atom, a halogen atom,
an alkyl group having 1 to 20 carbon atoms which may have a halogen atom as a substituent,
an aryl group having 6 to 20 carbon atoms which may have a halogen atom as a substituent,
an aralkyl group having 7 to 20 carbon atoms which may have a halogen atom as a substituent,
a substituted silyl group represented by —Si(R$^{12}$)$_3$, wherein the three R$^{12}$ groups each independently represent a hydrogen atom, a hydrocarbyl group or a halogenated hydrocarbyl group, and the total number of the carbon atoms in the three R$^{12}$ groups is 1 to 20, or
a disubstituted amino group represented by —N(R$^{13}$)$_2$, wherein the two R$^{13}$ groups each independently represent a hydrocarbyl group or a halogenated hydrocarbyl group, and the total number of the carbon atoms in the two R$^{13}$ groups is 2 to 20;
R$^{77}$, R$^{78}$ and R$^{79}$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si(R$^{12}$)$_3$, wherein the three R$^{12}$ groups each independently represent a hydrogen atom, a hydrocarbyl group or a halogenated hydrocarbyl group, and the total number of the carbon atoms in the three R$^{12}$ groups is 1 to 20, or
a disubstituted amino group represented by —N(R$^{13}$)$_2$, wherein the two R$^{13}$ groups each independently represent a hydrocarbyl group or a halogenated hydrocarbyl group, and the total number of the carbon atoms in the two R$^{13}$ groups is 2 to 20;
R$^{81}$ represents a methyl group;
R$^{82}$ represents an aryl group having 7 to 20 carbon atoms which may have a halogen atom as a substituent;
of R$^{76}$, R$^{77}$, R$^{78}$, R$^{79}$ and R$^{80}$, two groups bonded to two adjacent carbon atoms may be bonded to each other to form a ring together with the two carbon atoms to which the two groups are bonded;

R$^{81}$ and R$^{82}$ may be bonded to each other to form a ring together with the silicon atom to which R$^{81}$ and R$^{82}$ are bonded; and
the moiety

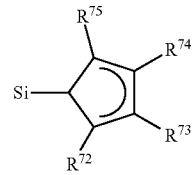

represents

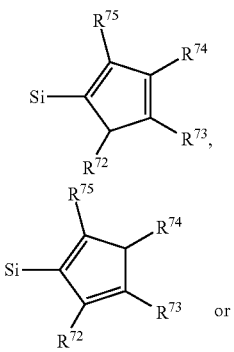

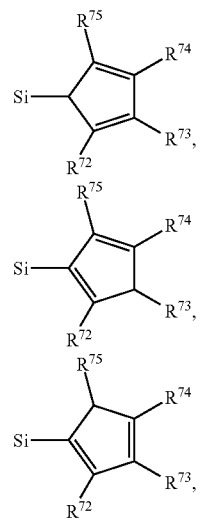

and
a substituted cyclopentadiene compound represented by general formula (6-6):

$$\text{(6-6)}$$

wherein R$^{83}$, R$^{84}$, R$^{85}$ and R$^{86}$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent, a substituted silyl group represented by —Si(R$^{12}$)$_3$, wherein the three R$^{12}$ groups each independently represent a hydrogen atom, a hydrocarbyl group or a halogenated hydrocarbyl group, and the total number of the carbon atoms in the three R$^{12}$ groups is 1 to 20, or a disubstituted amino group represented by —N(R$^{13}$)$_2$, wherein the two R$^{13}$ groups each independently represent a hydrocarbyl group or a halogenated hydrocarbyl group, and the total number of the carbon atoms in the two R$^{13}$ groups is 2 to 20, and at least one of R$^{83}$, R$^{84}$, R$^{85}$ and R$^{86}$ is a halogen atom, the alkyl group, the alkoxy group, the aryl group, the aryloxy group, the aralkyl group, the aralkyloxy group, the substituted silyl group or the disubstituted amino group, and not every groups of R$^{83}$, R$^{84}$, R$^{85}$ and R$^{86}$ are a methyl group at the same time;

each of R$^{87}$, R$^{88}$, R$^{89}$, R$^{90}$ and R$^{91}$ is a hydrogen atom; R$^{92}$ and R$^{93}$ each represent a methyl group; and the moiety

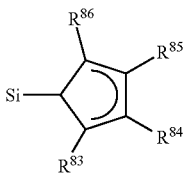

represents

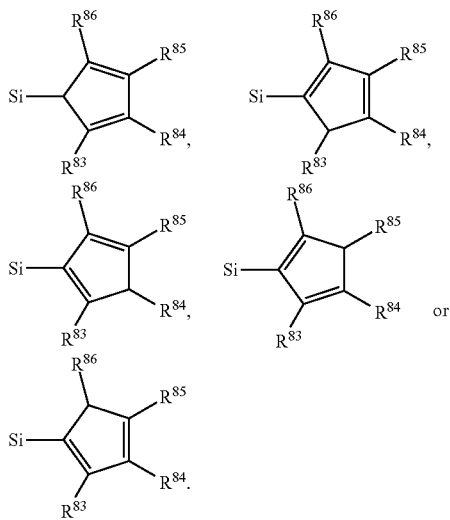

Moreover, a 7th aspect of the present invention relates to a process for producing the substituted cyclopentadiene compound represented by any of the general formulas (6-1) to (6-6).

Advantages of the Invention

The present invention can provide a transition metal complex that is suitable as a catalytic component capable of efficiently and highly selectively producing 1-hexene through the trimerization reaction of ethylene even under high temperature conditions. The present invention can further provide a process for economically producing an ethylenic polymer having a butyl branch even under high temperature conditions, comprising polymerizing ethylene in the presence of an olefin polymerization catalyst obtainable by bringing the transition metal complex, which is used as an ethylene trimerization catalyst, an olefin copolymerization catalyst and an activating co-catalyst into contact with each other.

DESCRIPTION OF EMBODIMENTS

Figure 1:
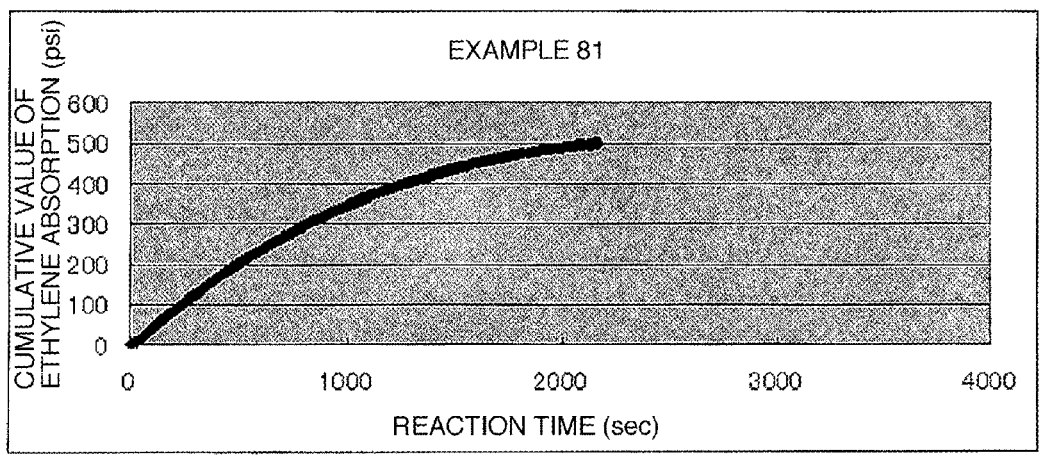
FIG. 1 graphically represents the time-dependent change of ethylene absorption in an embodiment of the present invention.

In the present invention, the term "polymerization" encompasses not only homopolymerization but also copolymerization. Moreover, in the present invention, the term "substituent" encompasses a halogen atom constituting a compound or a group.

Furthermore, in the present invention, substituted cyclopentadiene compounds represented by general formulae (6) and (6-1) to (6-6) respectively have isomers differing in the double bond position of each cyclopentadienyl ring. In the present invention, the substituted cyclopentadienyl compounds refer to any of them or a mixture of them.

<Transition Metal Complex (1) (Catalytic Component for Trimerization)>

Hereinafter, the transition metal complex represented by the general formula (1) will be described in detail.

In the transition metal complex (1), M$^1$ represents an element of Group 4 of the Periodic Table of the Elements, and examples thereof include titanium, zirconium and hafnium atoms. Among them, a titanium atom is preferable.

In the transition metal complex (1), the substituents R$^1$, R$^2$, R$^3$, R$^4$, R$^5$, R$^6$, R$^7$, R$^8$, R$^9$, R$^{10}$, R$^{11}$, X$^1$, X$^2$ and X$^3$ are as defined above, and specific examples thereof are shown below.

The halogen atom is a fluorine, chlorine, bromine or iodine atom and is preferably a chlorine atom.

Specific examples of the "alkyl group having 1 to 20 carbon atoms" in the alkyl group having 1 to 20 carbon atoms which may have a halogen atom as a substituent include methyl, ethyl, n-propyl, isopropyl, n-butyl, sec-butyl, tert-butyl, n-pentyl, neopentyl, amyl, n-hexyl, heptyl, n-octyl, n-nonyl, n-decyl, n-dodecyl, n-tridecyl, tetradecyl, pentadecyl, hexadecyl, heptadecyl, octadecyl, nonadecyl and n-eicosyl groups. Of these, a preferable alkyl group is an alkyl group having 1 to 10 carbon atoms, and more preferable examples thereof include methyl, ethyl, isopropyl, tert-butyl and amyl groups. Moreover, the phrase "may have a halogen atom as a substituent" in the "alkyl group which may have a halogen atom as a substituent" means that some or all of hydrogen atoms in the alkyl group may be substituted with a halogen atom. Specific examples of the halogen atom are as described above. When the alkyl group has a halogen atom as a substituent, the number of its carbon atoms is preferably in the range of 1 to 20, more preferably in the range of 1 to 10. Preferable examples of the alkyl group having a halogen atom as a substituent can include fluoromethyl, difluoromethyl, trifluoromethyl, chloromethyl, dichloromethyl, trichloromethyl, bromomethyl, dibromomethyl, tribromomethyl, fluoroethyl, perfluoropropyl, perfluorobutyl, perfluoropentyl and perfluorohexyl groups.

Specific examples of the "aryl group having 6 to 20 carbon atoms" in the aryl group having 6 to 20 carbon atoms which may have a halogen atom as a substituent include phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, naphthyl and anthracenyl groups. Of these, a preferable aryl group is an aryl group having 6 to 10 carbon atoms, and more preferable examples thereof include phenyl group. Moreover, the phrase "may have a halogen atom as a substituent" in the "aryl group which may have a halogen atom as a substituent" means that some or all of hydrogen atoms in the aryl group may be substituted with a halogen atom. Specific examples of the halogen atom are as described above. When the aryl group has a halogen atom as a substituent, the number of its carbon atoms is preferably in the range of 6 to 20, more preferably in the range of 6 to 10. Preferable examples of the aryl group having a halogen atom as a substituent can specifically include fluorophenyl, difluorophenyl, trifluorophenyl, tetrafluorophenyl, pentafluorophenyl, chlorophenyl, bromophenyl and iodophenyl groups.

Specific examples of the "aralkyl group having 7 to 20 carbon atoms" in the aralkyl group having 7 to 20 carbon atoms which may have a halogen atom as a substituent include benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (3,5-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, naphthylmethyl and anthracenylmethyl groups. Of these, a preferable aralkyl group is an aralkyl group having 7 to 10 carbon atoms, and more preferable examples thereof can include a benzyl group. Moreover, the phrase "may have a halogen atom as a substituent" in the "aralkyl group which may have a halogen atom as a substituent" means that some or all of hydrogen atoms in the aralkyl group may be substituted with a halogen atom. Specific examples of the halogen atom are as described above. When the aralkyl group has a halogen atom as a substituent, the number of its carbon atoms is preferably in the range of 7 to 20, more preferably in the range of 7 to 10.

Specific examples of the "alkoxy group having 1 to 20 carbon atoms" in the alkoxy group having 1 to 20 carbon atoms which may have a halogen atom as a substituent include methoxy, ethoxy, n-propoxy, isopropoxy, n-butoxy, sec-butoxy, tert-butoxy, n-pentyloxy, neopentyloxy, n-hexyloxy, n-octyloxy, n-nonyloxy, n-decyloxy, n-undecyloxy, n-dodecyloxy, tridecyloxy, tetradecyloxy, n-pentadecyloxy, hexadecyloxy, heptadecyloxy, octadecyloxy, nonadecyloxy and n-eicosyloxy groups. Of these, a preferable alkoxy group is an alkoxy group having 1 to 10 carbon atoms, and more preferable examples thereof include methoxy, ethoxy and tert-butoxy groups. Moreover, the phrase "may have a halogen atom as a substituent" in the "alkoxy group which may have a halogen atom as a substituent" means that some or all of hydrogen atoms in the alkoxy group may be substituted with a halogen atom. Specific examples of the halogen atom are as described above. When the alkoxy group has a halogen atom as a substituent, the number of its carbon atoms is preferably in the range of 1 to 20, more preferably in the range of 1 to 10.

Specific examples of the "alkoxy group having 2 to 20 carbon atoms" in the alkoxy group having 2 to 20 carbon atoms which may have a halogen atom as a substituent include ethoxy, n-propoxy, isopropoxy, n-butoxy, sec-butoxy, tert-butoxy, n-pentyloxy, neopentyloxy, n-hexyloxy, n-octyloxy, n-nonyloxy, n-decyloxy, n-undecyloxy, n-dodecyloxy, tridecyloxy, tetradecyloxy, n-pentadecyloxy, hexadecyloxy, heptadecyloxy, octadecyloxy, nonadecyloxy and n-eicosyloxy groups. Of these, a preferable alkoxy group is an alkoxy group having 2 to 10 carbon atoms, and more preferable examples thereof include ethoxy and tert-butoxy groups. Moreover, the phrase "may have a halogen atom as a substituent" in the "alkoxy group which may have a halogen atom as a substituent" means that some or all of hydrogen atoms in the alkoxy group may be substituted with a halogen atom. Specific examples of the halogen atom are as described above. When the alkoxy group has a halogen atom as a substituent, the number of its carbon atoms is preferably in the range of 2 to 20, more preferably in the range of 2 to 10.

Specific examples of the "aryloxy group having 6 to 20 carbon atoms" in the aryloxy group having 6 to 20 carbon atoms which may have a halogen atom as a substituent include phenoxy, 2-methylphenoxy, 3-methylphenoxy, 4-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2,3,4-trimethylphenoxy, 2,3,5-trimethylphenoxy, 2,3,6-trimethylphenoxy, 2,4,5-trimethylphenoxy, 2,4,6-trimethylphenoxy, 3,4,5-trimethylphenoxy, 2,3,4,5-tetramethylphenoxy, 2,3,4,6-tetramethylphenoxy, 2,3,5,6-tetramethylphenoxy, pentamethylphenoxy, ethylphenoxy, n-propylphenoxy, isopropylphenoxy, n-butylphenoxy, sec-butylphenoxy, tert-butylphenoxy, n-hexylphenoxy, n-octylphenoxy, n-decylphenoxy, n-tetradecylphenoxy, naphthoxy and anthracenoxy groups. Of these, a preferable aryloxy group is an aryloxy group having 6 to 10 carbon atoms, and more preferable examples thereof include phenoxy, 2-methylphenoxy, 3-methylphenoxy and 4-methylphenoxy groups. Moreover, the phrase "may have a halogen atom as a substituent" in the "aryloxy group which may have a halogen atom as a substituent" means that some or all of hydrogen atoms in the aryloxy group may be substituted with a halogen atom. Specific examples of the halogen atom are as described above. When the aryloxy group has a halogen atom as a substituent, the number of its carbon atoms is preferably in the range of 6 to 20, more preferably in the range of 6 to 10.

Specific examples of the "aralkyloxy group having 7 to 20 carbon atoms" in the aralkyloxy group having 7 to 20 carbon atoms which may have a halogen atom as a substituent include benzyloxy, (2-methylphenyl)methoxy, (3-methylphenyl)methoxy, (4-methylphenyl)methoxy, (2,3-dimethylphenyl)methoxy, (2,4-dimethylphenyl)methoxy, (2,5-dimethylphenyl)methoxy, (2,6-dimethylphenyl)methoxy, (3,4-dimethylphenyl)methoxy, (3,5-dimethylphenyl)methoxy, (2,3,4-trimethylphenyl)methoxy, (2,3,5-trimethylphenyl)methoxy, (2,3,6-trimethylphenyl)methoxy, (2,4,5-trimethylphenyl)methoxy, (2,4,6-trimethylphenyl)methoxy, (3,4,5-trimethylphenyl)methoxy, (2,3,4,5-tetramethylphenyl)methoxy, (2,3,4,6-tetramethylphenyl)methoxy, (2,3,5,6-tetramethylphenyl)methoxy, (pentamethylphenyl)methoxy, (ethylphenyl)methoxy, (n-propylphenyl)methoxy, (isopropylphenyl)methoxy, (n-butylphenyl)methoxy, (sec-butylphenyl)methoxy, (tert-butylphenyl)methoxy, (n-hexylphenyl)methoxy, (n-octylphenyl)methoxy, (n-decylphenyl)methoxy, naphthylmethoxy and anthracenylmethoxy groups. Of these, a preferable aralkyloxy group is an aralkyloxy group having 7 to 10 carbon atoms, and more preferable examples thereof include benzyloxy group. Moreover, the phrase "may have a halogen atom as a substituent" in the "aralkyloxy group which may have a halogen atom as a substituent" means that some or all of hydrogen atoms in the aralkyloxy group may be substituted with a halogen atom. Specific examples of the halogen atom are as described above. When the aralkyloxy group has a halogen atom as a substituent, the number of its carbon atoms is preferably in the range of 7 to 20, more preferably in the range of 7 to 10.

In the substituted silyl group represented by $-Si(R^{12})_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, the $R^{12}$ groups are each independently a hydrogen atom; a hydrocarbyl group such as an alkyl group having 1 to 10 carbon atoms (e.g., methyl, ethyl, n-propyl, isopropyl, n-butyl, sec-butyl, tert-butyl, isobutyl, n-pentyl, n-hexyl, cyclohexyl, n-heptyl, n-octyl, n-nonyl and n-decyl groups) and an aryl group (e.g., phenyl group); or a halogenated hydrocarbyl group obtained by substituting some or all of hydrogen atoms in the hydrocarbyl group with a halogen atom, and the total number of carbon atoms in the three $R^{12}$ groups is in the range of 1 to 20. The total number of the carbon atoms in the these three $R^{12}$ groups is preferably in the range of 3 to 18. Specific examples of the substituted silyl group include: monosubstituted silyl groups having one hydrocarbyl or halogenated hydrocarbyl group, such as methylsilyl, ethylsilyl and phenylsilyl groups, and groups obtained by substituting some or all of hydrogen atoms in the hydrocarbyl groups of these groups with a halogen atom; disubstituted silyl groups having two hydrocarbyl and/or halogenated hydrocarbyl groups, such as dimethylsilyl, diethylsilyl and diphenylsilyl groups, and groups obtained by substituting some or all of hydrogen atoms in the hydrocarbyl groups of these groups with a halogen atom; and trisubstituted silyl group having three hydrocarbyl and/or halogenated hydrocarbyl groups, such as trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyl-dimethylsilyl, tri-n-pentylsilyl, tri-n-hexylsilyl, tricyclohexylsilyl and triphenylsilyl groups, and groups obtained by substituting some or all of hydrogen atoms in the hydrocarbyl groups of these groups with a halogen atom. Of these, trisubstituted silyl groups are preferable, and trimethylsilyl, tert-butyldimethylsilyl and triphenylsilyl groups, and groups obtained by substituting some or all of hydrogen atoms in these groups with a halogen atom are more preferable.

In the disubstituted amino group represented by $-N(R^{13})_2$, wherein the two $R^{13}$ groups each independently represent a hydrocarbyl group or a halogenated hydrocarbyl group, and the total number of the carbon atoms in the two $R^{13}$ groups is 2 to 20, the $R^{13}$ groups each independently represent a hydrocarbyl group or a halogenated hydrocarbyl group, and the total number of the carbon atoms in the two $R^{13}$ groups is in the range of 2 to 20, more preferably in the range of 2 to 10. The hydrocarbyl group and the halogenated hydrocarbyl group are the same as those described as the hydrocarbyl group and the halogenated hydrocarbyl group for the substituted silyl group. Moreover, these two $R^{13}$ groups may be bonded to each other to form a ring together with the nitrogen atom to which these two $R^{13}$ groups are bonded. Examples of such a disubstituted amino group include dimethylamino, diethylamino, di-n-propylamino, diisopropylamino, di-n-butylamino, di-sec-butylamino, di-tert-butylamino, di-isobutylamino, tert-butylisopropylamino, di-n-hexylamino, di-n-octylamino, di-n-decylamino, diphenylamino, bistrimethyl silylamino, bis-tert-butyldimethylsilylamino, pyrrolyl, pyrrolidinyl, piperidinyl, carbazolyl, dihydroindolyl and dihydroisoindolyl groups, and groups obtained by substituting some or all of hydrogen atoms in these groups with a halogen atom. Of these, dimethylamino, diethylamino, pyrrolidinyl and piperidinyl groups, and groups obtained by substituting some or all of hydrogen atoms in these groups with a halogen atom are preferable.

Of $R^1$, $R^2$, $R^3$ and $R^4$, two groups bonded to two adjacent carbon atoms may be bonded to each other to form a ring together with the carbon atoms to which the two groups are bonded, $R^{10}$ and $R^{11}$ may be bonded to each other to form a ring together with the silicon atom to which $R^{10}$ and $R^{11}$ are bonded, and of $R^5$, $R^6$, $R^7$, $R^8$ and $R^9$, two groups bonded to two adjacent carbon atoms may be bonded to each other to form a ring together with the carbon atoms to which the two groups are bonded. In this context, the ring is a saturated or unsaturated hydrocarbyl ring substituted with a hydrocarbyl group having 1 to 20 carbon atoms, a saturated or unsaturated silahydrocarbyl ring substituted by a hydrocarbyl group having 1 to 20 carbon atoms, etc. Specific examples thereof include cyclopropane, cyclopropene, cyclobutane, cyclobutene, cyclopentane, cyclopentene, cyclohexane, cyclohexene, cycloheptane, cycloheptene, cyclooctane, cyclooctene, benzene, naphthalene, anthracene, silacyclopropane, silacyclobutane, silacyclopropane and silacyclohexane rings.

In the transition metal complex (1), at least one of $R^1$, $R^2$, $R^3$ and $R^4$ is a substituent other than hydrogen and is preferably a hydrogen atom, a halogen atom, an alkyl group having 1 to carbon atoms, an aryl group having 6 to 20 carbon atoms or an aralkyl group having 7 to 20 carbon atoms.

Specific examples of $R^1$, $R^2$, $R^3$ and $R^4$ are those that can provide a cyclopentadienyl substructure represented by substructural formula (15):

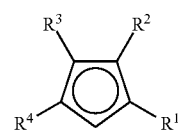

(15)

wherein $R^1$, $R^2$, $R^3$ and $R^4$ are as defined above, and at least one thereof is a substituent other than hydrogen.

For example, the following substructures can be exemplified:

methylcyclopentadienyl, ethylcyclopentadienyl, n-propylcyclopentadienyl, isopropylcyclopentadienyl, n-butylcyclopentadienyl, sec-butylcyclopentadienyl, tert-butylcyclopentadienyl, dimethylcyclopentadienyl, trimethylcyclopentadienyl, tetramethylcyclopentadienyl, phenylcyclopentadienyl, benzylcyclopentadienyl, indenyl, fluorenyl, tetrahydroindenyl, methyltetrahydroindenyl, dimethyltetrahydroindenyl and octahydrofluorenyl.

Of the cyclopentadienyl substructures exemplified above, the preferable cyclopentadienyl substructures are tetramethylcyclopentadienyl, etc.

In the transition metal complex (1), $R^5$, $R^6$, $R^7$, $R^8$ and $R^9$ are preferably a hydrogen atom, a halogen atom, an alkyl group having 1 to 20 carbon atoms, an aryl group having 6 to 20 carbon atoms or an aralkyl group having 7 to 20 carbon atoms.

Examples of the preferable combination of the moieties represented by $R^5$, $R^6$, $R^7$, $R^8$ and $R^9$ can include those that can provide the following substructures represented by substructural formula (16):

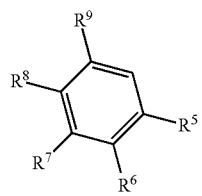

(16)

wherein $R^5$, $R^6$, $R^7$, $R^8$ and $R^9$ are as defined above.

For example, the following substructures can be exemplified:

phenyl, methylphenyl, dimethylphenyl, trimethylphenyl, tetramethylphenyl, pentamethylphenyl, tert-butylphenyl, di-tert-butylphenyl, tert-butylmethylphenyl, di(tert-butyl)methylphenyl, naphthyl, anthracenyl, chlorophenyl, dichlorophenyl, fluorophenyl, pentafluorophenyl, bis(trifluoromethyl)phenyl and methoxyphenyl.

Of the substructures exemplified above, the preferable substructures are phenyl, methylphenyl, dimethylphenyl, trimethylphenyl, etc.

In the transition metal complex (1), $R^{10}$ and $R^{11}$ are preferably a hydrogen atom, an alkyl group having 1 to 20 carbon atoms, an aryl group having 6 to 20 carbon atoms or an aralkyl group having 7 to 20 carbon atoms, and specific examples thereof include methyl, ethyl, n-propyl, isopropyl, n-butyl, sec-butyl, tert-butyl, phenyl, 4-methylphenyl, 3-methylphenyl, 2-methylphenyl, naphthyl and benzyl group.

Examples of a preferable combination of the moieties represented by $R^{10}$ and $R^{11}$ can include those that can provide the following substructures represented by substructural formula (17):

(17)

wherein $R^{10}$ and $R^{11}$ are as defined above:

For example, the following substructures can be exemplified:

dimethylsilylene, diethylsilylene, ethylmethylsilylene, di(n-propyl)silylene, methyl(n-propyl)silylene, di(n-butyl)silylene, n-butylmethylsilylene, n-hexylmethylsilylene, methyl(n-octyl)silylene, n-decylmethylsilylene, methyl(n-octadecyl)silylene, cyclohexylmethylsilylene, cyclotetramethylenesilylene, diphenylsilylene and methylphenylsilylene.

Preferable examples thereof can include a substructure represented by the substructural formula (17), wherein $R^{10}$ is a methyl group, and $R^{11}$ is an alkyl group having 2 to 20 carbon atoms which may have a halogen atom as a substituent, or an aryl group having 6 to 20 carbon atoms which may have a halogen atom as a substituent; or $R^{10}$ and $R^{11}$ are the same and represent an alkyl group having 1 to 20 carbon atoms which may have a halogen atom as a substituent, or an aryl group having 6 to 20 carbon atoms which may have a halogen atom as a substituent.

Specifically, the substructure can be dimethylsilylene, diethylsilylene, ethylmethylsilylene, n-butylmethylsilylene, cyclohexylmethylsilylene, cyclotetramethylenesilylene, diphenylsilylene, methylphenylsilylene, etc.

Preferable examples of the transition metal complex of the formula (1) can include transition metal complexes, wherein $R^6$ and $R^8$ are an alkyl group having 1 to 20 carbon atoms which may have a halogen atom as a substituent, or an aryl group having 6 to 20 carbon atoms which may have a halogen atom as a substituent, and $R^{10}$ and $R^{11}$ are an aryl group having 6 to 20 carbon atoms which may have a halogen atom as a substituent.

Specific examples of the transition metal complex (1) can include the following complexes:

titanium chloride complexes such as [1-dimethylphenylsilyl-2-methylcyclopentadienyl]titanium trichloride, [1-dimethylphenylsilyl-3-methylcyclopentadienyl]titanium trichloride, [1-dimethylphenylsilyl-2,3-dimethylcyclopentadienyl]titanium trichloride, [1-dimethylphenylsilyl-2,4-dimethylcyclopentadienyl]titanium trichloride, [1-dimethylphenylsilyl-2,5-dimethylcyclopentadienyl]titanium trichloride, [1-dimethylphenylsilyl-2,3,5-trimethylcyclopentadienyl]titanium trichloride, [1-dimethylphenylsilyl-2,3,4,5-tetramethylcyclopentadienyl]titanium trichloride, [1-dimethylphenylsilyl-2-ethylcyclopentadienyl]titanium trichloride, [1-dimethylphenylsilyl-3-ethylcyclopentadienyl]titanium trichloride, [1-dimethylphenylsilyl-2-n-propylcyclopentadienyl]titanium trichloride, [1-dimethylphenyl silyl-3-n-propylcyclopentadienyl]titanium trichloride, [1-dimethylphenylsilyl-2-isopropylcyclopentadienyl]titanium trichloride, [1-dimethylphenylsilyl-2-n-butylcyclopentadienyl]titanium trichloride, [1-dimethylphenylsilyl-3-n-butylcyclopentadienyl]titanium trichloride, [1-dimethylphenylsilyl-2-sec-butylcyclopentadienyl]titanium trichloride, [1-dimethylphenylsilyl-3-sec-butylcyclopentadienyl]titanium trichloride, [1-dimethylphenylsilyl-2-tert-butylcyclopentadienyl]titanium trichloride, [1-dimethylphenylsilyl-3-tert-butylcyclopentadienyl]titanium trichloride, [1-dimethylphenylsilyl-2-phenylcyclopentadienyl]titanium trichloride, [1-dimethylphenylsilyl-3-phenylcyclopentadienyl]titanium trichloride, [1-dimethylphenylsilyl-2-benzylcyclopentadienyl]titanium trichloride, [1-dimethylphenylsilyl-3-benzylcyclopentadienyl]titanium trichloride, [1-dimethylphenylsilyl-indenyl]titanium trichloride, [1-dimethylphenyl silyl-2-methylindenyl]titanium trichloride, [9-dimethylphenylsilylfluorenyl]titanium trichloride, [1-dimethylphenylsilyl-tetrahydroindenyl]titanium trichloride,

[1-dimethylphenylsilyl-2-methyltetrahydroindenyl]titanium trichloride, [9-dimethylphenylsilyl-octahydrofluorenyl]titanium trichloride,

[1-diethylphenylsilyl-2-methylcyclopentadienyl]titanium trichloride, [1-diethylphenylsilyl-3-methylcyclopentadienyl]titanium trichloride, [1-diethylphenylsilyl-2,3-dimethylcyclopentadienyl]titanium trichloride, [1-diethylphenylsilyl-2,4-dimethylcyclopentadienyl]titanium trichloride, [1-diethylphenylsilyl-2,5-dimethylcyclopentadienyl]titanium trichloride, [1-diethylphenylsilyl-2,3,5-trimethylcyclopentadienyl]titanium trichloride, [1-diethylphenylsilyl-2,3,4,5-tetramethylcyclopentadienyl]titanium trichloride, [1-diethylphenylsilyl-2-ethylcyclopentadienyl]titanium trichloride, [1-diethylphenylsilyl-3-ethylcyclopentadienyl]titanium trichloride, [1-diethylphenylsilyl-2-n-propylcyclopentadienyl]titanium trichloride, [1-diethylphenyl silyl-3-n-propylcyclopentadienyl]titanium trichloride, [1-diethylphenylsilyl-2-isopropylcyclopentadienyl]titanium trichloride, [1-diethylphenylsilyl-3-isopropylcyclopentadienyl]titanium trichloride, [1-diethylphenylsilyl-2-n-butylcyclopentadienyl]titanium trichloride, [1-diethylphenylsilyl-3-n-butylcyclopentadienyl]titanium trichloride, [1-diethylphenylsilyl-2-sec-butylcyclopentadienyl]titanium trichloride, [1-diethylphenylsilyl-3-sec-butylcyclopentadienyl]titanium trichloride, [1-diethylphenylsilyl-2-tert-butylcyclopentadienyl]titanium trichloride, [1-diethylphenylsilyl-3-tert-butylcyclopentadienyl]titanium trichloride, [1-diethylphenylsilyl-2-phenylcyclopentadienyl]titanium trichloride, [1-diethylphenylsilyl-3-phenylcyclopentadienyl]titanium trichloride, [1-diethylphenyl silyl-2-benzylcyclopentadienyl]titanium trichloride, [1-diethylphenylsilyl-3-benzylcyclopentadienyl]titanium trichloride, [1-diethylphenylsilyl-indenyl]titanium trichloride, [1-diethylphenyl silyl-2-methylindenyl]titanium trichloride, [9-diethylphenyl silyl-fluorenyl]titanium trichloride, [1-diethylphenylsilyl-tetrahydroindenyl]titanium trichloride, [1-diethylphenylsilyl-2-methyltetrahydroindenyl]titanium trichloride, [9-diethylphenylsilyl-octahydrofluorenyl]titanium trichloride,

[1-cyclotetramethylene(phenyl)silyl-2-methylcyclopentadienyl]titanium trichloride, [1-cyclotetramethylene(phenyl)silyl-3-methylcyclopentadienyl]titanium trichloride, [1-cyclotetramethylene(phenyl)silyl-2,3-dimethylcyclopentadienyl]titanium trichloride, [1-cyclotetramethylene(phenyl)silyl-2,4-dimethylcyclopentadienyl]titanium trichloride, [1-cyclotetramethylene(phenyl)silyl-2,5-dimethylcyclopentadienyl]titanium trichloride, [1-cyclotetramethylene(phenyl)silyl-2,3,5-trimethylcyclopentadienyl]titanium trichloride, [1-cyclotetramethylene(phenyl)silyl-2,3,4,5-tetramethylcyclopentadienyl]titanium trichloride, [1-cyclotetramethylene(phenyl)silyl-2-ethylcyclopentadienyl]titanium trichloride, [1-cyclotetramethylene(phenyl)silyl-3-ethylcyclopentadienyl]titanium trichloride, [1-cyclotetramethylene(phenyl)silyl-2-n-propylcyclopentadienyl]titanium trichloride, [1-cyclotetramethylene(phenyl)silyl-3-n-propylcyclopentadienyl]titanium trichloride, [1-cyclotetramethylene(phenyl)silyl-2-isopropylcyclopentadienyl]titanium trichloride, [1-cyclotetramethylene(phenyl)silyl-3-isopropylcyclopentadienyl]titanium trichloride, [1-cyclotetramethylene(phenyl)silyl-2-n-butylcyclopentadienyl]titanium trichloride, [1-cyclotetramethylene(phenyl)silyl-3-n-butylcyclopentadienyl]titanium trichloride, [1-cyclotetramethylene(phenyl)silyl-2-sec-butylcyclopentadienyl]titanium trichloride, [1-cyclotetramethylene(phenyl)silyl-3-sec-butylcyclopentadienyl]titanium trichloride, [1-cyclotetramethylene(phenyl)silyl-2-tert-butylcyclopentadienyl]titanium trichloride, [1-cyclotetramethylene(phenyl)silyl-3-tert-butylcyclopentadienyl]titanium trichloride, [1-cyclotetramethylene(phenyl)silyl-2-phenylcyclopentadienyl]titanium trichloride, [1-cyclotetramethylene(phenyl)silyl-3-phenylcyclopentadienyl]titanium trichloride, [1-cyclotetramethylene(phenyl)silyl-2-benzylcyclopentadienyl]titanium trichloride, [1-cyclotetramethylene(phenyl)silyl-3-benzylcyclopentadienyl]titanium trichloride, [1-cyclotetramethylene(phenyl)silyl-indenyl]titanium trichloride, [1-cyclotetramethylene(phenyl)silyl-2-methylindenyl]titanium trichloride, [9-cyclotetramethylene(phenyl)silyl-fluorenyl]titanium trichloride, [1-cyclotetramethylene(phenyl)silyl-tetrahydroindenyl]titanium trichloride, [1-cyclotetramethylene(phenyl)silyl-2-methyltetrahydroindenyl]titanium trichloride, [9-cyclotetramethylene(phenyl)silyl-octahydrofluorenyl]titanium trichloride,

[1-ethylmethylphenylsilyl-2-methylcyclopentadienyl]titanium trichloride, [1-ethylmethylphenyl silyl-3-methylcyclopentadienyl]titanium trichloride, [1-ethylmethylphenylsilyl-2,3-dimethylcyclopentadienyl]titanium trichloride, [1-ethylmethylphenylsilyl-2,4-dimethylcyclopentadienyl]titanium trichloride, [1-ethylmethylphenyl silyl-2, 5-dimethylcyclopentadienyl]titanium trichloride, [1-ethylmethylphenylsilyl-2,3,5-trimethylcyclopentadienyl]titanium trichloride, [1-ethylmethylphenylsilyl-2,3,4,5-tetramethylcyclopentadienyl]titanium trichloride, [1-ethylmethylphenylsilyl-2-ethylcyclopentadienyl]titanium trichloride, [1-ethylmethylphenylsilyl-3-ethylcyclopentadienyl]titanium trichloride, [1-ethylmethylphenylsilyl-2-n-propylcyclopentadienyl]titanium trichloride, [1-ethylmethylphenylsilyl-3-n-propylcyclopentadienyl]titanium trichloride, [1-ethylmethylphenylsilyl-2-isopropylcyclopentadienyl]titanium trichloride, [1-ethylmethylphenylsilyl-3-isopropylcyclopentadienyl]titanium trichloride, [1-ethylmethylphenylsilyl-2-n-butylcyclopentadienyl]titanium trichloride, [1-ethylmethylphenylsilyl-3-n-butylcyclopentadienyl]titanium trichloride, [1-ethylmethylphenylsilyl-2-sec-butylcyclopentadienyl]titanium trichloride, [1-ethylmethylphenylsilyl-3-sec-butylcyclopentadienyl]titanium trichloride, [1-ethylmethylphenylsilyl-2-tert-butylcyclopentadienyl]titanium trichloride, [1-ethylmethylphenylsilyl-3-tert-butylcyclopentadienyl]titanium trichloride, [1-ethylmethylphenylsilyl-2-phenylcyclopentadienyl]titanium trichloride, [1-ethylmethylphenylsilyl-3-phenylcyclopentadienyl]titanium trichloride, [1-ethylmethylphenylsilyl-2-benzylcyclopentadienyl]titanium trichloride, [1-ethylmethylphenylsilyl-3-benzylcyclopentadienyl]titanium trichloride, [1-ethylmethylphenylsilyl-indenyl]titanium trichloride, [1-ethylmethylphenylsilyl-2-methylindenyl]titanium trichloride, [9-ethylmethylphenylsilyl-fluorenyl]titanium trichloride, [1-ethylmethylphenylsilyl-tetrahydroindenyl]titanium trichloride, [1-ethylmethylphenylsilyl-2-methyltetrahydroindenyl]titanium trichloride, [9-ethylmethylphenylsilyl-octahydrofluorenyl]titanium trichloride,

[1-n-butylmethylphenylsilyl-2-methylcyclopentadienyl]titanium trichloride, [1-n-butylmethylphenyl silyl-3-methylcyclopentadienyl]titanium trichloride, [1-n-butylmethylphenylsilyl-2,3-dimethylcyclopentadienyl]titanium trichloride, [1-n-butylmethylphenylsilyl-2,4-dimethylcyclopentadienyl]titanium trichloride, [1-n-butylmethylphenylsilyl-2,5-dimethylcyclopentadienyl]titanium trichloride, [1-n-butylmethylphenylsilyl-2,3,5-trimethylcyclopentadienyl]titanium trichloride, [1-n-butylmethylphenylsilyl-2,3,4,5-tetramethylcyclopentadienyl]titanium trichloride, [1-n-butylmethylphenylsilyl-2-ethylcyclopentadienyl]titanium trichloride, [1-n-butylmethylphenylsilyl-3-ethylcyclopentadienyl]titanium trichloride, [1-n-butylmethylphenylsilyl-2-n-propylcyclopentadienyl]titanium trichloride, [1-n-butylmethylphenylsilyl-3-n-propylcyclopentadienyl]titanium trichloride, [1-n-butylmethylphenylsilyl-2-isopropylcyclopentadienyl]titanium trichloride, [1-n-butylmethylphenylsilyl-3-isopropylcyclopentadienyl]titanium trichloride, [1-n-butylmethylphenylsilyl-2-n-butylcyclopentadienyl]titanium trichloride, [1-n-butylmethylphenylsilyl-3-n-butylcyclopentadienyl]titanium trichloride, [1-n-butylmethylphenylsilyl-2-sec-butylcyclopentadienyl]titanium trichloride, [1-n-butylmethylphenylsilyl-3-sec-butylcyclopentadienyl]titanium trichloride, [1-n-butylmethylphenylsilyl-2-tert-butylcyclopentadienyl]titanium trichloride, [1-n-butylmethylphenylsilyl-3-tert-butylcyclopentadienyl]titanium trichloride, [1-n-butylmethylphenylsilyl-2-phenylcyclopentadienyl]titanium trichloride, [1-n-butylmethylphenylsilyl-3-phenylcyclopentadienyl]titanium trichloride, [1-n-butylmethylphenylsilyl-2-benzylcyclopentadienyl]titanium trichloride, [1-n-butylmethylphenylsilyl-3-benzylcyclopentadienyl]titanium trichloride, [1-n-butylmethylphenylsilyl-indenyl]titanium trichloride, [1-n-butylmethylphenylsilyl-2-methylindenyl]titanium trichloride, [9-n-butylmethylphenyl silyl-fluorenyl]titanium trichloride, [1-n-butylmethylphenylsilyl-tetrahydroindenyl]titanium trichloride, [1-n-butylmethylphenylsilyl-2-methyltetrahydroindenyl]titanium trichloride, [9-n-butylmethylphenylsilyl-octahydrofluorenyl]titanium trichloride,

[1-methyldiphenyl silyl-2-methylcyclopentadienyl]titanium trichloride, [1-methyldiphenylsilyl-3-methylcyclopentadienyl]titanium trichloride, [1-methyldiphenylsilyl-2,3-dimethylcyclopentadienyl]titanium trichloride, [1-methyldiphenylsilyl-2,4-dimethylcyclopentadienyl]titanium trichloride, [1-methyldiphenylsilyl-2,5-dimethylcyclopentadienyl]titanium trichloride, [1-methyldiphenylsilyl-2,3,5-trimethylcyclopentadienyl]titanium trichloride, [1-methyldiphenylsilyl-2,3,4,5-tetramethylcyclopentadienyl]titanium trichloride, [1-methyldiphenylsilyl-2-ethylcyclopentadienyl]titanium trichloride, [1-methyldiphenylsilyl-3-ethylcyclopentadienyl]titanium trichloride, [1-methyldiphenylsilyl-2-n-propylcyclopentadienyl]titanium trichloride, [1-methyldiphenylsilyl-3-n-propylcyclopentadienyl]titanium trichloride, [1-methyldiphenylsilyl-2-isopropylcyclopentadienyl]titanium trichloride, [1-methyldiphenylsilyl-2-n-butylcyclopentadienyl]titanium trichloride, [1-methyldiphenylsilyl-3-n-butylcyclopentadienyl]titanium trichloride, [1-methyldiphenylsilyl-2-sec-butylcyclopentadienyl]titanium trichloride, [1-methyldiphenylsilyl-3-sec-butylcyclopentadienyl]titanium trichloride, [1-methyldiphenylsilyl-2-tert-butylcyclopentadienyl]titanium trichloride, [1-methyldiphenylsilyl-3-tert-butylcyclopentadienyl]titanium trichloride, [1-methyldiphenylsilyl-2-phenylcyclopentadienyl]titanium trichloride, [1-methyldiphenylsilyl-3-phenylcyclopentadienyl]titanium trichloride, [1-methyldiphenylsilyl-2-benzylcyclopentadienyl]titanium trichloride, [1-methyldiphenylsilyl-3-benzylcyclopentadienyl]titanium trichloride, [1-methyldiphenylsilyl-indenyl]titanium trichloride, [1-methyldiphenyl silyl-2-methylindenyl]titanium trichloride, [9-methyldiphenyl silyl-fluorenyl]titanium trichloride, [1-methyldiphenylsilyl-tetrahydroindenyl]titanium trichloride, [1-methyldiphenylsilyl-2-methyltetrahydroindenyl]titanium trichloride, [9-methyldiphenylsilyl-octahydrofluorenyl]titanium trichloride,

[1-methylbis(3,5-dimethylphenyl)silyl-2-methylcyclopentadienyl]titanium trichloride, [1-methylbis(3,5-dimethylphenyl)silyl-3-methylcyclopentadienyl]titanium trichloride, [1-methylbis(3,5-dimethylphenyl)silyl-2,3-dimethylcyclopentadienyl]titanium trichloride, [1-methylbis(3,5-dimethylphenyl)silyl-2,4-dimethylcyclopentadienyl]titanium trichloride, [1-methylbis(3,5-dimethylphenyl)silyl-2,5-dimethylcyclopentadienyl]titanium trichloride, [1-methylbis(3,5-dimethylphenyl)silyl-2,3,5-trimethylcyclopentadienyl]titanium trichloride, [1-methylbis(3,5-dimethylphenyl)silyl-2,3,4,5-tetramethylcyclopentadienyl]titanium trichloride, [1-methylbis(3,5-dimethylphenyl)silyl-2-ethylcyclopentadienyl]titanium trichloride, [1-methylbis(3,5-dimethylphenyl)silyl-3-ethylcyclopentadienyl]titanium trichloride, [1-methylbis(3,5-dimethylphenyl)silyl-2-n-propylcyclopentadienyl]titanium trichloride, [1-methylbis(3,5-dimethylphenyl)silyl-3-n-propylcyclopentadienyl]titanium trichloride, [1-methylbis(3,5-dimethylphenyl)silyl-2-isopropylcyclopentadienyl]titanium trichloride, [1-methylbis(3,5-dimethylphenyl)silyl-2-n-butylcyclopentadienyl]titanium trichloride, [1-methylbis(3,5-dimethylphenyl)silyl-3-n-butylcyclopentadienyl]titanium trichloride, [1-methylbis(3,5-dimethylphenyl)silyl-2-sec-butylcyclopentadienyl]titanium trichloride, [1-methylbis(3,5-dimethylphenyl)silyl-3-sec-butylcyclopentadienyl]titanium trichloride, [1-methylbis(3,5-dimethylphenyl)silyl-2-tert-butylcyclopentadienyl]titanium trichloride, [1-methylbis(3,5-dimethylphenyl)silyl-3-tert-butylcyclopentadienyl]titanium trichloride, [1-methylbis(3,5-dimethylphenyl)silyl-2-phenylcyclopentadienyl]titanium trichloride, [1-methylbis(3,5-dimethylphenyl)silyl-3-phenylcyclopentadienyl]titanium trichloride, [1-methylbis(3,5-dimethylphenyl)silyl-2-benzylcyclopentadienyl]titanium trichloride, [1-methylbis(3,5-dimethylphenyl)silyl-3-benzylcyclopentadienyl]titanium trichloride, [1-methylbis(3,5-dimethylphenyl)silyl-indenyl]titanium trichloride, [1-methylbis(3,5-dimethylphenyl)silyl-2-methylindenyl]titanium trichloride, [9-methylbis(3,5-dimethylphenyl)silyl-fluorenyl]titanium trichloride, [1-methylbis(3,5-dimethylphenyl)silyl-tetrahydroindenyl]titanium trichloride, [1-methylbis(3,5-dimethylphenyl)silyl-2-methyltetrahydroindenyl]titanium trichloride, [9-methylbis(3,5-dimethylphenyl)silyl-octahydrofluorenyl]titanium trichloride,

[1-cyclohexylmethylphenylsilyl-2-methylcyclopentadienyl]titanium trichloride, [1-cyclohexylmethylphenylsilyl-3-methylcyclopentadienyl]titanium trichloride, [1-cyclohexylmethylphenylsilyl-2,3-dimethylcyclopentadienyl]titanium trichloride, [1-cyclohexylmethylphenylsilyl-2,4-dimethylcyclopentadienyl]titanium trichloride, [1-cyclohexylmethylphenylsilyl-2,5-dimethylcyclopentadienyl]titanium trichloride, [1-cyclohexylmethylphenylsilyl-2,3,5-trimethylcyclopentadienyl]titanium trichloride, [1-cyclohexylmethylphenylsilyl-2,3,4,5-tetramethylcyclopentadienyl]titanium trichloride, [1-cyclohexylmethylphenylsilyl-2-ethylcyclopentadienyl]titanium trichloride, [1-cyclohexylmethylphenylsilyl-3-ethylcyclopentadienyl]titanium trichloride, [1-cyclohexylmethylphenylsilyl-2-n-propylcyclopentadienyl]titanium trichloride, [1-cyclohexylmethylphenylsilyl-3-n-propylcyclopentadienyl]titanium trichloride, [1-cyclohexylmethylphenylsilyl-2-isopropylcyclopentadienyl]titanium trichloride, [1-cyclohexylmethylphenylsilyl-3-isopropylcyclopentadienyl]titanium trichloride, [1-cyclohexylmethylphenylsilyl-2-n-butylcyclopentadienyl]titanium trichloride, [1-cyclohexylmethylphenylsilyl-3-n-butylcyclopentadienyl]titanium trichloride, [1-cyclohexylmethylphenylsilyl-2-sec-butylcyclopentadienyl]titanium trichloride, [1-cyclohexylmethylphenylsilyl-3-sec-butylcyclopentadienyl]titanium trichloride, [1-cyclohexylmethylphenylsilyl-2-tert-butylcyclopentadienyl]titanium trichloride, [1-cyclohexylmethylphenylsilyl-3-tert-butylcyclopentadienyl]titanium trichloride,

[1-cyclohexylmethylphenylsilyl-2-phenylcyclopentadienyl]titanium trichloride, [1-cyclohexylmethylphenylsilyl-3-phenylcyclopentadienyl]titanium trichloride, [1-cyclohexylmethylphenylsilyl-2-benzylcyclopentadienyl]titanium trichloride, [1-cyclohexylmethylphenylsilyl-3-benzylcyclopentadienyl]titanium trichloride, [1-cyclohexylmethylphenylsilyl-indenyl]titanium trichloride, [1-cyclohexylmethylphenylsilyl-2-methylindenyl]titanium trichloride, [9-cyclohexylmethylphenylsilyl-fluorenyl]titanium trichloride, [1-cyclohexylmethylphenylsilyl-tetrahydroindenyl]titanium trichloride, [1-cyclohexylmethylphenylsilyl-2-methyltetrahydroindenyl]titanium trichloride, [9-cyclohexylmethylphenylsilyl-octahydrofluorenyl]titanium trichloride,

[1-methyl(n-octadecyl)phenylsilyl-2-methylcyclopentadienyl]titanium trichloride, [1-methyl(n-octadecyl)phenylsilyl-3-methylcyclopentadienyl]titanium trichloride, [1-methyl(n-octadecyl)phenylsilyl-2,3-dimethylcyclopentadienyl]titanium trichloride, [1-methyl(n-octadecyl)phenylsilyl-2,4-dimethylcyclopentadienyl]titanium trichloride, [1-methyl(n-octadecyl)phenylsilyl-2,5-dimethylcyclopentadienyl]titanium trichloride, [1-methyl(n-octadecyl)phenylsilyl-2,3,5-trimethylcyclopentadienyl]titanium trichloride, [1-methyl(n-octadecyl)phenylsilyl-2,3,4,5-tetramethylcyclopentadienyl]titanium trichloride, [1-methyl(n-octadecyl)phenylsilyl-2-ethylcyclopentadienyl]titanium trichloride, [1-methyl(n-octadecyl)phenylsilyl-3-ethylcyclopentadienyl]titanium trichloride, [1-methyl(n-octadecyl)phenylsilyl-2-n-propylcyclopentadienyl]titanium trichloride, [1-methyl(n-octadecyl)phenylsilyl-3-n-propylcyclopentadienyl]titanium trichloride, [1-methyl(n-octadecyl)phenylsilyl-2-isopropylcyclopentadienyl]titanium trichloride, [1-methyl(n-octadecyl)phenylsilyl-3-isopropylcyclopentadienyl]titanium trichloride, [1-methyl(n-octadecyl)phenylsilyl-2-n-butylcyclopentadienyl]titanium trichloride, [1-methyl(n-octadecyl)phenylsilyl-3-n-butylcyclopentadienyl]titanium trichloride, [1-methyl(n-octadecyl)phenylsilyl-2-sec-butylcyclopentadienyl]titanium trichloride, [1-methyl(n-octadecyl)phenylsilyl-3-sec-butylcyclopentadienyl]titanium trichloride, [1-methyl(n-octadecyl)phenylsilyl-2-tert-butylcyclopentadienyl]titanium trichloride, [1-methyl(n-octadecyl)phenylsilyl-3-tert-butylcyclopentadienyl]titanium trichloride, [1-methyl(n-octadecyl)phenylsilyl-2-phenylcyclopentadienyl]titanium trichloride, [1-methyl(n-octadecyl)phenylsilyl-3-phenylcyclopentadienyl]titanium trichloride, [1-methyl(n-octadecyl)phenylsilyl-2-benzylcyclopentadienyl]titanium trichloride, [1-methyl(n-octadecyl)phenylsilyl-3-benzylcyclopentadienyl]titanium trichloride, [1-methyl(n-octadecyl)phenylsilyl-indenyl]titanium trichloride, [1-methyl(n-octadecyl)phenylsilyl-2-methylindenyl]titanium trichloride, [9-methyl(n-octadecyl)phenylsilyl-fluorenyl]titanium trichloride, [1-methyl(n-octadecyl)phenylsilyl-tetrahydroindenyl]titanium trichloride, [1-methyl(n-octadecyl)phenylsilyl-2-methyltetrahydroindenyl]titanium trichloride, [9-methyl(n-octadecyl)phenylsilyl-octahydrofluorenyl]titanium trichloride,

[1-triphenylsilyl-2-methylcyclopentadienyl]titanium trichloride, [1-triphenylsilyl-3-methylcyclopentadienyl]titanium trichloride, [1-triphenylsilyl-2,3-dimethylcyclopentadienyl]titanium trichloride, [1-triphenylsilyl-2,4-dimethylcyclopentadienyl]titanium trichloride, [1-triphenylsilyl-2,5-dimethylcyclopentadienyl]titanium trichloride, [1-triphenylsilyl-2,3,5-trimethylcyclopentadienyl]titanium trichloride, [1-triphenylsilyl-2,3,4,5-tetramethylcyclopentadienyl]titanium trichloride, [1-triphenylsilyl-2-ethylcyclopentadienyl]titanium trichloride, [1-triphenylsilyl-3-ethylcyclopentadienyl]titanium trichloride, [1-triphenylsilyl-2-n-propylcyclopentadienyl]titanium trichloride, [1-triphenyl silyl-3-n-propylcyclopentadienyl]titanium trichloride, [1-triphenylsilyl-2-isopropylcyclopentadienyl]titanium trichloride, [1-triphenylsilyl-3-isopropylcyclopentadienyl]titanium trichloride, [1-triphenylsilyl-2-n-butylcyclopentadienyl]titanium trichloride, [1-triphenyl silyl-3-n-butylcyclopentadienyl]titanium trichloride, [1-triphenylsilyl-2-sec-butylcyclopentadienyl]titanium trichloride, [1-triphenylsilyl-3-sec-butylcyclopentadienyl]titanium trichloride, [1-triphenyl silyl-2-tert-butylcyclopentadienyl]titanium trichloride, [1-triphenylsilyl-3-tert-butylcyclopentadienyl]titanium trichloride, [1-triphenylsilyl-2-phenylcyclopentadienyl]titanium trichloride, [1-triphenylsilyl-3-phenylcyclopentadienyl]titanium trichloride, [1-triphenylsilyl-2-benzylcyclopentadienyl]titanium trichloride, [1-triphenylsilyl-3-benzylcyclopentadienyl]titanium trichloride, [1-triphenylsilyl-indenyl]titanium trichloride, [1-triphenylsilyl-2-methylindenyl]titanium trichloride, [9-triphenyl silyl-fluorenyl]titanium trichloride, [1-triphenylsilyl-tetrahydroindenyl]titanium trichloride, [1-triphenylsilyl-2-methyltetrahydroindenyl]titanium trichloride, [9-triphenyl silyl-octahydrofluorenyl]titanium trichloride,

[1-tri(4-n-butylphenyl)silyl-2-methylcyclopentadienyl]titanium trichloride, [1-tri(4-n-butylphenyl)silyl-3-methylcyclopentadienyl]titanium trichloride, [1-tri(4-n-butylphenyl)silyl-2,3-dimethylcyclopentadienyl]titanium trichloride, [1-tri(4-n-butylphenyl)silyl-2,4-dimethylcyclopentadienyl]titanium trichloride, [1-tri(4-n-butylphenyl)silyl-2,5-dimethylcyclopentadienyl]titanium trichloride, [1-tri(4-n-butylphenyl)silyl-2,3,5-trimethylcyclopentadienyl]titanium trichloride, [1-tri(4-n-butylphenyl)silyl-2,3,4,5-tetramethylcyclopentadienyl]titanium trichloride, [1-tri(4-n-butylphenyl)silyl-2-ethylcyclopentadienyl]titanium trichloride, [1-tri(4-n-butylphenyl)silyl-3-ethylcyclopentadienyl]titanium trichloride, [1-tri(4-n-butylphenyl)silyl-2-n-propylcyclopentadienyl]titanium trichloride, [1-tri(4-n-butylphenyl)silyl-3-n-propylcyclopentadienyl]titanium trichloride, [1-tri(4-n-butylphenyl)silyl-2-isopropylcyclopentadienyl]titanium trichloride, [1-tri(4-n-butylphenyl)silyl-3-isopropylcyclopentadienyl]titanium trichloride, [1-tri(4-n-butylphenyl)silyl-2-n-butylcyclopentadienyl]titanium trichloride, [1-tri(4-n-butylphenyl)silyl-3-n-butylcyclopentadienyl]titanium trichloride, [1-tri(4-n-butylphenyl)silyl-2-sec-butylcyclopentadienyl]titanium trichloride, [1-tri(4-n-butylphenyl)silyl-3-sec-butylcyclopentadienyl]titanium trichloride, [1-tri(4-n-butylphenyl)silyl-2-tert-butylcyclopentadienyl]titanium trichloride, [1-tri(4-n-butylphenyl)silyl-3-tert-butylcyclopentadienyl]titanium trichloride, [1-tri(4-n-butylphenyl)silyl-2-phenylcyclopentadienyl]titanium trichloride, [1-tri(4-n-butylphenyl)silyl-3-phenylcyclopentadienyl]titanium trichloride, [1-tri(4-n-butylphenyl)silyl-2-benzylcyclopentadienyl]titanium trichloride, [1-tri(4-n-butylphenyl)silyl-3-benzylcyclopentadienyl]titanium trichloride, [1-tri(4-n-butylphenyl)silyl-indenyl]titanium trichloride, [1-tri(4-n-butylphenyl)silyl-2-methylindenyl]titanium trichloride, [9-tri(4-n-butylphenyl)silyl-fluorenyl]titanium trichloride, [1-tri(4-n-butylphenyl)silyl-tetrahydroindenyl]titanium trichloride, [1-tri(4-n-butylphenyl)silyl-2-methyltetrahydroindenyl]titanium trichloride, [9-tri(4-n-butylphenyl)silyl-octahydrofluorenyl]titanium trichloride,

[1-tri(3-methylphenyl)silyl-2-methylcyclopentadienyl]titanium trichloride, [1-tri(3-methylphenyl)silyl-3-methylcyclopentadienyl]titanium trichloride, [1-tri(3-methylphenyl)silyl-2,3-dimethylcyclopentadienyl]titanium trichloride, [1-tri(3-methylphenyl)silyl-2,4-dimethylcyclopentadienyl]

titanium trichloride, [1-tri(3-methylphenyl)silyl-2,5-dimethylcyclopentadienyl]titanium trichloride, [1-tri(3-methylphenyl)silyl-2,3,5-trimethylcyclopentadienyl]titanium trichloride, [1-tri(3-methylphenyl)silyl-2,3,4,5-tetramethylcyclopentadienyl]titanium trichloride, [1-tri(3-methylphenyl)silyl-2-ethylcyclopentadienyl]titanium trichloride, [1-tri(3-methylphenyl)silyl-3-ethylcyclopentadienyl]titanium trichloride, [1-(3-methylphenyl)silyl-2-n-propylcyclopentadienyl]titanium trichloride, [1-tri(3-methylphenyl)silyl-3-n-propylcyclopentadienyl]titanium trichloride, [1-tri(3-methylphenyl)silyl-2-isopropylcyclopentadienyl]titanium trichloride, [1-tri(3-methylphenyl)silyl-3-isopropylcyclopentadienyl]titanium trichloride, [1-tri(3-methylphenyl)silyl-2-n-butylcyclopentadienyl]titanium trichloride, [1-tri(3-methylphenyl)silyl-3-n-butylcyclopentadienyl]titanium trichloride, [1-tri(3-methylphenyl)silyl-2-sec-butylcyclopentadienyl]titanium trichloride, [1-tri(3-methylphenyl)silyl-3-sec-butylcyclopentadienyl]titanium trichloride, [1-tri(3-methylphenyl)silyl-2-tert-butylcyclopentadienyl]titanium trichloride, [1-tri(3-methylphenyl)silyl-3-tert-butylcyclopentadienyl]titanium trichloride, [1-tri(3-methylphenyl)silyl-2-phenylcyclopentadienyl]titanium trichloride, [1-tri(3-methylphenyl)silyl-3-phenylcyclopentadienyl]titanium trichloride, [1-tri(3-methylphenyl)silyl-2-benzylcyclopentadienyl]titanium trichloride, [1-tri(3-methylphenyl)silyl-3-benzylcyclopentadienyl]titanium trichloride, [1-tri(3-methylphenyl)silyl-indenyl]titanium trichloride, [1-tri(3-methylphenyl)silyl-2-methylindenyl]titanium trichloride, [9-tri(3-methylphenyl)silyl-fluorenyl]titanium trichloride, [1-tri(3-methylphenyl)silyl-tetrahydroindenyl]titanium trichloride, [1-tri(3-methylphenyl)silyl-2-methyltetrahydroindenyl]titanium trichloride, [9-tri(3-methylphenyl)silyl-octahydrofluorenyl]titanium trichloride,

[1-tri(3-isopropylphenyl)silyl-2-methylcyclopentadienyl]titanium trichloride, [1-tri(3-isopropylphenyl)silyl-3-methylcyclopentadienyl]titanium trichloride, [1-tri(3-isopropylphenyl)silyl-2,3-dimethylcyclopentadienyl]titanium trichloride, [1-tri(3-isopropylphenyl)silyl-2,4-dimethylcyclopentadienyl]titanium trichloride, [1-tri(3-isopropylphenyl)silyl-2, 5-dimethylcyclopentadienyl]titanium trichloride, [1-tri(3-isopropylphenyl)silyl-2,3,5-trimethylcyclopentadienyl]titanium trichloride, [1-tri(3-isopropylphenyl)silyl-2,3,4,5-tetramethylcyclopentadienyl]titanium trichloride, [1-tri(3-isopropylphenyl)silyl-2-ethylcyclopentadienyl]titanium trichloride, [1-tri(3-isopropylphenyl)silyl-3-ethylcyclopentadienyl]titanium trichloride, [1-(3-isopropylphenyl)silyl-2-n-propylcyclopentadienyl]titanium trichloride, [1-tri(3-isopropylphenyl)silyl-3-n-propylcyclopentadienyl]titanium trichloride, [1-tri(3-isopropylphenyl)silyl-2-isopropylcyclopentadienyl]titanium trichloride, [1-tri(3-isopropylphenyl)silyl-3-isopropylcyclopentadienyl]titanium trichloride, [1-tri(3-isopropylphenyl)silyl-2-n-butylcyclopentadienyl]titanium trichloride, [1-tri(3-isopropylphenyl)silyl-3-n-butylcyclopentadienyl]titanium trichloride, [1-tri(3-isopropylphenyl)silyl-2-sec-butylcyclopentadienyl]titanium trichloride, [1-tri(3-isopropylphenyl)silyl-3-sec-butylcyclopentadienyl]titanium trichloride, [1-tri(3-isopropylphenyl)silyl-2-tert-butylcyclopentadienyl]titanium trichloride, [1-tri(3-isopropylphenyl)silyl-3-tert-butylcyclopentadienyl]titanium trichloride, [1-tri(3-isopropylphenyl)silyl-2-phenylcyclopentadienyl]titanium trichloride, [1-tri(3-isopropylphenyl)silyl-3-phenylcyclopentadienyl]titanium trichloride, [1-tri(3-isopropylphenyl)silyl-2-benzylcyclopentadienyl]titanium trichloride, [1-tri(3-isopropylphenyl)silyl-3-benzylcyclopentadienyl]titanium trichloride, [1-tri(3-isopropylphenyl)silyl-indenyl]titanium trichloride, [1-tri(3-isopropylphenyl)silyl-2-methylindenyl]titanium trichloride, [9-tri(3-isopropylphenyl)silyl-fluorenyl]titanium trichloride, [1-tri(3-isopropylphenyl)silyl-tetrahydroindenyl]titanium trichloride, [1-tri(3-isopropylphenyl)silyl-2-methyltetrahydroindenyl]titanium trichloride, [9-tri(3-isopropylphenyl)silyl-octahydrofluorenyl]titanium trichloride,

[1-dimethyl(3,5-dimethylphenyl)silyl-2-methylcyclopentadienyl]titanium trichloride, [1-dimethyl(3,5-dimethylphenyl)silyl-3-methylcyclopentadienyl]titanium trichloride, [1-dimethyl(3,5-dimethylphenyl)silyl-2,3-dimethylcyclopentadienyl]titanium trichloride, [1-dimethyl(3,5-dimethylphenyl)silyl-2,4-dimethylcyclopentadienyl]titanium trichloride, [1-dimethyl(3,5-dimethylphenyl)silyl-2,5-dimethylcyclopentadienyl]titanium trichloride, [1-dimethyl(3,5-dimethylphenyl)silyl-2,3,5-trimethylcyclopentadienyl]titanium trichloride, [1-dimethyl(3,5-dimethylphenyl)silyl-2,3,4,5-tetramethylcyclopentadienyl]titanium trichloride, [1-dimethyl(3,5-dimethylphenyl)silyl-2-ethylcyclopentadienyl]titanium trichloride, [1-dimethyl(3,5-dimethylphenyl)silyl-3-ethylcyclopentadienyl]titanium trichloride, [1-dimethyl(3,5-dimethylphenyl)silyl-2-n-propylcyclopentadienyl]titanium trichloride, [1-dimethyl(3,5-dimethylphenyl)silyl-3-n-propylcyclopentadienyl]titanium trichloride, [1-dimethyl(3,5-dimethylphenyl)silyl-2-isopropylcyclopentadienyl]titanium trichloride, [1-dimethyl(3,5-dimethylphenyl)silyl-3-isopropylcyclopentadienyl]titanium trichloride, [1-dimethyl(3,5-dimethylphenyl)silyl-2-n-butylcyclopentadienyl]titanium trichloride, [1-dimethyl(3,5-dimethylphenyl)silyl-3-n-butylcyclopentadienyl]titanium trichloride, [1-dimethyl(3,5-dimethylphenyl)silyl-2-sec-butylcyclopentadienyl]titanium trichloride, [1-dimethyl(3,5-dimethylphenyl)silyl-3-sec-butylcyclopentadienyl]titanium trichloride, [1-dimethyl(3,5-dimethylphenyl)silyl-2-tert-butylcyclopentadienyl]titanium trichloride, [1-dimethyl(3,5-dimethylphenyl)silyl-3-tert-butylcyclopentadienyl]titanium trichloride, [1-dimethyl(3,5-dimethylphenyl)silyl-2-phenylcyclopentadienyl]titanium trichloride, [1-dimethyl(3,5-dimethylphenyl)silyl-3-phenylcyclopentadienyl]titanium trichloride, [1-dimethyl(3,5-dimethylphenyl)silyl-2-benzylcyclopentadienyl]titanium trichloride, [1-dimethyl(3,5-dimethylphenyl)silyl-3-benzylcyclopentadienyl]titanium trichloride, [1-dimethyl(3,5-dimethylphenyl)silyl-indenyl]titanium trichloride, [1-dimethyl(3,5-dimethylphenyl)silyl-2-methylindenyl]titanium trichloride, [9-dimethyl(3,5-dimethylphenyl)silyl-fluorenyl]titanium trichloride, [1-dimethyl(3,5-dimethylphenyl)silyl-tetrahydroindenyl]titanium trichloride, [1-dimethyl(3,5-dimethylphenyl)silyl-2-methyltetrahydroindenyl]titanium trichloride, [9-dimethyl(3,5-dimethylphenyl)silyl-octahydrofluorenyl]titanium trichloride,

[1-dimethyl(3, 5-di-n-hexylphenyl)silyl-2-methylcyclopentadienyl]titanium trichloride, [1-dimethyl(3,5-di-n-hexylphenyl)silyl-3-methylcyclopentadienyl]titanium trichloride, [1-dimethyl(3,5-di-n-hexylphenyl)silyl-2,3-dimethylcyclopentadienyl]titanium trichloride, [1-dimethyl(3,5-di-n-hexylphenyl)silyl-2,4-dimethylcyclopentadienyl]titanium trichloride, [1-dimethyl(3,5-di-n-hexylphenyl)silyl-2,5-dimethylcyclopentadienyl]titanium trichloride, [1-dimethyl(3,5-di-n-hexylphenyl)silyl-2,3,5-trimethylcyclopentadienyl]titanium trichloride, [1-dimethyl(3,5-di-n-hexylphenyl)silyl-2,3,4,5-tetramethylcyclopentadienyl]titanium trichloride, [1-dimethyl(3,5-di-n-hexylphenyl)silyl-2-ethylcyclopentadienyl]titanium trichloride, [1-dimethyl(3,5-di-n-hexylphenyl)silyl-3-ethylcyclopentadienyl]titanium trichloride, [1-dimethyl(3,5-di-n-hexylphenyl)silyl-2-n-propylcyclopentadienyl]titanium trichloride, [1-dimethyl(3,5-di-n-hexylphenyl)silyl-3-n-propylcyclopentadienyl]titanium trichloride, [1-dimethyl(3,5-di-n-hexylphenyl)silyl-2-isopropylcyclopentadienyl]titanium trichloride, [1-dimethyl(3,5-di-n-hexylphenyl)silyl-3-isopropylcyclopentadienyl] titanium trichloride, [1-dimethyl(3,5-di-n-hexylphenyl)silyl-2-n-butylcyclopentadienyl]titanium trichloride, [1-dimethyl(3,5-di-n-hexylphenyl)silyl-3-n-butylcyclopentadienyl]titanium trichloride, [1-dimethyl(3,5-di-n-hexylphenyl)silyl-2-sec-butylcyclopentadienyl]titanium trichloride, [1-dimethyl(3,5-di-n-hexylphenyl)silyl-3-sec-butylcyclopentadienyl]titanium trichloride, [1-dimethyl(3,5-di-n-hexylphenyl)silyl-2-tert-butylcyclopentadienyl] titanium trichloride, [1-dimethyl(3,5-di-n-hexylphenyl)silyl-3-tert-butylcyclopentadienyl]titanium trichloride, [1-dimethyl(3,5-di-n-hexylphenyl)silyl-2-phenylcyclopentadienyl]titanium trichloride, [1-dimethyl(3,5-di-n-hexylphenyl)silyl-3-phenylcyclopentadienyl]titanium trichloride, [1-dimethyl(3,5-di-n-hexylphenyl)silyl-2-benzylcyclopentadienyl]titanium trichloride, [1-dimethyl(3,5-di-n-hexylphenyl)silyl-3-benzylcyclopentadienyl]titanium trichloride, [1-dimethyl(3,5-di-n-hexylphenyl)silyl-indenyl]titanium trichloride, [1-dimethyl(3,5-di-n-hexylphenyl)silyl-2-methylindenyl]titanium trichloride, [9-dimethyl(3,5-di-n-hexylphenyl)silyl-fluorenyl]titanium trichloride, [1-dimethyl(3,5-di-n-hexylphenyl)silyl-tetrahydroindenyl]titanium trichloride, [1-dimethyl(3,5-di-n-hexylphenyl)silyl-2-methyltetrahydroindenyl]titanium trichloride, [9-dimethyl(3,5-di-n-hexylphenyl)silyl-octahydrofluorenyl]titanium trichloride,

[1-n-butylmethyl(3,5-dimethylphenyl)silyl-2-methylcyclopentadienyl]titanium trichloride, [1-n-butylmethyl(3,5-dimethylphenyl)silyl-3-methylcyclopentadienyl]titanium trichloride, [1-n-butylmethyl(3,5-dimethylphenyl)silyl-2,3-dimethylcyclopentadienyl]titanium trichloride, [1-n-butylmethyl(3,5-dimethylphenyl)silyl-2,4-dimethylcyclopentadienyl]titanium trichloride, [1-n-butylmethyl(3,5-dimethylphenyl)silyl-2,5-dimethylcyclopentadienyl]titanium trichloride, [1-n-butylmethyl(3,5-dimethylphenyl)silyl-2,3,5-trimethylcyclopentadienyl]titanium trichloride, [1-n-butylmethyl(3,5-dimethylphenyl)silyl-2,3,4,5-tetramethylcyclopentadienyl]titanium trichloride, [1-n-butylmethyl(3,5-dimethylphenyl)silyl-2-ethylcyclopentadienyl]titanium trichloride, [1-n-butylmethyl(3,5-dimethylphenyl)silyl-3-ethylcyclopentadienyl]titanium trichloride, [1-n-butylmethyl(3,5-dimethylphenyl)silyl-2-n-propylcyclopentadienyl]titanium trichloride, [1-n-butylmethyl(3,5-dimethylphenyl)silyl-3-n-propylcyclopentadienyl]titanium trichloride, [1-n-butylmethyl(3,5-dimethylphenyl)silyl-2-isopropylcyclopentadienyl]titanium trichloride, [1-n-butylmethyl(3,5-dimethylphenyl)silyl-3-isopropylcyclopentadienyl]titanium trichloride, [1-n-butylmethyl(3,5-dimethylphenyl)silyl-2-n-butylcyclopentadienyl]titanium trichloride, [1-n-butylmethyl(3,5-dimethylphenyl)silyl-3-n-butylcyclopentadienyl]titanium trichloride, [1-n-butylmethyl(3,5-dimethylphenyl)silyl-2-sec-butylcyclopentadienyl]titanium trichloride, [1-n-butylmethyl(3,5-dimethylphenyl)silyl-3-sec-butylcyclopentadienyl]titanium trichloride, [1-n-butylmethyl(3,5-dimethylphenyl)silyl-2-tert-butylcyclopentadienyl]titanium trichloride, [1-n-butylmethyl(3,5-dimethylphenyl)silyl-3-tert-butylcyclopentadienyl]titanium trichloride, [1-n-butylmethyl(3,5-dimethylphenyl)silyl-2-phenylcyclopentadienyl]titanium trichloride, [1-n-butylmethyl(3,5-dimethylphenyl)silyl-3-phenylcyclopentadienyl]titanium trichloride, [1-n-butylmethyl(3,5-dimethylphenyl)silyl-2-benzylcyclopentadienyl]titanium trichloride, [1-n-butylmethyl(3,5-dimethylphenyl)silyl-3-benzylcyclopentadienyl]titanium trichloride, [1-n-butylmethyl(3,5-dimethylphenyl)silyl-indenyl]titanium trichloride, [1-n-butylmethyl(3,5-dimethylphenyl)silyl-2-methylindenyl]titanium trichloride, [9-n-butylmethyl(3,5-dimethylphenyl)silyl-fluorenyl]titanium trichloride, [1-n-butylmethyl(3,5-dimethylphenyl)silyl-tetrahydroindenyl] titanium trichloride, [1-n-butylmethyl(3,5-dimethylphenyl)silyl-2-methyltetrahydroindenyl]titanium trichloride, [9-n-butylmethyl(3,5-dimethylphenyl)silyl-octahydrofluorenyl] titanium trichloride,

[1-tris(3,5-dimethylphenyl)silyl-2-methylcyclopentadienyl]titanium trichloride, [1-tris(3,5-dimethylphenyl)silyl-3-methylcyclopentadienyl]titanium trichloride, [1-tris(3,5-dimethylphenyl)silyl-2,3-dimethylcyclopentadienyl] titanium trichloride, [1-tris(3,5-dimethylphenyl)silyl-2,4-dimethylcyclopentadienyl]titanium trichloride, [1-tris(3,5-dimethylphenyl)silyl-2,5-dimethylcyclopentadienyl] titanium trichloride, [1-tris(3,5-dimethylphenyl)silyl-2,3,5-trimethylcyclopentadienyl]titanium trichloride, [1-tris(3,5-dimethylphenyl)silyl-2,3,4,5-tetramethylcyclopentadienyl] titanium trichloride, [1-tris(3,5-dimethylphenyl)silyl-2-ethylcyclopentadienyl]titanium trichloride, [1-tris(3,5-dimethylphenyl)silyl-3-ethylcyclopentadienyl]titanium trichloride, [1-tris(3,5-dimethylphenyl)silyl-2-n-propylcyclopentadienyl]titanium trichloride, [1-tris(3,5-dimethylphenyl)silyl-3-n-propylcyclopentadienyl]titanium trichloride, [1-tris(3,5-dimethylphenyl)silyl-2-isopropylcyclopentadienyl]titanium trichloride, [1-tris(3,5-dimethylphenyl)silyl-3-isopropylcyclopentadienyl]titanium trichloride, [1-tris(3,5-dimethylphenyl)silyl-2-n-butylcyclopentadienyl]titanium trichloride, [1-tris(3,5-dimethylphenyl)silyl-3-n-butylcyclopentadienyl]titanium trichloride, [1-tris(3,5-dimethylphenyl)silyl-2-sec-butylcyclopentadienyl]titanium trichloride, [1-tris(3,5-dimethylphenyl)silyl-3-sec-butylcyclopentadienyl]titanium trichloride, [1-tris(3,5-dimethylphenyl)silyl-2-tert-butylcyclopentadienyl] titanium trichloride, [1-tris(3,5-dimethylphenyl)silyl-3-tert-butylcyclopentadienyl]titanium trichloride, [1-tris(3,5-dimethylphenyl)silyl-2-phenylcyclopentadienyl]titanium trichloride, [1-tris(3,5-dimethylphenyl)silyl-3-phenylcyclopentadienyl]titanium trichloride, [1-tris(3,5-dimethylphenyl)silyl-2-benzylcyclopentadienyl]titanium trichloride, [1-tris(3,5-dimethylphenyl)silyl-3-benzylcyclopentadienyl] titanium trichloride, [1-tris(3,5-dimethylphenyl)silyl-indenyl]titanium trichloride, [1-tris(3,5-dimethylphenyl)silyl-2-methylindenyl]titanium trichloride, [9-tris(3,5-dimethylphenyl)silyl-fluorenyl]titanium trichloride, [1-tris(3,5-dimethylphenyl)silyl-tetrahydroindenyl]titanium trichloride, [1-tris(3,5-dimethylphenyl)silyl-2-methyltetrahydroindenyl]titanium trichloride, [9-tris(3,5-dimethylphenyl)silyl-octahydrofluorenyl]titanium trichloride,

[1-tris(3,5-diethylphenyl)silyl-2-methylcyclopentadienyl]titanium trichloride, [1-tris(3,5-diethylphenyl)silyl-3-methylcyclopentadienyl]titanium trichloride, [1-tris(3,5-diethylphenyl)silyl-2,3-dimethylcyclopentadienyl]titanium trichloride, [1-tris(3,5-diethylphenyl)silyl-2,4-dimethylcyclopentadienyl]titanium trichloride, [1-tris(3,5-diethylphenyl)silyl-2,5-dimethylcyclopentadienyl]titanium trichloride, [1-tris(3,5-diethylphenyl)silyl-2,3,5-trimethylcyclopentadienyl]titanium trichloride, [1-tris(3,5-diethylphenyl)silyl-2,3,4,5-tetramethylcyclopentadienyl]titanium trichloride, [1-tris(3,5-diethylphenyl)silyl-2-ethylcyclopentadienyl]titanium trichloride, [1-tris(3,5-diethylphenyl)silyl-3-ethylcyclopentadienyl]titanium trichloride, [1-tris(3,5-diethylphenyl)silyl- 2-n-propylcyclopentadienyl]titanium trichloride, [1-tris(3,5-diethylphenyl)silyl-3-n-propylcyclopentadienyl]titanium trichloride, [1-tris(3,5-diethylphenyl)silyl-2-isopropylcyclopentadienyl]titanium trichloride, [1-tris(3,5-diethylphenyl)silyl-3-isopropylcyclopentadienyl]titanium trichloride, [1-tris(3,5-diethylphenyl)silyl-2-n-butylcyclopentadienyl]titanium trichloride, [1-tris(3,5-diethylphenyl)silyl-3-n-butylcyclopentadienyl]titanium trichloride, [1-tris(3,5-diethylphenyl)silyl-2-sec-butylcyclopentadienyl]titanium trichloride, [1-tris(3,5-diethylphenyl)silyl-3-sec-butylcyclopentadienyl]titanium trichloride, [1-tris(3,5-diethylphenyl)silyl-2-tert-butylcyclopentadienyl]titanium trichloride, [1-tris(3,5-diethylphenyl)silyl-3-tert-butylcyclopentadienyl]titanium trichloride, [1-tris(3,5-diethylphenyl)silyl-2-phenylcyclopentadienyl]titanium trichloride, [1-tris(3,5-diethylphenyl)silyl-3-phenylcyclopentadienyl]titanium trichloride, [1-tris(3,5-diethylphenyl)silyl-2-benzylcyclopentadienyl]titanium trichloride, [1-tris(3,5-diethylphenyl)silyl-3-benzylcyclopentadienyl]titanium trichloride, [1-tris(3,5-diethylphenyl)silyl-indenyl]titanium trichloride, [1-tris(3,5-diethylphenyl)silyl-2-methylindenyl]titanium trichloride, [9-tris(3,5-diethylphenyl)silyl-fluorenyl]titanium trichloride, [1-tris(3,5-diethylphenyl)silyl-tetrahydroindenyl]titanium trichloride, [1-tris(3,5-diethylphenyl)silyl-2-methyltetrahydroindenyl]titanium trichloride, [9-tris(3,5-diethylphenyl)silyl-octahydrofluorenyl]titanium trichloride,

[1-tris(3,5-diisopropylphenyl)silyl-2-methylcyclopentadienyl]titanium trichloride, [1-tris(3,5-diisopropylphenyl)silyl-3-methylcyclopentadienyl]titanium trichloride, [1-tris(3,5-diisopropylphenyl)silyl-2,3-dimethylcyclopentadienyl]titanium trichloride, [1-tris(3,5-diisopropylphenyl)silyl-2,4-dimethylcyclopentadienyl]titanium trichloride, [1-tris(3,5-diisopropylphenyl)silyl-2,5-dimethylcyclopentadienyl]titanium trichloride, [1-tris(3,5-diisopropylphenyl)silyl-2,3,5-trimethylcyclopentadienyl]titanium trichloride, [1-tris(3,5-diisopropylphenyl)silyl-2,3,4,5-tetramethylcyclopentadienyl]titanium trichloride, [1-tris(3,5-diisopropylphenyl)silyl-2-ethylcyclopentadienyl]titanium trichloride, [1-tris(3,5-diisopropylphenyl)silyl-3-ethylcyclopentadienyl]titanium trichloride, [1-tris(3,5-diisopropylphenyl)silyl-2-n-propylcyclopentadienyl]titanium trichloride, [1-tris(3,5-diisopropylphenyl)silyl-3-n-propylcyclopentadienyl]titanium trichloride, [1-tris(3,5-diisopropylphenyl)silyl-2-isopropylcyclopentadienyl]titanium trichloride, [1-tris(3,5-diisopropylphenyl)silyl-3-isopropylcyclopentadienyl]titanium trichloride, [1-tris(3,5-diisopropylphenyl)silyl-2-n-butylcyclopentadienyl]titanium trichloride, [1-tris(3,5-diisopropylphenyl)silyl-3-n-butylcyclopentadienyl]titanium trichloride, [1-tris(3,5-diisopropylphenyl)silyl-2-sec-butylcyclopentadienyl]titanium trichloride, [1-tris(3,5-diisopropylphenyl)silyl-3-sec-butylcyclopentadienyl]titanium trichloride, [1-tris(3,5-diisopropylphenyl)silyl-2-tert-butylcyclopentadienyl]titanium trichloride, [1-tris(3,5-diisopropylphenyl)silyl-3-tert-butylcyclopentadienyl]titanium trichloride, [1-tris(3,5-diisopropylphenyl)silyl-2-phenylcyclopentadienyl]titanium trichloride, [1-tris(3,5-diisopropylphenyl)silyl-3-phenylcyclopentadienyl]titanium trichloride, [1-tris(3,5-diisopropylphenyl)silyl-2-benzylcyclopentadienyl]titanium trichloride, [1-tris(3,5-diisopropylphenyl)silyl-3-benzylcyclopentadienyl]titanium trichloride, [1-tris(3,5-diisopropylphenyl)silyl-indenyl]titanium trichloride, [1-tris(3,5-diisopropylphenyl)silyl-2-methylindenyl]titanium trichloride, [9-tris(3,5-diisopropylphenyl)silyl-fluorenyl]titanium trichloride, [1-tris(3,5-diisopropylphenyl)silyl-tetrahydroindenyl]titanium trichloride, [1-tris(3,5-diisopropylphenyl)silyl-2-methyltetrahydroindenyl]titanium trichloride, [9-tris(3,5-diisopropylphenyl)silyl-octahydrofluorenyl]titanium trichloride,

[1-tris(3,5-di-tert-butylphenyl)silyl-2-methylcyclopentadienyl]titanium trichloride, [1-tris(3,5-di-tert-butylphenyl)silyl-3-methylcyclopentadienyl]titanium trichloride, [1-tris(3,5-di-tert-butylphenyl)silyl-2,3-dimethylcyclopentadienyl]titanium trichloride, [1-tris(3,5-di-tert-butylphenyl)silyl-2,4-dimethylcyclopentadienyl]titanium trichloride, [1-tris(3,5-di-tert-butylphenyl)silyl-2,5-dimethylcyclopentadienyl]titanium trichloride, [1-tris(3,5-di-tert-butylphenyl)silyl-2,3,5-trimethylcyclopentadienyl]titanium trichloride, [1-tris(3,5-di-tert-butylphenyl)silyl-2,3,4,5-tetramethylcyclopentadienyl]titanium trichloride, [1-tris(3,5-di-tert-butylphenyl)silyl-2-ethylcyclopentadienyl]titanium trichloride, [1-tris(3,5-di-tert-butylphenyl)silyl-3-ethylcyclopentadienyl]titanium trichloride, [1-tris(3,5-di-tert-butylphenyl)silyl-2-n-propylcyclopentadienyl]titanium trichloride, [1-tris(3,5-di-tert-butylphenyl)silyl-3-n-propylcyclopentadienyl]titanium trichloride, [1-tris(3,5-di-tert-butylphenyl)silyl-2-isopropylcyclopentadienyl]titanium trichloride, [1-tris(3,5-di-tert-butylphenyl)silyl-3-isopropylcyclopentadienyl]titanium trichloride, [1-tris(3,5-di-tert-butylphenyl)silyl-2-n-butylcyclopentadienyl]titanium trichloride, [1-tris(3,5-di-tert-butylphenyl)silyl-3-n-butylcyclopentadienyl]titanium trichloride, [1-tris(3,5-di-tert-butylphenyl)silyl-2-sec-butylcyclopentadienyl]titanium trichloride, [1-tris(3,5-di-tert-butylphenyl)silyl-3-sec-butylcyclopentadienyl]titanium trichloride, [1-tris(3,5-di-tert-butylphenyl)silyl-2-tert-butylcyclopentadienyl]titanium trichloride, [1-tris(3,5-di-tert-butylphenyl)silyl-3-tert-butylcyclopentadienyl]titanium trichloride, [1-tris(3,5-di-tert-butylphenyl)silyl-2-phenylcyclopentadienyl]titanium trichloride, [1-tris(3,5-di-tert-butylphenyl)silyl-3-phenylcyclopentadienyl]titanium trichloride, [1-tris(3,5-di-tert-butylphenyl)silyl-2-benzylcyclopentadienyl]titanium trichloride, [1-tris(3,5-di-tert-butylphenyl)silyl-3-benzylcyclopentadienyl]titanium trichloride, [1-tris(3,5-di-tert-butylphenyl)silyl-indenyl]titanium trichloride, [1-tris(3,5-di-tert-butylphenyl)silyl-2-methylindenyl]titanium trichloride, [9-tris(3,5-di-tert-butylphenyl)silyl-fluorenyl]titanium trichloride, [1-tris(3,5-di-tert-butylphenyl)silyl-tetrahydroindenyl]titanium trichloride, [1-tris(3,5-di-tert-butylphenyl)silyl-2-methyltetrahydroindenyl]titanium trichloride, [9-tris(3,5-di-tert-butylphenyl)silyl-octahydrofluorenyl]titanium trichloride,

[1-tris(3,5-di-n-hexylphenyl)silyl-2-methylcyclopentadienyl]titanium trichloride, [1-tris(3,5-di-n-hexylphenyl)silyl-3-methylcyclopentadienyl]titanium trichloride, [1-tris(3,5-di-n-hexylphenyl)silyl-2,3-dimethylcyclopentadienyl]titanium trichloride, [1-tris(3,5-di-n-hexylphenyl)silyl-2,4-dimethylcyclopentadienyl]titanium trichloride, [1-tris(3,5-di-n-hexylphenyl)silyl-2,5-dimethylcyclopentadienyl]titanium trichloride, [1-tris(3,5-di-n-hexylphenyl)silyl-2,3,5-trimethylcyclopentadienyl]titanium trichloride, [1-tris(3,5-di-n-hexylphenyl)silyl-2,3,4,5-tetramethylcyclopentadienyl]titanium trichloride, [1-tris(3,5-di-n-hexylphenyl)silyl-2-ethylcyclopentadienyl]titanium trichloride, [1-tris(3,5-di-n-hexylphenyl)silyl-3-ethylcyclopentadienyl]titanium trichloride, [1-tris(3,5-di-n-hexylphenyl)silyl-2-n-propylcyclopentadienyl]titanium trichloride, [1-tris(3,5-di-n-hexylphenyl)silyl-3-n-propylcyclopentadienyl]titanium trichloride, [1-tris(3,5-di-n-hexylphenyl)silyl-2-isopropylcyclopentadienyl]titanium trichloride, [1-tris(3,5-di-n-hexylphenyl)silyl-3-isopropylcyclopentadienyl]titanium trichloride, [1-tris(3,5-di-n-hexylphenyl)silyl-2-n-butylcyclopentadienyl]titanium trichloride, [1-tris(3,5-di-n-hexylphenyl)silyl-3-n-butylcyclopentadienyl]titanium trichloride, [1-tris(3,5-di-n-hexylphenyl)silyl-2-sec-butylcyclopentadienyl]titanium trichloride, [1-tris(3,5-di-n-hexylphenyl)silyl-3-sec-butylcyclopentadienyl]titanium trichloride, [1-tris(3,5-di-n-hexylphenyl)silyl-2-tert-butylcyclopentadienyl]titanium trichloride, [1-tris(3,5-di-n-hexylphenyl)silyl-3-tert-butylcyclopentadienyl]titanium trichloride, [1-tris(3,5-di-n-hexylphenyl)silyl-2-phenylcyclopentadienyl]titanium trichloride, [1-tris(3,5-di-n-hexylphenyl)silyl-3-phenylcyclopentadienyl]titanium trichloride, [1-tris(3,5-di-n-hexylphenyl)silyl-2-benzylcyclopentadienyl]titanium trichloride, [1-tris(3,5-di-n-hexylphenyl)silyl-3-benzylcyclopentadienyl]titanium trichloride, [1-tris(3,5-di-n-hexylphenyl)silyl-indenyl]titanium trichloride, [1-tris(3,5-di-n-hexylphenyl)silyl-2-methylindenyl]titanium trichloride, [9-tris(3,5-di-n-hexylphenyl)silyl-fluorenyl]titanium trichloride, [1-tris(3,5-di-n-hexylphenyl)silyl-tetrahydroindenyl]titanium trichloride, [1-tris(3,5-di-n-hexylphenyl)silyl-2-methyltetrahydroindenyl]titanium trichloride, [9-tris(3,5-di-n-hexylphenyl)silyl-octahydrofluorenyl]titanium trichloride,

[1-n-butylmethyl(2,4,6-trimethylphenyl)silyl-2-methylcyclopentadienyl]titanium trichloride, [1-n-butylmethyl(2,4,6-trimethylphenyl)silyl-3-methylcyclopentadienyl]titanium trichloride, [1-n-butylmethyl(2,4,6-trimethylphenyl)silyl-2,3-dimethylcyclopentadienyl]titanium trichloride, [1-n-butylmethyl(2,4,6-trimethylphenyl)silyl)-2,4-dimethylcyclopentadienyl]titanium trichloride, [1-n-butylmethyl(2,4,6-trimethylphenyl)silyl-2,5-dimethylcyclopentadienyl]titanium trichloride, [1-n-butylmethyl(2,4,6-trimethylphenyl)silyl-2,3,5-trimethylcyclopentadienyl]titanium trichloride, [1-n-butylmethyl(2,4,6-trimethylphenyl)silyl-2,3,4,5-tetramethylcyclopentadienyl]titanium trichloride, [1-n-butylmethyl(2,4,6-trimethylphenyl)silyl-2-ethylcyclopentadienyl]titanium trichloride, [1-n-butylmethyl(2,4,6-trimethylphenyl)silyl-3-ethylcyclopentadienyl]titanium trichloride, [1-n-butylmethyl(2,4,6-trimethylphenyl)silyl-2-n-propylcyclopentadienyl]titanium trichloride, [1-n-butylmethyl(2,4,6-trimethylphenyl)silyl-3-n-propylcyclopentadienyl]titanium trichloride, [1-n-butylmethyl(2,4,6-trimethylphenyl)silyl-2-isopropylcyclopentadienyl]titanium trichloride, [1-n-butylmethyl(2,4,6-trimethylphenyl)silyl-3-isopropylcyclopentadienyl]titanium trichloride, [1-n-butylmethyl(2,4,6-trimethylphenyl)silyl-2-n-butylcyclopentadienyl]titanium trichloride, [1-n-butylmethyl(2,4,6-trimethylphenyl)silyl-3-n-butylcyclopentadienyl]titanium trichloride, [1-n-butylmethyl(2,4,6-trimethylphenyl)silyl-2-sec-butylcyclopentadienyl]titanium trichloride, [1-n-butylmethyl(2,4,6-trimethylphenyl)silyl-3-sec-butylcyclopentadienyl]titanium trichloride, [1-n-butylmethyl(2,4,6-trimethylphenyl)silyl-2-tert-butylcyclopentadienyl]titanium trichloride, [1-n-butylmethyl(2,4,6-trimethylphenyl)silyl-3-tert-butylcyclopentadienyl]titanium trichloride, [1-n-butylmethyl(2,4,6-trimethylphenyl)silyl-2-phenylcyclopentadienyl]titanium trichloride, [1-n-butylmethyl(2,4,6-trimethylphenyl)silyl-3-phenylcyclopentadienyl]titanium trichloride, [1-n-butylmethyl(2,4,6-trimethylphenyl)silyl-2-benzylcyclopentadienyl]titanium trichloride, [1-n-butylmethyl(2,4,6-trimethylphenyl)silyl-3-benzylcyclopentadienyl]titanium trichloride, [1-n-butylmethyl(2,4,6-trimethylphenyl)silyl-indenyl]titanium trichloride, [1-n-butylmethyl(2,4,6-trimethylphenyl)silyl-2-methylindenyl]titanium trichloride, [9-n-butylmethyl(2,4,6-trimethylphenyl)silyl-fluorenyl]titanium trichloride, [1-n-butylmethyl(2,4,6-trimethylphenyl)silyl-tetrahydroindenyl]titanium trichloride, [1-n-butylmethyl(2,4,6-trimethylphenyl)silyl-2-methyltetrahydroindenyl]titanium trichloride, [9-n-butylmethyl(2,4,6-trimethylphenyl)silyl-octahydrofluorenyl]titanium trichloride,

[1-n-butylmethyl(pentamethylphenyl)silyl-2-methylcyclopentadienyl]titanium trichloride, [1-n-butylmethyl(pentamethylphenyl)silyl-3-methylcyclopentadienyl]titanium trichloride, [1-n-butylmethyl(pentamethylphenyl)silyl-2,3-dimethylcyclopentadienyl]titanium trichloride, [1-n-butylmethyl(pentamethylphenyl)silyl-2,4-dimethylcyclopentadienyl]titanium trichloride, [1-n-butylmethyl(pentamethylphenyl)silyl-2,5-dimethylcyclopentadienyl]titanium trichloride, [1-n-butylmethyl(pentamethylphenyl)silyl-2,3,5-trimethylcyclopentadienyl]titanium trichloride, [1-n-butylmethyl(pentamethylphenyl)silyl-2,3,4,5-tetramethylcyclopentadienyl]titanium trichloride, [1-n-butylmethyl(pentamethylphenyl)silyl-2-ethylcyclopentadienyl]titanium trichloride, [1-n-butylmethyl(pentamethylphenyl)silyl-3-ethylcyclopentadienyl]titanium trichloride, [1-n-butylmethyl(pentamethylphenyl)silyl-2-n-propylcyclopentadienyl]titanium trichloride, [1-n-butylmethyl(pentamethylphenyl)silyl-3-n-propylcyclopentadienyl]titanium trichloride, [1-n-butylmethyl(pentamethylphenyl)silyl-2-isopropylcyclopentadienyl]titanium trichloride, [1-n-butylmethyl(pentamethylphenyl)silyl-3-isopropylcyclopentadienyl]titanium trichloride, [1-n-butylmethyl(pentamethylphenyl)silyl-2-n-butylcyclopentadienyl]titanium trichloride, [1-n-butylmethyl(pentamethylphenyl)silyl-3-n-butylcyclopentadienyl]titanium trichloride, [1-n-butylmethyl(pentamethylphenyl)silyl-2-sec-butylcyclopentadienyl]titanium trichloride, [1-n-butylmethyl(pentamethylphenyl)silyl-3-sec-butylcyclopentadienyl]titanium trichloride, [1-n-butylmethyl(pentamethylphenyl)silyl-2-tert-butylcyclopentadienyl]titanium trichloride, [1-n-butylmethyl(pentamethylphenyl)silyl-3-tert-butylcyclopentadienyl]titanium trichloride, [1-n-butylmethyl(pentamethylphenyl)silyl-2-phenylcyclopentadienyl]titanium trichloride, [1-n-butylmethyl(pentamethylphenyl)silyl-3-phenylcyclopentadienyl]titanium trichloride, [1-n-butylmethyl(pentamethylphenyl)silyl-2-benzylcyclopentadienyl]titanium trichloride, [1-n-butylmethyl(pentamethylphenyl)silyl-3-benzylcyclopentadienyl]titanium trichloride, [1-n-butylmethyl(pentamethylphenyl)silyl-indenyl]titanium trichloride, [1-n-butylmethyl(pentamethylphenyl)silyl-2-methylindenyl]titanium trichloride, [9-n-butylmethyl(pentamethylphenyl)silyl-fluorenyl]titanium trichloride, [1-n-butylmethyl(pentamethylphenyl)silyl-tetrahydroindenyl]titanium trichloride, [1-n-butylmethyl(pentamethylphenyl)silyl-2-methyltetrahydroindenyl]titanium trichloride and [9-n-butylmethyl(pentamethylphenyl)silyl-octahydrofluorenyl]titanium trichloride.

Moreover, examples of the transition metal complex (1) also include: transition metal chloride complexes such as zirconium chloride complexes in which "titanium" in the complexes exemplified above is replaced with "zirconium", and hafnium chloride complexes in which "titanium" is replaced with "hafnium"; titanium halide complexes such as titanium fluoride complexes in which "chloride" in the complexes are replaced with "fluoride", titanium bromide complexes in which "chloride" is replaced with "bromide" and titanium iodide complexes in which "chloride" is replaced with "iodide"; titanium hydride complexes in which "chloride" is replaced with "hydride"; alkylated titanium complexes such as a methylated titanium complex in which "chloride" is replaced with "methyl"; arylated titanium complexes such as a phenylated titanium complex in which "chloride" is replaced with "phenyl"; aralkylated titanium complexes such as a benzylated titanium complex in which "chloride" is replaced with "benzyl"; titanium alkoxide complexes such as a titanium methoxide complex in which "chloride" is replaced with "methoxide", a titanium n-butoxide complex in which "chloride" is replaced with "n-butoxide" and a titanium isopropoxide complex in which "chloride" is replaced with "isopropoxide"; titanium aryloxide complexes such as a titanium phenoxide complex in which "chloride" is replaced with "phenoxide"; titanium aralkyloxide complexes such as a titanium benzyloxide complex in which "chloride" is replaced with "benzyloxide"; and titanium amide complexes such as a titanium dimethylamide complex in which "chloride" is replaced with "dimethylamide" and a titanium diethylamide complex in which "chloride" is replaced with "diethylamide". Of these, alkylated titanium complexes are preferable, and trimethyl titanium complexes are more preferable.

Preferable examples of the transition metal complex of formula (1) include [1-dimethylphenylsilyl-2,3,4,5-tetramethylcyclopentadienyl]titanium trichloride, [1-diethylphenylsilyl-2,3,4,5-tetramethylcyclopentadienyl]titanium trichloride, [1-cyclotetramethylene(phenyl)silyl-2,3,4,5-tetramethylcyclopentadienyl]titanium trichloride, [1-ethylmethylphenylsilyl-2,3,4,5-tetramethylcyclopentadienyl]titanium trichloride, [1-n-butylmethylphenylsilyl-2,3,4,5-tetramethylcyclopentadienyl]titanium trichloride, [1-methyldiphenylsilyl-2,3,4,5-tetramethylcyclopentadienyl]titanium trichloride, [1-cyclohexylmethylphenylsilyl-2,3,4,5-tetramethylcyclopentadienyl]titanium trichloride, [1-methyl(n-octadecyl)phenylsilyl-2,3,4,5-tetramethylcyclopentadienyl]titanium trichloride, [1-triphenylsilyl-2,3,4,5-tetramethylcyclopentadienyl]titanium trichloride, [1-tri(4-n-butylphenyl)silyl-2,3,4,5-tetramethylcyclopentadienyl]titanium trichloride, [1-dimethyl(3,5-dimethylphenyl)silyl-2,3,4,5-tetramethylcyclopentadienyl]titanium trichloride, [1-n-butylmethyl(3,5-dimethylphenyl)silyl-2,3,4,5-tetramethylcyclopentadienyl]titanium trichloride, [1-tris(3,5-dimethylphenyl)silyl-2,3,4,5-tetramethylcyclopentadienyl]titanium trichloride and [1-methyldi(4-methylphenyl)silyl-2,3,4,5-tetramethylcyclopentadienyl]titanium trichloride. More preferable examples thereof include [1-n-butylmethylphenylsilyl-2,3,4,5-tetramethylcyclopentadienyl]titanium trichloride, [1-methyldiphenylsilyl-2,3,4,5-tetramethylcyclopentadienyl]titanium trichloride, [1-triphenylsilyl-2,3,4,5-tetramethylcyclopentadienyl]titanium trichloride and [1-tris(3,5-dimethylphenyl)silyl-2,3,4,5-tetramethylcyclopentadienyl]titanium trichloride.

<Process for Producing Transition Metal Complex (1)>

The transition metal complex (1) can be produced by, for example, a production process comprising the steps of:
reacting a substituted cyclopentadiene compound represented by a formula (6) (hereinafter, referred to as a "substituted cyclopentadiene compound (6)") with a base in the presence of an amine compound:

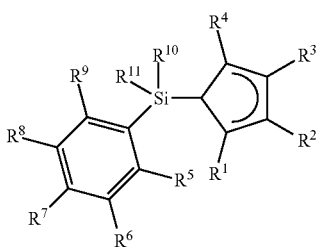

(6)

wherein $R^1$, $R^2$, $R^3$, $R^4$, $R^5$, $R^6$, $R^7$, $R^8$, $R^9$, $R^{10}$ and $R^{11}$ are as defined above; and reacting the reaction product of the substituted cyclopentadiene compound (6) and the base with a transition metal compound represented by the following general formula (7) (hereinafter, referred to as a "transition metal compound (7)"):

(7)

wherein $M^1$, $X^1$, $X^2$ and $X^3$ are as defined above, $X^{12}$ independently at each occurrence represent a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by $-Si(R^{12})_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by $-N(R^{13})_2$, wherein the two $R^{13}$ groups each independently represent a hydrocarbyl group or a halogenated hydrocarbyl group, and the total number of the carbon atoms in the two $R^{13}$ groups is 2 to 20, and m represents 0 or 1.

Hereinafter, the step of reacting a substituted cyclopentadiene compound (6) with a base in the presence of an amine compound may be referred to as a "1st reaction step", and the step of reacting the reaction product of the substituted cyclopentadiene compound (6) and the base with a transition metal compound (7) may be referred to as a "2nd reaction step".

Isomers of the substituted cyclopentadiene compound (6), differing in the double bond position of the cyclopentadiene ring include the following structural isomers:

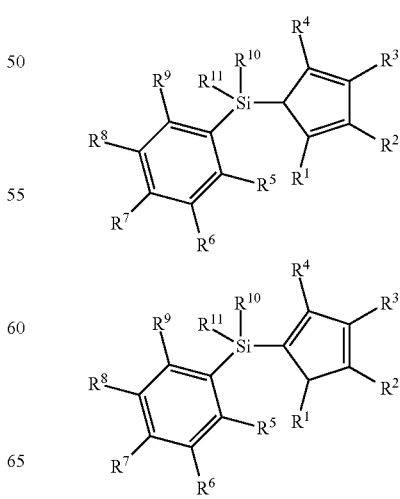

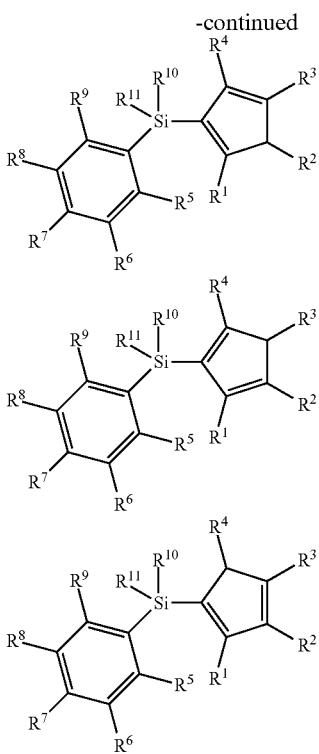

The compound represented by the general formula (6) has isomers differing in the double bond position of each cyclopentadienyl ring. In the present invention, it represents any of them or a mixture of them.

In the transition metal compound (7), the substituent $X^{12}$ is as defined above, and specific examples thereof can include the same as those exemplified for $X^1$, $X^2$ and $X^3$.

Examples of the transition metal compound (7) include: titanium halides such as titanium tetrachloride, titanium trichloride, titanium tetrabromide and titanium tetraiodide; titanium amidoes such as tetrakis(dimethylamino)titanium, dichlorobis(dimethylamino)titanium, trichloro(dimethylamino)titanium and tetrakis(diethylamino)titanium; and titanium alkoxides titanium such as tetraisopropoxytitanium, tetra-n-butoxytitanium, dichlorodiisopropoxytitanium and trichloroisopropoxytitanium. Moreover, examples of the transition metal compound (7) include compounds in which "titanium" in any of these compounds is replaced with "zirconium" or "hafnium". Of them, a preferable transition metal compound (7) is titanium tetrachloride.

Examples of the base reacted with the substituted cyclopentadiene compound (6) in the 1st reaction step include organic alkali metal compounds typified by organic lithium compounds such as methyllithium, ethyllithium, n-butyllithium, sec-butyllithium, tert-butyllithium, lithiumtrimethylsilyl acetylide, lithium acetylide, trimethylsilylmethyllithium, vinyllithium, phenyllithium and allyllithium.

The amount of the base used may be in the range of 0.5 to 5 moles per one mole of the substituted cyclopentadienyl compound (6).

In the reaction of the substituted cyclopentadiene compound (6) with the base in the 1st reaction step, an amine compound is used together with the organic alkali metal compound. Examples of such an amine compound include: primary amine compounds such as methylamine, ethylamine, n-propylamine, isopropylamine, n-butylamine, tert-butylamine, n-octylamine, n-decylamine, aniline and ethylenediamine; secondary amine compounds such as dimethylamine, diethylamine, di-n-propylamine, diisopropylamine, di-n-butylamine, di-tert-butylamine, di-n-octylamine, di-n-decylamine, pyrrolidine, hexamethyldisilazane and diphenylamine; and tertiary amine compounds such as trimethylamine, triethylamine, tri-n-propylamine, tri-n-butylamine, diisopropylethylamine, tri-n-octylamine, tri-n-decylamine, triphenylamine, N,N-dimethylaniline, N,N,N',N'-tetramethylethylenediamine, N-methylpyrrolidine and 4-dimethylaminopyridine. The amount of such an amine compound used is preferably 10 moles or smaller, more preferably in the range of 0.5 to 10 moles, even more preferably in the range of 1 to 5 moles, per one mole of the organic alkali metal compound.

In the 1st reaction step, the reaction of the substituted cyclopentadiene compound (6) with the base is preferably performed in the presence of a solvent. Moreover, when the solvent is used, the substituted cyclopentadiene compound (6) and the base are reacted in the solvent and then a transition metal compound (7) can be added into this reaction mixture to thereby further react the transition metal compound (7) with the reaction product of the substituted cyclopentadiene compound (6) and the base. Solids may be deposited in the reaction mixture obtained by reacting the substituted cyclopentadiene compound (6) and the base. In this case, the solvent may be further added until the deposited solid is dissolved; or the deposited solid may be temporarily separated by filtration or the like, and the solvent may be added to the separated solid for dissolution or suspension, followed by the addition of a transition metal compound (7). When the solvent is used, the substituted cyclopentadiene compound (6), the base and the transition metal compound (7) can also be added simultaneously to the solvent to thereby perform the 1st reaction step and the 2nd reaction step almost simultaneously.

The solvent used in the 1st reaction step or in the 1st and 2nd reaction steps is an inert solvent that does not significantly hinder the progress of the reaction associated with these steps. Examples of such a solvent include aprotic solvents such as: aromatic hydrocarbyl solvents such as benzene and toluene; aliphatic hydrocarbyl solvents such as hexane and heptane; ether solvents such as diethyl ether, tetrahydrofuran and 1,4-dioxane; amide solvents such as hexamethylphosphoric amide and dimethylformamide; polar solvents such as acetonitrile, propionitrile, acetone, diethyl ketone, methyl isobutyl ketone and cyclohexanone; and halogenic solvents such as dichloromethane, dichloroethane, chlorobenzene and dichlorobenzene. These solvents can be used alone or as a mixture of two or more thereof, and the amount thereof used is preferably 1 to 200 parts by weight, more preferably 3 to 50 parts by weight, per one part by weight of the substituted cyclopentadiene compound (6).

The amount of the transition metal compound (7) used is preferably in the range of 0.5 to 3 moles, more preferably in the range of 0.7 to 1.5 moles, per one mole of the substituted cyclopentadiene compound (6).

The reaction temperature in the 1st and 2nd reaction steps needs only to be a temperature not less than −100° C. and not more than the boiling point of the solvent and is preferably in the range of −80 to 100° C.

From the reaction mixture thus obtained through the 1st and 2nd reaction steps, the produced transition metal complex (1) can be taken out by various purification methods known in the art. For example, the transition metal complex (1) of interest can be obtained by a method in which after the 1st and 2nd reaction steps, the formed precipitates are filtered off, and the filtrate is concentrated to deposit a transition metal complex, which is then collected by filtration.

<Method for Producing Transition Metal Complex (1-2)>

The transition metal complex (1-2) can be produced, for example, by reacting a transition metal halide complex represented by general formula (1-1):

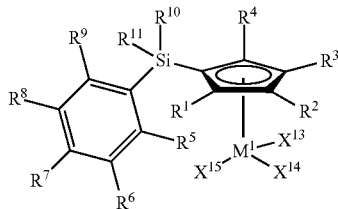

(1-1)

wherein $M^1$, $R^1$, $R^2$, $R^3$, $R^4$, $R^5$, $R^6$, $R^7$, $R^8$, $R^9$, $R^{10}$ and $R^{11}$ are as defined above, and
$X^{13}$, $X^{14}$ and $X^{15}$ are a halogen atom,
with an alkali metal compound represented by a formula (8):

$M^6$-$R^{20}$ (8)

wherein $M^6$ represents an alkali metal, and $R^{20}$ represents an alkyl group having 1 to 20 carbon atoms which may have a halogen atom as a substituent,
an aryl group having 6 to 20 carbon atoms which may have a halogen atom as a substituent, or
an aralkyl group having 7 to 20 carbon atoms which may have a halogen atom as a substituent, or
an alkaline earth metal compound represented by a formula (9):

(9)

wherein $M^7$ represents an alkaline earth metal, $R^{21}$ represents
an alkyl group having 1 to 20 carbon atoms which may have a halogen atom as a substituent,
an aryl group having 6 to 20 carbon atoms which may have a halogen atom as a substituent, or
an aralkyl group having 7 to 20 carbon atoms which may have a halogen atom as a substituent,
$X^{16}$ represents a halogen atom, r is 1 or 2, and the total sum of r and s is 2.

Examples of the transition metal complex (1-2) include alkylated titanium, arylated titanium and aralkylated titanium complexes.

In the transition metal complex (1-2), the substituents $R^{22}$, $R^{23}$ and $R^{24}$ are as defined above, and specific examples thereof can include the same as those exemplified for $R^1$.

Examples of the transition metal halide complex (1-1) include titanium chloride, titanium fluoride, titanium bromide and titanium iodide complexes.

In the transition metal compound (1-1), the substituents $X^{13}$, $X^{14}$ and $X^{15}$ are as defined above, and specific examples thereof can include the same as those exemplified for $X^1$, $X^2$ and $X^3$.

In the alkali metal compound (8), $M^6$ represents an alkali metal of the Periodic Table of the Elements, and examples thereof include lithium, sodium and potassium atoms. Among them, lithium and sodium atoms are preferable, and a lithium atom is particularly preferable.

In the alkali metal compound (8), the substituent $R^{20}$ is as defined above, and specific examples thereof can include the same as those exemplified for $R^1$.

In the alkaline earth metal compound (9), $M^7$ represents an alkaline earth metal of the Periodic Table of the Elements, and examples thereof include magnesium, calcium and strontium atoms. Among them, a magnesium atom is preferable.

In the alkaline earth metal compound (9), the substituent $R^{21}$ is as defined above, and specific examples thereof can include the same as those exemplified for $R^1$.

In the alkaline earth metal compound (9), the substituent $X^{16}$ is as defined above, and specific examples thereof can include the same as those exemplified for $X^1$, $X^2$ and $X^3$.

In the alkaline earth metal compound (9), r is 1 or 2, and the total sum of r and s is 2.

Examples of the alkali metal compound (8) include:
alkyllithiums such as methyllithium, ethyllithium, n-propyllithium, isopropyllithium, n-butyllithium, sec-butyllithium, tert-butyllithium, n-pentyllithium, neopentyllithium, amyllithium, n-hexyllithium, n-octyllithium, n-decyllithium, n-dodecyllithium, n-pentadecyllithium and n-eicosyllithium;
aralkyllithiums such as benzyllithium, (2-methylphenyl)methyllithium, (3-methylphenyl)methyllithium, (4-methylphenyl)methyllithium, (2,3-dimethylphenyl)methyllithium, (2,4-dimethylphenyl)methyllithium, (2,5-dimethylphenyl)methyllithium, (2,6-dimethylphenyl)methyllithium, (3,4-dimethylphenyl)methyllithium, (2,3,4-trimethylphenyl)methyllithium, (2,3,5-trimethylphenyl)methyllithium, (2,3,6-trimethylphenyl)methyllithium, (3,4,5-trimethylphenyl)methyllithium, (2,4,6-trimethylphenyl)methyllithium, (2,3,4,5-tetramethylphenyl)methyllithium, (2,3,4,6-tetramethylphenyl)methyllithium, (2,3,5,6-tetramethylphenyl)methyllithium, (pentamethylphenyl)methyllithium, (ethylphenyl)methyllithium, (n-propylphenyl)methyllithium, (isopropylphenyl)methyllithium, (n-butylphenyl)methyllithium, (sec-butylphenyl)methyllithium, (tert-butylphenyl)methyllithium, (n-pentylphenyl)methyllithium, (neopentylphenyl)methyllithium, (n-hexylphenyl)methyllithium, (n-octylphenyl)methyllithium, (n-decylphenyl)methyllithium, (n-dodecylphenyl)methyllithium, (n-tetradecylphenyl)methyllithium, naphthylmethyllithium and anthracenylmethyllithium; and
aryllithiums such as phenyllithium, 2-tolyllithium, 3-tolyllithium, 4-tolyllithium, 2,3-xylyllithium, 2,4-xylyllithium, 2,5-xylyllithium, 2,6-xylyllithium, 3,4-xylyllithium, 3,5-xylyllithium, 2,3,4-trimethylphenyllithium, 2,3,5-trimethylphenyllithium, 2,3,6-trimethylphenyllithium, 2,4,6-trimethylphenyllithium, 3,4,5-trimethylphenyllithium, 2,3,4,5-tetramethylphenyllithium, 2,3,4,6-tetramethylphenyllithium, 2,3,5,6-tetramethylphenyllithium, pentamethylphenyllithium, ethylphenyllithium, n-propylphenyllithium, isopropylphenyllithium, n-butylphenyllithium, sec-butylphenyllithium, tert-butylphenyllithium, n-pentylphenyllithium, neopentylphenyllithium, n-hexylphenyllithium, n-octylphenyllithium, n-decylphenyllithium, n-dodecylphenyllithium, n-tetradecylphenyllithium, naphthyllithium and anthracenyllithium. Methyllithium, benzyllithium and phenyllithium are preferable.

The amount of the alkali metal compound (8) used is usually in the range of 2- to 10-fold by mol, preferably in the range of 1- to 3-fold by mol, with respect to the transition metal halide complex (1-1).

Examples of the alkaline earth metal compound (9) include: dialkylmagnesiums and asymmetric dialkylmagnesiums such as dimethylmagnesium, diethylmagnesium, di-n-propylmagnesium, diisopropylmagnesium, di-n-butylmagnesium, di-sec-butylmagnesium, di-tert-butylmagnesium, di-n-pentylmagnesium, di-neopentylmagnesium, diamylmagnesium, di-n-hexylmagnesium, di-n-octylmagnesium, di-n-decylmagnesium, di-n-dodecylmagnesium, di-n-pentadecylmagnesium and di-n-eicosylmagnesium;

diaralkylmagnesiums and asymmetric diaralkylmagnesiums such as dibenzylmagnesium, di-(2-methylphenyl)methylmagnesium, di-(3-methylphenyl)methylmagnesium, di-(4-methylphenyl)methylmagnesium, di-(2,3-dimethylphenyl)methylmagnesium, di-(2,4-dimethylphenyl)methylmagnesium, di-(2,5-dimethylphenyl)methylmagnesium, di-(2,6-dimethylphenyl)methylmagnesium, di-(3,4-dimethylphenyl)methylmagnesium, di-(2,3,4-trimethylphenyl)methylmagnesium, di-(2,3,5-trimethylphenyl)methylmagnesium, di-(2,3,6-trimethylphenyl)methylmagnesium, di-(3,4,5-trimethylphenyl)methylmagnesium, di-(2,4,6-trimethylphenyl)methylmagnesium, di-(2,3,4,5-tetramethylphenyl)methylmagnesium, di-(2,3,4,6-tetramethylphenyl)methylmagnesium, di-(2,3,5,6-tetramethylphenyl)methylmagnesium, di-(pentamethylphenyl)methylmagnesium, di-(ethylphenyl)methylmagnesium, di-(n-propylphenyl)methylmagnesium, di-(isopropylphenyl)methylmagnesium, di-(n-butylphenyl)methylmagnesium, di-(sec-butylphenyl)methylmagnesium, di-(tert-butylphenyl)methylmagnesium, di-(n-pentylphenyl)methylmagnesium, di-(neopentylphenyl)methylmagnesium, di-(n-hexylphenyl)methylmagnesium, di-(n-octylphenyl)methylmagnesium, di-(n-decylphenyl)methylmagnesium, di-(n-dodecylphenyl)methylmagnesium, di-(n-tetradecylphenyl)methylmagnesium, dinaphthylmethylmagnesium and dianthracenylmethylmagnesium;

diarylmagnesiums and asymmetric diarylmagnesiums such as diphenylmagnesium, di-2-tolylmagnesium, di-3-tolylmagnesium, di-4-tolylmagnesium, di-2,3-xylylmagnesium, di-2,4-xylylmagnesium, di-2,5-xylylmagnesium, di-2,6-xylylmagnesium, di-3,4-xylylmagnesium, di-3,5-xylylmagnesium, di-2,3,4-trimethylphenylmagnesium, di-2,3,5-trimethylphenylmagnesium, di-2,3,6-trimethylphenylmagnesium, di-2,4,6-trimethylphenylmagnesium, di-3,4,5-trimethylphenylmagnesium, di-2,3,4,5-tetramethylphenylmagnesium, di-2,3,4,6-tetramethylphenylmagnesium, di-2,3,5,6-tetramethylphenylmagnesium, di-pentamethylphenylmagnesium, di-ethylphenylmagnesium, di-n-propylphenylmagnesium, di-isopropylphenylmagnesium, di-n-butylphenylmagnesium, di-sec-butylphenylmagnesium, di-tert-butylphenylmagnesium, di-n-pentylphenylmagnesium, di-neopentylphenylmagnesium, di-n-hexylphenylmagnesium, di-n-octylphenylmagnesium, di-n-decylphenylmagnesium, di-n-dodecylphenylmagnesium, di-n-tetradecylphenylmagnesium, dinaphthylmagnesium and dianthracenylmagnesium;

asymmetric organic magnesium compounds such as alkylaralkylmagnesiums, alkylarylmagnesiums and aralkylarylmagnesiums;

alkylmagnesium chlorides such as methylmagnesium chloride, ethylmagnesium chloride, n-propylmagnesium chloride, isopropylmagnesium chloride, n-butylmagnesium chloride, sec-butylmagnesium chloride, tert-butylmagnesium chloride, n-pentylmagnesium chloride, neopentylmagnesium chloride, amylmagnesium chloride, n-hexylmagnesium chloride, n-octylmagnesium chloride, n-decylmagnesium chloride, n-dodecylmagnesium chloride, n-pentadecylmagnesium chloride and n-eicosylmagnesium chloride;

aralkylmagnesium chlorides such as benzylmagnesium chloride, (2-methylphenyl)methylmagnesium chloride, (3-methylphenyl)methylmagnesium chloride, (4-methylphenyl)methylmagnesium chloride, (2,3-dimethylphenyl)methylmagnesium chloride, (2,4-dimethylphenyl)methylmagnesium chloride, (2,5-dimethylphenyl)methylmagnesium chloride, (2,6-dimethylphenyl)methylmagnesium chloride, (3,4-dimethylphenyl)methylmagnesium chloride, (2,3,4-trimethylphenyl)methylmagnesium chloride, (2,3,5-trimethylphenyl)methylmagnesium chloride, (2,3,6-trimethylphenyl)methylmagnesium chloride, (3,4,5-trimethylphenyl)methylmagnesium chloride, (2,4,6-trimethylphenyl)methylmagnesium chloride, (2,3,4,5-tetramethylphenyl)methylmagnesium chloride, (2,3,4,6-tetramethylphenyl)methylmagnesium chloride, (2,3,5,6-tetramethylphenyl)methylmagnesium chloride, (pentamethylphenyl)methylmagnesium chloride, (ethylphenyl)methylmagnesium chloride, (n-propylphenyl)methylmagnesium chloride, (isopropylphenyl)methylmagnesium chloride, (n-butylphenyl)methylmagnesium chloride, (sec-butylphenyl)methylmagnesium chloride, (tert-butylphenyl)methylmagnesium chloride, (n-pentylphenyl)methylmagnesium chloride, (neopentylphenyl)methylmagnesium chloride, (n-hexylphenyl)methylmagnesium chloride, (n-octylphenyl)methylmagnesium chloride, (n-decylphenyl)methylmagnesium chloride, (n-dodecylphenyl)methylmagnesium chloride, (n-tetradecylphenyl)methylmagnesium chloride, naphthylmethylmagnesium chloride and anthracenylmethylmagnesium chloride;

arylmagnesium chlorides such as phenylmagnesium chloride, 2-tolylmagnesium chloride, 3-tolylmagnesium chloride, 4-tolylmagnesium chloride, 2,3-xylylmagnesium chloride, 2,4-xylylmagnesium chloride, 2,5-xylylmagnesium chloride, 2,6-xylylmagnesium chloride, 3,4-xylylmagnesium chloride, 3,5-xylylmagnesium chloride, 2,3,4-trimethylphenylmagnesium chloride, 2,3,5-trimethylphenylmagnesium chloride, 2,3,6-trimethylphenylmagnesium chloride, 2,4,6-trimethylphenylmagnesium chloride, 3,4,5-trimethylphenylmagnesium chloride, 2,3,4,5-tetramethylphenylmagnesium chloride, 2,3,4,6-tetramethylphenylmagnesium chloride, 2,3,5,6-tetramethylphenylmagnesium chloride, pentamethylphenylmagnesium chloride, ethylphenylmagnesium chloride, n-propylphenylmagnesium chloride, isopropylphenylmagnesium chloride, n-butylphenylmagnesium chloride, sec-butylphenylmagnesium chloride, tert-butylphenylmagnesium chloride, n-pentylphenylmagnesium chloride, neopentylphenylmagnesium chloride, n-hexylphenylmagnesium chloride, n-octylphenylmagnesium chloride, n-decylphenylmagnesium chloride, n-dodecylphenylmagnesium chloride, n-tetradecylphenylmagnesium chloride, naphthylmagnesium chloride and anthracenylmagnesium chloride; and compounds in which chloride is replaced with bromide or iodide in these compounds. Preferable examples thereof include dimethylmagnesium, dibenzylmagnesium, diphenylmagnesium, methylmagnesium bromide, benzylmagnesium bromide phenylmagnesium bromide, and so on.

The amount of the alkaline earth metal compound (9) used is usually in the range of 1- to 10-fold by mol, preferably in the range of 1- to 3-fold by mol, with respect to the transition metal halide complex (1-1).

The reaction method is not particularly limited, and the reaction is usually preferably performed by adding the organic alkali metal or alkaline earth metal compound to the transition metal halide complex (1-1) in the presence of a solvent in an inert atmosphere of nitrogen, argon, or the like.

Examples of the solvent for the reaction can include: aliphatic hydrocarbyl solvents such as pentane, hexane, cyclohexane, heptane and octane; aromatic hydrocarbyl solvents such as benzene, toluene, xylene, mesitylene and ethylbenzene; halogenated hydrocarbyl solvents such as chloroform, methylene dichloride, monochlorobenzene and dichlorobenzene; and ethers such as diethyl ether, dibutyl ether, methyl-t-butyl ether and tetrahydrofuran. These solvents are used alone or as a mixture of two or more thereof, and the amount thereof used is usually in the range of 1- to 200-fold by weight, preferably in the range of 3- to 30-fold by weight, with respect to the transition metal halide complex (1-1).

The temperature of the reaction is usually −100° C. to the boiling point of the solvent, preferably −80° C. to 30° C. The reaction time is not particularly limited. After the completion of the reaction, for example, insoluble matter is filtered off, and the filtrate is then concentrated to obtain a crystal, which can then be collected by filtration to obtain the transition metal complex (1-2) of interest.

<Method for Producing Transition Metal Complex (1-3)>

The transition metal complex (1-3) can be produced, for example, by reacting a transition metal halide complex represented by general formula (1-1):

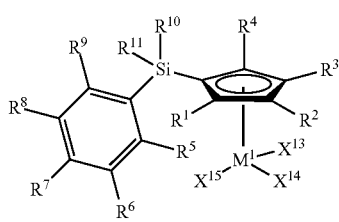

(1-1)

wherein $M^1$, $R^1$, $R^2$, $R^4$, $R^5$, $R^6$, $R^7$, $R^8$, $R^9$, $R^{10}$, $R^{11}$, $X^{13}$, $X^{14}$ and $X^{15}$ are as defined above,
with an alkali metal compound represented by general formula (10):

$$M^6\text{-}OR^{20} \qquad (10)$$

wherein $M^6$ and $R^{20}$ are as defined above, or
an alkaline earth metal compound represented by formula (11):

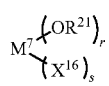

(11)

wherein $M^7$, $R^{21}$, $X^{16}$, r and s are as defined above.

Examples of the transition metal complex (1-3) include titanium alkoxide, titanium aryloxide and titanium aralkyloxide complexes.

In the transition metal complex (1-3), the substituents $R^{25}$, $R^{26}$ and $R^{27}$ are as defined above, and specific examples thereof can include the same as those exemplified for $R^1$.

Examples of the transition metal halide complex (1-1) include titanium chloride, titanium fluoride, titanium bromide and titanium iodide complexes.

In the transition metal compound (1-1), the substituents $X^{13}$, $X^{14}$ and $X^{15}$ are as defined above, and specific examples thereof can include the same as those exemplified for $X^1$, $X^2$ and $X^3$.

In the alkali metal compound (10), $M^6$ represents an alkali metal of the Periodic Table of the Elements, and examples thereof include lithium, sodium and potassium atoms. Among them, lithium and sodium atoms are preferable, and a lithium atom is particularly preferable.

In the alkali metal compound (10), the substituent $R^{20}$ is as defined above, and specific examples thereof can include the same as those exemplified for $R^1$.

In the alkaline earth metal compound (11), $M^7$ represents an alkaline earth metal of the Periodic Table of the Elements, and examples thereof include magnesium, calcium and strontium atoms. Among them, a magnesium atom is preferable.

In the alkaline earth metal compound (11), the substituent $R^{21}$ is as defined above, and specific examples thereof can include the same as those exemplified for $R^1$.

In the alkaline earth metal compound (11), the substituent $X^{16}$ is as defined above, and specific examples thereof can include the same as those exemplified for $X^1$, $X^2$ and $X^3$.

In the alkaline earth metal compound (11), r is 1 or 2, and the total sum of r and s is 2.

The transition metal complex (1-3) can be produced by a process in which the alkali metal compound (10) is allowed to act on the transition metal complex (1-1) (hereinafter, referred to as process A-1) or by a process in which the alkaline earth metal compound (11) is allowed to act thereon (hereinafter, referred to as process A-2).

Moreover, the transition metal complex (1-3) can also be produced by a process in which an alcohol compound is allowed to act on the transition metal complex (1-1) in the presence of a base (hereinafter, referred to as process B).

Examples of the alkali metal compound represented by the general formula (10) include: sodium methoxide, sodium ethoxide, sodium n-propoxide, sodium isopropoxide, sodium n-butoxide, sodium sec-butoxide, sodium tert-butoxide, sodium n-pentoxide, sodium neopentoxide, sodium methoxyethoxide, sodium ethoxyethoxide, sodium benzyloxide, sodium 1-phenylethoxide, and alkali metal alkoxides derived from monools, in which sodium is replaced with lithium or potassium in these compounds;

lithium phenoxide, lithium 2-methylphenoxide, lithium 3-methylphenoxide, lithium 4-methylphenoxide, lithium 2,3-dimethylphenoxide, lithium 2,4-dimethylphenoxide, lithium 2,5-dimethylphenoxide, lithium 2,6-dimethylphenoxide, lithium 3,4-dimethylphenoxide, lithium 2,3,4-trimethylphenoxide, lithium 2,3,5-trimethylphenoxide, lithium 2,3,6-trimethylphenoxide, lithium 3,4,5-trimethylphenoxide, lithium 2,4,6-trimethylphenoxide, lithium 2,3,4,5-tetramethylphenoxide, lithium 2,3,4,6-tetramethylphenoxide, lithium 2,3,5,6-tetramethylphenoxide, lithium pentamethylphenoxide, lithium ethylphenoxide, lithium n-propylphenoxide, lithium isopropylphenoxide, lithium n-butylphenoxide, lithium sec-butylphenoxide, lithium tert-butylphenoxide, lithium n-pentylphenoxide, lithium neopentylphenoxide, lithium n-hexylphenoxide, lithium n-octylphenoxide, lithium n-decylphenoxide, lithium n-dodecylphenoxide, lithium n-tetradecylphenoxide, lithium naphthyloxide, and lithium anthracenyloxide; compounds in which lithium is replaced with sodium or potassium in these compounds; alkali metal haloaryloxides in which these compounds are substituted with a halogen such as fluorine, chlorine or bromine atom; alkali metal alkoxyaryloxide, obtained by arbitrarily changing a halogen atom in the haloaralkyl group into a methoxy, ethoxy, n-propoxy, isopropoxy, n-butoxy, sec-butoxy or tert-butoxy group; alkali metal cyanoaryloxides; and alkali metal nitroaryloxides. Preferable examples thereof include lithium phenoxide, lithium 4-methylphenoxide, lithium 2,4,6-trimethylphenoxide, sodium phenoxide, sodium 4-methylphenoxide and sodium 2,4,6-trimethylphenoxide.

A commercially available product or the like can be used as the alkali metal compound (10). Alternatively, the alkali metal compound (10) can also be produced in the system, for use, through the reaction between an alcohol compound and an alkali metal compound.

Examples of such an alkali metal compound used in the production of the alkali metal compound (10) in the system include: alkyllithiums such as methyllithium, ethyllithium, n-propyllithium, isopropyllithium, n-butyllithium, sec-butyllithium, tert-butyllithium, n-pentyllithium, neopentyllithium, amyllithium, n-hexyllithium, n-octyllithium, n-decyllithium, n-dodecyllithium, n-pentadecyllithium and n-eicosyllithium;

aralkyllithiums such as benzyllithium, (2-methylphenyl)methyllithium, (3-methylphenyl)methyllithium, (4-methylphenyl)methyllithium, (2,3-dimethylphenyl)methyllithium, (2,4-dimethylphenyl)methyllithium, (2,5-dimethylphenyl)methyllithium, (2,6-dimethylphenyl)methyllithium, (3,4-dimethylphenyl)methyllithium, (2,3,4-trimethylphenyl)methyllithium, (2,3,5-trimethylphenyl)methyllithium, (2,3,6-trimethylphenyl)methyllithium, (3,4,5-trimethylphenyl)methyllithium, (2,4,6-trimethylphenyl)methyllithium, (2,3,4,5-tetramethylphenyl)methyllithium, (2,3,4,6-tetramethylphenyl)methyllithium, (2,3,5,6-tetramethylphenyl)methyllithium, (pentamethylphenyl)methyllithium, (ethylphenyl)methyllithium, (n-propylphenyl)methyllithium, (isopropylphenyl)methyllithium, (n-butylphenyl)methyllithium, (sec-butylphenyl)methyllithium, (tert-butylphenyl)methyllithium, (n-pentylphenyl)methyllithium, (neopentylphenyl)methyllithium, (n-hexylphenyl)methyllithium, (n-octylphenyl)methyllithium, (n-decylphenyl)methyllithium, (n-dodecylphenyl)methyllithium, (n-tetradecylphenyl)methyllithium, naphthylmethyllithium and anthracenylmethyllithium; and aryllithiums such as phenyllithium, 2-tolyllithium, 3-tolyllithium, 4-tolyllithium, 2,3-xylyllithium, 2,4-xylyllithium, 2,5-xylyllithium, 2,6-xylyllithium, 3,4-xylyllithium, 3,5-xylyllithium, 2,3,4-trimethylphenyllithium, 2,3,5-trimethylphenyllithium, 2,3,6-trimethylphenyllithium, 2,4,6-trimethylphenyllithium, 3,4,5-trimethylphenyllithium, 2,3,4,5-tetramethylphenyllithium, 2,3,4,6-tetramethylphenyllithium, 2,3,5,6-tetramethylphenyllithium, pentamethylphenyllithium, ethylphenyllithium, n-propylphenyllithium, isopropylphenyllithium, n-butylphenyllithium, sec-butylphenyllithium, tert-butylphenyllithium, n-pentylphenyllithium, neopentylphenyllithium, n-hexylphenyllithium, n-octylphenyllithium, n-decylphenyllithium, n-dodecylphenyllithium, n-tetradecylphenyllithium, naphthyllithium and anthracenyllithium. Methyllithium, benzyllithium and phenyllithium are preferable.

Moreover, examples of the alcohol compound used include monools such as methanol, ethanol, n-propanol, isopropanol, n-butanol, sec-butanol, tert-butanol, n-pentanol, neopentyl alcohol, ethylene glycol monomethyl ether, ethylene glycol monoethyl ether, phenol, benzyl alcohol, 1-phenylethanol, and so on.

Examples of the alkaline earth metal compound represented by the general formula (11) include: alkaline earth metal alkoxides derived from monools, such as magnesium dimethoxide, magnesium diethoxide, magnesium di-n-propoxide, magnesium diisopropoxide, magnesium di-n-butoxide, magnesium di-sec-butoxide, magnesium di-tert-butoxide, magnesium di-n-pentoxide, magnesium dineopentoxide, magnesium dimethoxyethoxide, magnesium diethoxyethoxide, magnesium dibenzyloxide, and magnesium di-1-phenylethoxide, and those obtained by changing magnesium in these compounds to calcium, strontium or barium; and alkaline earth metal alkoxides derived from diols, such as magnesium ethylenedioxide, magnesium methylethylenedioxide, magnesium 1,2-dimethylethylenedioxide, magnesium tetramethylethylenedioxide, magnesium phenylethylenedioxide, magnesium 1,2-diphenylethylenedioxide, magnesium tetraphenylethylenedioxide, magnesium cyclopentane-1,2-dioxide, magnesium cyclohexane-1,2-dioxide, magnesium propylene-1,3-dioxide, magnesium 1,3-dimethylpropylene-1,3-dioxide, and magnesium 1,3-diphenylpropylene-1,3-dioxide, and those obtained by arbitrarily changing magnesium in these compounds into calcium, strontium or barium. These compounds encompass all stereoisomers and optical isomers thereof.

A commercially available product or the like can be used as the alkaline earth metal compound (11). Alternatively, the alkaline earth metal compound (11) can also be produced in the system, for use, through the reaction between an alcohol compound and an alkaline earth metal compound.

Examples of such an alkaline earth metal compound used in the production of the alkaline earth alkoxides in the system include Grignard reagents such as methylmagnesium chloride, phenylmagnesium chloride, benzylmagnesium chloride, methylmagnesium bromide, phenylmagnesium bromide and benzylmagnesium bromide. Preferable examples thereof include methylmagnesium chloride and methylmagnesium bromide. Moreover, examples of the alcohol compound used include: monools such as methanol, ethanol, n-propanol, isopropanol, n-butanol, sec-butanol, tert-butanol, n-pentanol, neopentyl alcohol, ethylene glycol monomethyl ether, ethylene glycol monoethyl ether, phenol, benzyl alcohol and 1-phenylethanol; and diols such as ethylene glycol, propylene glycol, 2,3-butanediol, tetramethylethylene glycol, phenylethylene glycol, hydrobenzoin, tetraphenylethylene glycol, cyclopentane-1,2-diol, cyclohexane-1,2-diol, 1,3-propanediol, 2,4-pentanediol, 1,3-diphenyl-1,3-propanediol and tartaric acid. These compounds encompass all stereoisomers and optical isomers thereof.

Examples of the alcohol compound used in the method B include monools such as methanol, ethanol, n-propanol, isopropanol, n-butanol, sec-butanol, tert-butanol, n-pentanol, neopentyl alcohol, ethylene glycol monomethyl ether, ethylene glycol monoethyl ether, phenol, benzyl alcohol and 1-phenylethanol.

Examples of the base include: inorganic bases such as alkali metal hydroxides and alkali metal carbonates; and organic bases such as amine compounds, and preferably include amine compounds. Examples of the amine compounds include, but not particularly limited to: primary amines such as aniline, chloroaniline, bromoaniline, fluoroaniline, toluidine, anisidine, naphthylamine, benzylamine, propylamine, butylamine and pentylamine; secondary amines such as N-methylaniline, N-ethylaniline, diphenylamine, N-methylchloroaniline, N-methylbromoaniline, N-methylfluoroaniline, pyrrolidine, morpholine and piperidine; tertiary amines such as trimethylamine, triethylamine, diisopropylethylamine, N,N-dimethylaniline, N,N-dimethylchloroaniline, N,N-dimethylbromoaniline, N,N-dimethylfluoroaniline, N-methylpyrrolidine, N-methylmorpholine, N-methylpiperidine, 1,4-diazabicyclo[2,2,2]octane, 1,5-diazabicyclo[4,3,0]non-5-ene and 1,8-diazabicyclo[5,4,0]undec-7-ene; and pyridines such as pyridine, N,N-dimethylaminopyridine, picoline and pipecoline.

The reaction process is not particularly limited, and the reaction is preferably performed by reacting the transition metal complex (1-1) with the alkali metal compound (10) (process A-1) or the alkaline earth metal compound (11) (process A-2) or with the alcohol compound in the presence of a base (process B), in the presence of a solvent in an inert atmosphere of nitrogen, argon, or the like.

In process A-1, the amount of the alkali metal compound (10) used with respect to the transition metal complex (1-1) is usually approximately 0.5- to 15-fold by mol, preferably approximately 0.8- to 3-fold by mol.

In the method A-2, the amount of the alkaline earth metal compound (11) used with respect to the transition metal complex (1-1) is usually approximately 0.3- to 10-fold by mol, preferably approximately 0.5- to 2-fold by mol.

In the method B, the amount of the alcohol compound used with respect to the transition metal complex (1-1) is usually approximately 0.5- to 10-fold by mol, preferably approximately 0.8- to 3-fold by mol, and the amount of the base used with respect to the transition metal complex (1-1) is usually approximately 0.5- to 5-fold by mol, preferably approximately 0.8- to 3-fold by mol.

Examples of the solvent that can be used in the reactions include, but not particularly limited to: aliphatic hydrocarbyl solvents such as pentane, hexane, heptane, octane and decane; aromatic hydrocarbyl solvents such as benzene, toluene, xylene and mesitylene; halogenated aliphatic hydrocarbyl solvents such as dichloromethane, chloroform and dichloroethane; halogenated aromatic hydrocarbyl solvents such as monochlorobenzene and dichlorobenzene; ethers such as diethyl ether, dibutyl ether, methyl t-butyl ether and tetrahydrofuran; alcohols correspond to the alkali metal compound (10); and mixtures thereof. The amount thereof used is usually 1- to 200-fold by weight, preferably approximately 3- to 30-fold by weight, with respect to the transition metal complex (1-1) in each of the processes A-1, A-2 and B.

The reaction temperature is usually −100° C. to the boiling point of the solvent, preferably approximately −80 to 30° C.

After the reaction, for example, insoluble solid is removed, and the solvent can be distilled off to obtain the transition metal complex (1-3). The transition metal complex (1-3) can be purified, if necessary, by a usual method such as recrystallization and sublimation.

<Substituted Cyclopentadienes (6-1) to (6-6)>

In the substituted cyclopentadiene compound (6-1), the substituents $R^{28}$, $R^{29}$, $R^{30}$, $R^{31}$, $R^{32}$, $R^{33}$, $R^{34}$, $R^{35}$, $R^{36}$, $R^{37}$ and $R^{38}$ are as defined above.

Examples of the substituted cyclopentadiene compound (6-1) can include the following compounds:

1-(ethylmethylphenylsilyl)-2-methylcyclopentadiene, 1-(ethylmethylphenylsilyl)-3-methylcyclopentadiene, 1-(ethylmethylphenylsilyl)-2,3-dimethylcyclopentadiene, 1-(ethylmethylphenylsilyl)-2,4-dimethylcyclopentadiene, 1-(ethylmethylphenylsilyl)-2,5-dimethylcyclopentadiene, 1-(ethylmethylphenylsilyl)-2,3,5-trimethylcyclopentadiene, 1-(ethylmethylphenylsilyl)-2,3,4,5-tetramethylcyclopentadiene, 1-(ethylmethylphenylsilyl)-2-ethylcyclopentadiene, 1-(ethylmethylphenylsilyl)-2-n-propylcyclopentadiene, 1-(ethylmethylphenylsilyl)-2-isopropylcyclopentadiene, 1-(ethylmethylphenylsilyl)-2-n-butylcyclopentadiene, 1-(ethylmethylphenylsilyl)-2-tert-butylcyclopentadiene, 1-(ethylmethylphenylsilyl)-2-phenylcyclopentadiene, 1-(ethylmethylphenylsilyl)-2-benzylcyclopentadiene, 1-(diethylphenylsilyl)-2-methylcyclopentadiene, 1-(diethylphenylsilyl)-3-methylcyclopentadiene, 1-(diethylphenylsilyl)-2,3-dimethylcyclopentadiene, 1-(diethylphenylsilyl)-2,4-dimethylcyclopentadiene, 1-(diethylphenylsilyl)-2,5-dimethylcyclopentadiene, 1-(diethylphenylsilyl)-2,3,5-trimethylcyclopentadiene, 1-(diethylphenylsilyl)-2,3,4,5-tetramethylcyclopentadiene, 1-(diethylphenylsilyl)-2-ethylcyclopentadiene, 1-(diethylphenylsilyl)-2-n-propylcyclopentadiene, 1-(diethylphenyl silyl)-2-isopropylcyclopentadiene, 1-(diethylphenylsilyl)-2-n-butylcyclopentadiene, 1-(diethylphenylsilyl)-2-tert-butylcyclopentadiene, 1-(diethylphenylsilyl)-2-phenylcyclopentadiene, 1-(diethylphenylsilyl)-2-benzylcyclopentadiene, 1-(n-butylmethylphenylsilyl)-2-methylcyclopentadiene, 1-(n-butylmethylphenylsilyl)-3-methylcyclopentadiene, 1-(n-butylmethylphenylsilyl)-2,3-dimethylcyclopentadiene, 1-(n-butylmethylphenylsilyl)-2,4-dimethylcyclopentadiene, 1-(n-butylmethylphenylsilyl)-2,5-dimethylcyclopentadiene, 1-(n-butylmethylphenylsilyl)-2,3,5-trimethylcyclopentadiene, 1-(n-butylmethylphenylsilyl)-2,3,4,5-tetramethylcyclopentadiene, 1-(n-butylmethylphenylsilyl)-2-ethylcyclopentadiene, 1-(n-butylmethylphenylsilyl)-2-n-propylcyclopentadiene, 1-(n-butylmethylphenylsilyl)-2-isopropylcyclopentadiene, 1-(n-butylmethylphenyl silyl)-2-n-butylcyclopentadiene, 1-(n-butylmethylphenylsilyl)-2-tert-butylcyclopentadiene, 1-(n-butylmethylphenylsilyl)-2-phenylcyclopentadiene, 1-(n-butylmethylphenylsilyl)-2-benzylcyclopentadiene, 1-(cyclohexylmethylphenylsilyl)-2-methylcyclopentadiene, 1-(cyclohexylmethylphenylsilyl)-3-methylcyclopentadiene, 1-(cyclohexylmethylphenylsilyl)-2,3-dimethylcyclopentadiene, 1-(cyclohexylmethylphenylsilyl)-2,4-dimethylcyclopentadiene, 1-(cyclohexylmethylphenylsilyl)-2,5-dimethylcyclopentadiene, 1-(cyclohexylmethylphenylsilyl)-2,3,5-trimethylcyclopentadiene, 1-(cyclohexylmethylphenylsilyl)-2,3,4,5-tetramethylcyclopentadiene, 1-(cyclohexylmethylphenylsilyl)-2-ethylcyclopentadiene, 1-(cyclohexylmethylphenylsilyl)-2-n-propylcyclopentadiene, 1-(cyclohexylmethylphenylsilyl)-2-isopropylcyclopentadiene, 1-(cyclohexylmethylphenylsilyl)-2-n-butylcyclopentadiene, 1-(cyclohexylmethylphenylsilyl)-2-tert-butylcyclopentadiene, 1-(cyclohexylmethylphenylsilyl)-2-phenylcyclopentadiene, 1-(cyclohexylmethylphenylsilyl)-2-benzylcyclopentadiene, 1-(methyl(n-octadecyl)phenylsilyl)-2-methylcyclopentadiene, 1-(methyl(n-octadecyl)phenylsilyl)-3-methylcyclopentadiene, 1-(methyl(n-octadecyl)phenylsilyl)-2,3-dimethylcyclopentadiene, 1-(methyl(n-octadecyl)phenylsilyl)-2,4-dimethylcyclopentadiene, 1-(methyl(n-octadecyl)phenylsilyl)-2,5-dimethylcyclopentadiene, 1-(methyl(n-octadecyl)phenylsilyl)-2,3,5-trimethylcyclopentadiene, 1-(methyl(n-octadecyl)phenylsilyl)-2,3,4,5-tetramethylcyclopentadiene, 1-(methyl(n-octadecyl)phenylsilyl)-2-ethylcyclopentadiene, 1-(methyl(n-octadecyl)phenylsilyl)-2-n-propylcyclopentadiene, 1-(methyl(n-octadecyl)phenylsilyl)-2-isopropylcyclopentadiene, 1-(methyl(n-octadecyl)phenylsilyl)-2-n-butylcyclopentadiene, 1-(methyl(n-octadecyl)phenylsilyl)-2-tert-butylcyclopentadiene, 1-(methyl(n-octadecyl)phenylsilyl)-2-phenylcyclopentadiene, 1-(methyl(n-octadecyl)phenylsilyl)-2-benzylcyclopentadiene, 1-(benzyldiphenylsilyl)-2-methylcyclopentadiene, 1-(benzyldiphenylsilyl)-3-methylcyclopentadiene, 1-(benzyldiphenylsilyl)-2,3-dimethylcyclopentadiene, 1-(benzyldiphenylsilyl)-2,4-dimethylcyclopentadiene, 1-(benzyldiphenylsilyl)-2,5-dimethylcyclopentadiene, 1-(benzyldiphenylsilyl)-2,3,5-trimethylcyclopentadiene, 1-(benzyldiphenylsilyl)-2,3,4,5-tetramethylcyclopentadiene, 1-(benzyldiphenylsilyl)-2-ethylcyclopentadiene, 1-(benzyldiphenylsilyl)-2-n-propylcyclopentadiene, 1-(benzyldiphenylsilyl)-2-isopropylcyclopentadiene, 1-(benzyldiphenylsilyl)-2-n-butylcyclopentadiene, 1-(benzyldiphenylsilyl)-2-tert-butylcyclopentadiene, 1-(benzyldiphenylsilyl)-2-phenylcyclopentadiene and 1-(benzyldiphenylsilyl)-2-benzylcyclopentadiene.

The substituted cyclopentadiene compounds exemplified above may have isomers differing in the double bond position of the cyclopentadiene ring. A mixture of these isomers may also be used in the present invention.

In the substituted cyclopentadiene compound (6-2), the substituents $R^{39}$, $R^{40}$, $R^{41}$, $R^{42}$, $R^{43}$, $R^{44}$, $R^{45}$, $R^{46}$, $R^{47}$, $R^{48}$ and $R^{49}$ are as defined above.

Examples of the substituted cyclopentadiene compound (6-2) can include the following compounds:

1-triphenylsilyl-2-methylcyclopentadiene, 1-triphenylsilyl-3-methylcyclopentadiene, 1-triphenylsilyl-2,3-dimethylcyclopentadiene, 1-triphenylsilyl-2,4-dimethylcyclopentadiene, 1-triphenylsilyl-2,5-dimethylcyclopentadiene, 1-triphenylsilyl-2,3,5-trimethylcyclopentadiene, 1-triphenylsilyl-2,3,4,5-tetramethylcyclopentadiene, 1-triphenylsilyl-2-ethylcyclopentadiene, 1-triphenylsilyl-2-n-propylcyclopentadiene, 1-triphenylsilyl-2-isopropylcyclopentadiene, 1-triphenyl silyl-2-n-butylcyclopentadiene, 1-triphenylsilyl-2-tert-butylcyclopentadiene, 1-triphenyl silyl-2-phenylcyclopentadiene, 1-triphenylsilyl-2-benzylcyclopentadiene, 1-(3-methylphenyl)diphenylsilyl-2-methylcyclopentadiene, 1-(3-methylphenyl)diphenylsilyl-3-methylcyclopentadiene, 1-(3-methylphenyl)diphenylsilyl-2,3-dimethylcyclopentadiene, 1-(3-methylphenyl)diphenylsilyl-2,4-dimethylcyclopentadiene, 1-(3-methylphenyl)diphenylsilyl-2,5-dimethylcyclopentadiene, 1-(3-methylphenyl)diphenylsilyl-2,3,5-trimethylcyclopentadiene, 1-(3-methylphenyl)diphenylsilyl-2,3,4,5-tetramethylcyclopentadiene, 1-(3-methylphenyl)diphenylsilyl-2-ethylcyclopentadiene, 1-(3-methylphenyl)diphenylsilyl-2-n-propylcyclopentadiene, 1-(3-methylphenyl)diphenylsilyl-2-isopropylcyclopentadiene, 1-(3-methylphenyl)diphenylsilyl-2-n-butylcyclopentadiene, 1-(3-methylphenyl)diphenylsilyl-2-tert-butylcyclopentadiene, 1-(3-methylphenyl)diphenylsilyl-2-phenylcyclopentadiene, 1-(3-methylphenyl)diphenylsilyl-2-benzylcyclopentadiene, 1-(4-methylphenyl)diphenylsilyl-2-methylcyclopentadiene, 1-(4-methylphenyl)diphenylsilyl-3-methylcyclopentadiene, 1-(4-methylphenyl)diphenylsilyl-2,3-dimethylcyclopentadiene, 1-(4-methylphenyl)diphenylsilyl-2,4-dimethylcyclopentadiene, 1-(4-methylphenyl)diphenylsilyl-2,5-dimethylcyclopentadiene, 1-(4-methylphenyl)diphenylsilyl-2,3,5-trimethylcyclopentadiene, 1-(4-methylphenyl)diphenylsilyl-2,3,4,5-tetramethylcyclopentadiene, 1-(4-methylphenyl)diphenylsilyl-2-ethylcyclopentadiene, 1-(4-methylphenyl)diphenylsilyl-2-n-propylcyclopentadiene, 1-(4-methylphenyl)diphenylsilyl-2-isopropylcyclopentadiene, 1-(4-methylphenyl)diphenylsilyl-2-n-butylcyclopentadiene, 1-(4-methylphenyl)diphenylsilyl-2-tert-butylcyclopentadiene, 1-(4-methylphenyl)diphenylsilyl-2-phenylcyclopentadiene, 1-(4-methylphenyl)diphenylsilyl-2-benzylcyclopentadiene, 1-(3,5-dimethylphenyl)diphenylsilyl-2-methylcyclopentadiene, 1-(3,5-dimethylphenyl)diphenylsilyl-3-methylcyclopentadiene, 1-(3,5-dimethylphenyl)diphenylsilyl-2,3-dimethylcyclopentadiene, 1-(3,5-dimethylphenyl)diphenylsilyl-2,4-dimethylcyclopentadiene, 1-(3,5-dimethylphenyl)diphenylsilyl-2,5-dimethylcyclopentadiene, 1-(3,5-dimethylphenyl)diphenylsilyl-2,3,5-trimethylcyclopentadiene, 1-(3,5-dimethylphenyl)diphenylsilyl-2,3,4,5-tetramethylcyclopentadiene, 1-(3,5-dimethylphenyl)diphenylsilyl-2-ethylcyclopentadiene, 1-(3,5-dimethylphenyl)diphenylsilyl-2-n-propylcyclopentadiene, 1-(3,5-dimethylphenyl)diphenylsilyl-2-isopropylcyclopentadiene, 1-(3,5-dimethylphenyl)diphenylsilyl-2-n-butylcyclopentadiene, 1-(3,5-dimethylphenyl)diphenylsilyl-2-tert-butylcyclopentadiene, 1-(3,5-dimethylphenyl)diphenylsilyl-2-phenylcyclopentadiene, 1-(3,5-dimethylphenyl)diphenylsilyl-2-benzylcyclopentadiene, 1-bis(3,5-dimethylphenyl)phenylsilyl-2-methylcyclopentadiene, 1-bis(3,5-dimethylphenyl)phenylsilyl-3-methylcyclopentadiene, 1-bis(3,5-dimethylphenyl)phenylsilyl-2,3-dimethylcyclopentadiene, 1-bis(3,5-dimethylphenyl)phenylsilyl-2,4-dimethylcyclopentadiene, 1-bis(3,5-dimethylphenyl)phenylsilyl-2,5-dimethylcyclopentadiene, 1-bis(3,5-dimethylphenyl)phenylsilyl-2,3,5-trimethylcyclopentadiene, 1-bis(3,5-dimethylphenyl)phenylsilyl-2,3,4,5-tetramethylcyclopentadiene, 1-bis(3,5-dimethylphenyl)phenylsilyl-2-ethylcyclopentadiene, 1-bis(3,5-dimethylphenyl)phenylsilyl-2-n-propylcyclopentadiene, 1-bis(3,5-dimethylphenyl)phenylsilyl-2-isopropylcyclopentadiene, 1-bis(3,5-dimethylphenyl)phenylsilyl-2-n-butylcyclopentadiene, 1-bis(3,5-dimethylphenyl)phenylsilyl-2-tert-butylcyclopentadiene, 1-bis(3,5-dimethylphenyl)phenylsilyl-2-phenylcyclopentadiene, 1-bis(3,5-dimethylphenyl)phenylsilyl-2-benzylcyclopentadiene, 1-tris(3,5-dimethylphenyl)silyl-2-methylcyclopentadiene, 1-tris(3,5-dimethylphenyl)silyl-3-methylcyclopentadiene, 1-tris(3,5-dimethylphenyl)silyl-2,3-dimethylcyclopentadiene, 1-tris(3,5-dimethylphenyl)silyl-2,4-dimethylcyclopentadiene, 1-tris(3,5-dimethylphenyl)silyl-2,5-dimethylcyclopentadiene, 1-tris(3,5-dimethylphenyl)silyl-2,3,5-trimethylcyclopentadiene, 1-tris(3,5-dimethylphenyl)silyl-2,3,4,5-tetramethylcyclopentadiene, 1-tris(3,5-dimethylphenyl)silyl-2-ethylcyclopentadiene, 1-tris(3,5-dimethylphenyl)silyl-2-n-propylcyclopentadiene, 1-tris(3,5-dimethylphenyl)silyl-2-isopropylcyclopentadiene, 1-tris(3,5-dimethylphenyl)silyl-2-n-butylcyclopentadiene, 1-tris(3,5-dimethylphenyl)silyl-2-tert-butylcyclopentadiene, 1-tris(3,5-dimethylphenyl)silyl-2-phenylcyclopentadiene, 1-tris(3,5-dimethylphenyl)silyl-2-benzylcyclopentadiene, 1-(4-n-butylphenyl)diphenylsilyl-2-methylcyclopentadiene, 1-(4-n-butylphenyl)diphenylsilyl-3-methylcyclopentadiene, 1-(4-n-butylphenyl)diphenylsilyl-2,3-dimethylcyclopentadiene, 1-(4-n-butylphenyl)diphenylsilyl-2,4-dimethylcyclopentadiene, 1-(4-n-butylphenyl)diphenylsilyl-2,5-dimethylcyclopentadiene, 1-(4-n-butylphenyl)diphenylsilyl-2,3,5-trimethylcyclopentadiene, 1-(4-n-butylphenyl)diphenylsilyl-2,3,4,5-tetramethylcyclopentadiene, 1-(4-n-butylphenyl)diphenylsilyl-2-ethylcyclopentadiene, 1-(4-n-butylphenyl)diphenylsilyl-2-n-propylcyclopentadiene, 1-(4-n-butylphenyl)diphenylsilyl-2-isopropylcyclopentadiene, 1-(4-n-butylphenyl)diphenylsilyl-2-n-butylcyclopentadiene, 1-(4-n-butylphenyl)diphenylsilyl-2-tert-butylcyclopentadiene, 1-(4-n-butylphenyl)diphenylsilyl-2-phenylcyclopentadiene, 1-(4-n-butylphenyl)diphenylsilyl-2-benzylcyclopentadiene, 1-di(4-n-butylphenyl)phenylsilyl-2-methylcyclopentadiene, 1-di(4-n-butylphenyl)phenylsilyl-3-methylcyclopentadiene, 1-di(4-n-butylphenyl)phenylsilyl-2,3-dimethylcyclopentadiene, 1-di(4-n-butylphenyl)phenylsilyl-2,4-dimethylcyclopentadiene, 1-di(4-n-butylphenyl)phenylsilyl-2,5-dimethylcyclopentadiene, 1-di(4-n-butylphenyl)phenylsilyl-2,3,5-trimethylcyclopentadiene, 1-di(4-n-butylphenyl)phenylsilyl-2,3,4,5-tetramethylcyclopentadiene, 1-di(4-n-butylphenyl)phenylsilyl-2-ethylcyclopentadiene, 1-di(4-n-butylphenyl)phenylsilyl-2-n-propylcyclopentadiene, 1-di(4-n-butylphenyl)phenylsilyl-2-isopropylcyclopentadiene, 1-di(4-n-butylphenyl)phenylsilyl-2-n-butylcyclopentadiene, 1-di(4-n-butylphenyl)phenylsilyl-2-tert-butylcyclopentadiene, 1-di(4-n-butylphenyl)phenylsilyl-2-phenylcyclopentadiene, 1-di(4-n-butylphenyl)phenylsilyl-2-benzylcyclopentadiene, 1-tri(4-n-butylphenyl)silyl-2-methylcyclopentadiene, 1-tri(4-n-butylphenyl)silyl-3-methylcyclopentadiene, 1-tri(4-n-butylphenyl)silyl-2,3-dimethylcyclopentadiene, 1-tri(4-n-butylphenyl)silyl-2,4-dimethylcyclopentadiene, 1-tri(4-n-butylphenyl)silyl-2,5-dimethylcyclopentadiene, 1-tri(4-n-butylphenyl)silyl-2,3,5-trimethylcyclopentadiene, 1-tri(4-n-butylphenyl)silyl-2,3,4,5-tetramethylcyclopentadiene, 1-tri(4-n-butylphenyl)silyl-2-ethylcyclopentadiene, 1-tri(4-n-butylphenyl)silyl-2-n-propylcyclopentadiene, 1-tri(4-n-butylphenyl)silyl-2-isopropylcyclopentadiene, 1-tri(4-n-butylphenyl)silyl-2-n-butylcyclopentadiene, 1-tri(4-n-butylphenyl)silyl-2-tert-butylcyclopentadiene, 1-tri(4-n-butylphenyl)silyl-2-phenylcyclopentadiene and 1-tri(4-n-butylphenyl)silyl-2-benzylcyclopentadiene.

The substituted cyclopentadiene compounds exemplified above may have isomers differing in the double bond position of the cyclopentadiene ring. A mixture of these isomers may also be used in the present invention.

In the substituted cyclopentadiene compound (6-3), the substituents $R^{50}$, $R^{51}$, $R^{52}$, $R^{53}$, $R^{54}$, $R^{55}$, $R^{56}$, $R^{57}$, $R^{58}$, $R^{59}$ and $R^{60}$ are as defined above.

Examples of the substituted cyclopentadiene compound (6-3) can include the following compounds:
1-dimethylphenylsilyl-tetrahydroindene, 1-dimethylphenylsilyl-2-methyltetrahydroindene, 1-dimethylphenylsilyl-3-methyltetrahydroindene, 9-dimethylphenylsilyl-octahydrofluorene, 1-ethylmethylphenylsilyl-tetrahydroindene, 1-ethylmethylphenyl silyl-2-methyltetrahydroindene, 1-ethylmethylphenylsilyl-3-methyltetrahydroindene, 9-ethylmethylphenylsilyl-octahydrofluorene, 1-diethylphenylsilyl-tetrahydroindene, 1-diethylphenylsilyl-2-methyltetrahydroindene, 1-diethylphenyl silyl-3-methyltetrahydroindene, 9-diethylphenylsilyl-octahydrofluorene, 1-n-butylmethylphenylsilyl-tetrahydroindene, 1-n-butylmethylphenylsilyl-2-methyltetrahydroindene, 1-n-butylmethylphenylsilyl-3-methyltetrahydroindene, 9-n-butylmethylphenylsilyl-octahydrofluorene, 1-cyclohexylmethylphenylsilyl-tetrahydroindene, 1-cyclohexylmethylphenylsilyl-2-methyltetrahydroindene, 1-cyclohexylmethylphenylsilyl-3-methyltetrahydroindene, 9-cyclohexylmethylphenylsilyl-octahydrofluorene, 1-methyldiphenylsilyl-tetrahydroindene, 1-methyldiphenylsilyl-2-methyltetrahydroindene, 1-methyldiphenylsilyl-3-methyltetrahydroindene, 9-methyldiphenylsilyl-octahydrofluorene, 1-triphenylsilyl-tetrahydroindene, 1-triphenylsilyl-2-methyltetrahydroindene, 1-triphenylsilyl-3-methyltetrahydroindene and 9-triphenylsilyl-octahydrofluorene.

The substituted cyclopentadiene compounds exemplified above may have isomers differing in the double bond position of the cyclopentadiene ring. A mixture of these isomers may also be used in the present invention.

In the substituted cyclopentadiene compound (6-4), the substituents $R^{61}$, $R^{62}$, $R^{63}$, $R^{64}$, $R^{65}$, $R^{66}$, $R^{67}$, $R^{68}$, $R^{69}$, $R^{70}$ and $R^{71}$ are as defined above.

Examples of the substituted cyclopentadiene compound (6-4) can include the following compounds:
1-dimethyl(4-methylphenyl)silyl-2-methylcyclopentadiene, 1-dimethyl(4-methylphenyl)silyl-3-methylcyclopentadiene, 1-dimethyl(4-methylphenyl)silyl-2,3-dimethylcyclopentadiene, 1-dimethyl(4-methylphenyl)silyl-2,4-dimethylcyclopentadiene, 1-dimethyl(4-methylphenyl)silyl-2, 5-dimethylcyclopentadiene, 1-dimethyl(4-methylphenyl)silyl-2,3,5-trimethylcyclopentadiene, 1-dimethyl(4-methylphenyl)silyl-2,3,4,5-tetramethylcyclopentadiene, 1-dimethyl(4-methylphenyl)silyl-2-ethylcyclopentadiene, 1-dimethyl(4-methylphenyl)silyl-2-n-propylcyclopentadiene, 1-dimethyl(4-methylphenyl)silyl-2-isopropylcyclopentadiene, 1-dimethyl(4-methylphenyl)silyl-2-n-butylcyclopentadiene, 1-dimethyl(4-methylphenyl)silyl-2-tert-butylcyclopentadiene, 1-dimethyl(4-methylphenyl)silyl-2-phenylcyclopentadiene, 1-dimethyl(4-methylphenyl)silyl-2-benzylcyclopentadiene, 1-dimethyl(3,5-dimethylphenyl)silyl-2-methylcyclopentadiene, 1-dimethyl(3,5-dimethylphenyl)silyl-3-methylcyclopentadiene, 1-dimethyl(3,5-dimethylphenyl)silyl-2,3-dimethylcyclopentadiene, 1-dimethyl(3,5-dimethylphenyl)silyl-2,4-dimethylcyclopentadiene, 1-dimethyl(3,5-dimethylphenyl)silyl-2,5-dimethylcyclopentadiene, 1-dimethyl(3,5-dimethylphenyl)silyl-2,3,5-trimethylcyclopentadiene, 1-dimethyl(3,5-dimethylphenyl)silyl-2,3,4,5-tetramethylcyclopentadiene, 1-dimethyl(3,5-dimethylphenyl)silyl-2-ethylcyclopentadiene, 1-dimethyl(3,5-dimethylphenyl)silyl-2-n-propylcyclopentadiene, 1-dimethyl(3,5-dimethylphenyl)silyl-2-isopropylcyclopentadiene, 1-dimethyl(3,5-dimethylphenyl)silyl-2-n-butylcyclopentadiene, 1-dimethyl(3,5-dimethylphenyl)silyl-2-tert-butylcyclopentadiene, 1-dimethyl(3,5-dimethylphenyl)silyl-2-phenylcyclopentadiene, 1-dimethyl(3,5-dimethylphenyl)silyl-2-benzylcyclopentadiene, 1-dimethyl(2,4,6-trimethylphenyl)silyl-2-methylcyclopentadiene, 1-dimethyl(2,4,6-trimethylphenyl)silyl-3-methylcyclopentadiene, 1-dimethyl(2,4,6-trimethylphenyl)silyl-2,3-dimethylcyclopentadiene, 1-dimethyl(2,4,6-trimethylphenyl)silyl-2,4-dimethylcyclopentadiene, 1-dimethyl(2,4,6-trimethylphenyl)silyl-2, 5-dimethylcyclopentadiene, 1-dimethyl(2,4,6-trimethylphenyl)silyl-2,3,5-trimethylcyclopentadiene, 1-dimethyl(2,4,6-trimethylphenyl)silyl-2,3,4,5-tetramethylcyclopentadiene, 1-dimethyl(2,4,6-trimethylphenyl)silyl-2-ethylcyclopentadiene, 1-dimethyl(2,4,6-trimethylphenyl)silyl-2-n-propylcyclopentadiene, 1-dimethyl(2,4,6-trimethylphenyl)silyl-2-isopropylcyclopentadiene, 1-dimethyl(2,4,6-trimethylphenyl)silyl-2-n-butylcyclopentadiene, 1-dimethyl(2,4,6-trimethylphenyl)silyl-2-tert-butylcyclopentadiene, 1-dimethyl(2,4,6-trimethylphenyl)silyl-2-phenylcyclopentadiene, 1-dimethyl(2,4,6-trimethylphenyl)silyl-2-benzylcyclopentadiene, 1-dimethyl(4-methoxyphenyl)silyl-2-methylcyclopentadiene, 1-dimethyl(4-methoxyphenyl)silyl-3-methylcyclopentadiene, 1-dimethyl(4-methoxyphenyl)silyl-2,3-dimethylcyclopentadiene, 1-dimethyl(4-methoxyphenyl)silyl-2,4-dimethylcyclopentadiene, 1-dimethyl(4-methoxyphenyl)silyl-2,5-dimethylcyclopentadiene, 1-dimethyl(4-methoxyphenyl)silyl-2,3,5-trimethylcyclopentadiene, 1-dimethyl(4-methoxyphenyl)silyl-2,3,4,5-tetramethylcyclopentadiene, 1-dimethyl(4-methoxyphenyl)silyl-2-ethylcyclopentadiene, 1-dimethyl(4-methoxyphenyl)silyl-2-n-propylcyclopentadiene, 1-dimethyl(4-methoxyphenyl)silyl- 2-isopropylcyclopentadiene, 1-dimethyl(4-methoxyphenyl)silyl-2-n-butylcyclopentadiene, 1-dimethyl(4-methoxyphenyl)silyl-2-tert-butylcyclopentadiene, 1-dimethyl(4-methoxyphenyl)silyl-2-phenylcyclopentadiene, 1-dimethyl(4-methoxyphenyl)silyl-2-benzylcyclopentadiene, 1-(3,5-bis(trifluoromethyl)phenyl)dimethylsilyl-2-methylcyclopentadiene, 1-(3,5-bis(trifluoromethyl)phenyl)dimethylsilyl-3-methylcyclopentadiene, 1-(3,5-bis(trifluoromethyl)phenyl)dimethylsilyl-2,3-dimethylcyclopentadiene, 1-(3,5-bis(trifluoromethyl)phenyl)dimethylsilyl-2,4-dimethylcyclopentadiene, 1-(3,5-bis(trifluoromethyl)phenyl)dimethylsilyl-2,5-dimethylcyclopentadiene, 1-(3,5-bis(trifluoromethyl)phenyl)dimethylsilyl-2,3,5-trimethylcyclopentadiene, 1-(3,5-bis(trifluoromethyl)phenyl)dimethylsilyl-2,3,4,5-tetramethylcyclopentadiene, 1-(3,5-bis(trifluoromethyl)phenyl)dimethylsilyl-2-ethylcyclopentadiene, 1-(3,5-bis(trifluoromethyl)phenyl)dimethylsilyl-2-n-propylcyclopentadiene, 1-(3,5-bis(trifluoromethyl)phenyl)dimethylsilyl-2-isopropylcyclopentadiene, 1-(3,5-bis(trifluoromethyl)phenyl)dimethylsilyl-2-n-butylcyclopentadiene, 1-(3,5-bis(trifluoromethyl)phenyl)dimethylsilyl-2-tert-butylcyclopentadiene, 1-(3,5-bis(trifluoromethyl)phenyl)dimethylsilyl-2-phenylcyclopentadiene, 1-(3,5-bis(trifluoromethyl)phenyl)dimethylsilyl-2-benzylcyclopentadiene, 1-(9-anthryl)dimethylsilyl-2-methylcyclopentadiene, 1-(9-anthryl)dimethylsilyl-3-methylcyclopentadiene, 1-(9-anthryl)dimethylsilyl-2,3-dimethylcyclopentadiene, 1-(9-anthryl)dimethylsilyl-2,4-dimethylcyclopentadiene, 1-(9-anthryl)dimethylsilyl-2,5-dimethylcyclopentadiene, 1-(9-anthryl)dimethylsilyl-2,3,5-trimethylcyclopentadiene, 1-(9-anthryl)dimethylsilyl-2,3,4,5-tetramethylcyclopentadiene, 1-(9-anthryl)dimethylsilyl-2-ethylcyclopentadiene, 1-(9-anthryl)dimethylsilyl-2-n-propylcyclopentadiene, 1-(9-anthryl)dimethylsilyl-2-isopropylcyclopentadiene, 1-(9-anthryl)dimethylsilyl-2-n-butylcyclopentadiene, 1-(9-anthryl)dimethylsilyl-2-tert-butylcyclopentadiene, 1-(9-anthryl)dimethylsilyl-2-phenylcyclopentadiene and 1-(9-anthryl)dimethylsilyl-2-benzylcyclopentadiene.

The substituted cyclopentadiene compounds exemplified above may have isomers differing in the double bond position of the cyclopentadiene ring. A mixture of these isomers may also be used in the present invention.

In the substituted cyclopentadiene compound (6-5), the substituents $R^{72}$, $R^{73}$, $R^{74}$, $R^{75}$, $R^{76}$, $R^{77}$, $R^{78}$, $R^{79}$, $R^{80}$, $R^{81}$ and $R^{82}$ are as defined above.

Examples of the substituted cyclopentadiene compound (6-5) can include the following compounds:

1-methyl(4-methylphenyl)phenylsilyl-2-methylcyclopentadiene, 1-methyl(4-methylphenyl)phenylsilyl-3-methylcyclopentadiene, 1-methyl(4-methylphenyl)phenylsilyl-2,3-dimethylcyclopentadiene, 1-methyl(4-methylphenyl)phenylsilyl-2,4-dimethylcyclopentadiene, 1-methyl(4-methylphenyl)phenylsilyl-2,5-dimethylcyclopentadiene, 1-methyl(4-methylphenyl)phenylsilyl-2,3,5-trimethylcyclopentadiene, 1-methyl(4-methylphenyl)phenylsilyl-2,3,4,5-tetramethylcyclopentadiene, 1-methyl(4-methylphenyl)phenylsilyl-2-ethylcyclopentadiene, 1-methyl(4-methylphenyl)phenylsilyl-2-n-propylcyclopentadiene, 1-methyl(4-methylphenyl)phenylsilyl-2-isopropylcyclopentadiene, 1-methyl(4-methylphenyl)phenylsilyl-2-n-butylcyclopentadiene, 1-methyl(4-methylphenyl)phenylsilyl-2-tert-butylcyclopentadiene, 1-methyl(4-methylphenyl)phenylsilyl-2-phenylcyclopentadiene, 1-methyl(4-methylphenyl)phenylsilyl-2-benzylcyclopentadiene, 1-(4-n-butylphenyl)methylphenylsilyl-2-methylcyclopentadiene, 1-(4-n-butylphenyl)methylphenylsilyl-3-methylcyclopentadiene, 1-(4-n-butylphenyl)methylphenylsilyl-2,3-dimethylcyclopentadiene, 1-(4-n-butylphenyl)methylphenylsilyl-2,4-dimethylcyclopentadiene, 1-(4-n-butylphenyl)methylphenylsilyl-2,5-dimethylcyclopentadiene, 1-(4-n-butylphenyl)methylphenylsilyl-2,3,5-trimethylcyclopentadiene, 1-(4-n-butylphenyl)methylphenylsilyl-2,3,4,5-tetramethylcyclopentadiene, 1-(4-n-butylphenyl)methylphenylsilyl-2-ethylcyclopentadiene, 1-(4-n-butylphenyl)methylphenylsilyl-2-n-propylcyclopentadiene, 1-(4-n-butylphenyl)methylphenylsilyl-2-isopropylcyclopentadiene, 1-(4-n-butylphenyl)methylphenylsilyl-2-n-butylcyclopentadiene, 1-(4-n-butylphenyl)methylphenylsilyl-2-tert-butylcyclopentadiene, 1-(4-n-butylphenyl)methylphenylsilyl-2-phenylcyclopentadiene, 1-(4-n-butylphenyl)methylphenylsilyl-2-benzylcyclopentadiene, 1-di(4-n-butylphenyl)methylsilyl-2-methylcyclopentadiene, 1-di(4-n-butylphenyl)methylsilyl-3-methylcyclopentadiene, 1-di(4-n-butylphenyl)methylsilyl-2,3-dimethylcyclopentadiene, 1-di(4-n-butylphenyl)methylsilyl-2,4-dimethylcyclopentadiene, 1-di(4-n-butylphenyl)methylsilyl-2,5-dimethylcyclopentadiene, 1-di(4-n-butylphenyl)methylsilyl-2,3,5-trimethylcyclopentadiene, 1-di(4-n-butylphenyl)methylsilyl-2,3,4,5-tetramethylcyclopentadiene, 1-di(4-n-butylphenyl)methylsilyl-2-ethylcyclopentadiene, 1-di(4-n-butylphenyl)methylsilyl-2-n-propylcyclopentadiene, 1-di(4-n-butylphenyl)methylsilyl-2-isopropylcyclopentadiene, 1-di(4-n-butylphenyl)methylsilyl-2-n-butylcyclopentadiene, 1-di(4-n-butylphenyl)methylsilyl-2-tert-butylcyclopentadiene, 1-di(4-n-butylphenyl)methylsilyl-2-phenylcyclopentadiene, 1-di(4-n-butylphenyl)methylsilyl-2-benzylcyclopentadiene, 1-methyl(3,5-dimethylphenyl)phenylsilyl-2-methylcyclopentadiene, 1-methyl(3,5-dimethylphenyl)phenylsilyl-3-methylcyclopentadiene, 1-methyl(3,5-dimethylphenyl)phenylsilyl-2,3-dimethylcyclopentadiene, 1-methyl(3,5-dimethylphenyl)phenylsilyl-2,4-dimethylcyclopentadiene, 1-methyl(3,5-dimethylphenyl)phenylsilyl-2,5-dimethylcyclopentadiene, 1-methyl(3,5-dimethylphenyl)phenylsilyl-2,3,5-trimethylcyclopentadiene, 1-methyl(3,5-dimethylphenyl)phenylsilyl-2,3,4,5-tetramethylcyclopentadiene, 1-methyl(3,5-dimethylphenyl)phenylsilyl-2-ethylcyclopentadiene, 1-methyl(3,5-dimethylphenyl)phenylsilyl-2-n-propylcyclopentadiene, 1-methyl(3,5-dimethylphenyl)phenylsilyl-2-isopropylcyclopentadiene, 1-methyl(3,5-dimethylphenyl)phenylsilyl-2-n-butylcyclopentadiene, 1-methyl(3,5-dimethylphenyl)phenylsilyl-2-tert-butylcyclopentadiene, 1-methyl(3,5-dimethylphenyl)phenylsilyl-2-phenylcyclopentadiene, 1-methyl(3,5-dimethylphenyl)phenylsilyl-2-benzylcyclopentadiene, 1-methylbis(3,5-dimethylphenyl)silyl-2-methylcyclopentadiene, 1-methylbis(3,5-dimethylphenyl)silyl-3-methylcyclopentadiene, 1-methylbis(3,5-dimethylphenyl)silyl-2,3-dimethylcyclopentadiene, 1-methylbis(3,5-dimethylphenyl)silyl-2,4-dimethylcyclopentadiene, 1-methylbis(3,5-dimethylphenyl)silyl-2,5-dimethylcyclopentadiene, 1-methylbis(3,5-dimethylphenyl)silyl-2,3,5-trimethylcyclopentadiene, 1-methylbis(3,5-dimethylphenyl)silyl-2,3,4,5-tetramethylcyclopentadiene, 1-methylbis(3,5-dimethylphenyl)silyl-2-ethylcyclopentadiene, 1-methylbis(3,5-dimethylphenyl)silyl-2-n-propylcyclopentadiene, 1-methylbis(3,5-dimethylphenyl)silyl-2-isopropylcyclopentadiene, 1-methylbis(3,5-dimethylphenyl)silyl-2-n-butylcyclopentadiene, 1-methylbis(3,5-dimethylphenyl)silyl-2-tert-butylcyclopentadiene, 1-methylbis(3,5-dimethylphenyl)

silyl-2-phenylcyclopentadiene and 1-methylbis(3,5-dimethylphenyl)silyl-2-benzylcyclopentadiene.

The substituted cyclopentadiene compounds exemplified above may have isomers differing in the double bond position of the cyclopentadiene ring. A mixture of these isomers may also be used in the present invention.

In the substituted cyclopentadiene compound (6-6), the substituents $R^{83}$, $R^{84}$, $R^{85}$, $R^{86}$, $R^{87}$, $R^{88}$, $R^{89}$, $R^{90}$, $R^{91}$, $R^{92}$ and $R^{93}$ are as defined above.

Examples of the substituted cyclopentadiene compound (6-6) can include the following compounds:

1-dimethylphenylsilyl-2-methylcyclopentadiene, 1-dimethylphenylsilyl-3-methylcyclopentadiene, 1-dimethylphenylsilyl-2,3-dimethylcyclopentadiene, 1-dimethylphenylsilyl-2,4-dimethylcyclopentadiene, 1-dimethylphenylsilyl-2,5-dimethylcyclopentadiene, 1-dimethylphenylsilyl-2,3,5-trimethylcyclopentadiene, 1-dimethylphenylsilyl-2-ethylcyclopentadiene, 1-dimethylphenylsilyl-2-n-propylcyclopentadiene, 1-dimethylphenylsilyl-2-isopropylcyclopentadiene, 1-dimethylphenylsilyl-2-n-butylcyclopentadiene, 1-dimethylphenylsilyl-2-tert-butylcyclopentadiene, 1-dimethylphenylsilyl-2-phenylcyclopentadiene and 1-dimethylphenyl silyl-2-benzylcyclopentadiene.

<Process for Producing Substituted Cyclopentadienes (6-1) to (6-6)>

The substituted cyclopentadiene compounds represented by the general formulas (6-1) to (6-6) can be produced, for example, by the steps of: reacting substituted cyclopentadiene compounds represented by general formulas (12-1) to (12-6) with a base in the presence of an amine compound; and reacting the reaction products of the substituted cyclopentadiene compounds (12-1) to (12-6) and the base with silicon halide compounds represented by general formulas (13-1) to (13-6).

The substituted cyclopentadiene compounds represented by the general formulas (12-1) to (12-6) are as follows:

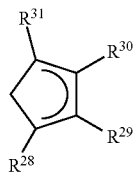

(12-1)

wherein $R^{28}$, $R^{29}$, $R^{30}$ and $R^{31}$ are as defined above, and the moiety

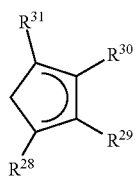

represents

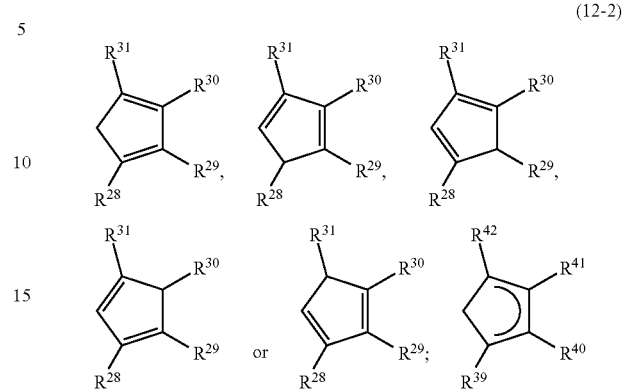

(12-2)

wherein $R^{39}$, $R^{40}$, $R^{41}$ and $R^{42}$ are as defined above, and the moiety

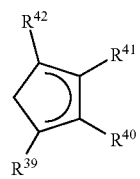

represents

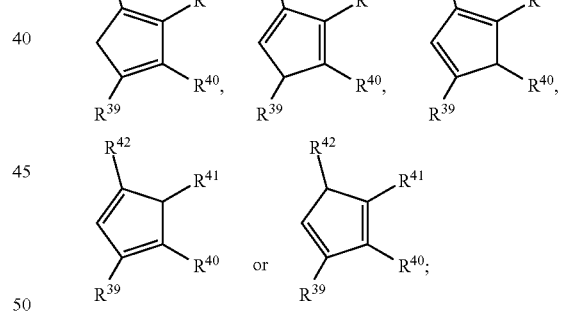

a substituted cyclopentadiene compound represented by

(12-3)

wherein $R^{49}$, $R^{50}$, $R^{51}$ and $R^{52}$ are as defined above, and the moiety represents 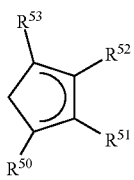

(12-4) 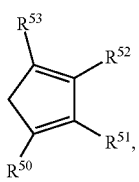 , 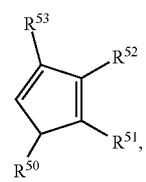 , 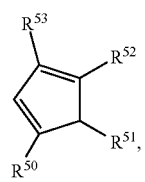 ,

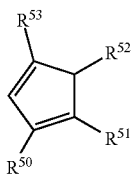 or 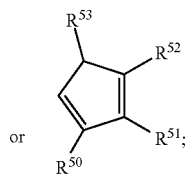 ; 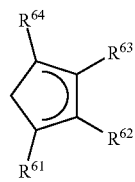

wherein $R^{61}$, $R^{62}$, $R^{63}$ and $R^{64}$ are as defined above, and the moiety

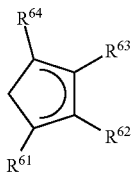

represents (12-5) 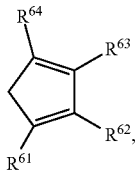 , 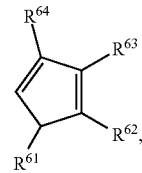 , 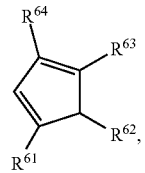 ,

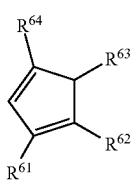 or 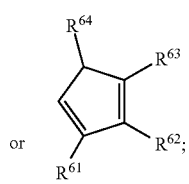 ; 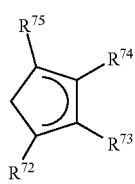

wherein $R^{72}$, $R^{73}$, $R^{74}$ and $R^{75}$ are as defined above, and the moiety represents 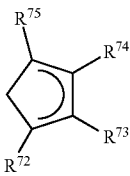

(12-6) 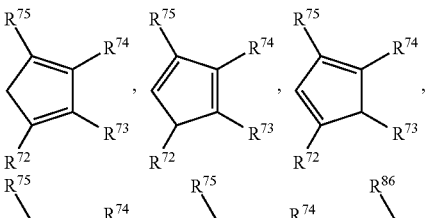

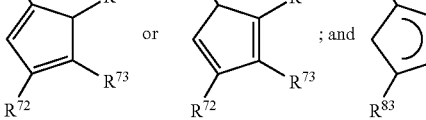

wherein $R^{83}$, $R^{84}$, $R^{85}$ and $R^{86}$ are as defined above, and the moiety

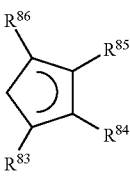

represents

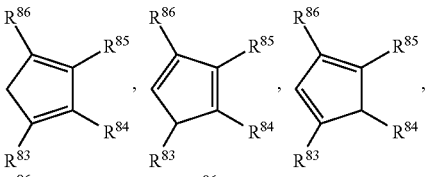

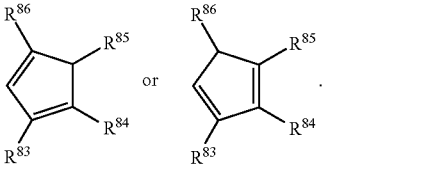

Examples of the substituted cyclopentadiene compounds (12-1), (12-2), (12-4) and (12-5) can include the following compounds:

methylcyclopentadiene, 1,2-dimethylcyclopentadiene, 1,3-dimethylcyclopentadiene, 1,2,3-trimethylcyclopentadiene, 1,3,4-trimethylcyclopentadiene, 1,2,3,4-tetramethylcyclopentadiene, ethylcyclopentadiene, 1,2-diethylcyclopentadiene, 1,3-diethylcyclopentadiene, 1,2,3-triethylcyclopentadiene, 1,3,4-triethylcyclopentadiene, 1,2,3,4-tetraethylcyclopentadiene, n-propylcyclopentadiene, isopropylcyclopentadiene, n-butylcyclopentadiene, sec-butylcyclopentadiene, tert-butylcyclopentadiene, n-pentylcyclopentadiene, neopentylcyclopentadiene, n-hexylcyclopentadiene, n-octylcyclopentadiene, phenylcyclopentadiene, naphthylcyclopentadiene, trimethylsilylcyclopentadiene, triethylsilylcyclopentadiene and tert-butyldimethylsilylcyclopentadiene.

Examples of the substituted cyclopentadiene compound (12-3) can include the following compounds:
tetrahydroindene, 2-methyltetrahydroindene, 3-methyltetrahydroindene, 2,3-dimethyltetrahydroindene, 2-ethyltetrahydroindene, 2-n-propyltetrahydroindene, 2-isopropyltetrahydroindene, 2-n-butyltetrahydroindene, 2-sec-butyltetrahydroindene, 2-tert-butyltetrahydroindene, 2-n-pentyltetrahydroindene, 2-neopentyltetrahydroindene, 2-amyltetrahydroindene, 2-n-hexyltetrahydroindene, 2-cyclohexyltetrahydroindene, 2-n-octyltetrahydroindene, 2-n-decyltetrahydroindene, 2-phenyltetrahydroindene, 2-benzyltetrahydroindene, 2-naphthyltetrahydroindene, 2-methoxytetrahydroindene, 2-phenoxytetrahydroindene, 2-benzyloxytetrahydroindene, 2-dimethylaminotetrahydroindene, 2-trimethylsilyltetrahydroindene and octahydrofluorene.

Examples of the substituted cyclopentadiene compound (12-6) can include the following compounds:
methylcyclopentadiene, 1,2-dimethylcyclopentadiene, 1,3-dimethylcyclopentadiene, 1,2,3-trimethylcyclopentadiene, 1,3,4-trimethylcyclopentadiene, ethylcyclopentadiene, 1,2-diethylcyclopentadiene, 1,3-diethylcyclopentadiene, 1,2,3-triethylcyclopentadiene, 1,3,4-triethylcyclopentadiene, 1,2,3,4-tetraethylcyclopentadiene, n-propylcyclopentadiene, isopropylcyclopentadiene, n-butylcyclopentadiene, sec-butylcyclopentadiene, tert-butylcyclopentadiene, n-pentylcyclopentadiene, neopentylcyclopentadiene, n-hexylcyclopentadiene, n-octylcyclopentadiene, phenylcyclopentadiene, naphthylcyclopentadiene, trimethylsilylcyclopentadiene, triethyl silylcyclopentadiene and tert-butyldimethylsilylcyclopentadiene.

The silicon halide compounds represented by the general formulas (13-1) to (13-6) are as follows:

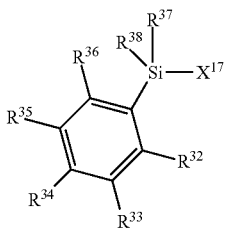
(13-1)

wherein $R^{32}$, $R^{33}$, $R^{34}$, $R^{3}$, $R^{36}$, $R^{37}$ and $R^{38}$ are as defined above, and $X^{17}$ is a halogen atom;

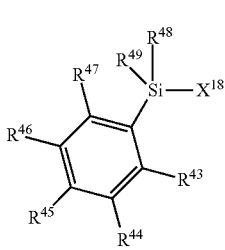
(13-2)

wherein $R^{43}$, $R^{44}$, $R^{45}$, $R^{46}$, $R^{47}$, $R^{48}$ and $R^{49}$ are as defined above, and $X^{18}$ is a halogen atom;

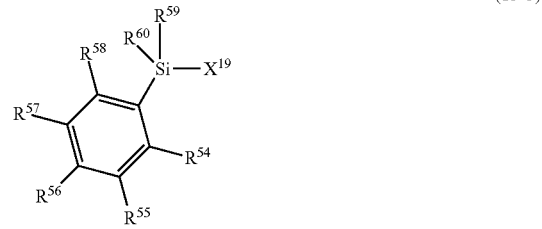
(13-3)

wherein $R^{54}$, $R^{55}$, $R^{56}$, $R^{57}$, $R^{58}$, $R^{59}$ and $R^{60}$ are as defined above, and $X^{19}$ is a halogen atom;

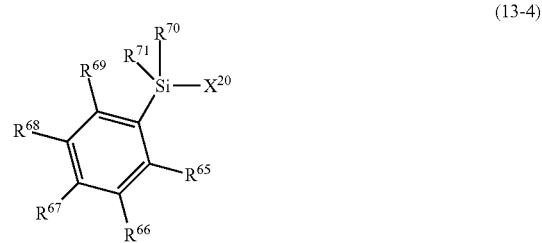
(13-4)

wherein $R^{65}$, $R^{66}$, $R^{67}$, $R^{68}$, $R^{69}$, $R^{70}$ and $R^{71}$ are as defined above, and $X^{20}$ is a halogen atom;

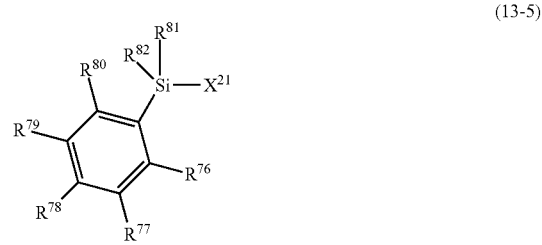
(13-5)

wherein $R^{76}$, $R^{77}$, $R^{78}$, $R^{79}$, $R^{80}$, $R^{81}$ and $R^{82}$ are as defined above, and $X^{21}$ is a halogen atom; and

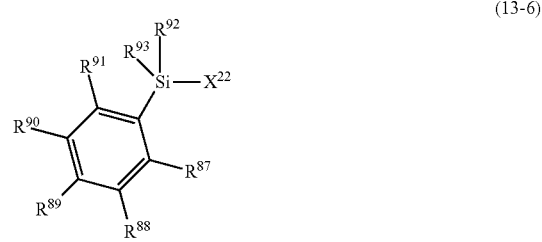
(13-6)

wherein $R^{87}$, $R^{88}$, $R^{89}$, $R^{90}$, $R^{91}$, $R^{92}$ and $R^{93}$ are as defined above, and $X^{22}$ is a halogen atom.

Examples of the silicon halide compound (13-1) can include the following compounds:
chloroethylmethylphenylsilane, chlorodiethylphenylsilane, chloromethyl(n-propyl)phenylsilane, chloromethyl(isopropyl)phenylsilane, chloro(n-butyl)methylphenylsilane, chloro(sec-butyl)methylphenylsilane, chloro(tert-butyl)methylphenylsilane, chloromethyl(n-pentyl)phenylsilane, chloromethyl(neopentyl)phenylsilane, amylchloromethylphenylsilane, chloro(n-hexyl)methylphenylsilane, chlorocyclohexylmethylphenylsilane, chloromethyl(n-octyl)phenylsilane, chloro(n-decyl)methylphenylsilane, chloro(n-dodecyl)methylphenylsilane, chloromethyl(n-octadecyl)phenylsilane, chlorobenzyldiphenylsilane, chloro(n-butyl)methyl(3-methylphenyl)silane, chloro(n-butyl)methyl(4-methylphenyl)silane, chloro(n-butyl)methyl(3,5-dimethylphenyl)silane, chloro(n-butyl)methyl(4-n-butylphenyl)silane, chloro(n-butyl)methyl(4-phenylphenyl)silane, chloro(n-butyl)methyl(4-methoxyphenyl)silane, chloro(n-butyl)methyl(4-phenoxyphenyl)silane, chloro(n-butyl)methyl(4-trimethylsilylphenyl)silane, chloro(n-butyl)methyl(4-dimethylaminophenyl)silane and chloro(n-butyl)methyl(4-benzyloxyphenyl)silane. Moreover, compounds in which "chloro" in these compounds exemplified above are replaced with "fluoro", "bromo" or "iodo" are also included therein.

Examples of the silicon halide compound (13-2) can include the following compounds:

chlorotriphenylsilane, chloro(2-methylphenyl)diphenylsilane, chloro(3-methylphenyl)diphenylsilane, chloro(4-methylphenyl)diphenylsilane, chloro(2,3-dimethylphenyl)diphenylsilane, chloro(2,4-dimethylphenyl)diphenylsilane, chloro(2,5-dimethylphenyl)diphenylsilane, chloro(2,6-dimethylphenyl)diphenylsilane, chloro(3,4-dimethylphenyl)diphenylsilane, chloro(3,5-dimethylphenyl)diphenylsilane, chloro(3,6-dimethylphenyl)diphenylsilane, chloro(2,3,4-trimethylphenyl)diphenylsilane, chloro(2,3,5-trimethylphenyl)diphenylsilane, chloro(2,3,6-trimethylphenyl)diphenylsilane, chloro(2,4,5-trimethylphenyl)diphenylsilane, chloro(2,4,6-trimethylphenyl)diphenylsilane, chloro(2,3,4,5-tetramethylphenyl)diphenylsilane, chloro(2,3,4,6-tetramethylphenyl)diphenylsilane, chloro(2,3,4,5,6-pentamethylphenyl)diphenylsilane, chloro(4-ethylphenyl)diphenylsilane, chloro(4-isopropylphenyl)diphenylsilane, chloro(4-n-butylphenyl)diphenylsilane, chloro(4-sec-butylphenyl)diphenylsilane, chloro(4-tert-butylphenyl)diphenylsilane, chloro(4-trimethylsilylphenyl)diphenylsilane, chloro(4-methoxyphenyl)diphenylsilane, chloro(4-dimethylaminophenyl)diphenylsilane, chloro(4-phenoxyphenyl)diphenylsilane, chloro(4-benzyloxyphenyl)diphenylsilane, chlorobis(2,3-dimethylphenyl)diphenylsilane, chlorotris(2,3-dimethylphenyl)silane, chlorodi(n-butylphenyl)phenylsilane and chlorotri(n-butylphenyl)silane. Moreover, compounds in which "chloro" in these compounds exemplified above are replaced with "fluoro", "bromo" or "iodo" are also included therein.

Examples of the silicon halide compound (13-3) can include the following compounds:

chlorodimethylphenylsilane, chloroethylmethylphenylsilane, chlorodiethylphenylsilane, chloromethyl(n-propyl)phenylsilane, chloromethyl(isopropyl)phenylsilane, chloro(n-butyl)methylphenylsilane, chloro(sec-butyl)methylphenylsilane, chloro(tert-butyl)methylphenylsilane, chloromethyl(n-pentyl)phenylsilane, chloromethyl(neopentyl)phenylsilane, amylchloromethylphenylsilane, chloro(n-hexyl)methylphenylsilane, chlorocyclohexylmethylphenylsilane, chloromethyl(n-octyl)phenylsilane, chloro(n-decyl)methylphenylsilane, chloro(n-dodecyl)methylphenylsilane, chloromethyl(n-octadecyl)phenylsilane, chlorobenzyldiphenylsilane, chlorodimethyl(3-methylphenyl)silane, chlorodimethyl(4-methylphenyl)silane, chlorodimethyl(3,5-dimethylphenyl)silane, chlorodimethyl(4-n-butylphenyl)silane, chlorodimethyl(4-phenylphenyl)silane, chlorodimethyl(4-methoxyphenyl)silane, chlorodimethyl(4-phenoxyphenyl)silane, chlorodimethyl(4-trimethylsilylphenyl)silane, chlorodimethyl(4-dimethylaminophenyl)silane, chlorodimethyl(4-benzyloxyphenyl)silane, chloro(n-butyl)methyl(3-methylphenyl)silane, chloro(n-butyl)methyl(4-methylphenyl)silane, chloro(n-butyl)methyl(3,5-dimethylphenyl)silane, chloro(n-butyl)methyl(4-n-butylphenyl)silane, chloro(n-butyl)methyl(4-phenylphenyl)silane, chloro(n-butyl)methyl(4-methoxyphenyl)silane, chloro(n-butyl)methyl(4-phenoxyphenyl)silane, chloro(n-butyl)methyl(4-trimethylsilylphenyl)silane, chloro(n-butyl)methyl(4-dimethylaminophenyl)silane, chloro(n-butyl)methyl(4-benzyloxyphenyl)silane, chloromethyldiphenylsilane, chloromethyl(2-methylphenyl)phenylsilane, chloromethyl(3-methylphenyl)phenylsilane, chloromethyl(4-methylphenyl)phenylsilane, chloromethyl(2,3-dimethylphenyl)phenylsilane, chloromethyl(2,4-dimethylphenyl)phenylsilane, chloromethyl(2,5-dimethylphenyl)phenylsilane, chloromethyl(2,6-dimethylphenyl)phenylsilane, chloromethyl(3,4-dimethylphenyl)phenylsilane, chloromethyl(3,5-dimethylphenyl)phenylsilane, chloromethyl(3,6-dimethylphenyl)phenylsilane, chloromethyl(2,3,4-trimethylphenyl)phenylsilane, chloromethyl(2,3,5-trimethylphenyl)phenylsilane, chloromethyl(2,3,6-trimethylphenyl)phenylsilane, chloromethyl(2,4,5-trimethylphenyl)phenylsilane, chloromethyl(2,4,6-trimethylphenyl)phenylsilane, chloromethyl(2,3,4,5-tetramethylphenyl)phenylsilane, chloromethyl(2,3,4,6-tetramethylphenyl)phenylsilane, chloromethyl(2,3,4,5,6-pentamethylphenyl)phenylsilane, chloromethyl(4-ethylphenyl)phenylsilane, chloromethyl(4-isopropylphenyl)phenylsilane, chloromethyl(4-n-butylphenyl)phenylsilane, chloromethyl(4-sec-butylphenyl)phenylsilane, chloromethyl(4-tert-butylphenyl)phenylsilane, chloromethyl(4-trimethylsilylphenyl)phenylsilane, chloromethyl(4-methoxyphenyl)phenylsilane, chloromethyl(4-dimethylaminophenyl)phenylsilane, chloromethyl(4-phenoxyphenyl)phenylsilane, chloromethyl(4-benzyloxyphenyl)phenylsilane, chloromethylbis(2,3-dimethylphenyl)silane, chloromethyldi(4-n-butylphenyl)silane, chlorotriphenylsilane, chloro(2-methylphenyl)diphenylsilane, chloro(3-methylphenyl)diphenylsilane, chloro(4-methylphenyl)diphenylsilane, chloro(2,3-dimethylphenyl)diphenylsilane, chloro(2,4-dimethylphenyl)diphenylsilane, chloro(2,5-dimethylphenyl)diphenylsilane, chloro(2,6-dimethylphenyl)diphenylsilane, chloro(3,4-dimethylphenyl)diphenylsilane, chloro(3,5-dimethylphenyl)diphenylsilane, chloro(3,6-dimethylphenyl)diphenylsilane, chloro(2,3,4-trimethylphenyl)diphenylsilane, chloro(2,3,5-trimethylphenyl)diphenylsilane, chloro(2,3,6-trimethylphenyl)diphenylsilane, chloro(2,4,5-trimethylphenyl)diphenylsilane, chloro(2,4,6-trimethylphenyl)diphenylsilane, chloro(2,3,4,5-tetramethylphenyl)diphenylsilane, chloro(2,3,4,6-tetramethylphenyl)diphenylsilane, chloro(2,3,4,5,6-pentamethylphenyl)diphenylsilane, chloro(4-ethylphenyl)diphenylsilane, chloro(4-isopropylphenyl)diphenylsilane, chloro(4-n-butylphenyl)diphenylsilane, chloro(4-sec-butylphenyl)diphenylsilane, chloro(4-tert-butylphenyl)diphenylsilane, chloro(4-trimethylsilylphenyl)diphenylsilane, chloro(4-methoxyphenyl)diphenylsilane, chloro(4-dimethylaminophenyl)diphenylsilane, chloro(4-phenoxyphenyl)diphenylsilane, chloro(4-benzyloxyphenyl)diphenylsilane, chlorobis(2,3-dimethylphenyl)phenylsilane, chlorotris(2,3-dimethylphenyl)silane, chlorodi(n-butylphenyl)phenylsilane and chlorotri(n-butylphenyl)silane. Moreover, compounds in which "chloro" in these compounds exemplified above are replaced with "fluoro", "bromo" or "iodo" are also included therein.

Examples of the silicon halide compound (13-4) can include the following compounds:

chlorodimethyl(2-methylphenyl)silane, chlorodimethyl(3-methylphenyl)silane, chlorodimethyl(4-methylphenyl)silane, chlorodimethyl(2,3-dimethylphenyl)silane, chlorodimethyl(2,4-dimethylphenyl)silane, chlorodimethyl(2,5-dimethylphenyl)silane, chlorodimethyl(2,6-dimethylphenyl)silane, chlorodimethyl(3,4-dimethylphenyl)silane, chlorodimethyl(3,5-dimethylphenyl)silane, chlorodimethyl(3,6-dimethylphenyl)silane, chlorodimethyl(2,3,4-trimethylphenyl)silane, chlorodimethyl(2,3,5-trimethylphenyl)silane, chlorodimethyl(2,3,6-trimethylphenyl)silane, chlorodimethyl(2,3,4,5-tetramethylphenyl)silane, chlorodimethyl(2,3,4,6-tetramethylphenyl)silane, chlorodimethyl(2,3,4,5,6-pentamethylphenyl)silane, chlorodimethyl(4-n-butylphenyl)silane, chlorodimethyl(4-tert-butylphenyl)silane, chlorodimethyl(3,5-di-tert-butylphenyl)silane, chlorodimethyl(3-tert-butyl-5-methylphenyl)silane, chlorodimethyl(3,5-tert-butyl-4-methylphenyl)silane, (9-anthryl)chlorodimethylsilane, chloro(3,5-bis(trifluoromethyl)phenyl)dimethylsilane, chlorodimethyl(4-chlorophenyl)silane, chlorodimethyl(3,5-dichlorophenyl)silane, chlorodimethyl(4-fluorophenyl)silane and chlorodimethyl(4-bromophenyl)silane. Moreover, compounds in which "chloro" in these compounds exemplified above are replaced with "fluoro", "bromo" or "iodo" are also included therein.

Examples of the silicon halide compound (13-5) can include the following compounds:

chloromethyl(2-methylphenyl)phenylsilane, chloromethyl(3-methylphenyl)phenylsilane, chloromethyl(4-methylphenyl)phenylsilane, chloromethyl(2,3-dimethylphenyl)phenylsilane, chloromethyl(2,4-dimethylphenyl)phenylsilane, chloromethyl(2,5-dimethylphenyl)phenylsilane, chloromethyl(2,6-dimethylphenyl)phenylsilane, chloromethyl(3,4-dimethylphenyl)phenylsilane, chloromethyl(3,5-dimethylphenyl)phenylsilane, chloromethyl(3,6-dimethylphenyl)phenylsilane, chloromethyl(2,3,4-trimethylphenyl)phenylsilane, chloromethyl(2,3,5-trimethylphenyl)phenylsilane, chloromethyl(2,3,6-trimethylphenyl)phenylsilane, chloromethyl(2,4,5-trimethylphenyl)phenylsilane, chloromethyl(2,4,6-trimethylphenyl)phenylsilane, chloromethyl(2,3,4,5-tetramethylphenyl)phenylsilane, chloromethyl(2,3,4,6-tetramethylphenyl)phenylsilane, chloromethyl(2,3,4,5,6-pentamethylphenyl)phenylsilane, chloromethyl(4-ethylphenyl)phenylsilane, chloromethyl(4-isopropylphenyl)phenylsilane, chloromethyl(4-n-butylphenyl)phenylsilane, chloromethyl(4-sec-butylphenyl)phenylsilane, chloromethyl(4-tert-butylphenyl)phenylsilane, chloromethyl(4-trimethylsilylphenyl)(4-methylphenyl)silane, chloromethyl(4-methoxyphenyl)(4-methylphenyl)silane, chloromethyl(4-dimethylaminophenyl)(4-methylphenyl)silane, chloromethyl(4-phenoxyphenyl)(4-methylphenyl)silane, chloromethyl(4-benzyloxyphenyl)(4-methylphenyl)silane, chloromethyl(4-methylphenyl)(2,3-dimethylphenyl)silane and chloromethyl(4-n-butylphenyl)(4-methylphenyl)silane. Moreover, compounds in which "chloro" in these compounds exemplified above are replaced with "fluoro", "bromo" or "iodo" are also included therein.

Examples of the silicon halide compound (13-6) can include the following compounds:

chlorodimethylphenylsilane, bromodimethylphenylsilane, fluorodimethylphenylsilane and iododimethylphenylsilane.

Examples of the base to be reacted with the substituted cyclopentadiene compounds (12-1) to (12-6) include: alkali metal hydrides such as lithium hydride, sodium hydride and potassium hydride; alkaline earth metal hydrides such as calcium hydride; and organic alkali metal compounds typified by organic lithium compounds such as methyllithium, ethyllithium, n-butyllithium, sec-butyllithium, tert-butyllithium, lithiumtrimethylsilyl acetylide, lithium acetylide, trimethylsilylmethyllithium, vinyllithium, phenyllithium and allyllithium. The amount thereof used is usually in the range of 0.5- to 3-fold by mol, preferably in the range of 0.9- to 2-fold by mol, with respect to the substituted cyclopentadiene compound. A usual commercially available mineral oil-containing product can be used directly as sodium hydride or potassium hydride. Of course, prior to the usage, the mineral oil may be removed, by washing with a hydrocarbyl solvent such as hexane.

Examples of the amine compound include: Primary amines including primary anilines such as aniline, chloroaniline, bromoaniline, fluoroaniline, dichloroaniline, dibromoaniline, difluoroaniline, trichloroaniline, tribromoaniline, trifluoroaniline, tetrachloroaniline, tetrabromoaniline, tetrafluoroaniline, pentachloroaniline, pentafluoroaniline, nitroaniline, dinitroaniline, hydroxyaniline, phenylenediamine, anisidine, dimethoxyaniline, trimethoxyaniline, ethoxyaniline, diethoxyaniline, triethoxyaniline, n-propoxyaniline, isopropoxyaniline, n-butoxyaniline, sec-butoxyaniline, isobutoxyaniline, t-butoxyaniline, phenoxyaniline, methylaniline, ethylaniline, n-propylaniline, isopropylaniline, n-butylaniline, sec-butylaniline, isobutylaniline, t-butylaniline, dimethylaniline, diethylaniline, di-n-propylaniline, diisopropylaniline, di-n-butylaniline, di-sec-butylaniline, diisobutylaniline, di-t-butylaniline, trimethylaniline, triethylaniline, diisopropylaniline, phenylaniline, benzylaniline, aminobenzoic acid, methyl aminobenzoate, ethyl aminobenzoate, n-propyl aminobenzoate, isopropyl aminobenzoate, n-butyl aminobenzoate, isobutyl aminobenzoate, sec-butyl aminobenzoate and t-butyl aminobenzoate, and further including other primary amines including naphthylamine, naphthylmethylamine, benzylamine, propylamine, butylamine, pentylamine, hexylamine, cyclohexylamine, heptylamine, octylamine, 2-aminopyridine, 3-aminopyridine and 4-aminopyridine;

secondary amines such as N-methylaniline, N-ethylaniline, diphenylamine, N-methylchloroaniline, N-methylbromoaniline, N-methylfluoroaniline, N-methylanisidine, N-methylmethylaniline, N-methylethylaniline, N-methyl-n-propylaniline, N-methylisopropylaniline, diethylamine, dipropylamine, diisopropylamine, dipentylamine, dihexylamine, dicyclohexylamine, diheptylamine, dioctylamine, morpholine, piperidine, 2,2,6,6-tetramethylpiperidine, pyrrolidine, 2-methylaminopyridine, 3-methylaminopyridine and 4-methylaminopyridine; and tertiary amines such as N,N-dimethylaniline, N,N-dimethylchloroaniline, N,N-dimethylbromoaniline, N,N-dimethylfluoroaniline, N,N-dimethylanisidine, N-methylmethylaniline, N,N-dimethylethylaniline, N,N-dimethyl-n-propylaniline, N,N-dimethylisopropylaniline, 1,4-diazabicyclo[2.2.2]octane, 1,5-diazabicyclo[4.3.0]non-5-ene, 1,8-diazabicyclo[5.4.0]undec-7-ene, 2-dimethylaminopyridine, 3-dimethylaminopyridine, 4-dimethylaminopyridine, trimethylamine, triethylamine, tri-n-propylamine, tri-n-butylamine, diisopropylethylamine, trin-octylamine, tri-n-decylamine and triphenylamine. Preferably primary or secondary amines, more preferably primary amines are used.

The amount thereof used is usually in the range of 0.001- to 2-fold by mol, preferably in the range of 0.01- to 0.5-fold by mol, with respect to the metal hydride. The reaction is usually performed in a solvent inert to the reaction. Examples of such a solvent include aprotic solvents such as: aromatic hydrocarbyl solvents such as benzene, toluene and xylene; aliphatic hydrocarbyl solvents such as pentane, hexane, heptane, octane and cyclohexane; ether solvents such as diethyl ether, methyl t-butyl ether, tetrahydrofuran and 1,4-dioxane; amide solvents such as hexamethylphosphoric amide, dimethylformamide, dimethylacetamide and N-methylpyrrolidone; and halogen solvents such as chlorobenzene and dichlorobenzene. These solvents are used alone or as a mixture of two or more thereof, and the amount thereof used is usually in the range of 1- to 200-fold by weight, preferably in the range of 3- to 30-fold by weight, with respect to the cyclopentadiene.

For the reaction, for example, any of the substituted cyclopentadiene compounds (12-1) to (12-6), the base and the amine compound may be mixed simultaneously in a solvent, or the base and the amine compound are mixed in advance and then any of the substituted cyclopentadiene compounds (12-1) to (12-6) may be added to the mixture. The reaction temperature is not particularly limited, and a temperature region that eliminates the need of low temperature equipment is industrially preferable and is, for example, in the range of 0 to 70° C., preferably in the range of 10 to 60° C. This reaction efficiently produces a metal salt of any of the substituted cyclopentadiene compounds (12-1) to (12-6). The metal salt of any of the substituted cyclopentadiene compounds (12-1) to (12-6) thus obtained may be used directly in the form of the reaction mixture or may be taken from the reaction mixture. The former case usually suffices.

The reaction for obtaining any of the substituted cyclopentadiene compounds (6-1) to (6-6) is usually performed in a solvent inert to the reaction. Examples of such a solvent include aprotic solvents such as: aromatic hydrocarbyl solvents such as benzene, toluene and xylene; aliphatic hydrocarbyl solvents such as pentane, hexane, heptane, octane and cyclohexane; ether solvents such as diethyl ether, methyl t-butyl ether, tetrahydrofuran and 1,4-dioxane; amide solvents such as hexamethylphosphoric amide, dimethylformamide, dimethylacetamide and N-methylpyrrolidone; and halogen solvents such as chlorobenzene and dichlorobenzene. These solvents are used alone or as a mixture of two or more thereof, and the amount thereof used is usually in the range of 1- to 200-fold by weight, preferably in the range of 3- to 30-fold by weight, with respect to any of the substituted cyclopentadiene compounds (12-1) to (12-6). This reaction is usually performed, for example, by mixing the base, the amine compound and any of the substituted cyclopentadiene compounds (12-1) to (12-6) in a solvent and then adding any of the silicon halide compounds (13-1) to (13-6) to the mixture. However, even when a method in which these components are mixed simultaneously is employed, the substituted cyclopentadiene compounds (12-1) to (12-6) of interest can be produced. The reaction temperature is not particularly limited, and a temperature region that eliminates the need of low temperature equipment is industrially advantageous and is, for example, in the range of 0 to 70° C., preferably in the range of 10 to 60° C.

The amount of the substituted cyclopentadienes (12-1) to (12-6) used is usually in the range of 0.5- to 5-fold by mol, preferably in the range of 0.8- to 3-fold by mol, with respect to the silicon halide compounds (13-1) to (13-6).

After the completion of the reaction, water, an aqueous sodium bicarbonate solution, an aqueous sodium carbonate solution, an aqueous ammonium chloride solution or an aqueous solution of hydrochloric acid or the like is added to the obtained reaction mixture. Then, organic and aqueous layers are separated to obtain solutions of any of the substituted cyclopentadiene compounds (12-1) to (12-6) as the organic layer. When water-compatible solvent is used in the reaction or when the amount of the solvent used in the reaction is too small to easily separate organic and aqueous layers, a water-insoluble organic solvent such as toluene, ethyl acetate or chlorobenzene may be added to the reaction mixture as needed, followed by separation into organic and aqueous layers. The obtained organic layer is concentrated to obtain any of the substituted cyclopentadiene compounds (12-1) to (12-6). The obtained substituted cyclopentadiene compound may be purified, if necessary, by a method such as distillation or column chromatography treatment.

<Activating Co-Catalytic Component>

Examples of the activating co-catalytic component can include compounds (A) and (B) shown below. These compounds (A) and (B) may be used in combination.

Compound (A): one or more aluminum compounds selected from the compound group consisting of the following compounds (A1) to (A3):

(A1): an organic aluminum compound represented by a general formula $(E^1)_a Al(G)_{3-a}$, (A2): a cyclic aluminoxane having a structure represented by a general formula $\{-Al(E^2)-O-\}_b$, and (A3): a linear aluminoxane having a structure represented by a general formula $E^3\{-Al(E^3)-O-\}_c Al(E^3)_2$, wherein $E^1$, $E^2$ and $E^3$ each represent a hydrocarbyl group having 1 to 8 carbon atoms; G represents a hydrogen atom or a halogen atom; a represents an integer of 1 to 3; b represents an integer of 2 or more; c represents an integer of 1 or more; in the case that more than one $E^1$ groups exist, the $E^1$ groups may be the same or different from each other; in the case that more than one G groups exist, the G groups may be the same or different from each other; the $E^2$ groups may be the same or different from each other; and the $E^3$ groups may be the same or different from each other; and Compound (B): one or more boron compounds selected from the compound group consisting of the following compounds (B1) to (B3):

(B1): a boron compound represented by a general formula $BQ^1Q^2Q^3$, (B2): a borate compound represented by a general formula $T^+(BQ^1Q^2Q^3Q^4)^-$, and (B3): a borate compound represented by a general formula $(L-H)^+(BQ^1Q^2Q^3Q^4)^-$, wherein B represents a trivalent boron atom; $Q^1$, $Q^2$, $Q^3$ and $Q^4$ are the same as or different from each other and each represent a halogen atom, a hydrocarbyl group having 1 to 20 carbon atoms which may be substituted with a halogen atom, a hydrocarbylsilyl group having 1 to 20 carbon atoms, an alkoxy group having 1 to 20 carbon atoms or a dihydrocarbylamino group having 2 to 20 carbon atoms; $T^+$ represents an inorganic or organic cation; and $(L-H)^+$ represents a Broensted acid.

In the compounds (A1) to (A3), examples of the hydrocarbyl group having 1 to 8 carbon atoms in $E^1$, $E^2$ and $E^3$ include alkyl having 1 to 8 carbon atoms. Examples of the alkyl groups having 1 to 8 carbon atoms include methyl, ethyl, normal propyl, isopropyl, normal butyl, isobutyl, normal pentyl and neopentyl groups.

Examples of the organic aluminum compound (A1) represented by the general formula $(E^1)_aAl(G)_{3-a}$ include trialkylaluminums, dialkylaluminum chlorides, alkylaluminum dichlorides and dialkylaluminum hydrides. Examples of the trialkylaluminum include trimethylaluminum, triethylaluminum, tripropylaluminum, triisobutylaluminum and trihexylaluminum. Examples of the dialkylaluminum chloride include dimethylaluminum chloride, diethylaluminum chloride, dipropylaluminum chloride, diisobutylaluminum chloride and dihexylaluminum chloride. Examples of the alkylaluminum dichloride include methylaluminum dichloride, ethylaluminum dichloride, propylaluminum dichloride, isobutylaluminum dichloride and hexylaluminum dichloride. Examples of the dialkylaluminum hydride include dimethylaluminum hydride, diethylaluminum hydride, dipropylaluminum hydride, diisobutylaluminum hydride and dihexylaluminum hydride.

Examples of $E^2$ and $E^3$ in (A2): cyclic aluminoxane having a structure represented by the general formula $\{-Al(E^2)-O-\}_b$ and (A3): linear aluminoxane having a structure represented by the general formula $E^3\{-Al(E^3)-O-\}_cAl(E^3)_2$ include alkyl groups such as methyl, ethyl, normal propyl, isopropyl, normal butyl, isobutyl, normal pentyl and neopentyl groups. b is an integer of 2 or more, and c is an integer of 1 or more. Preferably, $E^2$ and $E^3$ are each independently a methyl group or an isobutyl group, b is 2 to 40, and C is 1 to 40.

These aluminoxanes are prepared by various methods. The methods are not particularly limited, and they may be prepared according to methods known in the art. For example, a solution containing a trialkylaluminum (e.g., trimethylaluminum) dissolved in an appropriate organic solvent (e.g., benzene or aliphatic hydrocarbyl) is contacted with water to prepare the aluminoxanes. Another preparation method can involve, for example, contacting a trialkylaluminum (e.g., trimethylaluminum) with a metal salt (e.g., copper sulfate hydrate) containing crystalline water.

In the compounds (B1) to (B3), $Q^1$, $Q^2$, $Q^3$ and $Q^4$ are preferably a halogen atom or a hydrocarbyl group having 1 to 20 carbon atoms which may be substituted by a halogen atom. Examples of the inorganic cation in $T^+$ include ferrocenium cation, alkyl-substituted ferrocenium cations and silver cation. Examples of the organic cation in $T^+$ include triphenylmethyl cation. Examples of $(BQ^1Q^2Q^3Q^4)^-$ include tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,3,4-trifluorophenyl)borate, phenyltris(pentafluorophenyl)borate and tetrakis(3,5-bistrifluoromethylphenyl)borate. Examples of the Broensted acid represented by $(L-H)^+$ include trialkyl-substituted ammonium, N,N-dialkylanilinium, dialkylammonium and triarylphosphonium.

Examples of the boron compound (B1) represented by the general formula $BQ^1Q^2Q^3$ include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane and phenylbis(pentafluorophenyl)borane.

Examples of the borate compound (B2) represented by the general formula $T^+(BQ^1Q^2Q^3Q^4)^-$ include ferrocenium tetrakis(pentafluorophenyl)borate, 1,1'-bis-trimethylsilylferrocenium tetrakis(pentafluorophenyl)borate, silver tetrakis(pentafluorophenyl)borate, triphenylmethyl tetrakis(pentafluorophenyl)borate and triphenylmethyl tetrakis(3,5-bistrifluoromethylphenyl)borate.

Examples of the borate compound (B3) represented by the general formula $(L-H)^+(BQ^1Q^2Q^3Q^4)^-$ include triethylammonium tetrakis(pentafluorophenyl)borate, tripropylammonium tetrakis(pentafluorophenyl)borate, tri(normal butyl) ammonium tetrakis(pentafluorophenyl)borate, tri(normal butyl)ammonium tetrakis(3,5-bistrifluoromethylphenyl)borate, N,N-bis-trimethylsilylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-bis-trimethylsilylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate and tri(bis-trimethylsilylphenyl)phosphonium tetrakis(pentafluorophenyl)borate.

<Trimerization Catalyst>

The trimerization catalyst of the present invention is a trimerization catalyst comprising the transition metal complex (1) and is a catalyst capable of producing 1-hexene by ethylene trimerization. For example, the transition metal complex (1) can be brought into contact with an activating co-catalytic component to obtain a catalytic component for trimerization.

Examples of such an activating co-catalytic component can include the compounds (A) and (B) described above. Moreover, these compounds (A) and (B) may be used in combination.

Regarding the amount of each catalytic component used, a molar ratio between the compound (A) (in terms of the aluminum atom) and the transition metal complex (1) used as a catalytic component (compound (A) (in terms of the aluminum atom)/transition metal complex (1)) is usually 0.01 to 10000, preferably 5 to 5000. Also, a molar ratio between the compound (B) and the transition metal complex (1) used as a catalytic component (compound (B)/transition metal complex (1)) is usually 0.01 to 100, preferably 0.5 to 10.

When each catalytic component is used in a solution state, the concentration of the transition metal complex (1) used as a catalytic component is usually 0.0001 to 5 mmol/L, preferably 0.001 to 1 mmol/L. The concentration of the compound (A) is usually 0.01 to 500 mmol/L, preferably 0.1 to 100 mmol/L, in terms of the aluminum atom. The concentration of the compound (B) is usually 0.0001 to 5 mmol/L, preferably 0.001 to 1 mmol/L.

The method for contacting each catalytic component is not particularly limited. The transition metal complex (1) may be brought into contact with the activating co-catalytic component to prepare a trimerization catalyst in advance, and then is supplied to a reactor. Alternatively, these catalytic components may be supplied to a reactor in any order and subjected to contact treatment in the reactor.

<Process for Producing 1-Hexene>

The process for producing 1-hexene according to the present invention is a process for producing 1-hexene from ethylene and is a process for producing 1-hexene through the trimerization reaction of ethylene.

The trimerization reaction is not particularly limited and may be, for example, trimerization reaction using an aliphatic hydrocarbyl (e.g., butane, pentane, hexane, heptane and octane), an aromatic hydrocarbyl (e.g., benzene and toluene), or a hydrocarbyl halide (e.g., methylene dichloride and chlorobenzene) as a solvent, trimerization reaction in a slurry state, or trimerization reaction in ethylene in a gas state can be carried out.

The trimerization reaction can be performed by any of batch, semi-continuous and continuous process.

The pressure of ethylene is usually in the range of normal pressure to 10 MPa, preferably in the range of normal pressure to 5 MPa.

The temperature of the trimerization reaction can usually be in the range of −50° C. to 220° C. and is preferably in the range of 0° C. to 170° C., more preferably in the range of 50° C. to 120° C.

The time of the trimerization reaction can generally be determined appropriately according to the reaction apparatus of interest and can be in the range of 1 minute to 20 hours.

<Catalytic Component for Olefin Polymerization>

Examples of the catalytic component for olefin polymerization used in the present invention can include a solid catalytic component containing titanium, magnesium and a halogen as essential ingredients; and a catalytic component comprising a metallocene transition metal complex. In addition, examples of the catalytic component for olefin polymerization can include a complex having a phenoxyimine ligand as reported in EP0874005.

Examples of the solid catalytic component containing titanium, magnesium and a halogen as essential ingredients can include solid catalytic components described in, for example, JP 63-142008 A, JP 4-227604 A, JP 5-339319 A, JP 6-179720 A, JP 9-31119 A, JP 11-80234 A, JP 11-322833 A or the like.

Examples of the catalytic component for olefin polymerization comprising a transition metal complex containing metallocene can include a transition metal complex represented by the following general formula (2):

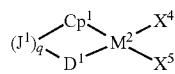
(2)

wherein $M^2$ represents a transition metal atom of Group 4 of the Periodic Table of the Elements; $Cp^1$ represents a group having a cyclopentadiene-type anionic skeleton; $J^1$ represents a group linking $Cp^1$ and $D^1$ by one or two atoms of Group 14 of the Periodic Table of the Elements; q represents 0 or 1;

when q is 1, $D^1$ represents a group having a cyclopentadiene-type anionic skeleton or a group which links $J^1$ and $M^2$ and which is bonded to $M^2$ at its atom of Group 15 or 16 of the Periodic Table of the Elements, and when q is 0, $D^1$ represents a group having a cyclopentadiene-type anionic skeleton; and $X^4$ and $X^5$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20.

Preferable examples of the catalytic component for olefin polymerization can include transition metal complexes represented by the following general formulas (3), (4) or (5):

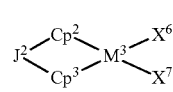
(3)

wherein $M^3$ represents a transition metal atom of Group 4 of the Periodic Table of the Elements; $Cp^2$ and $Cp^3$ represent a group having a cyclopentadiene-type anionic skeleton; $J^2$ represents a group linking $Cp^2$ and $Cp^3$ by one or two atoms of Group 14 of the Periodic Table of the Elements; and $X^6$ and $X^7$ each independently represent
a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20,

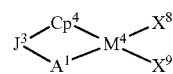
(4)

wherein $M^4$ represents a transition metal atom of Group 4 of the Periodic Table of the Elements; $Cp^4$ represents a group having a cyclopentadiene-type anionic skeleton; $J^3$ represents a group linking $Cp^4$ and $A^1$ by one or two atoms of Group 14 of the Periodic Table of the Elements; $A^1$ represents a group which links $J^3$ and $M^4$ and which is bonded to $M^4$ at its atom of Group 15 or 16 of the Periodic Table of the Elements; and $X^8$ and $X^9$ each independently represent
a hydrogen atom, a halogen atom,
an alkyl group having 1 to 20 carbon atoms which may have a halogen atom as a substituent, an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by $-Si(R^{12})_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by $-N(R^{13})_2$, wherein the two $R^{13}$ groups each independently represent a hydrocarbyl group or a halogenated hydrocarbyl group, and the total number of the carbon atoms in the two $R^{13}$ groups is 2 to 20, and

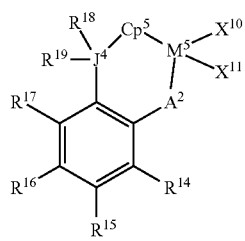

(5)

wherein
$M^5$ represents a transition metal atom of Group 4 of the Periodic Table of the Elements;
$A^2$ represents an atom of Group 16 of the Periodic Table of the Elements;
$J^4$ represents an atom of Group 14 of the Periodic Table of the Elements;
$Cp^5$ represents a group having a cyclopentadiene-type anionic skeleton;
$X^1$, $X^{11}$, $R^{14}$, $R^{15}$, $R^{16}$ and $R^{17}$ each independently represent a hydrogen atom, a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by $-Si(R^{12})_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by $-N(R^{13})_2$, wherein the two $R^{13}$ groups each independently represent a hydrocarbyl group or a halogenated hydrocarbyl group, and the total number of the carbon atoms in the two $R^{13}$ groups is 2 to 20; and $R^{18}$ and $R^{19}$ each independently represent
a hydrogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by $-Si(R^{12})_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by $-N(R^{13})_2$, wherein the two $R^{13}$ groups each independently represent a hydrocarbyl group or a halogenated hydrocarbyl group, and the total number of the carbon atoms in the two $R^{13}$ groups is 2 to 20;
of $R^{14}$, $R^{15}$, $R^{16}$ and $R^{17}$, two groups bonded to two adjacent carbon atoms may be bonded to each other to form a ring together with the two carbon atoms to which the two groups are bonded; $X^{10}$ and $X^{11}$ may be bonded to each other to form a ring together with $M^5$; and $R^{18}$ and $R^{19}$ may be bonded to each other to form a ring together with $J^4$.

The transition metal complex represented by the general formula (2) will be described in detail.

Examples of the transition metal atom of Group 4 of the Periodic Table of the Elements (IUPAC Nomenclature of Inorganic Chemistry, Revised, 1989) in $M^2$ include titanium, zirconium and hafnium atoms, for example.

Examples of the group having a cyclopentadiene-type anionic skeleton, represented by $Cp^1$ or $D^1$ include $\eta^5$-cyclopentadienyl, $\eta^5$-methylcyclopentadienyl, $\eta^5$-dimethylcyclopentadienyl, $\eta^5$-trimethylcyclopentadienyl, $\eta^5$-tetramethylcyclopentadienyl, $\eta^5$-ethylcyclopentadienyl, $\eta^5$-n-propylcyclopentadienyl, $\eta^5$-isopropylcyclopentadienyl, $\eta^5$-n-butylcyclopentadienyl, $\eta^5$-sec-butylcyclopentadienyl, $\eta^5$-tert-butylcyclopentadienyl, $\eta^5$-n-pentylcyclopentadienyl, $\eta^5$-neopentylcyclopentadienyl, $\eta^5$-n-hexylcyclopentadienyl, $\eta^5$-n-octylcyclopentadienyl, $\eta^5$-phenylcyclopentadienyl, $\eta^5$-naphthylcyclopentadienyl, $\eta^5$-trimethylsilylcyclopentadienyl, $\eta^5$-triethylsilylcyclopentadienyl, $\eta^5$-tert-butyldimethylsilylcyclopentadienyl, $\eta^5$-indenyl, $\eta^5$-methylindenyl, $\eta^5$-dimethylindenyl, $\eta^5$-ethylindenyl, $\eta^5$-n-propylindenyl, $\eta^5$-isopropylindenyl, $\eta^5$-n-butylindenyl, $\eta^5$-sec-butylindenyl, $\eta^5$-tert-butylindenyl, $\eta^5$-n-pentylindenyl, $\eta^5$-neopentylindenyl, $\eta^5$-n-hexylindenyl, $\eta^5$-n-octylindenyl, $\eta^5$-n-decylindenyl, $\eta^5$-phenylindenyl, $\eta^5$-methylphenylindenyl, $\eta^5$-naphthylindenyl, $\eta^5$-trimethylsilylindenyl, $\eta^5$-triethylsilylindenyl, $\eta^5$-tert-butyldimethylsilylindenyl, $\eta^5$-tetrahydroindenyl, $\eta^5$-fluorenyl, $\eta^5$-methylfluorenyl, $\eta^5$-dimethylfluorenyl, $\eta^5$-ethylfluorenyl, $\eta^5$-diethylfluorenyl, $\eta^5$-n-propylfluorenyl, $\eta^5$-di-n-propylfluorenyl, $\eta^5$-isopropylfluorenyl, $\eta^5$-diisopropylfluorenyl, $\eta^5$-n-butylfluorenyl, $\eta^5$-sec-butylfluorenyl, $\eta^5$-tert-butylfluorenyl, $\eta^5$-di-n-butylfluorenyl, $\eta^5$-di-sec-butylfluorenyl, $\eta^5$-di-tert-butylfluorenyl, $\eta^5$-n-pentylfluorenyl, $\eta^5$-neopentylfluorenyl, $\eta^5$-n-hexylfluorenyl, $\eta^5$-n-octylfluorenyl, $\eta^5$-n-decylfluorenyl, $\eta^5$-n-dodecylfluorenyl, $\eta^5$-phenylfluorenyl, $\eta^5$-di-phenylfluorenyl, $\eta^5$-methylphenylfluorenyl, $\eta^5$-naphthylfluorenyl, η⁵-trimethylsilylfluorenyl, η⁵-bis-trimethylsilylfluorenyl, η⁵-triethylsilylfluorenyl, η⁵-tert-butyldimethylsilylfluorenyl and η⁵-azulenyl groups. η⁵-cyclopentadienyl, η⁵-methylcyclopentadienyl, η⁵-tert-butylcyclopentadienyl, η⁵-tetramethylcyclopentadienyl, η⁵-indenyl, η⁵-fluorenyl and η⁵-azulenyl groups, etc. are preferable.

J¹ is a group linking Cp¹ and D¹ by one or two atoms of Group 14 of the Periodic Table of the Elements. J¹ is —SiR₂—, —CR₂—, —SiR₂SiR₂—, —CR₂CR₂—, —CR═CR—, —CR₂SiR₂— or —GeR₂—. R is a hydrogen atom, an alkyl group having up to 20 carbon atoms which may have a halogen atom as a substituent, an aralkyl group having up to 20 carbon atoms which may have a halogen atom as a substituent, an aryl group having up to 20 carbon atoms which may have a halogen atom as a substituent or a hydrocarbyl-substituted silyl group having up to 20 carbon atoms which may have a halogen atom as a substituent. R groups may be the same or different.

Examples of R include: alkyl groups such as methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl and n-eicosyl groups; aralkyl groups such as benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (3,5-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl and anthracenylmethyl groups; aryl groups such as phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, naphthyl and anthracenyl groups; hydrocarbyl-substituted silyl groups such as methylsilyl, ethylsilyl, phenylsilyl, dimethylsilyl, diethylsilyl, diphenylsilyl, trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyl-dimethylsilyl, tri-n-pentylsilyl, tri-n-hexylsilyl, tricyclohexylsilyl and triphenylsilyl groups; and groups obtained by substituting some or all of hydrogen atoms in these groups by a halogen atom. J¹ is preferably —SiR₂—, —CR₂— or —CR₂CR₂—, and R is preferably a hydrogen atom or a methyl group.

The group which links J¹ and M² and which is bonded to M² at its atom of Group 15 or 16 of the Periodic Table of the Elements, represented by D¹ is, for example, —O—, —S—, —NR— or —PR—, preferably —NR—. R is a hydrogen atom, an alkyl group having up to 20 carbon atoms which may have a halogen atom as a substituent, an aralkyl group having up to 20 carbon atoms which may have a halogen atom as a substituent, an aryl group having up to 20 carbon atoms which may have a halogen atom as a substituent or a hydrocarbyl-substituted silyl group having up to 20 carbon atoms which may have a halogen atom as a substituent.

Examples of R include: alkyl groups such as methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl and n-eicosyl groups; aralkyl groups such as benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (3,5-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl and anthracenylmethyl groups; aryl groups such as phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, naphthyl and anthracenyl groups; hydrocarbyl-substituted silyl groups such as methylsilyl, ethylsilyl, phenylsilyl, dimethylsilyl, diethylsilyl, diphenylsilyl, trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyl-dimethylsilyl, tri-n-pentylsilyl, tri-n-hexylsilyl, tricyclohexylsilyl and triphenylsilyl groups; and groups obtained by substituting some or all of hydrogen atoms in these groups by a halogen atom. R is preferably a methyl, ethyl, propyl, butyl, pentyl, hexyl, norbornyl, benzyl or phenyl group, etc.

Furthermore, examples of the group which links J¹ and M² and which is bonded to M² at its atom of Group 15 or 16 of the Periodic Table of the Elements, represented by D¹ include groups represented by the following general formulas (2-1), (2-2), (2-3) and (2-4):

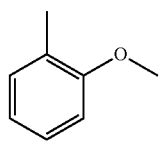

(2-1)

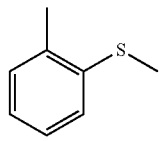

(2-2)

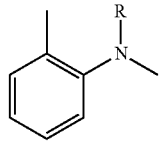

(2-3)

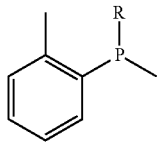

(2-4)

The general formula (2-1) is preferable. R is a hydrogen atom, an alkyl group having up to 20 carbon atoms which may have a halogen atom as a substituent, an aralkyl group having up to 20 carbon atoms which may have a halogen atom as a substituent, an aryl group having up to 20 carbon atoms which may have a halogen atom as a substituent or a hydrocarbyl-substituted silyl group having up to 20 carbon atoms which may have a halogen atom as a substituent. Examples of R include: alkyl groups such as methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl and n-eicosyl groups; aralkyl groups such as benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (3,5-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl and anthracenylmethyl groups; aryl groups such as phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, naphthyl and anthracenyl groups; hydrocarbyl-substituted silyl groups such as methylsilyl, ethylsilyl, phenylsilyl, dimethylsilyl, diethylsilyl, diphenylsilyl, trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyl-dimethylsilyl, tri-n-pentylsilyl, tri-n-hexylsilyl, tricyclohexylsilyl and triphenylsilyl groups; and groups obtained by substituting some or all of hydrogen atoms in these groups by a halogen atom. R is preferably a methyl, ethyl, propyl, butyl, pentyl, hexyl, norbornyl, benzyl or phenyl group, etc.

Moreover, a hydrogen atom on the benzene ring in the general formulas (2-1), (2-2), (2-3) and (2-4) may be substituted with
a halogen atom,
an alkyl group having 1 to 20 carbon atoms which may have a halogen atom as a substituent,
an alkoxy group having 1 to 20 carbon atoms which may have a halogen atom as a substituent,
an aryl group having 6 to 20 carbon atoms which may have a halogen atom as a substituent,
an aryloxy group having 6 to 20 carbon atoms which may have a halogen atom as a substituent,
an aralkyl group having 7 to 20 carbon atoms which may have a halogen atom as a substituent,
an aralkyloxy group having 7 to 20 carbon atoms which may have a halogen atom as a substituent,
a substituted silyl group represented by $-Si(R^{12})_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or
a disubstituted amino group represented by $-N(R^{13})_2$, wherein the two $R^{13}$ groups each independently represent a hydrocarbyl group or a halogenated hydrocarbyl group, and the total number of the carbon atoms in the two $R^{13}$ groups is 2 to 20.

Examples of the halogen atom in $X^4$, $X^5$ and the substituent on the benzene ring in the general formulas (2-1), (2-2), (2-3) and (2-4) include fluorine, chlorine, bromine and iodine atoms.

Examples of the alkyl group having 1 to 20 carbon atoms in $X^4$, $X^5$ and the substituent on the benzene ring in the general formulas (2-1), (2-2), (2-3) and (2-4) include methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl and n-eicosyl groups.

Moreover, the phrase "may have a halogen atom as a substituent" in the "alkyl group which may have a halogen atom as a substituent" means that some or all of hydrogen atoms in the alkyl group may be substituted with a halogen atom. Examples of the halogen atom include fluorine, chlorine, bromine and iodine atoms. Examples of the alkyl group having 1 to 20 carbon atoms having a halogen atom as a substituent include fluoromethyl, difluoromethyl, trifluoromethyl, chloromethyl, dichloromethyl, trichloromethyl, bromomethyl, dibromomethyl, tribromomethyl, iodomethyl, diiodomethyl, triiodomethyl, fluoroethyl, difluoroethyl, trifluoroethyl, tetrafluoroethyl, pentafluoroethyl, chloroethyl, dichloroethyl, trichloroethyl, tetrachloroethyl, pentachloroethyl, bromoethyl, dibromoethyl, tribromoethyl, tetrabromoethyl, pentabromoethyl, perfluoropropyl, perfluorobutyl, perfluoropentyl, perfluorohexyl, perfluorooctyl, perfluorododecyl, perfluoropentadecyl, perfluoroeicosyl, perchloropropyl, perchlorobutyl, perchloropentyl, perchlorohexyl, perchlorooctyl, perchlorododecyl, perchloropentadecyl, perchloroeicosyl, perbromopropyl, perbromobutyl, perbromopentyl, perbromohexyl, perbromooctyl, perbromododecyl, perbromopentadecyl and perbromoeicosyl groups.

Examples of the aryl group having 6 to 20 carbon atoms in $X^4$, $X^5$ and the substituent on the benzene ring in the general formulas (2-1), (2-2), (2-3) and (2-4) include phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, naphthyl and anthracenyl groups.

Moreover, the phrase "may have a halogen atom as a substituent" in the "aryl group which may have a halogen atom as a substituent" means that some or all of hydrogen atoms in the aryl group may be substituted with a halogen atom. Examples of the halogen atom include fluorine, chlorine, bromine and iodine atoms. Examples of the aryl group having 6 to 20 carbon atoms having a halogen atom as a substituent include fluorophenyl, difluorophenyl, trifluorophenyl, tetrafluorophenyl, pentafluorophenyl, chlorophenyl, bromophenyl and iodophenyl groups.

Examples of the aralkyl group having 7 to 20 carbon atoms in $X^4$, $X^5$ and the substituent on the benzene ring in the general formulas (2-1), (2-2), (2-3) and (2-4) include benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (3,5-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl and anthracenylmethyl groups.

Any of these aralkyl groups may be substituted by a halogen atom. Examples of the halogen atom include fluorine, chlorine, bromine and iodine atoms.

Moreover, the phrase "may have a halogen atom as a substituent" in the "aralkyl group which may have a halogen atom as a substituent" means that some or all of hydrogen atoms in the aralkyl group may be substituted with a halogen atom. Examples of the halogen atom include fluorine, chlorine, bromine and iodine atoms. Examples of the aralkyl group having 7 to 20 carbon atoms having a halogen atom as a substituent include groups obtained by substituting some or all hydrogen atoms in the aralkyl group by a halogen atom.

Examples of the alkoxy group having 1 to 20 carbon atoms in $X^4$, $X^5$ and the substituent on the benzene ring in the general formulas (2-1), (2-2), (2-3) and (2-4) include methoxy, ethoxy, n-propoxy, isopropoxy, n-butoxy, sec-butoxy, tert-butoxy, n-pentoxy, neopentoxy, n-hexoxy, n-octoxy, n-dodecoxy, n-pentadecoxy and n-eicosoxy.

Moreover, the phrase "may have a halogen atom as a substituent" in the "alkoxy group which may have a halogen atom as a substituent" means that some or all of hydrogen atoms in the alkoxy group may be substituted with a halogen atom. Examples of the halogen atom include fluorine, chlorine, bromine and iodine atoms. Examples of the alkoxy group having 1 to 20 carbon atoms having a halogen atom as a substituent include groups obtained by substituting some or all hydrogen atoms in the alkoxy group by a halogen atom.

Examples of the aryloxy group having 6 to 20 carbon atoms in $X^4$, $X^5$ and the substituent on the benzene ring in the general formulas (2-1), (2-2), (2-3) and (2-4) include aryloxy groups having 6 to 20 carbon atoms, such as phenoxy, 2-methylphenoxy, 3-methylphenoxy, 4-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2,3,4-trimethylphenoxy, 2,3,5-trimethylphenoxy, 2,3,6-trimethylphenoxy, 2,4,5-trimethylphenoxy, 2,4,6-trimethylphenoxy, 3,4,5-trimethylphenoxy, 2,3,4,5-tetramethylphenoxy, 2,3,4,6-tetramethylphenoxy, 2,3,5,6-tetramethylphenoxy, pentamethylphenoxy, ethylphenoxy, n-propylphenoxy, isopropylphenoxy, n-butylphenoxy, sec-butylphenoxy, tert-butylphenoxy, n-hexylphenoxy, n-octylphenoxy, n-decylphenoxy, n-tetradecylphenoxy, naphthoxy and anthracenoxy groups.

Moreover, the phrase "may have a halogen atom as a substituent" in the "aryloxy group which may have a halogen atom as a substituent" means that some or all of hydrogen atoms in the aryloxy group may be substituted with a halogen atom. Examples of the halogen atom include fluorine, chlorine, bromine and iodine atoms. Examples of the aryloxy group having 6 to 20 carbon atoms having a halogen atom as a substituent include groups obtained by substituting some or all hydrogen atoms in the aryloxy group by a halogen atom.

Examples of the aralkyloxy group having 7 to 20 carbon atoms in $X^4$, $X^5$ and the substituent on the benzene ring in the general formulas (2-1), (2-2), (2-3) and (2-4) include benzyloxy, (2-methylphenyl)methoxy, (3-methylphenyl)methoxy, (4-methylphenyl)methoxy, (2,3-dimethylphenyl)methoxy, (2,4-dimethylphenyl)methoxy, (2,5-dimethylphenyl)methoxy, (2,6-dimethylphenyl)methoxy, (3,4-dimethylphenyl)methoxy, (3,5-dimethylphenyl)methoxy, (2,3,4-trimethylphenyl)methoxy, (2,3,5-trimethylphenyl)methoxy, (2,3,6-trimethylphenyl)methoxy, (2,4,5-trimethylphenyl)methoxy, (2,4,6-trimethylphenyl)methoxy, (3,4,5-trimethylphenyl)methoxy, (2,3,4,5-tetramethylphenyl)methoxy, (2,3,4,6-tetramethylphenyl)methoxy, (2,3,5,6-tetramethylphenyl)methoxy, (pentamethylphenyl)methoxy, (ethylphenyl)methoxy, (n-propylphenyl)methoxy, (isopropylphenyl)methoxy, (n-butylphenyl)methoxy, (sec-butylphenyl)methoxy, (tert-butylphenyl)methoxy, (n-hexylphenyl)methoxy, (n-octylphenyl)methoxy, (n-decylphenyl)methoxy, (n-tetradecylphenyl)methoxy, naphthylmethoxy and anthracenylmethoxy groups.

Moreover, the phrase "may have a halogen atom as a substituent" in the "aralkyloxy group which may have a halogen atom as a substituent" means that some or all of hydrogen atoms in the aralkyloxy group may be substituted with a halogen atom. Examples of the halogen atom include fluorine, chlorine, bromine and iodine atoms. Examples of the aralkyloxy group having 7 to 20 carbon atoms having a halogen atom as a substituent include groups obtained by substituting some or all hydrogen atoms in the aralkyloxy group by a halogen atom.

In the substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, in $X^4$, $X^5$ and the substituent on the benzene ring in the general formulas (2-1), (2-2), (2-3) and (2-4), the $R^{12}$ groups are each independently a hydrogen atom; a hydrocarbyl group such as an alkyl group having 1 to 10 carbon atoms (e.g., methyl, ethyl, n-propyl, isopropyl, n-butyl, sec-butyl, tert-butyl, isobutyl, n-pentyl, n-hexyl, cyclohexyl, n-heptyl, n-octyl, n-nonyl and n-decyl groups) and an aryl group (e.g., a phenyl group); or a halogenated hydrocarbyl group obtained by substituting some or all hydrogen atoms in the hydrocarbyl group by a halogen atom, and the total number of the carbon atoms in the three $R^{12}$ groups is in the range of 1 to 20. The total number of the carbon atoms in these three $R^{12}$ groups is preferably in the range of 3 to 18. Specific examples of the substituted silyl group include: monosubstituted silyl groups having one hydrocarbyl or halogenated hydrocarbyl group, such as methylsilyl, ethylsilyl and phenylsilyl groups, and groups obtained by substituting some or all hydrogen atoms in the hydrocarbyl groups of these groups by a halogen atom; disubstituted silyl groups having two hydrocarbyl and/or hydrocarbyl halide groups, such as dimethylsilyl, diethylsilyl and diphenylsilyl groups, and groups obtained by substituting some or all hydrogen atoms in the hydrocarbyl groups of these groups by a halogen atom; and trisubstituted silyl groups having three hydrocarbyl and/or hydrocarbyl halide groups, such as trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyldimethylsilyl, tri-n-pentylsilyl, tri-n-hexylsilyl, tricyclohexylsilyl and triphenylsilyl groups, and groups obtained by substituting some or all hydrogen atoms in the hydrocarbyl groups of these groups by a halogen atom. Of them, trisubstituted silyl groups are preferable, and trimethylsilyl, tert-butyldimethylsilyl and triphenylsilyl groups, and groups obtained by substituting some or all hydrogen atoms in these groups by a halogen atom are more preferable.

In the disubstituted amino group represented by $-N(R^{13})_2$, wherein the two $R^{13}$ groups each independently represent a hydrocarbyl group or a halogenated hydrocarbyl group, and the total number of the carbon atoms in the two $R^{13}$ groups is 2 to 20, in $X^4$, $X^5$ and the substituent on the benzene ring in the general formulas (2-1), (2-2), (2-3) and (2-4), the $R^{13}$ groups each independently represent a hydrocarbyl group or a halogenated hydrocarbyl group, and the total number of the carbon atoms in the two $R^{13}$ groups is in the range of 2 to 20, more preferably in the range of 2 to 10. The hydrocarbyl group and the halogenated hydrocarbyl group are the same as those described as a hydrocarbyl group and a halogenated hydrocarbyl group for the substituted silyl group. Moreover, these two $R^{13}$ groups may be bonded to each other to form a ring together with the nitrogen atom to which the two $R^{13}$ groups are bonded. Examples of such a disubstituted amino group include dimethylamino, diethylamino, di-n-propylamino, diisopropylamino, di-n-butylamino, di-sec-butylamino, di-tert-butylamino, di-isobutylamino, tert-butylisopropylamino, di-n-hexylamino, di-n-octylamino, di-n-decylamino, diphenylamino, bistrimethyl silylamino, bis-tert-butyldimethylsilylamino, pyrrolyl, pyrrolidinyl, piperidinyl, carbazolyl, dihydroindolyl and dihydroisoindolyl groups, and groups obtained by substituting some or all hydrogen atoms in these groups by a halogen atom. Of them, dimethylamino, diethylamino, pyrrolidinyl and piperidinyl groups, and groups obtained by substituting some or all hydrogen atoms in these groups by a halogen atom are preferable.

The transition metal complex represented by the general formula (2) is preferably a complex wherein q is 1, more preferably wherein q is 1, and $D^1$ is a group binding to $M^2$ by a nitrogen atom or a group represented by the general formula (2-1), even more preferably wherein q is 1, and $D^1$ is a group represented by the general formula (2-1).

The transition metal complexes represented by the general formulas (3) and (4) will be described in detail.

Examples of the transition metal atom of Group 4 of the Periodic Table of the Elements (IUPAC Nomenclature of Inorganic Chemistry, Revised, 1989) in $M^3$ include titanium, zirconium and hafnium atoms. Zirconium and hafnium atoms are preferable.

Examples of the transition metal atom of Group 4 of the Periodic Table of the Elements (IUPAC Nomenclature of Inorganic Chemistry, Revised, 1989) in $M^4$ include titanium, zirconium and hafnium atoms. Titanium and zirconium atoms are preferable.

$A^1$ is a group linking $J^3$ and $M^4$ by an oxygen, sulfur, nitrogen or phosphorus atom. $A^1$ is, for example, $-O-$, $-S-$, $-NR-$ or $-PR-$, preferably $-NR-$. However, R is a hydrogen atom, an alkyl group having up to 20 carbon atoms which may have a halogen atom as a substituent, an aralkyl group having up to 20 carbon atoms which may have a halogen atom as a substituent, an aryl group having up to 20 carbon atoms which may have a halogen atom as a substituent or a hydrocarbyl-substituted silyl group having up to 20 carbon atoms which may have a halogen atom as a substituent.

Examples of R include: alkyl groups such as methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl and n-eicosyl groups; aralkyl groups such as benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (3,5-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl and anthracenylmethyl groups; aryl groups such as phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, naphthyl and anthracenyl groups; hydrocarbyl-substituted silyl groups such as methylsilyl, ethylsilyl, phenylsilyl, dimethylsilyl, diethylsilyl, diphenylsilyl, trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyl-dimethylsilyl, tri-n-pentylsilyl, tri-n-hexylsilyl, tricyclohexylsilyl and triphenylsilyl groups; and groups obtained by substituting some or all hydrogen atoms in these groups by a halogen atom. R is preferably a methyl, ethyl, propyl, butyl, pentyl, hexyl, norbornyl, benzyl or phenyl group, etc.

$J^2$ is a group linking $Cp^2$ and $Cp^3$ by one or two atoms of Group 14 of the Periodic Table of the Elements, and $J^3$ is a group linking $Cp^4$ and $A^1$ by one or two atoms of Group 14 of the Periodic Table of the Elements. $J^2$ and $J^3$ are each independently $-SiR_2-$, $-CR_2-$, $-SiR_2SiR_2-$, $-CR_2CR_2-$, $-CR=CR-$, $-CR_2SiR_2-$ or $-GeR_2-$. However, R is a hydrogen atom, an alkyl group having up to 20 carbon atoms which may have a halogen atom as a substituent, an aralkyl group having up to 20 carbon atoms which may have a halogen atom as a substituent, an aryl group having up to 20 carbon atoms which may have a halogen atom as a substituent or a hydrocarbyl-substituted silyl group having up to 20 carbon atoms which may have a halogen atom as a substituent. A plurality of R moieties may be the same or different.

Examples of R include: alkyl groups such as methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl and n-eicosyl groups; aralkyl groups such as benzyl, (2-methylphenyl)methyl, (3-methylphenyl)

methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (3,5-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl and anthracenylmethyl groups; aryl groups such as phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, naphthyl and anthracenyl groups; hydrocarbyl-substituted silyl groups such as methylsilyl, ethylsilyl, phenylsilyl, dimethylsilyl, diethylsilyl, diphenylsilyl, trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyl-dimethylsilyl, tri-n-pentylsilyl, tri-n-hexylsilyl, tricyclohexylsilyl and triphenylsilyl groups; and groups obtained by substituting some or all hydrogen atoms in these groups by a halogen atom. $J^2$ and $J^3$ are preferably —$SiR_2$—, —$CR_2$— or —$CR_2CR_2$—, and R is preferably a hydrogen atom or a methyl group.

Examples of the group having a cyclopentadiene-type anionic skeleton represented by the substituents $Cp^2$, $Cp^3$ and $Cp^4$ include $\eta^5$-cyclopentadienyl, $\eta^5$-methylcyclopentadienyl, $\eta^5$-dimethylcyclopentadienyl, $\eta^5$-trimethylcyclopentadienyl, $\eta^5$-tetramethylcyclopentadienyl, $\eta^5$-ethylcyclopentadienyl, $\eta^5$-n-propylcyclopentadienyl, $\eta^5$-isopropylcyclopentadienyl, $\eta^5$-n-butylcyclopentadienyl, $\eta^5$-sec-butylcyclopentadienyl, $\eta^5$-tert-butylcyclopentadienyl, $\eta^5$-n-pentylcyclopentadienyl, $\eta^5$-neopentylcyclopentadienyl, $\eta^5$-n-hexylcyclopentadienyl, $\eta^5$-n-octylcyclopentadienyl, $\eta^5$-phenylcyclopentadienyl, $\eta^5$-naphthylcyclopentadienyl, $\eta^5$-trimethylsilylcyclopentadienyl, $\eta^5$-triethylsilylcyclopentadienyl, $\eta^5$-tert-butyldimethylsilylcyclopentadienyl, $\eta^5$-indenyl, $\eta^5$-methylindenyl, $\eta^5$-dimethylindenyl, $\eta^5$-ethylindenyl, $\eta^5$-n-propylindenyl, $\eta^5$-isopropylindenyl, $\eta^5$-n-butylindenyl, $\eta^5$-sec-butylindenyl, $\eta^5$-tert-butylindenyl, $\eta^5$-n-pentylindenyl, $\eta^5$-neopentylindenyl, $\eta^5$-n-hexylindenyl, $\eta^5$-n-octylindenyl, $\eta^5$-n-decylindenyl, $\eta^5$-phenylindenyl, $\eta^5$-methylphenylindenyl, $\eta^5$-naphthylindenyl, $\eta^5$-trimethylsilylindenyl, $\eta^5$-triethylsilylindenyl, $\eta^5$-tert-butyldimethylsilylindenyl, $\eta^5$-tetrahydroindenyl, $\eta^5$-fluorenyl, $\eta^5$-methylfluorenyl, $\eta^5$-dimethylfluorenyl, $\eta^5$-ethylfluorenyl, $\eta^5$-diethylfluorenyl, $\eta^5$-n-propylfluorenyl, $\eta^5$-di-n-propylfluorenyl, $\eta^5$-isopropylfluorenyl, $\eta^5$-diisopropylfluorenyl, $\eta^5$-n-butylfluorenyl, $\eta^5$-sec-butylfluorenyl, $\eta^5$-tert-butylfluorenyl, $\eta^5$-di-n-butylfluorenyl, $\eta^5$-di-sec-butylfluorenyl, $\eta^5$-di-tert-butylfluorenyl, $\eta^5$-n-pentylfluorenyl, $\eta^5$-neopentylfluorenyl, $\eta^5$-n-hexylfluorenyl, $\eta^5$-n-octylfluorenyl, $\eta^5$-n-decylfluorenyl, $\eta^5$-n-dodecylfluorenyl, $\eta^5$-phenylfluorenyl, $\eta^5$-di-phenylfluorenyl, $\eta^5$-methylphenylfluorenyl, $\eta^5$-naphthylfluorenyl, $\eta^5$-trimethylsilylfluorenyl, $\eta^5$-bis-trimethylsilylfluorenyl, $\eta^5$-triethylsilylfluorenyl, $\eta^5$-tert-butyldimethylsilylfluorenyl and $\eta^5$-azulenyl groups. $\eta^5$-cyclopentadienyl, $\eta^5$-methylcyclopentadienyl, $\eta^5$-tert-butylcyclopentadienyl, $\eta^5$-tetramethylcyclopentadienyl, $\eta^5$-indenyl, $\eta^5$-fluorenyl and $\eta^5$-azulenyl groups, etc. are preferable.

Examples of the halogen atom in $X^6$, $X^7$, $X^8$ and $X^9$ include fluorine, chlorine, bromine and iodine atoms.

Examples of the alkyl group having 1 to 20 carbon atoms in $X^6$, $X^7$, $X^8$ and $X^9$ include methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl and n-eicosyl groups.

Moreover, the phrase "may have a halogen atom as a substituent" in the "alkyl group which may have a halogen atom as a substituent" means that some or all of hydrogen atoms in the alkyl group may be substituted with a halogen atom. Examples of the halogen atom include fluorine, chlorine, bromine and iodine atoms. Examples of the alkyl group having 1 to 20 carbon atoms having a halogen atom as a substituent include fluoromethyl, difluoromethyl, trifluoromethyl, chloromethyl, dichloromethyl, trichloromethyl, bromomethyl, dibromomethyl, tribromomethyl, iodomethyl, diiodomethyl, triiodomethyl, fluoroethyl, difluoroethyl, trifluoroethyl, tetrafluoroethyl, pentafluoroethyl, chloroethyl, dichloroethyl, trichloroethyl, tetrachloroethyl, pentachloroethyl, bromoethyl, dibromoethyl, tribromoethyl, tetrabromoethyl, pentabromoethyl, perfluoropropyl, perfluorobutyl, perfluoropentyl, perfluorohexyl, perfluorooctyl, perfluorododecyl, perfluoropentadecyl, perfluoroeicosyl, perchloropropyl, perchlorobutyl, perchloropentyl, perchlorohexyl, perchlorooctyl, perchlorododecyl, perchloropentadecyl, perchloroeicosyl, perbromopropyl, perbromobutyl, perbromopentyl, perbromohexyl, perbromooctyl, perbromododecyl, perbromopentadecyl and perbromoeicosyl groups.

Examples of the aryl group having 6 to 20 carbon atoms in $X^6$, $X^7$, $X^8$ and $X^9$ include phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, naphthyl and anthracenyl groups.

Moreover, the phrase "may have a halogen atom as a substituent" in the "aryl group which may have a halogen atom as a substituent" means that some or all of hydrogen atoms in the aryl group may be substituted with a halogen atom. Examples of the halogen atom include fluorine, chlorine, bromine and iodine atoms. Examples of the aryl group having 6 to 20 carbon atoms having a halogen atom as a substituent include fluorophenyl, difluorophenyl, trifluorophenyl, tetrafluorophenyl, pentafluorophenyl, chlorophenyl, bromophenyl and iodophenyl groups.

Examples of the aralkyl group having 7 to 20 carbon atoms in $X^6$, $X^7$, $X^8$ and $X^9$ include benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (3,5-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)

methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl and anthracenylmethyl groups.

Any of these aralkyl groups may be substituted by a halogen atom. Examples of the halogen atom include fluorine, chlorine, bromine and iodine atoms.

Moreover, the phrase "may have a halogen atom as a substituent" in the "aralkyl group which may have a halogen atom as a substituent" means that some or all of hydrogen atoms in the aralkyl group may be substituted with a halogen atom. Examples of the halogen atom include fluorine, chlorine, bromine and iodine atoms. Examples of the aralkyl group having 7 to 20 carbon atoms having a halogen atom as a substituent include groups obtained by substituting some or all of hydrogen atoms in the aralkyl group with a halogen atom.

Examples of the alkoxy group having 1 to 20 carbon atoms in $X^6$, $X^7$, $X^8$ and $X^9$ include methoxy, ethoxy, n-propoxy, isopropoxy, n-butoxy, sec-butoxy, tert-butoxy, n-pentoxy, neopentoxy, n-hexoxy, n-octoxy, n-dodecoxy, n-pentadecoxy and n-eicosoxy.

Moreover, the phrase "may have a halogen atom as a substituent" in the "alkoxy group which may have a halogen atom as a substituent" means that some or all of hydrogen atoms in the alkoxy group may be substituted with a halogen atom. Examples of the halogen atom include fluorine, chlorine, bromine and iodine atoms. Examples of the alkoxy group having 1 to 20 carbon atoms having a halogen atom as a substituent include groups obtained by substituting some or all of hydrogen atoms in the alkoxy group with a halogen atom.

Examples of the aryloxy group having 6 to 20 carbon atoms in $X^6$, $X^7$, $X^8$ and $X^9$ include aryloxy groups having 6 to 20 carbon atoms, such as phenoxy, 2-methylphenoxy, 3-methylphenoxy, 4-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2,3,4-trimethylphenoxy, 2,3,5-trimethylphenoxy, 2,3,6-trimethylphenoxy, 2,4,5-trimethylphenoxy, 2,4,6-trimethylphenoxy, 3,4,5-trimethylphenoxy, 2,3,4,5-tetramethylphenoxy, 2,3,4,6-tetramethylphenoxy, 2,3,5,6-tetramethylphenoxy, pentamethylphenoxy, ethylphenoxy, n-propylphenoxy, isopropylphenoxy, n-butylphenoxy, sec-butylphenoxy, tert-butylphenoxy, n-hexylphenoxy, n-octylphenoxy, n-decylphenoxy, n-tetradecylphenoxy, naphthoxy and anthracenoxy groups.

Moreover, the phrase "may have a halogen atom as a substituent" in the "aryloxy group which may have a halogen atom as a substituent" means that some or all of hydrogen atoms in the aryloxy group may be substituted with a halogen atom. Examples of the halogen atom include fluorine, chlorine, bromine and iodine atoms. Examples of the aryloxy group having 6 to 20 carbon atoms having a halogen atom as a substituent include groups obtained by substituting some or all of hydrogen atoms in the aryloxy group with a halogen atom.

Examples of the aralkyloxy group having 7 to 20 carbon atoms in $X^6$, $X^7$, $X^8$ and $X^9$ include benzyloxy, (2-methylphenyl)methoxy, (3-methylphenyl)methoxy, (4-methylphenyl)methoxy, (2,3-dimethylphenyl)methoxy, (2,4-dimethylphenyl)methoxy, (2,5-dimethylphenyl)methoxy, (2,6-dimethylphenyl)methoxy, (3,4-dimethylphenyl)methoxy, (3,5-dimethylphenyl)methoxy, (2,3,4-trimethylphenyl)methoxy, (2,3,5-trimethylphenyl)methoxy, (2,3,6-trimethylphenyl)methoxy, (2,4,5-trimethylphenyl)methoxy, (2,4,6-trimethylphenyl)methoxy, (3,4,5-trimethylphenyl)methoxy, (2,3,4,5-tetramethylphenyl)methoxy, (2,3,4,6-tetramethylphenyl)methoxy, (2,3,5,6-tetramethylphenyl)methoxy, (pentamethylphenyl)methoxy, (ethylphenyl)methoxy, (n-propylphenyl)methoxy, (isopropylphenyl)methoxy, (n-butylphenyl)methoxy, (sec-butylphenyl)methoxy, (tert-butylphenyl)methoxy, (n-hexylphenyl)methoxy, (n-octylphenyl)methoxy, (n-decylphenyl)methoxy, (n-tetradecylphenyl)methoxy, naphthylmethoxy and anthracenylmethoxy groups.

Moreover, the phrase "may have a halogen atom as a substituent" in the "aralkyloxy group which may have a halogen atom as a substituent" means that some or all of hydrogen atoms in the aralkyloxy group may be substituted with a halogen atom. Examples of the halogen atom include fluorine, chlorine, bromine and iodine atoms. Examples of the aralkyloxy group having 7 to 20 carbon atoms having a halogen atom as a substituent include groups obtained by substituting some or all of hydrogen atoms in the aralkyloxy group with a halogen atom.

In the substituted silyl group represented by $-Si(R^{12})_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, in $X^6$, $X^7$, $X^8$ and $X^9$, the $R^{12}$ groups are each independently a hydrogen atom; a hydrocarbyl group such as an alkyl group having 1 to 10 carbon atoms (e.g., methyl, ethyl, n-propyl, isopropyl, n-butyl, sec-butyl, tert-butyl, isobutyl, n-pentyl, n-hexyl, cyclohexyl, n-heptyl, n-octyl, n-nonyl and n-decyl groups) and an aryl group (e.g., a phenyl group); or a halogenated hydrocarbyl group obtained by substituting some or all hydrogen atoms in the hydrocarbyl group by a halogen atom, and the total number of the carbon atoms in the three $R^{12}$ groups is in the range of 1 to 20. The total number of the carbon atoms in these three $R^{12}$ groups is preferably in the range of 3 to 18. Specific examples of the substituted silyl group include: monosubstituted silyl groups having one hydrocarbyl or halogenated hydrocarbyl group, such as methylsilyl, ethylsilyl and phenylsilyl groups, and groups obtained by substituting some or all hydrogen atoms in the hydrocarbyl groups of these groups by a halogen atom; disubstituted silyl groups having two hydrocarbyl and/or halogenated hydrocarbyl groups, such as dimethylsilyl, diethylsilyl and diphenylsilyl groups, and groups obtained by substituting some or all hydrogen atoms in the hydrocarbyl groups of these groups by a halogen atom; and trisubstituted silyl groups having three hydrocarbyl and/or halogenated hydrocarbyl groups, such as trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyl-dimethylsilyl, tri-n-pentylsilyl, tri-n-hexylsilyl, tricyclohexylsilyl and triphenylsilyl groups, and groups obtained by substituting some or all hydrogen atoms in the hydrocarbyl groups of these groups by a halogen atom. Of them, trisubstituted silyl groups are preferable, and trimethylsilyl, tert-butyldimethylsilyl and triphenylsilyl groups, and groups obtained by substituting some or all hydrogen atoms in these groups by a halogen atom are more preferable.

In the disubstituted amino group represented by $-N(R^{13})_2$, wherein the two $R^{13}$ groups each independently represent a hydrocarbyl group or a halogenated hydrocarbyl group, and the total number of the carbon atoms in the two $R^{13}$ groups is 2 to 20, in $X^6$, $X^7$, $X^8$ and $X^9$, the $R^{13}$ groups each independently represent a hydrocarbyl group or a halogenated hydrocarbyl group, and the total number of the carbon atoms in the two $R^{13}$ groups is in the range of 2 to 20, more preferably in the range of 2 to 10. The hydrocarbyl group and the halogenated hydrocarbyl group are the same as those described as a hydrocarbyl group and a halogenated hydrocarbyl group for the substituted silyl group. Moreover, these two $R^{13}$ groups may be bonded to each other to form a ring together with the nitrogen atom to which the two $R^{13}$ groups are bonded thereto. Examples of such a disubstituted amino group include dimethylamino, diethylamino, di-n-propylamino, diisopropylamino, di-n-butylamino, di-sec-butylamino, di-tert-butylamino, di-isobutylamino, tert-butylisopropylamino, di-n-hexylamino, di-n-octylamino, di-n-decylamino, diphenylamino, bistrimethyl silylamino, bis-tert-butyldimethyl silylamino, pyrrolyl, pyrrolidinyl, piperidinyl, carbazolyl, dihydroindolyl and dihydroisoindolyl groups, and groups obtained by substituting some or all hydrogen atoms in these groups by a halogen atom. Of them, dimethylamino, diethylamino, pyrrolidinyl and piperidinyl groups, and groups obtained by substituting some or all hydrogen atoms in these groups by a halogen atom are preferable.

The transition metal complex represented by the general formula (3) can be produced, for example, by a method described in JP 3290218B.

Examples of the complex represented by the general formula (3) include methylenebis(cyclopentadienyl)zirconium dichloride, isopropylidenebis(cyclopentadienyl)zirconium dichloride, diphenylmethylenebis(cyclopentadienyl)zirconium dichloride, 1,2-ethylene-bis(cyclopentadienyl)zirconium dichloride, dimethylsilylenebis(cyclopentadienyl)zirconium dichloride, diphenylsilylenebis(cyclopentadienyl)zirconium dichloride, 1,2-tetramethyldisilylene-bis(cyclopentadienyl)zirconium dichloride, methylenebis(methylcyclopentadienyl)zirconium dichloride, isopropylidenebis(methylcyclopentadienyl)zirconium dichloride, diphenylmethylenebis(methylcyclopentadienyl)zirconium dichloride, 1,2-ethylene-bis(methylcyclopentadienyl)zirconium dichloride, dimethylsilylenebis(methylcyclopentadienyl)zirconium dichloride, diphenylsilylenebis(methylcyclopentadienyl)zirconium dichloride, 1,2-tetramethyldisilylene-bis(methylcyclopentadienyl)zirconium dichloride, methylenebis(n-butylcyclopentadienyl)zirconium dichloride, isopropylidenebis(n-butylcyclopentadienyl)zirconium dichloride, diphenylmethylenebis(n-butylcyclopentadienyl)zirconium dichloride, 1,2-ethylene-bis(n-butylcyclopentadienyl)zirconium dichloride, dimethylsilylenebis(n-butylcyclopentadienyl)zirconium dichloride, diphenylsilylenebis(n-butylcyclopentadienyl)zirconium dichloride, 1,2-tetramethyldisilylene-bis(n-butylcyclopentadienyl)zirconium dichloride, methylenebis(tert-butylcyclopentadienyl)zirconium dichloride, isopropylidenebis(tert-butylcyclopentadienyl)zirconium dichloride, diphenylmethylenebis(tert-butylcyclopentadienyl)zirconium dichloride, 1,2-ethylene-bis(tert-butylcyclopentadienyl)zirconium dichloride, dimethylsilylenebis(tert-butylcyclopentadienyl)zirconium dichloride, diphenylsilylenebis(tert-butylcyclopentadienyl)zirconium dichloride, 1,2-tetramethyldisilylene-bis(tert-butylcyclopentadienyl)zirconium dichloride, methylenebis(tetramethylcyclopentadienyl)zirconium dichloride, isopropylidenebis(tetramethylcyclopentadienyl)zirconium dichloride, diphenylmethylenebis(tetramethylcyclopentadienyl)zirconium dichloride, 1,2-ethylene-bis(tetramethylcyclopentadienyl)zirconium dichloride, dimethylsilylenebis(tetramethylcyclopentadienyl)zirconium dichloride, diphenylsilylenebis(tetramethylcyclopentadienyl)zirconium dichloride, 1,2-tetramethyldisilylene-bis(tetramethylcyclopentadienyl)zirconium dichloride, methylenebis(indenyl)zirconium dichloride, isopropylidenebis(indenyl)zirconium dichloride, diphenylmethylenebis(indenyl)zirconium dichloride, 1,2-ethylene-bis(indenyl)zirconium dichloride, dimethylsilylenebis(indenyl)zirconium dichloride, diphenylsilylenebis(indenyl)zirconium dichloride, 1,2-tetramethyldisilylene-bis(indenyl)zirconium dichloride, methylenebis(fluorenyl)zirconium dichloride, isopropylidenebis(fluorenyl)zirconium dichloride, diphenylmethylenebis(fluorenyl)zirconium dichloride, 1,2-ethylene-bis(fluorenyl)zirconium dichloride, dimethylsilylenebis(fluorenyl)zirconium dichloride, diphenylsilylenebis(fluorenyl)zirconium dichloride, 1,2-tetramethyldisilylene-bis(fluorenyl)zirconium dichloride, methylenebis(azulenyl)zirconium dichloride, isopropylidenebis(azulenyl)zirconium dichloride, diphenylmethylenebis(azulenyl)zirconium dichloride, 1,2-ethylene-bis(azulenyl)zirconium dichloride, dimethylsilylenebis(azulenyl)zirconium dichloride, diphenylsilylenebis(azulenyl)zirconium dichloride, 1,2-tetramethyldisilylene-bis(azulenyl)zirconium dichloride, methylenebis[2-ethyl-4-(2-fluoro-4-biphenylyl)-4H-azulenyl]zirconium dichloride, isopropylidenebis[2-ethyl-4-(2-fluoro-4-biphenylyl)-4H-azulenyl]zirconium dichloride, diphenylmethylenebis[2-ethyl-4-(2-fluoro-4-biphenylyl)-4H-azulenyl]zirconium dichloride, 1,2-ethylenebis[2-ethyl-4-(2-fluoro-4-biphenylyl)-4H-azulenyl]zirconium dichloride, dimethylsilylenebis[2-ethyl-4-(2-fluoro-4-biphenylyl)-4H-azulenyl]zirconium dichloride, diphenylsilylenebis[2-ethyl-4-(2-fluoro-4-biphenylyl)-4H-azulenyl]zirconium dichloride, 1,2-tetramethyldisilylenebis[2-ethyl-4-(2-fluoro-4-biphenylyl)-4H-azulenyl]zirconium dichloride, methylene(cyclopentadienyl)(tetramethylcyclopentadienyl)zirconium dichloride, isopropylidene(cyclopentadienyl)(tetramethylcyclopentadienyl)zirconium dichloride, diphenylmethylene(cyclopentadienyl)(tetramethylcyclopentadienyl)zirconium dichloride, 1,2-ethylene-(cyclopentadienyl)(tetramethylcyclopentadienyl)zirconium dichloride, dimethylsilylene(cyclopentadienyl)(tetramethylcyclopentadienyl)zirconium dichloride, diphenylsilylene(cyclopentadienyl)(tetramethylcyclopentadienyl)zirconium dichloride, 1,2-tetramethyldisilylene-(cyclopentadienyl)(tetramethylcyclopentadienyl)zirconium dichloride, methylene(cyclopentadienyl)(indenyl)zirconium dichloride, isopropylidene(cyclopentadienyl)(indenyl)zirconium dichloride, diphenylmethylene(cyclopentadienyl)(indenyl)zirconium dichloride, 1,2-ethylene-(cyclopentadienyl)(indenyl)zirconium dichloride, dimethylsilylene(cyclopentadienyl)(indenyl)zirconium dichloride, diphenylsilylene(cyclopentadienyl)(indenyl)zirconium dichloride, 1,2-tetramethyldisilylene-(cyclopentadienyl)(indenyl)zirconium dichloride, methylene(cyclopentadienyl)(fluorenyl)zirconium dichloride, isopropylidene(cyclopentadienyl)(fluorenyl)zirconium dichloride, diphenylmethylene(cyclopentadienyl)(fluorenyl)zirconium dichloride, 1,2-ethylene-(cyclopentadienyl)(fluorenyl)zirconium dichloride, dimethylsilylene(cyclopentadienyl)(fluorenyl)zirconium dichloride, diphenylsilylene(cyclopentadienyl)(fluorenyl)zirconium dichloride, 1,2-tetramethyldisilylene-(cyclopentadienyl)(fluorenyl)zirconium dichloride, methylene(3-tert-butyl-5-methylcyclopentadienyl)(3,6-di-tert-butylfluorenyl)zirconium dichloride, isopropylidene (3-tert-butyl-5-methylcyclopentadienyl)(3,6-di-tert-butylfluorenyl)zirconium dichloride, diphenylmethylene(3-tert-butyl-5-methylcyclopentadienyl)(3,6-di-tert-butylfluorenyl)zirconium dichloride, 1,2-ethylene-(3-tert-butyl-5-methylcyclopentadienyl)(3,6-di-tert-butylfluorenyl)zirconium dichloride, dimethylsilylene(3-tert-butyl-5-methylcyclopentadienyl)(3,6-di-tert-butylfluorenyl)zirconium dichloride, diphenylsilylene(3-tert-butyl-5-methylcyclopentadienyl)(3,6-di-tert-butylfluorenyl)zirconium dichloride, 1,2-tetramethyldisilylene-(3-tert-butyl-5-methylcyclopentadienyl)(3,6-di-tert-butylfluorenyl)zirconium dichloride, methylenebis(cyclopentadienyl)hafnium dichloride, isopropylidenebis(cyclopentadienyl)hafnium dichloride, diphenylmethylenebis(cyclopentadienyl)hafnium dichloride, 1,2-ethylene-bis(cyclopentadienyl)hafnium dichloride, dimethylsilylenebis(cyclopentadienyl)hafnium dichloride, diphenylsilylenebis(cyclopentadienyl)hafnium dichloride, 1,2-tetramethyldisilylene-bis(cyclopentadienyl)hafnium dichloride, methylenebis(methylcyclopentadienyl)hafnium dichloride, isopropylidenebis(methylcyclopentadienyl)hafnium dichloride, diphenylmethylenebis(methylcyclopentadienyl)hafnium dichloride, 1,2-ethylene-bis(methylcyclopentadienyl)hafnium dichloride, dimethylsilylenebis(methylcyclopentadienyl)hafnium dichloride, diphenylsilylenebis(methylcyclopentadienyl)hafnium dichloride, 1,2-tetramethyldisilylene-bis(methylcyclopentadienyl)hafnium dichloride, methylenebis(n-butylcyclopentadienyl)hafnium dichloride, isopropylidenebis(n-butylcyclopentadienyl)hafnium dichloride, diphenylmethylenebis(n-butylcyclopentadienyl)hafnium dichloride, 1,2-ethylene-bis(n-butylcyclopentadienyl)hafnium dichloride, dimethylsilylenebis(n-butylcyclopentadienyl)hafnium dichloride, diphenylsilylenebis(n-butylcyclopentadienyl)hafnium dichloride, 1,2-tetramethyldisilylene-bis(n-butylcyclopentadienyl)hafnium dichloride, methylenebis(tert-butylcyclopentadienyl)hafnium dichloride, isopropylidenebis(tert-butylcyclopentadienyl)hafnium dichloride, diphenylmethylenebis(tert-butylcyclopentadienyl)hafnium dichloride, 1,2-ethylene-bis(tert-butylcyclopentadienyl)hafnium dichloride, dimethylsilylenebis(tert-butylcyclopentadienyl)hafnium dichloride, diphenylsilylenebis(tert-butylcyclopentadienyl)hafnium dichloride, 1,2-tetramethyldisilylene-bis(tert-butylcyclopentadienyl)hafnium dichloride, methylenebis(tetramethylcyclopentadienyl)hafnium dichloride, isopropylidenebis(tetramethylcyclopentadienyl)hafnium dichloride, diphenylmethylenebis(tetramethylcyclopentadienyl)hafnium dichloride, 1,2-ethylene-bis(tetramethylcyclopentadienyl)hafnium dichloride, dimethylsilylenebis(tetramethylcyclopentadienyl)hafnium dichloride, diphenylsilylenebis(tetramethylcyclopentadienyl)hafnium dichloride, 1,2-tetramethyldisilylene-bis(tetramethylcyclopentadienyl)hafnium dichloride, methylenebis(indenyl)hafnium dichloride, isopropylidenebis(indenyl)hafnium dichloride, diphenylmethylenebis(indenyl)hafnium dichloride, 1,2-ethylene-bis(indenyl)hafnium dichloride, dimethylsilylenebis(indenyl)hafnium dichloride, diphenylsilylenebis(indenyl)hafnium dichloride, 1,2-tetramethyldisilylene-bis(indenyl)hafnium dichloride, methylenebis(fluorenyl)hafnium dichloride, isopropylidenebis(fluorenyl)hafnium dichloride, diphenylmethylenebis(fluorenyl)hafnium dichloride, 1,2-ethylene-bis(fluorenyl)hafnium dichloride, dimethylsilylenebis(fluorenyl)hafnium dichloride, diphenylsilylenebis(fluorenyl)hafnium dichloride, 1,2-tetramethyldisilylene-bis(fluorenyl)hafnium dichloride, methylenebis(azulenyl)hafnium dichloride, isopropylidenebis(azulenyl)hafnium dichloride, diphenylmethylenebis(azulenyl)hafnium dichloride, 1,2-ethylene-bis(azulenyl)hafnium dichloride, dimethylsilylenebis(azulenyl)hafnium dichloride, diphenylsilylenebis(azulenyl)hafnium dichloride, 1,2-tetramethyldisilylene-bis(azulenyl)hafnium dichloride, methylenebis[2-ethyl-4-(2-fluoro-4-biphenylyl)-4H-azulenyl]hafnium dichloride, isopropylidenebis[2-ethyl-4-(2-fluoro-4-biphenylyl)-4H-azulenyl]hafnium dichloride, diphenylmethylenebis[2-ethyl-4-(2-fluoro-4-biphenylyl)-4H-azulenyl]hafnium dichloride, 1,2-ethylenebis[2-ethyl-4-(2-fluoro-4-biphenylyl)-4H-azulenyl]hafnium dichloride, dimethylsilylenebis[2-ethyl-4-(2-fluoro-4-biphenylyl)-4H-azulenyl]hafnium dichloride, diphenylsilylenebis[2-ethyl-4-(2-fluoro-4-biphenylyl)-4H-azulenyl]hafnium dichloride, 1,2-tetramethyldisilylenebis[2-ethyl-4-(2-fluoro-4-biphenylyl)-4H-azulenyl]hafnium dichloride, methylene(cyclopentadienyl)(tetramethylcyclopentadienyl)hafnium dichloride, isopropylidene(cyclopentadienyl)(tetramethylcyclopentadienyl)hafnium dichloride, diphenylmethylene(cyclopentadienyl)(tetramethylcyclopentadienyl)hafnium dichloride, 1,2-ethylene-(cyclopentadienyl)(tetramethylcyclopentadienyl)hafnium dichloride, dimethylsilylene(cyclopentadienyl)(tetramethylcyclopentadienyl)hafnium dichloride, diphenylsilylene(cyclopentadienyl)(tetramethylcyclopentadienyl)hafnium dichloride, 1,2-tetramethyldisilylene-(cyclopentadienyl)(tetramethylcyclopentadienyl)hafnium dichloride, methylene(cyclopentadienyl)(indenyl)hafnium dichloride, isopropylidene(cyclopentadienyl)(indenyl)hafnium dichloride, diphenylmethylene(cyclopentadienyl)(indenyl)hafnium dichloride, 1,2-ethylene-(cyclopentadienyl)(indenyl)hafnium dichloride, dimethylsilylene(cyclopentadienyl)(indenyl)hafnium dichloride, diphenylsilylene(cyclopentadienyl)(indenyl)hafnium dichloride, 1,2-tetramethyldisilylene-(cyclopentadienyl)(indenyl)hafnium dichloride, methylene(cyclopentadienyl)(fluorenyl)hafnium dichloride, isopropylidene(cyclopentadienyl)(fluorenyl)hafnium dichloride, diphenylmethylene(cyclopentadienyl)(fluorenyl)hafnium dichloride, 1,2-ethylene-(cyclopentadienyl)(fluorenyl)hafnium dichloride, dimethylsilylene(cyclopentadienyl)(fluorenyl)hafnium dichloride, diphenylsilylene(cyclopentadienyl)(fluorenyl)hafnium dichloride, 1,2-tetramethyldisilylene-(cyclopentadienyl)(fluorenyl)hafnium dichloride, methylene(3-tert-butyl-5-methylcyclopentadienyl)(3,6-di-tert-butylfluorenyl)hafnium dichloride, isopropylidene(3-tert-butyl-5-methylcyclopentadienyl)(3,6-di-tert-butylfluorenyl)hafnium dichloride, diphenylmethylene(3-tert-butyl-5-methylcyclopentadienyl)(3,6-di-tert-butylfluorenyl)hafnium dichloride, 1,2-ethylene-(3-tert-butyl-5-methylcyclopentadienyl)(3,6-di-tert-butylfluorenyl)hafnium dichloride, dimethylsilylene(3-tert-butyl-5-methylcyclopentadienyl)(3,6-di-tert-butylfluorenyl)hafnium dichloride, diphenylsilylene(3-tert-butyl-5-methylcyclopentadienyl)(3,6-di-tert-butylfluorenyl)hafnium dichloride, 1,2-tetramethyldisilylene-(3-tert-butyl-5-methylcyclopentadienyl)(3,6-di-tert-butylfluorenyl)hafnium dichloride, and compounds obtained by replacing zirconium or hafnium in these compounds with titanium; replacing cyclopentadienyl therein with methylcyclopentadienyl, n-butylcyclopentadienyl, t-butylcyclopentadienyl, tetramethylcyclopentadienyl, indenyl or fluorenyl; or replacing chloride therein with bromide, iodide, hydride, methyl, phenyl, benzyl, methoxide, n-butoxide, isopropoxide, phenoxide, benzyloxide, dimethylamide or diethylamide.

The transition metal complex represented by the general formula (4) can be produced, for example, by a method described in JP 2535249B.

Examples of the complex represented by the general formula (4) include methylene(tert-butylamido)(cyclopentadienyl)titanium dichloride, methylene(cyclohexylamido)(cyclopentadienyl)titanium dichloride, methylene(phenylamido)(cyclopentadienyl)titanium dichloride, methylene(benzylamido)(cyclopentadienyl)titanium dichloride, methylene(tert-butylphosphido)(cyclopentadienyl)titanium dichloride, methylene(cyclohexylphosphido)(cyclopentadienyl)titanium dichloride, methylene(phenylphosphido)(cyclopentadienyl)titanium dichloride, methylene(benzylphosphido)(cyclopentadienyl)titanium dichloride, isopropylidene(tert-butylamido)(cyclopentadienyl)titanium dichloride, isopropylidene(cyclohexylamido)(cyclopentadienyl)titanium dichloride, isopropylidene(phenylamido)(cyclopentadienyl)titanium dichloride, isopropylidene(benzylamido)(cyclopentadienyl)titanium dichloride, isopropylidene(tert-butylphosphido)(cyclopentadienyl)titanium dichloride, isopropylidene(cyclohexylphosphido)(cyclopentadienyl)titanium dichloride, isopropylidene(phenylphosphido)(cyclopentadienyl)titanium dichloride, isopropylidene(benzylphosphido)(cyclopentadienyl)titanium dichloride, diphenylmethylene(tert-butylamido)(cyclopentadienyl)titanium dichloride, diphenylmethylene(cyclohexylamido)(cyclopentadienyl)titanium dichloride, diphenylmethylene(phenylamido)(cyclopentadienyl)titanium dichloride, diphenylmethylene(benzylamido)(cyclopentadienyl)titanium dichloride, diphenylmethylene(tert-butylphosphido)(cyclopentadienyl)titanium dichloride, diphenylmethylene(cyclohexylphosphido)(cyclopentadienyl)titanium dichloride, diphenylmethylene(phenylphosphido)(cyclopentadienyl)titanium dichloride, diphenylmethylene(benzylphosphido)(cyclopentadienyl)titanium dichloride, 1,2-ethylene(tert-butylamido)(cyclopentadienyl)titanium dichloride, 1,2-ethylene(cyclohexylamido)(cyclopentadienyl)titanium dichloride, 1,2-ethylene(phenylamido)(cyclopentadienyl)titanium dichloride, 1,2-ethylene(benzylamido)(cyclopentadienyl)titanium dichloride, 1,2-ethylene(tert-butylphosphido)(cyclopentadienyl)titanium dichloride, 1,2-ethylene(cyclohexylphosphido)(cyclopentadienyl)titanium dichloride, 1,2-ethylene(phenylphosphido)(cyclopentadienyl)titanium dichloride, 1,2-ethylene(benzylphosphido)(cyclopentadienyl)titanium dichloride, dimethylsilylene(tert-butylamido)(cyclopentadienyl)titanium dichloride, dimethylsilylene(cyclohexylamido)(cyclopentadienyl)titanium dichloride, dimethylsilylene(phenylamido)(cyclopentadienyl)titanium dichloride, dimethylsilylene(benzylamido)(cyclopentadienyl)titanium dichloride, dimethylsilylene(tert-butylphosphido)(cyclopentadienyl)titanium dichloride, dimethylsilylene(cyclohexylphosphido)(cyclopentadienyl)titanium dichloride, dimethylsilylene(phenylphosphido)(cyclopentadienyl)titanium dichloride, dimethylsilylene(benzylphosphido)(cyclopentadienyl)titanium dichloride, diphenylsilylene(tert-butylamido)(cyclopentadienyl)titanium dichloride, diphenylsilylene(cyclohexylamido)(cyclopentadienyl)titanium dichloride, diphenylsilylene(phenylamido)(cyclopentadienyl)titanium dichloride, diphenylsilylene(benzylamido)(cyclopentadienyl)titanium dichloride, diphenylsilylene(tert-butylphosphido)(cyclopentadienyl)titanium dichloride, diphenylsilylene(cyclohexylphosphido)(cyclopentadienyl)titanium dichloride, diphenylsilylene(phenylphosphido)(cyclopentadienyl)titanium dichloride, diphenylsilylene(benzylphosphido)(cyclopentadienyl)titanium dichloride, 1,2-tetramethyldisilylene(tert-butylamido)(cyclopentadienyl)titanium dichloride, 1,2-tetramethyldisilylene(cyclohexylamido)(cyclopentadienyl)titanium dichloride, 1,2-tetramethyldisilylene(phenylamido)(cyclopentadienyl)titanium dichloride, 1,2-tetramethyldisilylene(benzylamido)(cyclopentadienyl)titanium dichloride, 1,2-tetramethyldisilylene(tert-butylphosphido)(cyclopentadienyl)titanium dichloride, 1,2-tetramethyldisilylene(cyclohexylphosphido)(cyclopentadienyl)titanium dichloride, 1,2-tetramethyldisilylene(phenylphosphido)(cyclopentadienyl)titanium dichloride, 1,2-tetramethyldisilylene(benzylphosphido)(cyclopentadienyl)titanium dichloride, and compounds obtained by replacing titanium in these compounds with zirconium or hafnium; replacing cyclopentadienyl therein with methylcyclopentadienyl, n-butylcyclopentadienyl, t-butylcyclopentadienyl, tetramethylcyclopentadienyl, indenyl or fluorenyl; replacing t-butylamido therein with an oxygen or sulfur atom; or replacing chloride therein with bromide, iodide, hydride, methyl, phenyl, benzyl, methoxide, n-butoxide, isopropoxide, phenoxide, benzyloxide, dimethylamide or diethylamide.

The complex represented by the general formula (5) will be described in detail. Examples of the transition metal atom of Group 4 of the Periodic Table of the Elements (IUPAC Nomenclature of Inorganic Chemistry, Revised, 1989) in $M^5$ include titanium, zirconium and hafnium atoms. A titanium atom is preferable.

Examples of the atom of Group 16 of the Periodic Table of the Elements in $A^2$ include oxygen, sulfur and selenium atoms. An oxygen atom is preferable.

Examples of the atom of Group 14 of the Periodic Table of the Elements represented by $J^4$ include carbon, silicon and germanium atoms. Carbon and silicon atoms are preferable, and a carbon atom is more preferable.

Examples of the group having a cyclopentadiene-type anionic skeleton represented by the substituent $Cp^5$ include $\eta^5$-cyclopentadienyl, $\eta^5$-methylcyclopentadienyl, $\eta^5$-dimethylcyclopentadienyl, $\eta^5$-trimethylcyclopentadienyl, $\eta^5$-tetramethylcyclopentadienyl, $\eta^5$-ethylcyclopentadienyl, $\eta^5$-n-propylcyclopentadienyl, $\eta^5$-isopropylcyclopentadienyl, $\eta^5$-n-butylcyclopentadienyl, $\eta^5$-sec-butylcyclopentadienyl, $\eta^5$-tert-butylcyclopentadienyl, $\eta^5$-n-pentylcyclopentadienyl, $\eta^5$-neopentylcyclopentadienyl, $\eta^5$-n-hexylcyclopentadienyl, $\eta^5$-n-octylcyclopentadienyl, $\eta^5$-phenylcyclopentadienyl, $\eta^5$-naphthylcyclopentadienyl, $\eta^5$-trimethylsilylcyclopentadienyl, $\eta^5$-triethylsilylcyclopentadienyl, $\eta^5$-tert-butyldimethylsilylcyclopentadienyl, $\eta^5$-indenyl, $\eta^5$-methylindenyl, $\eta^5$-dimethylindenyl, $\eta^5$-ethylindenyl, $\eta^5$-n-propylindenyl, $\eta^5$-isopropylindenyl, $\eta^5$-n-butylindenyl, $\eta^5$-sec-butylindenyl, $\eta^5$-tert-butylindenyl, $\eta^5$-n-pentylindenyl, $\eta^5$-neopentylindenyl, $\eta^5$-n-hexylindenyl, $\eta^5$-n-octylindenyl, $\eta^5$-n-decylindenyl, $\eta^5$-phenylindenyl, $\eta^5$-methylphenylindenyl, $\eta^5$-naphthylindenyl, $\eta^5$-trimethylsilylindenyl, $\eta^5$-triethylsilylindenyl, $\eta^5$-tert-butyldimethylsilylindenyl, $\eta^5$-tetrahydroindenyl, $\eta^5$-fluorenyl, $\eta^5$-methylfluorenyl, $\eta^5$-dimethylfluorenyl, $\eta^5$-ethylfluorenyl, $\eta^5$-diethylfluorenyl, $\eta^5$-n-propylfluorenyl, $\eta^5$-di-n-propylfluorenyl, $\eta^5$-isopropylfluorenyl, $\eta^5$-diisopropylfluorenyl, $\eta^5$-n-butylfluorenyl, $\eta^5$-sec-butylfluorenyl, $\eta^5$-tert-butylfluorenyl, $\eta^5$-di-n-butylfluorenyl, $\eta^5$-disec-butylfluorenyl, $\eta^5$-di-tert-butylfluorenyl, $\eta^5$-n-pentylfluorenyl, $\eta^5$-neopentylfluorenyl, $\eta^5$-n-hexylfluorenyl, $\eta^5$-n-octylfluorenyl, $\eta^5$-n-decylfluorenyl, $\eta^5$-n-dodecylfluorenyl, $\eta^5$-phenylfluorenyl, $\eta^5$-di-phenylfluorenyl, $\eta^5$-methylphenylfluorenyl, $\eta^5$-naphthylfluorenyl, $\eta^5$-trimethylsilylfluorenyl, $\eta^5$-bis-trimethylsilylfluorenyl, $\eta^5$-triethylsilylfluorenyl and $\eta^5$-tert-butyldimethylsilylfluorenyl groups. $\eta^5$-cyclopentadienyl, $\eta^5$-methylcyclopentadienyl, $\eta^5$-tert-butylcyclopentadienyl, $\eta^5$-tetramethylcyclopentadienyl, $\eta^5$-indenyl and $\eta^5$-fluorenyl groups, etc. are preferable.

Examples of the halogen atom in $X^{10}$, $X^{11}$, $R^{14}$, $R^{15}$, $R^{16}$ and $R^{17}$ include fluorine, chlorine, bromine and iodine atoms.

Examples of the alkyl group having 1 to 20 carbon atoms in $X^{10}$, $X^{11}$, $R^{14}$, $R^{15}$, $R^{16}$, $R^{17}$, $R^{18}$ and $R^{19}$ include methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl and n-eicosyl groups.

Moreover, the phrase "may have a halogen atom as a substituent" in the "alkyl group which may have a halogen atom as a substituent" means that some or all of hydrogen atoms in the alkyl group may be substituted with a halogen atom. Examples of the halogen atom include fluorine, chlorine, bromine and iodine atoms. Examples of the alkyl group having 1 to 20 carbon atoms having a halogen atom as a substituent include fluoromethyl, difluoromethyl, trifluoromethyl, chloromethyl, dichloromethyl, trichloromethyl, bromomethyl, dibromomethyl, tribromomethyl, iodomethyl, diiodomethyl, triiodomethyl, fluoroethyl, difluoroethyl, trifluoroethyl, tetrafluoroethyl, pentafluoroethyl, chloroethyl, dichloroethyl, trichloroethyl, tetrachloroethyl, pentachloroethyl, bromoethyl, dibromoethyl, tribromoethyl, tetrabromoethyl, pentabromoethyl, perfluoropropyl, perfluorobutyl, perfluoropentyl, perfluorohexyl, perfluorooctyl, perfluorododecyl, perfluoropentadecyl, perfluoroeicosyl, perchloropropyl, perchlorobutyl, perchloropentyl, perchlorohexyl, perchlorooctyl, perchlorododecyl, perchloropentadecyl, perchloroeicosyl, perbromopropyl, perbromobutyl, perbromopentyl, perbromohexyl, perbromooctyl, perbromododecyl, perbromopentadecyl and perbromoeicosyl groups.

Examples of the aryl group having 6 to 20 carbon atoms in $X^{10}$, $X^{11}$, $R^{14}$, $R^{15}$, $R^{16}$, $R^{17}$, $R^{18}$ and $R^{19}$ include phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, naphthyl and anthracenyl groups.

Moreover, the phrase "may have a halogen atom as a substituent" in the "aryl group which may have a halogen atom as a substituent" means that some or all of hydrogen atoms in the aryl group may be substituted with a halogen atom. Examples of the halogen atom include fluorine, chlorine, bromine and iodine atoms. Examples of the aryl group having 6 to 20 carbon atoms having a halogen atom as a substituent include fluorophenyl, difluorophenyl, trifluorophenyl, tetrafluorophenyl, pentafluorophenyl, chlorophenyl, bromophenyl and iodophenyl groups.

Examples of the aralkyl group having 7 to 20 carbon atoms in $X^{10}$, $X^{11}$, $R^{14}$, $R^{15}$, $R^{16}$, $R^{17}$, $R^{18}$ and $R^{19}$ include benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (3,5-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl and anthracenylmethyl groups.

Moreover, the phrase "may have a halogen atom as a substituent" in the "aralkyl group which may have a halogen atom as a substituent" means that some or all of hydrogen atoms in the aralkyl group may be substituted with a halogen atom. Examples of the halogen atom include fluorine, chlorine, bromine and iodine atoms. Examples of the aralkyl group having 7 to 20 carbon atoms having a halogen atom as a substituent include groups obtained by substituting some or all of hydrogen atoms in the aralkyl group listed above with a halogen atom.

Examples of the alkoxy group having 1 to 20 carbon atoms in $X^{10}$, $X^{11}$, $R^{14}$, $R^{15}$, $R^{16}$, $R^{17}$, $R^{18}$ and $R^{19}$ include methoxy, ethoxy, n-propoxy, isopropoxy, n-butoxy, sec-butoxy, tert-butoxy, n-pentoxy, neopentoxy, n-hexoxy, n-octoxy, n-dodecoxy, n-pentadecoxy and n-eicosoxy.

Moreover, the phrase "may have a halogen atom as a substituent" in the "alkoxy group which may have a halogen atom as a substituent" means that some or all of hydrogen atoms in the alkoxy group may be substituted with a halogen atom. Examples of the halogen atom include fluorine, chlorine, bromine and iodine atoms. Examples of the alkoxy group having 1 to 20 carbon atoms having a halogen atom as a substituent include groups obtained by substituting some or all of hydrogen atoms in the alkoxy group listed above with a halogen atom.

Examples of the aryloxy group having 6 to 20 carbon atoms in $X^{10}$, $X^{11}$, $R^{14}$, $R^{15}$, $R^{16}$, $R^{17}$, $R^{18}$ and $R^{19}$ include aryloxy groups having 6 to 20 carbon atoms, such as phenoxy, 2-methylphenoxy, 3-methylphenoxy, 4-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2,3,4-trimethylphenoxy, 2,3,5-trimethylphenoxy, 2,3,6-trimethylphenoxy, 2,4,5-trimethylphenoxy, 2,4,6-trimethylphenoxy, 3,4,5-trimethylphenoxy, 2,3,4,5-tetramethylphenoxy, 2,3,4,6-tetramethylphenoxy, 2,3,5,6-tetramethylphenoxy, pentamethylphenoxy, ethylphenoxy, n-propylphenoxy, isopropylphenoxy, n-butylphenoxy, sec-butylphenoxy, tert-butylphenoxy, n-hexylphenoxy, n-octylphenoxy, n-decylphenoxy, n-tetradecylphenoxy, naphthoxy and anthracenoxy groups.

Moreover, the phrase "may have a halogen atom as a substituent" in the "aryloxy group which may have a halogen atom as a substituent" means that some or all of hydrogen atoms in the aryloxy group may be substituted with a halogen atom. Examples of the halogen atom include fluorine, chlorine, bromine and iodine atoms. Examples of the aryloxy group having 6 to 20 carbon atoms having a halogen atom as a substituent include groups obtained by substituting some or all of hydrogen atoms in the aryloxy group listed above with a halogen atom.

Examples of the aralkyloxy group having 7 to 20 carbon atoms in $X^{10}$, $X^{11}$, $R^{14}$, $R^{15}$, $R^{16}$, $R^{17}$, $R^{18}$ and $R^{19}$ include benzyloxy, (2-methylphenyl)methoxy, (3-methylphenyl)methoxy, (4-methylphenyl)methoxy, (2,3-dimethylphenyl)methoxy, (2,4-dimethylphenyl)methoxy, (2,5-dimethylphenyl)methoxy, (2,6-dimethylphenyl)methoxy, (3,4-dimethylphenyl)methoxy, (3,5-dimethylphenyl)methoxy, (2,3,4-trimethylphenyl)methoxy, (2,3,5-trimethylphenyl)methoxy, (2,3,6-trimethylphenyl)methoxy, (2,4,5-trimethylphenyl)methoxy, (2,4,6-trimethylphenyl)methoxy, (3,4,5-trimethylphenyl)methoxy, (2,3,4,5-tetramethylphenyl)methoxy, (2,3,4,6-tetramethylphenyl)methoxy, (2,3,5,6-tetramethylphenyl)methoxy, (pentamethylphenyl)methoxy, (ethylphenyl)methoxy, (n-propylphenyl)methoxy, (isopropylphenyl)methoxy, (n-butylphenyl)methoxy, (sec-butylphenyl)methoxy, (tert-butylphenyl)methoxy, (n-hexylphenyl)methoxy, (n-octylphenyl)methoxy, (n-decylphenyl)methoxy, (n-tetradecylphenyl)methoxy, naphthylmethoxy and anthracenylmethoxy groups.

Moreover, the phrase "may have a halogen atom as a substituent" in the "aralkyloxy group which may have a halogen atom as a substituent" means that some or all of hydrogen atoms in the aralkyloxy group may be substituted with a halogen atom. Examples of the halogen atom include fluorine, chlorine, bromine and iodine atoms. Examples of the aralkyloxy group having 7 to 20 carbon atoms having a halogen atom as a substituent include groups obtained by substituting some or all of hydrogen atoms in the aralkyloxy group listed above with a halogen atom.

In the substituted silyl group represented by $-Si(R^{12})_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, in $X^{10}$, $X^{11}$, $R^{14}$, $R^{15}$, $R^{16}$, $R^{17}$, $R^{18}$ and $R^{19}$, the $R^{12}$ groups are each independently a hydrogen atom; a hydrocarbyl group such as an alkyl group having 1 to 10 carbon atoms (e.g., methyl, ethyl, n-propyl, isopropyl, n-butyl, sec-butyl, tert-butyl, isobutyl, n-pentyl, n-hexyl, cyclohexyl, n-heptyl, n-octyl, n-nonyl and n-decyl groups) and an aryl group (e.g., a phenyl group); or a halogenated hydrocarbyl group obtained by substituting some or all hydrogen atoms in the hydrocarbyl group by a halogen atom, and the total number of the carbon atoms in the three $R^{12}$ groups is in the range of 1 to 20. The total number of the carbon atoms in these three $R^{12}$ groups is preferably in the range of 3 to 18. Specific examples of the substituted silyl group include: monosubstituted silyl groups having one hydrocarbyl or hydrocarbyl halide group, such as methylsilyl, ethylsilyl and phenylsilyl groups, and groups obtained by substituting some or all hydrogen atoms in the hydrocarbyl groups of these groups by a halogen atom; disubstituted silyl groups having two hydrocarbyl and/or halogenated hydrocarbyl groups, such as dimethylsilyl, diethylsilyl and diphenylsilyl groups, and groups obtained by substituting some or all hydrogen atoms in the hydrocarbyl groups of these groups by a halogen atom; and trisubstituted silyl groups having three hydrocarbyl and/or halogenated hydrocarbyl groups, such as trimethylsilyl, triethylsilyl, tri-n-propylsilyl, triisopropylsilyl, tri-n-butylsilyl, tri-sec-butylsilyl, tri-tert-butylsilyl, tri-isobutylsilyl, tert-butyl-dimethylsilyl, tri-n-pentylsilyl, tri-n-hexylsilyl, tricyclohexylsilyl and triphenylsilyl groups, and groups obtained by substituting some or all hydrogen atoms in the hydrocarbyl groups of these groups by a halogen atom. Of them, trisubstituted silyl groups are preferable, and trimethylsilyl, tert-butyldimethylsilyl and triphenylsilyl groups, and groups obtained by substituting some or all of hydrogen atoms in these groups with a halogen atom are more preferable.

In the disubstituted amino group represented by $-N(R^{13})_2$, wherein the two $R^{13}$ groups each independently represent a hydrocarbyl group or a halogenated hydrocarbyl group, and the total number of the carbon atoms in the two $R^{13}$ groups is 2 to 20, in $X^{10}$, $X^{11}$, $R^{14}$, $R^{15}$, $R^{16}$, $R^{17}$, $R^{18}$ and $R^{19}$, the $R^{13}$ moieties each independently represent a hydrocarbyl group or a halogenated hydrocarbyl group, and the total number of the carbon atoms in two $R^{13}$ groups is in the range of 2 to 20, more preferably in the range of 2 to 10. The hydrocarbyl group and the halogenated hydrocarbyl group are the same as those described as a hydrocarbyl group and a halogenated hydrocarbyl group for the substituted silyl group. Moreover, these two $R^{13}$ groups may be bonded to each other to form a ring together with the nitrogen atom to which the two $R^{13}$ groups are bonded. Examples of such a disubstituted amino group include dimethylamino, diethylamino, di-n-propylamino, diisopropylamino, di-n-butylamino, di-sec-butylamino, di-tert-butylamino, di-isobutylamino, tert-butylisopropylamino, di-n-hexylamino, di-n-octylamino, di-n-decylamino, diphenylamino, bistrimethyl silylamino, bis-tert-butyldimethylsilylamino, pyrrolyl, pyrrolidinyl, piperidinyl, carbazolyl, dihydroindolyl and dihydroisoindolyl groups, and groups obtained by substituting some or all hydrogen atoms in these groups by a halogen atom. Of them, dimethylamino, diethylamino, pyrrolidinyl and piperidinyl groups, and groups obtained by substituting some or all of hydrogen atoms in these groups with a halogen atom are preferable.

Of $R^{14}$, $R^{15}$, $R^{16}$ and $R^{17}$, two groups bonded to two adjacent carbon atoms may be bonded to each other to form a ring together with the two carbon atoms to which the two groups are bonded, and $R^{18}$ and $R^{19}$ may be bonded to each other to form a ring together with $J^4$ to which $R^{18}$ and $R^{19}$ are bonded. Examples of the ring include saturated or unsaturated hydrocarbyl rings and can specifically include cyclopropane, cyclopropene, cyclobutane, cyclobutene, cyclopentane, cyclopentene, cyclohexane, cyclohexene, cycloheptane, cycloheptene, cyclooctane, cyclooctene, benzene, naphthalene and anthracene rings. These rings may be substituted by a hydrocarbyl group having 1 to 20 carbon atoms or the like, or may contain a silicon atom. Examples of the ring containing a silicon atom include silacyclopropane, silacyclobutane, silacyclopentane and silacyclohexane rings.

The substituents $X^{10}$ and $X^{11}$ are preferably a halogen atom, an alkyl group having 1 to 20 carbon atoms which may have a halogen atom as a substituent, or an aralkyl group having 7 to carbon atoms which may have a halogen atom as a substituent, more preferably a halogen atom.

$R^{14}$ is preferably an alkyl group having 1 to 20 carbon atoms which may have a halogen atom as a substituent, an aryl group having 6 to 20 carbon atoms which may have a halogen atom as a substituent, an aralkyl group having 7 to 20 carbon atoms which may have a halogen atom as a substituent, or a substituted silyl group represented by $-Si(R^{12})_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20. Specific examples thereof include methyl, ethyl, isopropyl, tert-butyl, amyl, phenyl, benzyl, trimethylsilyl, tert-butyldimethylsilyl and triphenylsilyl groups. More preferable examples thereof include tert-butyl, trimethylsilyl, tert-butyldimethylsilyl and triphenylsilyl groups.

The transition metal complex represented by the general formula (5) can be produced, for example, by a method described in JP 9-87313 A.

Examples of the complex represented by the general formula (5) include: transition metal complexes represented by the general formula (5) wherein $J^4$ is a carbon atom, such as methylene(cyclopentadienyl)(3,5-dimethyl-2-phenoxy)titanium dichloride, methylene(cyclopentadienyl)(3-tert-butyl-2-phenoxy)titanium dichloride, methylene(cyclopentadienyl)(3-tert-butyl-5-methyl-2-phenoxy)titanium dichloride, methylene(cyclopentadienyl)(3-phenyl-2-phenoxy)titanium dichloride, methylene(cyclopentadienyl)(3-tert-butyldimethylsilyl-5-methyl-2-phenoxy)titanium dichloride, methylene(cyclopentadienyl)(3-trimethylsilyl-5-methyl-2-phenoxy)titanium dichloride, methylene(cyclopentadienyl)(3-tert-butyl-5-methoxy-2-phenoxy)titanium dichloride, methylene(cyclopentadienyl)(3-tert-butyl-5-chloro-2-phenoxy)titanium dichloride, methylene(methylcyclopentadienyl)(3,5-dimethyl-2-phenoxy)titanium dichloride, methylene(methylcyclopentadienyl)(3-tert-butyl-2-phenoxy)titanium dichloride, methylene(methylcyclopentadienyl)(3-tert-butyl-5-methyl-2-phenoxy)titanium dichloride, methylene(methylcyclopentadienyl)(3-phenyl-2-phenoxy)titanium dichloride, methylene(methylcyclopentadienyl)(3-tert-butyldimethylsilyl-5-methyl-2-phenoxy)titanium dichloride, methylene(methylcyclopentadienyl)(3-trimethylsilyl-5-methyl-2-phenoxy)titanium dichloride, methylene(methylcyclopentadienyl)(3-tert-butyl-5-methoxy-2-phenoxy)titanium dichloride, methylene(methylcyclopentadienyl)(3-tert-butyl-5-chloro-2-phenoxy)titanium dichloride, methylene(tert-butylcyclopentadienyl)(3,5-dimethyl-2-phenoxy)titanium dichloride, methylene(tert-butylcyclopentadienyl)(3-tert-butyl-2-phenoxy)titanium dichloride, methylene(tert-butylcyclopentadienyl)(3-tert-butyl-5-methyl-2-phenoxy)titanium dichloride, methylene(tert-butylcyclopentadienyl)(3-phenyl-2-phenoxy)titanium dichloride, methylene(tert-butylcyclopentadienyl)(3-tert-butyldimethylsilyl-5-methyl-2-phenoxy)titanium dichloride, methylene(tert-butylcyclopentadienyl)(3-trimethylsilyl-5-methyl-2-phenoxy)titanium dichloride, methylene(tert-butylcyclopentadienyl)(3-tert-butyl-5-methoxy-2-phenoxy)titanium dichloride, methylene(tert-butylcyclopentadienyl)(3-tert-butyl-5-chloro-2-phenoxy)titanium dichloride, methylene(tetramethylcyclopentadienyl)(3,5-dimethyl-2-phenoxy)titanium dichloride, methylene(tetramethylcyclopentadienyl)(3-tert-butyl-2-phenoxy)titanium dichloride, methylene(tetramethylcyclopentadienyl)(3-tert-butyl-5-methyl-2-phenoxy)titanium dichloride, methylene(tetramethylcyclopentadienyl)(3-phenyl-2-phenoxy)titanium dichloride, methylene(tetramethylcyclopentadienyl)(3-tert-butyldimethylsilyl-5-methyl-2-phenoxy)titanium dichloride, methylene(tetramethylcyclopentadienyl)(3-trimethylsilyl-5-methyl-2-phenoxy)titanium dichloride, methylene(tetramethylcyclopentadienyl)(3-tert-butyl-5-methoxy-2-phenoxy)titanium dichloride, methylene(tetramethylcyclopentadienyl)(3-tert-butyl-5-chloro-2-phenoxy)titanium dichloride, methylene(trimethylsilylcyclopentadienyl)(3,5-dimethyl-2-phenoxy)titanium dichloride, methylene(trimethylsilylcyclopentadienyl)(3-tert-butyl-2-phenoxy)titanium dichloride, methylene(trimethylsilylcyclopentadienyl)(3-tert-butyl-5-methyl-2-phenoxy)titanium dichloride, methylene(trimethylsilylcyclopentadienyl)(3-phenyl-2-phenoxy)titanium dichloride, methylene(trimethylsilylcyclopentadienyl)(3-tert-butyldimethylsilyl-5-methyl-2-phenoxy)titanium dichloride, methylene(trimethylsilylcyclopentadienyl)(3-trimethylsilyl-5-methyl-2-phenoxy)titanium dichloride, methylene(trimethylsilylcyclopentadienyl)(3-tert-butyl-5-methoxy-2-phenoxy)titanium dichloride, methylene(trimethylsilylcyclopentadienyl)(3-tert-butyl-5-chloro-2-phenoxy)titanium dichloride, methylene(fluorenyl)(3,5-dimethyl-2-phenoxy)titanium dichloride, methylene(fluorenyl)(3-tert-butyl-2-phenoxy)titanium dichloride, methylene(fluorenyl)(3-tert-butyl-5-methyl-2-phenoxy)titanium dichloride, methylene(fluorenyl)(3-phenyl-2-phenoxy)titanium dichloride, methylene(fluorenyl)(3-tert-butyldimethylsilyl-5-methyl-2-phenoxy)titanium dichloride, methylene(fluorenyl)(3-trimethylsilyl-5-methyl-2-phenoxy)titanium dichloride, methylene(fluorenyl)(3-tert-butyl-5-methoxy-2-phenoxy)titanium dichloride, methylene(fluorenyl)(3-tert-butyl-5-chloro-2-phenoxy)titanium dichloride, isopropylidene(cyclopentadienyl)(3,5-dimethyl-2-phenoxy)titanium dichloride, isopropylidene(cyclopentadienyl)(3-tert-butyl-2-phenoxy)titanium dichloride, isopropylidene(cyclopentadienyl)(3-tert-butyl-5-methyl-2-phenoxy)titanium dichloride, isopropylidene(cyclopentadienyl)(3-phenyl-2-phenoxy)titanium dichloride, isopropylidene(cyclopentadienyl)(3-tert-butyldimethylsilyl-5-methyl-2-phenoxy)titanium dichloride, isopropylidene(cyclopentadienyl)(3-trimethylsilyl-5-methyl-2-phenoxy)titanium dichloride, isopropylidene(cyclopentadienyl)(3-tert-butyl-5-methoxy-2-phenoxy)titanium dichloride, isopropylidene(cyclopentadienyl)(3-tert-butyl-5-chloro-2-phenoxy)titanium dichloride, isopropylidene(methylcyclopentadienyl)(3,5-dimethyl-2-phenoxy)titanium dichloride, isopropylidene(methylcyclopentadienyl)(3-tert-butyl-2-phenoxy)titanium dichloride, isopropylidene(methylcyclopentadienyl)(3-tert-butyl-5-methyl-2-phenoxy)titanium dichloride, isopropylidene(methylcyclopentadienyl)(3-phenyl-2-phenoxy)titanium dichloride, isopropylidene(methylcyclopentadienyl)(3-tert-butyldimethylsilyl-5-methyl-2-phenoxy)titanium dichloride, isopropylidene(methylcyclopentadienyl)(3-trimethylsilyl-5-methyl-2-phenoxy)titanium dichloride, isopropylidene(methylcyclopentadienyl)(3-tert-butyl-5-methoxy-2-phenoxy)titanium dichloride, isopropylidene(methylcyclopentadienyl)(3-tert-butyl-5-chloro-2-phenoxy)titanium dichloride, isopropylidene(tert-butylcyclopentadienyl)(3,5-dimethyl-2-phenoxy)titanium dichloride, isopropylidene(tert-butylcyclopentadienyl)(3-tert-butyl-2-phenoxy)titanium dichloride, isopropylidene(tert-butylcyclopentadienyl)(3-tert-butyl-5-methyl-2-phenoxy)titanium dichloride, isopropylidene(tert-butylcyclopentadienyl)(3-phenyl-2-phenoxy)titanium dichloride, isopropylidene(tert-butylcyclopentadienyl)(3-tert-butyldimethylsilyl-5-methyl-2-phenoxy)titanium dichloride, isopropylidene(tert-butylcyclopentadienyl)(3-trimethylsilyl-5-methyl-2-phenoxy)titanium dichloride, isopropylidene(tert-butylcyclopentadienyl)(3-tert-butyl-5-methoxy-2-phenoxy)titanium dichloride, isopropylidene(tert-butylcyclopentadienyl)(3-tert-butyl-5-chloro-2-phenoxy)titanium dichloride, isopropylidene(tetramethylcyclopentadienyl)(3,5-dimethyl-2-phenoxy)titanium dichloride, isopropylidene(tetramethylcyclopentadienyl)(3-tert-butyl-2-phenoxy)titanium dichloride, isopropylidene(tetramethylcyclopentadienyl)(3-tert-butyl-5-methyl-2-phenoxy)titanium dichloride, isopropylidene(tetramethylcyclopentadienyl)(3-phenyl-2-phenoxy)titanium dichloride, isopropylidene(tetramethylcyclopentadienyl)(3-tert-butyldimethylsilyl-5- methyl-2-phenoxy)titanium dichloride, isopropylidene(tetramethylcyclopentadienyl)(3-trimethylsilyl-5-methyl-2-phenoxy)titanium dichloride, isopropylidene(tetramethylcyclopentadienyl)(3-tert-butyl-5-methoxy-2-phenoxy)titanium dichloride, isopropylidene(tetramethylcyclopentadienyl)(3-tert-butyl-5-chloro-2-phenoxy)titanium dichloride, isopropylidene(trimethylsilylcyclopentadienyl)(3,5-dimethyl-2-phenoxy)titanium dichloride, isopropylidene(trimethylsilylcyclopentadienyl)(3-tert-butyl-2-phenoxy)titanium dichloride, isopropylidene(trimethylsilylcyclopentadienyl)(3-tert-butyl-5-methyl-2-phenoxy)titanium dichloride, isopropylidene(trimethylsilylcyclopentadienyl)(3-phenyl-2-phenoxy)titanium dichloride, isopropylidene(trimethylsilylcyclopentadienyl)(3-tert-butyldimethylsilyl-5-methyl-2-phenoxy)titanium dichloride, isopropylidene(trimethylsilylcyclopentadienyl)(3-trimethylsilyl-5-methyl-2-phenoxy)titanium dichloride, isopropylidene(trimethylsilylcyclopentadienyl)(3-tert-butyl-5-methoxy-2-phenoxy)titanium dichloride, isopropylidene(trimethylsilylcyclopentadienyl)(3-tert-butyl-5-chloro-2-phenoxy)titanium dichloride, isopropylidene(fluorenyl)(3,5-dimethyl-2-phenoxy)titanium dichloride, isopropylidene(fluorenyl)(3-tert-butyl-2-phenoxy)titanium dichloride, isopropylidene(fluorenyl)(3-tert-butyl-5-methyl-2-phenoxy)titanium dichloride, isopropylidene(fluorenyl)(3-phenyl-2-phenoxy)titanium dichloride, isopropylidene(fluorenyl)(3-tert-butyldimethylsilyl-5-methyl-2-phenoxy)titanium dichloride, isopropylidene(fluorenyl)(3-trimethylsilyl-5-methyl-2-phenoxy)titanium dichloride, isopropylidene(fluorenyl)(3-tert-butyl-5-methoxy-2-phenoxy)titanium dichloride, isopropylidene(fluorenyl)(3-tert-butyl-5-chloro-2-phenoxy)titanium dichloride, diphenylmethylene(cyclopentadienyl)(3,5-dimethyl-2-phenoxy)titanium dichloride, diphenylmethylene(cyclopentadienyl)(3-tert-butyl-2-phenoxy)titanium dichloride, diphenylmethylene(cyclopentadienyl)(3-tert-butyl-5-methyl-2-phenoxy)titanium dichloride, diphenylmethylene(cyclopentadienyl)(3-phenyl-2-phenoxy)titanium dichloride, diphenylmethylene(cyclopentadienyl)(3-tert-butyldimethylsilyl-5-methyl-2-phenoxy)titanium dichloride, diphenylmethylene(cyclopentadienyl)(3-trimethylsilyl-5-methyl-2-phenoxy)titanium dichloride, diphenylmethylene(cyclopentadienyl)(3-tert-butyl-5-methoxy-2-phenoxy)titanium dichloride, diphenylmethylene(cyclopentadienyl)(3-tert-butyl-5-chloro-2-phenoxy)titanium dichloride, diphenylmethylene(methylcyclopentadienyl)(3,5-dimethyl-2-phenoxy)titanium dichloride, diphenylmethylene(methylcyclopentadienyl)(3-tert-butyl-2-phenoxy)titanium dichloride, diphenylmethylene(methylcyclopentadienyl)(3-tert-butyl-5-methyl-2-phenoxy)titanium dichloride, diphenylmethylene(methylcyclopentadienyl)(3-phenyl-2-phenoxy)titanium dichloride, diphenylmethylene(methylcyclopentadienyl)(3-tert-butyldimethylsilyl-5-methyl-2-phenoxy)titanium dichloride, diphenylmethylene(methylcyclopentadienyl)(3-trimethylsilyl-5-methyl-2-phenoxy)titanium dichloride, diphenylmethylene(methylcyclopentadienyl)(3-tert-butyl-5-methoxy-2-phenoxy)titanium dichloride, diphenylmethylene(methylcyclopentadienyl)(3-tert-butyl-5-chloro-2-phenoxy)titanium dichloride, diphenylmethylene(tert-butylcyclopentadienyl)(3,5-dimethyl-2-phenoxy)titanium dichloride, diphenylmethylene(tert-butylcyclopentadienyl)(3-tert-butyl-2-phenoxy)titanium dichloride, diphenylmethylene(tert-butylcyclopentadienyl)(3-tert-butyl-5-methyl-2-phenoxy)titanium dichloride, diphenylmethylene(tert-butylcyclopentadienyl)(3-phenyl-2-phenoxy)titanium dichloride, diphenylmethylene(tert-butylcyclopentadienyl)(3-tert-butyldimethylsilyl-5-methyl-2-phenoxy)titanium dichloride, diphenylmethylene(tert-butylcyclopentadienyl)(3-trimethylsilyl-5-methyl-2-phenoxy)titanium dichloride, diphenylmethylene(tert-butylcyclopentadienyl)(3-tert-butyl-5-methoxy-2-phenoxy)titanium dichloride, diphenylmethylene(tert-butylcyclopentadienyl)(3-tert-butyl-5-chloro-2-phenoxy)titanium dichloride, diphenylmethylene(tetramethylcyclopentadienyl)(3,5-dimethyl-2-phenoxy)titanium dichloride, diphenylmethylene(tetramethylcyclopentadienyl)(3-tert-butyl-2-phenoxy)titanium dichloride, diphenylmethylene(tetramethylcyclopentadienyl)(3-tert-butyl-5-methyl-2-phenoxy)titanium dichloride, diphenylmethylene(tetramethylcyclopentadienyl)(3-phenyl-2-phenoxy)titanium dichloride, diphenylmethylene(tetramethylcyclopentadienyl)(3-tert-butyldimethylsilyl-5-methyl-2-phenoxy)titanium dichloride, diphenylmethylene(tetramethylcyclopentadienyl)(3-trimethylsilyl-5-methyl-2-phenoxy)titanium dichloride, diphenylmethylene(tetramethylcyclopentadienyl)(3-tert-butyl-5-methoxy-2-phenoxy)titanium dichloride, diphenylmethylene(tetramethylcyclopentadienyl)(3-tert-butyl-5-chloro-2-phenoxy)titanium dichloride, diphenylmethylene(trimethylsilylcyclopentadienyl)(3,5-dimethyl-2-phenoxy)titanium dichloride, diphenylmethylene(trimethylsilylcyclopentadienyl)(3-tert-butyl-2-phenoxy)titanium dichloride, diphenylmethylene(trimethylsilylcyclopentadienyl)(3-tert-butyl-5-methyl-2-phenoxy)titanium dichloride, diphenylmethylene(trimethylsilylcyclopentadienyl)(3-phenyl-2-phenoxy)titanium dichloride, diphenylmethylene(trimethylsilylcyclopentadienyl)(3-tert-butyldimethylsilyl-5-methyl-2-phenoxy)titanium dichloride, diphenylmethylene(trimethylsilylcyclopentadienyl)(3-trimethylsilyl-5-methyl-2-phenoxy)titanium dichloride, diphenylmethylene(trimethylsilylcyclopentadienyl)(3-tert-butyl-5-methoxy-2-phenoxy)titanium dichloride, diphenylmethylene(trimethylsilylcyclopentadienyl)(3-tert-butyl-5-chloro-2-phenoxy)titanium dichloride, diphenylmethylene(fluorenyl)(3,5-dimethyl-2-phenoxy)titanium dichloride, diphenylmethylene(fluorenyl)(3-tert-butyl-2-phenoxy)titanium dichloride, diphenylmethylene(fluorenyl)(3-tert-butyl-5-methyl-2-phenoxy)titanium dichloride, diphenylmethylene(fluorenyl)(3-phenyl-2-phenoxy)titanium dichloride, diphenylmethylene(fluorenyl)(3-tert-butyldimethylsilyl-5-methyl-2-phenoxy)titanium dichloride, diphenylmethylene(fluorenyl)(3-trimethylsilyl-5-methyl-2-phenoxy)titanium dichloride, diphenylmethylene(fluorenyl)(3-tert-butyl-5-methoxy-2-phenoxy)titanium dichloride, diphenylmethylene(fluorenyl)(3-tert-butyl-5-chloro-2-phenoxy)titanium dichloride, and compounds obtained by replacing titanium in these compounds with zirconium or hafnium; replacing chloride therein with bromide, iodide, hydride, methyl, phenyl, benzyl, methoxide, n-butoxide, isopropoxide, phenoxide, benzyloxide, dimethylamide or diethylamide; replacing (cyclopentadienyl) therein with (dimethylcyclopentadienyl), (trimethylcyclopentadienyl), (n-butylcyclopentadienyl), (tert-butyldimethylsilylcyclopentadienyl) or (indenyl); replacing 3,5-dimethyl-2-phenoxy therein with 2-phenoxy, 3-methyl-2-phenoxy, 3,5-di-tert-butyl-2-phenoxy, 3-phenyl-5-methyl-2- phenoxy, 3-tert-butyldimethylsilyl-2-phenoxy or 3-trimethylsilyl-2-phenoxy; or replacing methylene therein with diethylmethylene; and transition metal complexes represented by the general formula (5) wherein $J^4$ is an atom of Group 14 of the Periodic Table of the Elements other than a carbon atom, such as dimethylsilylene(cyclopentadienyl)(2-phenoxy)titanium dichloride, dimethylsilylene(cyclopentadienyl)(3-methyl-2-phenoxy)titanium dichloride, dimethylsilylene(cyclopentadienyl)(3,5-dimethyl-2-phenoxy)titanium dichloride, dimethylsilylene(cyclopentadienyl)(3-tert-butyl-2-phenoxy)titanium dichloride, dimethylsilylene(cyclopentadienyl)(3-tert-butyl-5-methyl-2-phenoxy)titanium dichloride, dimethylsilylene(cyclopentadienyl)(3,5-di-tert-butyl-2-phenoxy)titanium dichloride, dimethylsilylene(cyclopentadienyl)(5-methyl-3-phenyl-2-phenoxy)titanium dichloride, dimethylsilylene(cyclopentadienyl)(3-tert-butyldimethylsilyl-5-methyl-2-phenoxy)titanium dichloride, dimethylsilylene(cyclopentadienyl)(5-methyl-3-trimethylsilyl-2-phenoxy)titanium dichloride, dimethylsilylene(cyclopentadienyl)(3-tert-butyl-5-methoxy-2-phenoxy)titanium dichloride, dimethylsilylene(cyclopentadienyl)(3-tert-butyl-5-chloro-2-phenoxy)titanium dichloride, dimethylsilylene(cyclopentadienyl)(3,5-diamyl-2-phenoxy)titanium dichloride, dimethylsilylene(methylcyclopentadienyl)(2-phenoxy)titanium dichloride, dimethylsilylene(methylcyclopentadienyl)(3-methyl-2-phenoxy)titanium dichloride, dimethylsilylene(methylcyclopentadienyl)(3,5-dimethyl-2-phenoxy)titanium dichloride, dimethylsilylene(methylcyclopentadienyl)(3-tert-butyl-2-phenoxy)titanium dichloride, dimethylsilylene(methylcyclopentadienyl)(3-tert-butyl-5-methyl-2-phenoxy)titanium dichloride, dimethylsilylene(methylcyclopentadienyl)(3,5-di-tert-butyl-2-phenoxy)titanium dichloride, dimethylsilylene(methylcyclopentadienyl)(5-methyl-3-phenyl-2-phenoxy)titanium dichloride, dimethylsilylene(methylcyclopentadienyl)(3-tert-butyldimethylsilyl-5-methyl-2-phenoxy)titanium dichloride, dimethylsilylene(methylcyclopentadienyl)(5-methyl-3-trimethylsilyl-2-phenoxy)titanium dichloride, dimethylsilylene(methylcyclopentadienyl)(3-tert-butyl-5-methoxy-2-phenoxy)titanium dichloride, dimethylsilylene(methylcyclopentadienyl)(3-tert-butyl-5-chloro-2-phenoxy)titanium dichloride, dimethylsilylene(methylcyclopentadienyl)(3,5-diamyl-2-phenoxy)titanium dichloride, dimethylsilylene(n-butylcyclopentadienyl)(2-phenoxy)titanium dichloride, dimethylsilylene(n-butylcyclopentadienyl)(3-methyl-2-phenoxy)titanium dichloride, dimethylsilylene(n-butylcyclopentadienyl)(3,5-dimethyl-2-phenoxy)titanium dichloride, dimethylsilylene(n-butylcyclopentadienyl)(3-tert-butyl-2-phenoxy)titanium dichloride, dimethylsilylene(n-butylcyclopentadienyl)(3-tert-butyl-5-methyl-2-phenoxy)titanium dichloride, dimethylsilylene(n-butylcyclopentadienyl)(3,5-di-tert-butyl-2-phenoxy)titanium dichloride, dimethylsilylene(n-butylcyclopentadienyl)(5-methyl-3-phenyl-2-phenoxy)titanium dichloride, dimethylsilylene(n-butylcyclopentadienyl)(3-tert-butyldimethylsilyl-5-methyl-2-phenoxy)titanium dichloride, dimethylsilylene(n-butylcyclopentadienyl)(5-methyl-3-trimethylsilyl-2-phenoxy)titanium dichloride, dimethylsilylene(n-butylcyclopentadienyl)(3-tert-butyl-5-methoxy-2-phenoxy)titanium dichloride, dimethyl silylene(n-butylcyclopentadienyl)(3-tert-butyl-5-chloro-2-phenoxy) titanium dichloride, dimethylsilylene(n-butylcyclopentadienyl)(3,5-diamyl-2-phenoxy)titanium dichloride, dimethylsilylene(tert-butylcyclopentadienyl)(2-phenoxy)titanium dichloride, dimethylsilylene(tert-butylcyclopentadienyl)(3-methyl-2-phenoxy)titanium dichloride, dimethylsilylene(tert-butylcyclopentadienyl)(3,5-dimethyl-2-phenoxy)titanium dichloride, dimethylsilylene(tert-butylcyclopentadienyl)(3-tert-butyl-2-phenoxy)titanium dichloride, dimethylsilylene(tert-butylcyclopentadienyl)(3-tert-butyl-5-methyl-2-phenoxy)titanium dichloride, dimethylsilylene(tert-butylcyclopentadienyl)(3,5-di-tert-butyl-2-phenoxy)titanium dichloride, dimethylsilylene(tert-butylcyclopentadienyl)(5-methyl-3-phenyl-2-phenoxy)titanium dichloride, dimethylsilylene(tert-butylcyclopentadienyl)(3-tert-butyldimethylsilyl-5-methyl-2-phenoxy)titanium dichloride, dimethylsilylene(tert-butylcyclopentadienyl)(5-methyl-3-trimethylsilyl-2-phenoxy)titanium dichloride, dimethylsilylene(tert-butylcyclopentadienyl)(3-tert-butyl-5-methoxy-2-phenoxy)titanium dichloride, dimethylsilylene(tert-butylcyclopentadienyl)(3-tert-butyl-5-chloro-2-phenoxy)titanium dichloride, dimethylsilylene(tert-butylcyclopentadienyl)(3,5-diamyl-2-phenoxy)titanium dichloride, dimethylsilylene(tetramethylcyclopentadienyl)(2-phenoxy)titanium dichloride, dimethylsilylene(tetramethylcyclopentadienyl)(3-methyl-2-phenoxy)titanium dichloride, dimethylsilylene(tetramethylcyclopentadienyl)(3,5-dimethyl-2-phenoxy)titanium dichloride, dimethylsilylene(tetramethylcyclopentadienyl)(3-tert-butyl-2-phenoxy)titanium dichloride, dimethylsilylene(tetramethylcyclopentadienyl)(3-tert-butyl-5-methyl-2-phenoxy)titanium dichloride, dimethylsilylene(tetramethylcyclopentadienyl)(3,5-di-tert-butyl-2-phenoxy)titanium dichloride, dimethylsilylene(tetramethylcyclopentadienyl)(5-methyl-3-phenyl-2-phenoxy)titanium dichloride, dimethylsilylene(tetramethylcyclopentadienyl)(3-tert-butyldimethylsilyl-5-methyl-2-phenoxy)titanium dichloride, dimethylsilylene(tetramethylcyclopentadienyl)(5-methyl-3-trimethylsilyl-2-phenoxy)titanium dichloride, dimethylsilylene(tetramethylcyclopentadienyl)(3-tert-butyl-5-methoxy-2-phenoxy)titanium dichloride, dimethylsilylene(tetramethylcyclopentadienyl)(3-tert-butyl-5-chloro-2-phenoxy)titanium dichloride, dimethylsilylene(tetramethylcyclopentadienyl)(3,5-diamyl-2-phenoxy)titanium dichloride, dimethylsilylene(trimethylsilylcyclopentadienyl)(2-phenoxy)titanium dichloride, dimethylsilylene(trimethylsilylcyclopentadienyl)(3-methyl-2-phenoxy)titanium dichloride, dimethyl silylene(trimethylsilylcyclopentadienyl)(3,5-dimethyl-2-phenoxy)titanium dichloride, dimethylsilylene(trimethylsilylcyclopentadienyl)(3-tert-butyl-2-phenoxy)titanium dichloride, dimethylsilylene(trimethylsilylcyclopentadienyl)(3-tert-butyl-5-methyl-2-phenoxy)titanium dichloride, dimethylsilylene(trimethylsilylcyclopentadienyl)(3,5-di-tert-butyl-2-phenoxy)titanium dichloride, dimethylsilylene(trimethylsilylcyclopentadienyl)(5-methyl-3-phenyl-2-phenoxy)titanium dichloride, dimethylsilylene(trimethylsilylcyclopentadienyl)(3-tert-butyldimethylsilyl-5-methyl-2-phenoxy)titanium dichloride, dimethylsilylene(trimethylsilylcyclopentadienyl)(5-methyl-3-trimethylsilyl-2-phenoxy)titanium dichloride, dimethylsilylene(trimethylsilylcyclopentadienyl)(3-tert-butyl-5-methoxy-2-phenoxy)titanium dichloride, dimethylsilylene (trimethylsilylcyclopentadienyl)(3-tert-butyl-5-chloro-2-phenoxy)titanium dichloride, dimethylsilylene(trimethylsilylcyclopentadienyl)(3,5-diamyl-2-phenoxy)titanium dichloride, dimethylsilylene(indenyl)(2-phenoxy)titanium dichloride, dimethylsilylene(indenyl)(3-methyl-2-phenoxy)titanium dichloride, dimethylsilylene(indenyl)(3,5-dimethyl-2-phenoxy)titanium dichloride, dimethylsilylene(indenyl)(3-tert-butyl-2-phenoxy)titanium dichloride, dimethylsilylene(indenyl)(3-tert-butyl-5-methyl-2-phenoxy)titanium dichloride, dimethylsilylene(indenyl)(3,5-di-tert-butyl-2-phenoxy)titanium dichloride, dimethylsilylene(indenyl)(5-methyl-3-phenyl-2-phenoxy)titanium dichloride, dimethylsilylene(indenyl)(3-tert-butyldimethylsilyl-5-methyl-2-phenoxy)titanium dichloride, dimethylsilylene(indenyl)(5-methyl-3-trimethylsilyl-2-phenoxy)titanium dichloride, dimethylsilylene(indenyl)(3-tert-butyl-5-methoxy-2-phenoxy)titanium dichloride, dimethylsilylene(indenyl)(3-tert-butyl-5-chloro-2-phenoxy)titanium dichloride, dimethylsilylene(indenyl)(3,5-diamyl-2-phenoxy)titanium dichloride, dimethylsilylene(fluorenyl)(2-phenoxy)titanium dichloride, dimethylsilylene(fluorenyl)(3-methyl-2-phenoxy)titanium dichloride, dimethylsilylene(fluorenyl)(3,5-dimethyl-2-phenoxy)titanium dichloride, dimethylsilylene(fluorenyl)(3-tert-butyl-2-phenoxy)titanium dichloride, dimethylsilylene(fluorenyl)(3-tert-butyl-5-methyl-2-phenoxy)titanium dichloride, dimethylsilylene(fluorenyl)(3,5-di-tert-butyl-2-phenoxy)titanium dichloride, dimethylsilylene(fluorenyl)(5-methyl-3-phenyl-2-phenoxy)titanium dichloride, dimethylsilylene(fluorenyl)(3-tert-butyldimethylsilyl-5-methyl-2-phenoxy)titanium dichloride, dimethylsilylene(fluorenyl)(5-methyl-3-trimethylsilyl-2-phenoxy)titanium dichloride, dimethylsilylene(fluorenyl)(3-tert-butyl-5-methoxy-2-phenoxy)titanium dichloride, dimethylsilylene(fluorenyl)(3-tert-butyl-5-chloro-2-phenoxy)titanium dichloride, dimethylsilylene(fluorenyl)(3,5-diamyl-2-phenoxy)titanium dichloride, dimethylsilylene(tetramethylcyclopentadienyl)(1-naphthoxy-2-yl)titanium dichloride, and compounds obtained by replacing (cyclopentadienyl) in these compounds with (dimethylcyclopentadienyl), (trimethylcyclopentadienyl), (ethylcyclopentadienyl), (n-propylcyclopentadienyl), (isopropylcyclopentadienyl), (sec-butylcyclopentadienyl), (isobutylcyclopentadienyl), (tert-butyldimethylsilylcyclopentadienyl), (phenylcyclopentadienyl), (methylindenyl) or (phenylindenyl); replacing 2-phenoxy therein with 3-phenyl-2-phenoxy, 3-trimethyl silyl-2-phenoxy or 3-tert-butyldimethylsilyl-2-phenoxy, changing dimethylsilylene therein into diethylsilylene, diphenylsilylene or dimethoxysilylene, changing titanium therein into zirconium or hafnium; or replacing chloride therein with bromide, iodide, hydride, methyl, phenyl, benzyl, methoxide, n-butoxide, isopropoxide, phenoxide, benzyloxide, dimethylamide or diethylamide.

An unbridged bismetallocene complex can also be used as the catalytic component for olefin polymerization, and examples thereof include bis(cyclopentadienyl)zirconium dichloride, bis(methylcyclopentadienyl)zirconium dichloride, bis(n-butylcyclopentadienyl)zirconium dichloride, bis(t-butylcyclopentadienyl)zirconium dichloride, bis(pentamethylcyclopentadienyl)zirconium dichloride, bis(indenyl)zirconium dichloride, bis(fluorenyl)zirconium dichloride, (cyclopentadienyl)(methylcyclopentadienyl)zirconium dichloride, (cyclopentadienyl)(n-butylcyclopentadienyl)zirconium dichloride, (cyclopentadienyl)(t-butylcyclopentadienyl)zirconium dichloride, (cyclopentadienyl)(pentamethylcyclopentadienyl)zirconium dichloride, (cyclopentadienyl)(indenyl)zirconium dichloride, (cyclopentadienyl)(fluorenyl)zirconium dichloride, and compounds obtained by replacing zirconium in these compounds with titanium or hafnium; replacing cyclopentadienyl therein with methylcyclopentadienyl, n-butylcyclopentadienyl, t-butylcyclopentadienyl, tetramethylcyclopentadienyl, indenyl or fluorenyl; or replacing chloride therein with bromide, iodide, hydride, methyl, phenyl, benzyl, methoxide, n-butoxide, isopropoxide, phenoxide, benzyloxide, dimethylamide or diethylamide.

A transition metal complex of Group 4 of the Periodic Table of the Elements having an amide-pyridyl-aryl ligand can also be used as the catalytic component for olefin polymerization, and examples thereof include 2-(N-phenylamido-phenylmethyl)-6-(2-η-phenyl)-pyridyl hafnium dimethyl, 2-(N-phenylamido-phenylmethyl)-6-(2-η-1-naphthyl)-pyridyl hafnium dimethyl, 2-[N-(2,6-diisopropylphenylamido)-phenylmethyl]-6-(2-η-phenyl)-pyridyl hafnium dimethyl, 2-[(N-phenylamido)-o-isopropylphenylmethyl]-6-(2-η-phenyl)-pyridyl hafnium dimethyl, 2-[N-(2,6-diisopropylphenylamido)-phenylmethyl]-6-(2-η-1-naphthyl)-pyridyl hafnium dimethyl, 2-[(N-phenylamido)-o-isopropylphenylmethyl]-6-(2-η-1-naphthyl)-pyridyl hafnium dimethyl, 2-[N-(2,6-diisopropylphenylamido)-o-isopropylphenylmethyl]-6-(2-η-phenyl)-pyridyl hafnium dimethyl, 2-[N-(2,6-diisopropylphenylamido)-o-isopropylphenylmethyl]-6-(2-η-1-naphthyl)-pyridyl hafnium dimethyl, 2-[N-(2,6-diisopropylphenylamido)-o-cyclohexylphenylmethyl]-6-(2-η-1-naphthyl)-pyridyl hafnium dimethyl, 2-[N-(2,6-diisopropylphenylamido)-o-methylphenylmethyl]-6-(2-η-1-naphthyl)-pyridyl hafnium dimethyl, 2-[N-(2,6-diisopropylphenylamido)-o-phenylphenylmethyl]-6-(2-η-1-naphthyl)-pyridyl hafnium dimethyl, and compounds obtained by replacing hafnium in these compounds with titanium or zirconium; or replacing dimethyl therein into bistrimethylsilylmethyl. These compounds can be produced, for example, by a method described in US2004/0220050A1.

<Olefin Polymerization Catalyst>

The olefin polymerization catalyst used in the present invention is a catalyst obtainable by bringing a catalytic component for olefin polymerization comprising the transition metal complex represented by the general formula (2), a catalytic component for trimerization comprising the transition metal complex represented by the general formula (1) and the activating co-catalyst component into contact with each other.

In the amount of each catalytic component used, a molar ratio between the catalytic component for trimerization and the catalytic component for olefin polymerization (catalytic component for trimerization/catalytic component for olefin polymerization) is usually 0.0001 to 100, preferably 0.001 to 1, more preferably 0.01 to 0.5, even more preferably 0.05 to 0.15.

In the amount of each catalytic component used, a molar ratio between the compound (A) (in terms of the aluminum atom) and the transition metal complexes used as catalytic components (total of the catalytic component for trimerization and the catalytic component for olefin polymerization) (compound (A) (in terms of the aluminum atom)/transition metal complexes) is usually 0.01 to 10000, preferably 5 to 2000. Moreover, a molar ratio between the compound (B) and the transition metal complexes used as catalytic components (total of the catalytic component for trimerization and the catalytic component for olefin polymerization) (compound (B)/transition metal complexes) is usually 0.01 to 100, preferably 0.5 to 10.

Moreover, a ratio between the mole of aluminum atoms in the compound (A) and the mole of titanium atoms in the solid catalytic component (mole of aluminum atoms in the compound (A)/mole of titanium atoms in the solid catalytic component) is usually 1 to 10000, preferably 1 to 2000, more preferably 2 to 600.

When each catalytic component is used in a solution state, the concentration of the transition metal complex used as a catalytic component is usually 0.0001 to 5 mmol/L, preferably 0.001 to 1 mmol/L. The concentration of the compound (A) is usually 0.01 to 500 mmol/L, preferably 0.1 to 100 mmol/L, in terms of the aluminum atom. The concentration of the compound (B) is usually 0.0001 to 5 mmol/L, preferably 0.001 to 1 mmol/L.

A catalytic component for olefin polymerization comprising the transition metal complex represented by the general formula (2) and the activating co-catalytic component may be supported on a carrier for use. A porous substance is preferably used as a carrier. More preferably an inorganic substance or an organic polymer, even more preferably an inorganic substance, is used. The carrier will be described later.

The method for bringing each catalytic component into contact with each other is not particularly limited. The catalytic component for olefin polymerization, the catalytic component for trimerization and the activating co-catalytic component may be brought into contact with each other in advance to prepare a polymerization catalyst, which is then supplied to a polymerization reactor. Alternatively, these catalytic components may be supplied to a polymerization reactor in any order and subjected to contact treatment in the polymerization reactor. The catalytic component for olefin polymerization brought into contact with the catalytic component for trimerization in advance (including a simultaneous product of the catalytic component for olefin polymerization and the catalytic component for trimerization) may also be supplied to a polymerization reactor; the catalytic component for olefin polymerization brought into contact with the activating co-catalytic component in advance may be supplied thereto; or the catalytic component for trimerization brought into contact with the activating co-catalytic component in advance may be supplied thereto.

(Carrier)

Examples of the inorganic substance used as a carrier include inorganic oxides and magnesium compounds. Clay, clay mineral, or the like may also be used. They may be mixed for use.

Specific examples of the inorganic oxides used as a carrier can include $SiO_2$, $Al_2O_3$, MgO, $ZrO_2$, $TiO_2$, $B_2O_3$, CaO, ZnO, BaO, $ThO_2$ and mixtures thereof, for example, $SiO_2$—MgO, $SiO_2$—$Al_2O_3$, $SiO_2$—$TiO_2$, $SiO_2$—$V_2O_5$, $SiO_2$—$Cr_2O_3$ and $SiO_2$—$TiO_2$—MgO. Among these inorganic oxides, $SiO_2$ and $Al_2O_3$ are preferable, and $SiO_2$ is more preferable. These inorganic oxides may contain a small amount of a carbonate, sulfate, nitrate or oxide component such as $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_3$, $Na_2O$, $K_2O$, and $Li_2O$.

Moreover, the inorganic oxides usually have a hydroxy group formed on the surface. Modified inorganic oxides obtained by substituting active hydrogen in the surface hydroxy group by various substituents may be used as the inorganic oxides, and a preferable substituent is a silyl group. Specific examples of the modified inorganic oxides include inorganic oxides treated by contact with trialkylchlorosilane such as trimethylchlorosilane and tert-butyldimethylchlorosilane, triarylchlorosilane such as triphenylchlorosilane, dialkyldichlorosilane such as dimethyldichlorosilane, diaryldichlorosilane such as diphenyldichlorosilane, alkyltrichlorosilane such as methyltrichlorosilane, aryltrichlorosilane such as phenyltrichlorosilane, trialkylalkoxysilane such as trimethylmethoxysilane, triarylalkoxysilane such as triphenylmethoxysilane, dialkyldialkoxysilane such as dimethyldimethoxysilane, diaryldialkoxysilane such as diphenyldimethoxysilane, alkyltrialkoxysilane such as methyltrimethoxysilane, aryltrialkoxysilane such as phenyltrimethoxysilane, tetraalkoxysilane such as tetramethoxysilane, alkyldisilazane such as 1,1,1,3,3,3-hexamethyldisilazane, tetrachlorosilane, or the like.

Examples of the magnesium compounds used as a carrier can include: magnesium halide such as magnesium chloride, magnesium bromide, magnesium iodide and magnesium fluoride; alkoxy magnesium halide such as methoxy magnesium chloride, ethoxy magnesium chloride, isopropoxy magnesium chloride, butoxy magnesium chloride and octoxy magnesium chloride; aryloxy magnesium halide such as phenoxy magnesium chloride and methylphenoxy magnesium chloride; alkoxymagnesium such as ethoxymagnesium, isopropoxymagnesium, butoxymagnesium, n-octoxymagnesium and 2-ethylhexoxymagnesium; aryloxymagnesium such as phenoxymagnesium and dimethylphenoxymagnesium; and carboxylate of magnesium such as magnesium laurate and magnesium stearate. Among them, magnesium halide or alkoxymagnesium is preferable, and magnesium chloride or butoxymagnesium is more preferable.

Examples of the clay or clay mineral used as a carrier include kaolin, bentonite, kibushi clay, gairome clay, allophane, hisingerite, pyrophyllite, talc, micas isinglass, montmorillonites, vermiculite, chlorites, palygorskite, kaolinite, nacrite, dickite and halloysites. Among them, smectite, montmorillonite, hectorite, Laponite or saponite is preferable, and montmorillonite or hectorite is more preferable.

The inorganic substance used as a carrier is preferably inorganic oxide.

These inorganic substances used as a carrier are preferably dried, for use, by heat treatment. The temperature of the heat treatment is usually 100 to 1500° C., preferably 100 to 1000° C., more preferably 200 to 800° C. The time of the heat treatment is not particularly limited and is preferably 10 minutes to 50 hours, more preferably 1 hour to 30 hours. Examples of the method for the heat treatment include, but not limited to, a method in which after heating, for example, dried inert gas (e.g., nitrogen or argon) is circulated at a constant flow rate for a few hours or longer, and a method in which the pressure is reduced for a few hours.

The average particle size of the carrier comprising the inorganic substance is preferably 5 to 1000 μm, more preferably 10 to 500 μm, even more preferably 10 to 100 μm. The pore volume of the carrier comprising the inorganic substance is preferably 0.1 ml/g or larger, more preferably 0.3 to 10 ml/g. The specific surface of the carrier comprising the inorganic substance is preferably 10 to 1000 $m^2$/g, more preferably 100 to 500 $m^2$/g.

The organic polymer used as a carrier is not particularly limited, and two or more organic polymers may be used as a mixture. A polymer having a group having active hydrogen and/or a non-proton-donating Lewis-basic group is preferable.

The group having active hydrogen is not particularly limited as long as it has active hydrogen. Specific examples thereof include primary amino, secondary amino, imino, amide, hydrazide, amidino, hydroxy, hydroperoxy, carboxyl, formyl, carbamoyl, sulfonic acid, sulfinic acid, sulfenic acid, thiol, thioformyl, pyrrolyl, imidazolyl, piperidyl, indazolyl and carbazolyl groups. A primary amino, secondary amino, imino, amide, imide, hydroxy, formyl, carboxyl, sulfonic acid or thiol group is preferable. A primary amino, secondary amino, amide or hydroxy group is particularly preferable. These groups may be substituted by a halogen atom or a hydrocarbyl group having 1 to 20 carbon atoms.

The non-proton-donating Lewis-basic group is not particularly limited as long as it is a group having a Lewis base moiety free from an active hydrogen atom. Specific examples thereof include pyridyl, N-substituted imidazolyl, N-substituted indazolyl, nitrile, azide, N-substituted imino, N,N-substituted amino, N,N-substituted aminooxy, N,N,N-substituted hydrazino, nitroso, nitro, nitrooxy, furyl, carbonyl, thiocarbonyl, alkoxy, alkyloxycarbonyl, N,N-substituted carbamoyl, thioalkoxy, substituted sulfinyl, substituted sulfonyl and substituted sulfonic acid groups. Heterocyclic groups are preferable, and aromatic heterocyclic groups having oxygen and/or nitrogen atoms in the ring are more preferable. A pyridyl, N-substituted imidazolyl or N-substituted indazolyl group is particularly preferable, with a pyridyl group most preferred. These groups may be substituted by a halogen atom or a hydrocarbyl group having 1 to 20 carbon atoms.

The amount of the group having active hydrogen and the non-proton-donating Lewis-basic group in the polymer is preferably 0.01 to 50 mmol/g, more preferably 0.1 to 20 mmol/g, in terms of the molar amount of the group per unit gram of the polymer.

The polymer having such group(s) can be obtained, for example, by homopolymerizing monomers having the group having active hydrogen and/or the non-proton-donating Lewis-basic group and one or more polymerizable unsaturated groups or by copolymerizing this monomer with additional monomer(s) having one or more polymerizable unsaturated groups. Moreover, a crosslinking polymerizable monomer having two or more polymerizable unsaturated groups is preferably used as at least one of the additional monomers.

Examples of such monomers having the group having active hydrogen and/or the non-proton-donating Lewis-basic group and one or more polymerizable unsaturated groups can include monomers having the group having active hydrogen and one or more polymerizable unsaturated groups, and monomers having the group having a Lewis base moiety free from an active hydrogen atom and one or more polymerizable unsaturated groups. Examples of such polymerizable unsaturated groups include: alkenyl groups such as vinyl and allyl; and alkynyl groups such as an ethyne group.

Examples of the monomers having the group having active hydrogen and one or more polymerizable unsaturated groups can include vinyl group-containing primary amine, vinyl group-containing secondary amine, vinyl group-containing amide compounds and vinyl group-containing hydroxy compounds. Specific examples thereof include N-(1-ethenyl)amine, N-(2-propenyl)amine, N-(1-ethenyl)-N-methylamine, N-(2-propenyl)-N-methylamine, 1-ethenylamide, 2-propenylamide, N-methyl-(1-ethenyl)amide, N-methyl-(2-propenyl)amide, vinyl alcohol, 2-propen-1-ol and 3-buten-1-ol.

Specific examples of the monomers having the non-proton-donating Lewis-basic group and one or more polymerizable unsaturated groups can include vinylpyridine, vinyl (N-substituted) imidazole and vinyl (N-substituted) indazole.

Examples of the additional monomers having one or more polymerizable unsaturated groups include olefin and aromatic vinyl compounds and specifically include ethylene, propylene, 1-butene, 1-hexene, 4-methyl-1-pentene and styrene. Ethylene or styrene is preferable. These monomers may be used in combination of two or more thereof. Moreover, specific examples of the crosslinking polymerizable monomer having two or more polymerizable unsaturated groups include divinylbenzene.

The average particle size of the carrier comprising the organic polymer is preferably to 1000 μm, more preferably 10 to 500 μm. The pore volume of the carrier comprising the organic polymer is preferably 0.1 ml/g or larger, more preferably 0.3 to 10 ml/g. The specific surface of the carrier comprising the organic polymer is preferably 10 to 1000 $m^2/g$, more preferably 50 to 500 $m^2/g$.

These organic polymers used as a carrier are preferably dried, for use, by heat treatment. The temperature of the heat treatment is usually 30 to 400° C., preferably 50 to 200° C., more preferably 70 to 150° C. The time of the heat treatment is not particularly limited and is preferably 10 minutes to 50 hours, more preferably 1 hour to 30 hours. Examples of the method for the heat treatment include, but not limited to, a method in which after heating, for example, dried inert gas (e.g., nitrogen or argon) is circulated at a constant flow rate for a few hours or longer, and a method in which the pressure is reduced for a few hours.

The geometric standard deviation of the particle size of the carrier based on the volume is preferably 2.5 or lower, more preferably 2.0 or lower, even more preferably 1.7 or lower.

<Polymerization>

The present invention relates to a process for producing an ethylenic polymer, comprising polymerizing ethylene in the presence of the olefin polymerization catalyst. The polymerization may be performed by supplying only ethylene as a raw material monomer or by supplying an ethylene-copolymerizable monomer and ethylene.

Examples of the ethylene-copolymerizable monomer include: olefin having 3 to 20 carbon atoms, such as propylene, 1-butene, 1-pentene, 1-hexene, 1-heptene, 1-octene, 1-nonene, 1-decene, 1-dodecene, 4-methyl-1-pentene and 4-methyl-1-hexene; cyclic olefin such as norbornene; alkenyl aromatic hydrocarbyl such as styrene; unsaturated carboxylic acid such as acrylic acid and methacrylic acid; unsaturated carboxylic ester such as methyl acrylate, ethyl acrylate, butyl acrylate, methyl methacrylate and ethyl methacrylate; and vinyl ester compounds such as vinyl acetate. These monomers may be used alone or in combination of two or more thereof.

The polymerization process is not particularly limited and can be, for example, solvent polymerization using aliphatic hydrocarbyl (butane, pentane, hexane, heptane, octane, etc.), aromatic hydrocarbyl (benzene, toluene, etc.) or hydrocarbyl halide (methylene dichloride, etc.) as a solvent, slurry polymerization, gas-phase polymerization performed in monomers in a gas state, or the like. Moreover, both continuous polymerization and batch polymerization may be used.

The present invention can produce a polymer having a butyl branch even by polymerization using hexene supplied in small amounts as a raw material monomer or by polymerization using only ethylene supplied as a raw material monomer. Therefore, polymerization conditions that make the advantages of the present invention more significant involve an ethylene molar fraction (the total amount of ethylene and 1-hexene in the polymerization system is defined as 100 mol %) of preferably 90 mol % or larger, more preferably 95 mol % or larger, even more preferably, substantially 100 mol %, in the polymerization system, when the polymerization form is slurry polymerization. Moreover, when the polymerization form is gas-phase polymerization, the ethylene molar fraction (the total amount of ethylene and 1-hexene in the polymerization system is defined as 100 mol %) is preferably 97 mol % or larger, more preferably 98 mol % or larger, even more preferably, substantially 100 mol %, in the polymerization system.

For the solution polymerization and the slurry polymerization, the concentration of the olefin polymerization catalyst in the polymerization solution is usually 0.0001 to 5 mmol/L in terms of the mole of the transition metal complexes used as catalytic components (total of the catalytic component for trimerization and the catalytic component for olefin polymerization). The concentration of the olefin polymerization catalyst is preferably 2 mmol/L or lower, more preferably 1 mmol/L or lower, for enhancing the economy. Moreover, the concentration of the olefin polymerization catalyst is preferably 0.001 mmol/L or higher, more preferably 0.01 mmol/L or higher, even more preferably 0.1 mmol/L or higher, particularly preferably 0.5 mmol/L or higher, for more increasing the number of butyl branches.

The polymerization pressure is preferably normal pressure to 5 MPa. The polymerization time is generally determined appropriately according to the type of the polymer of interest and a reaction apparatus and can be in the range of 1 minute to 20 hours. Moreover, a chain transfer agent such as hydrogen can also be added for adjusting the molecular weight of the ethylenic polymer.

The polymerization temperature can be in the range of 0° C. to 220° C. The polymerization temperature is preferably 20° C. or higher, more preferably 40° C. or higher, even more preferably 50° C. or higher, most preferably 70° C. or higher, to improve the economic efficiency. Moreover, the polymerization temperature is preferably 130° C. or lower, more preferably 100° C. or lower, for more increasing the number of butyl branches.

<Polymer>

Examples of the ethylenic polymer obtained by the production process of the present invention include ethylene-1-hexene, ethylene-1-hexene-propylene, ethylene-1-hexene-1-butene, ethylene-1-hexene-1-octene, ethylene-1-hexene-4-methyl-1-pentene, ethylene-1-hexene-1-butene-1-octene, ethylene-1-hexene-1-butene-4-methyl-1-pentene, ethylene-1-hexene-styrene, ethylene-1-hexene-norbornene, ethylene-1-hexene-propylene-styrene and ethylene-1-hexene-propylene-norbornene copolymers.

The ethylenic polymer is preferably an ethylene-1-hexene, ethylene-1-hexene-propylene, ethylene-1-hexene-1-butene, ethylene-1-hexene-1-octene, ethylene-1-hexene-4-methyl-1-pentene, ethylene-1-hexene-styrene or ethylene-1-hexene-norbornene copolymer, more preferably an ethylene-1-hexene or ethylene-1-hexene-1-butene copolymer.

The number of butyl branches per 1000 carbon atoms in the ethylenic polymer is preferably 1 or more, more preferably 3 or more, even more preferably 5 or more, particularly preferably 10 or more, from the viewpoint of enhancing the mechanical strength of the ethylenic polymer. Moreover, the number of butyl branches is preferably 40 or less, more preferably 30 or less, even more preferably 25 or less, from the viewpoint of enhancing the stiffness of the ethylenic polymer. The number of butyl branches can be determined by a method such as carbon nuclear magnetic resonance ($^{13}$C-NMR) or IR.

The melting point of the ethylenic polymer is preferably lower than 130° C. from the viewpoint of enhancing the mechanical strength of the ethylenic polymer. The melting point can be determined using a differential scanning calorimeter.

The number of butyl branches per 1000 carbon atoms in the ethylenic polymer can be increased by increasing a molar ratio between the catalytic component for trimerization and the catalytic component for olefin polymerization (catalytic component for trimerization/catalytic component for olefin polymerization) used in the preparation of the polymerization catalyst or by lowering the polymerization temperature.

The molecular weight distribution (Mw/Mn) of the ethylenic polymer is preferably 1.5 or higher for enhancing the processability of the polymer. Moreover, Mw/Mn is preferably 20 or lower for enhancing the mechanical strength of the polymer. The molecular weight distribution (Mw/Mn) is a value (Mw/Mn) obtained by determining the weight-average molecular weight (Mw) and the number-average molecular weight (Mn) by gel permeation chromatography against polystyrene standards and dividing Mw by Mn.

The ethylenic polymer is molded, for use, into various moldings (e.g., films, sheets and containers (bottles, trays, etc.)) by a molding method known in the art, for example: extrusion methods such as inflation film molding and T-die film molding; hollow molding, injection molding; compression molding; and cross-linked foaming molding.

The ethylenic polymer may be blended with a resin known in the art and then molded. Moreover, the moldings may be monolayer molding containing the ethylenic polymer or may be multilayer molding containing the ethylenic polymer.

Examples of the moldings include films for food package, containers for food package, packaging materials for pharmaceuticals, surface-protective films, packaging materials for electronic parts used in package for semiconductor products or the like, cross-linked foamed moldings, injection foamed moldings, hollow moldings, blow bottles and squeeze bottles.

EXAMPLES

The present invention will be described by way of Examples and Comparative Examples below.
<Production of Transition Metal Complex>
Physical properties were measured according to the following methods.
(1) Proton Nuclear Magnetic Resonance Spectrum ($^1$H-NMR)
Apparatus: EX270 manufactured by JEOL Ltd.
Sample cell: Tube (5 mm in diameter)
Measurement solvent: CDCl$_3$ or CD$_2$Cl$_2$
Sample concentration: 10 mg/0.5 mL (CDCl$_3$ or CD$_2$Cl$_2$)
Measurement temperature: Room temperature (about 25° C.)
Measurement parameter: Probe (5 mm in diameter), EXMOD NON, OBNUC $^1$H, accumulated number 16 times or more
Repeat time: ACQTM 6 seconds, PD 1 second
Internal standard: CDCl$_3$ (7.26 ppm) or CD$_2$Cl$_2$ (5.32 ppm)

(2) Carbon Nuclear Magnetic Resonance Spectrum ($^{13}$C-NMR)
Apparatus: EX270 manufactured by JEOL Ltd.
Sample cell: Tube (5 mm in diameter)
Measurement solvent: $CDCl_3$ or $CD_2Cl_2$
Sample concentration: 30 mg/0.5 mL ($CDCl_3$ or $CD_2Cl_2$)
Measurement temperature: Room temperature (about 25° C.)
Measurement parameter: Probe (5 mm in diameter), EXMOD BCM, OBNUC $^{13}$C, accumulated number 256 times or more
Repeat time: ACQTM 1.79 seconds, PD 1.21 seconds
Internal standard: $CDCl_3$ (77.0 ppm) or $CD_2Cl_2$ (53.8 ppm)
(3) Mass Spectrum
[Electron ionization mass spectrometry (EI-MS)]
Apparatus: JMS-T100GC manufactured by JEOL Ltd.
Ionization voltage: 70 eV
Ion source temperature: 230° C.
Acceleration voltage: 7 kV
MASS RANGE: m/z 35-800

Example 1

Synthesis of [1-n-butylmethylphenyl silyl-2,3,4,5-tetramethylcyclopentadienyl]titanium trichloride (Hereinafter, Referred to as "Complex 1")

Synthesis of 1-n-butylmethylphenylsilyl-2,3,4,5-tetramethylcyclopentadiene

Under a nitrogen atmosphere, sodium hydride dispersed in mineral oil was washed with hexane to remove the mineral oil. Thereafter, the resultant sodium hydride (0.80 g, 33.47 mmol as pure sodium hydride) and tetrahydrofuran (38 mL) were mixed. This mixture was heated to 50° C. and aniline (0.21 g, 2.23 mmol) was added and stirred at 50° C. for one hour. To this, a solution of 1,2,3,4-tetramethylcyclopenta-1,3-diene (3.00 g, 24.55 mmol) dissolved in tetrahydrofuran (10 mL) was added dropwise and stirred at 50° C. for 2 hours, and then the resultant mixture was cooled to 0° C. To this solution, a solution of chloro(n-butyl)methylphenylsilane (4.75 g, 22.32 mmol) dissolved in toluene (10 mL) was added dropwise and stirred at 35° C. for 2 hours. The resultant mixture was added dropwise at 0° C. to a mixed solution of a 10% sodium hydrogen carbonate (24 mL) and a 10% sodium carbonate (24 mL). Toluene (24 mL) was added to separate an organic phase, and the organic phase was washed with water (40 mL) and further washed with saturated brine (20 mL). After the organic phase was dried over sodium sulfate and filtrated, the solvent was removed under reduced pressure to obtain 1-n-butylmethylphenylsilyl-2,3,4,5-tetramethylcyclopentadiene (5.16 g, yield 77.4%).
$^1$H-NMR ($CDCl_3$, δ ppm): 0.13 (s, 3H), 0.66-0.90 (m, 2H), 0.84 (t, J=7.0 Hz, 3H), 1.15-1.35 (m, 4H), 1.67 (s, 3H), 1.71 (s, 3H), 1.73 (s, 3H), 1.80 (s, 3H), 3.10 (s, 1H), 7.29-7.36 (m, 3H), 7.41-7.47 (m, 2H)
Mass Spectrum (EI-MS, m/z): 298 ($M^+$)

Synthesis of Complex 1

Under a nitrogen atmosphere, to a toluene solution (23 mL) of 1-n-butylmethylphenylsilyl-2,3,4,5-tetramethylcyclopentadiene (2.30 g, 7.70 mmol) and triethylamine (1.95 g, 19.25 mmol), a 1.55 M hexane solution of n-butyllithium (6.21 mL, 9.63 mmol) was added dropwise at −78° C. After the mixture was gradually warmed to room temperature, stirring was performed at 35° C. for 2.5 hours. The resultant mixture was cooled to −78° C. and a solution of titanium tetrachloride (2.19 g, 11.55 mmol) dissolved in toluene (12 mL) was added dropwise at the same temperature. The mixture was warmed and the internal temperature was set to 60° C. Thereafter, the mixture was stirred at the same temperature for 2 hours. After completion of the reaction, the solvent was removed under reduced pressure. Thereafter, the residue, to which heptane was added, was filtrated to remove insoluble materials. The solvent was removed under reduced pressure. Pentane was added and a precipitated white solid was removed by filtration. The resultant filtrate was cooled to −20° C. The resultant solid was filtrated and washed with a small amount of pentane, and then dried under reduced pressure to obtain complex 1 (0.25 g, yield 7.2%) as an orange solid.
$^1$H-NMR ($CDCl_3$, δ ppm): 0.76 (s, 3H), 0.87 (t, J=7.0 Hz, 3H), 1.23-1.42 (m, 6H), 2.27 (s, 3H), 2.28 (s, 3H), 2.36 (s, 3H), 2.46 (s, 3H), 7.30-7.42 (m, 3H), 7.43-7.52 (m, 2H)
$^{13}$C-NMR ($CDCl_3$, δ ppm): −2.61, 13.69, 14.13, 14.32, 14.90, 17.71, 17.81, 25.86, 26.51, 128.01, 129.53, 134.45, 136.25, 139.44, 141.96, 142.47, 144.63, 144.92
Mass Spectrum (EI-MS, m/z): 393 ($M^+$-Bu)

Example 2

Synthesis of [1-methyldiphenylsilyl-2,3,4,5-tetramethylcyclopentadienyl]titanium trichloride (Hereinafter, Referred to as "Complex 2")

Synthesis of 1-methyldiphenylsilyl-2,3,4,5-tetramethylcyclopentadiene

Under a nitrogen atmosphere, sodium hydride dispersed in mineral oil was washed with hexane to remove the mineral oil. Thereafter, the resultant sodium hydride (0.54 g, 22.32 mmol as pure sodium hydride) and tetrahydrofuran (28 mL) were mixed. This mixture was heated to 50° C. and aniline (0.14 g, 1.49 mmol) was added and stirred at 50° C. for one hour. To this, a solution of 1,2,3,4-tetramethylcyclopenta-1,3-diene (3.00 g, 24.55 mmol) dissolved in tetrahydrofuran (7 mL) was added dropwise and stirred at 50° C. for 2 hours, and then was cooled to 20° C. To this solution, a solution of chloromethyldiphenylsilane (3.46 g, 14.88 mmol) dissolved in toluene (7 mL) was added dropwise and stirred at 35° C. overnight. The resultant mixture was added dropwise at 0° C. to a mixed solution of a 10% sodium hydrogen carbonate (17 mL) and a 10% sodium carbonate (17 mL). Toluene (17 mL) was added to separate an organic phase, and the organic phase was dried over sodium sulfate and filtrated. The solvent was concentrated under reduced pressure to obtain 1-methyldiphenylsilyl-2,3,4,5-tetramethylcyclopentadiene (4.10 g, yield 86.5%).

Synthesis of Complex 2

Under a nitrogen atmosphere, to a toluene solution (38 mL) of 1-methyldiphenylsilyl-2,3,4,5-tetramethylcyclopentadiene (1.90 g, 5.97 mmol) and triethylamine (3.02 g, 29.86 mmol), a 1.55 M hexane solution of n-butyllithium (4.62 mL, 7.17 mmol) was added dropwise at −78° C. After the mixture was gradually warmed to room temperature, stirring was performed at 35° C. for 3 hours. The resultant mixture was cooled to −78° C. and a solution of titanium tetrachloride (1.25 g, 6.57 mmol) dissolved in toluene (7 mL) was added dropwise at the same temperature. The mixture was warmed and the internal temperature was set to 35° C. Thereafter, the mixture was stirred at the same temperature for one hour. After completion of the reaction, the solvent was removed under reduced pressure. The residue, to which heptane was added, was filtrated to remove insoluble materials. The solvent was removed under reduced pressure. Pentane was added, the resultant solid was filtrated and washed with a small amount of pentane and then dried under reduced pressure to obtain complex 2 (0.94 g, yield 33.2%) as an orange solid.

$^1$H-NMR (CDCl$_3$, δ ppm): 2.12 (s, 6H), 2.34 (s, 6H), 7.31-7.50 (m, 10H)

$^{13}$C-NMR (CDCl$_3$, δ ppm): −1.04, 14.27, 17.69, 128.11, 129.91, 135.08, 135.38, 137.44, 142.33, 145.22

Mass Spectrum (EI-MS, m/z): 470 (M$^+$)

Example 3

Synthesis of [1-cyclohexylmethylphenylsilyl-2,3,4,5-tetramethylcyclopentadienyl]titanium trichloride (Hereinafter, Referred to as "Complex 3")

Synthesis of 1-cyclohexylmethylphenylsilyl-2,3,4,5-tetramethylcyclopentadiene

Under a nitrogen atmosphere, sodium hydride dispersed in mineral oil was washed with hexane to remove the mineral oil. Thereafter, the resultant sodium hydride (1.21 g, 50.32 mmol as pure sodium hydride) and tetrahydrofuran (57 mL) were mixed. This mixture was heated to 50° C. and aniline (0.31 g, 3.35 mmol) was added and stirred at 50° C. for 1.5 hours. To this, a solution of 1,2,3,4-tetramethylcyclopenta-1,3-diene (4.51 g, 36.90 mmol) dissolved in tetrahydrofuran (14 mL) was added dropwise and stirred at 50° C. for 2 hours, and then was cooled to 0° C. To this solution, a solution of chlorocyclohexylmethylphenylsilane (8.01 g, 33.55 mmol) dissolved in toluene (14 mL) was added dropwise and stirred at room temperature for 3 hours. The resultant mixture was added dropwise at 0° C. to a 10% aqueous sodium carbonate solution (72 ml). Toluene (100 mL) was added to separate an organic phase, and the organic phase was washed with water (100 mL) twice and further washed with saturated saline (50 mL). After the organic phase was dried over sodium sulfate and filtrated, the solvent was removed under reduced pressure. Purification was performed by silica gel column chromatography to obtain 1-cyclohexylmethylphenylsilyl-2,3,4,5-tetramethylcyclopentadiene (6.57 g, yield 60.3%).

$^1$H-NMR (CDCl$_3$, δ ppm): 0.03 (s, 3H), 1.05-1.37 (m, 6H), 1.58-1.84 (m, 14H), 1.94 (s, 3H), 3.23 (s, 1H), 7.23-7.34 (m, 3H), 7.36-7.42 (m, 2H)

Mass Spectrum (EI-MS, m/z): 324 (M$^+$)

Synthesis of Complex 3

Under a nitrogen atmosphere, to a toluene solution (49 mL) of 1-cyclohexylmethylphenylsilyl-2,3,4,5-tetramethylcyclopentadiene (2.27 g, 7.00 mmol) and triethylamine (3.54 g, 35.00 mmol), a 1.65 M hexane solution of n-butyllithium (5.09 mL, 8.40 mmol) was added dropwise at −78° C. After the mixture was gradually warmed to room temperature, stirring was performed at room temperature for 2 hours. The resultant mixture was cooled to −78° C. and a solution of titanium tetrachloride (1.46 g, 7.70 mmol) dissolved in toluene (8 mL) was added dropwise at the same temperature. After the mixture was gradually warmed to room temperature, stirring was performed at room temperature for 2 hours. After completion of the reaction, the solvent was removed under reduced pressure. Thereafter, the residue, to which heptane was added, was filtrated to remove insoluble materials. The solvent was removed under reduced pressure. Pentane was added and the resultant solid was filtrated and washed with a small amount of pentane, and then, dried under reduced pressure to obtain complex 3 (1.19 g, yield 35.6%) as an orange solid.

$^1$H-NMR (CDCl$_3$, δ ppm): 0.80 (s, 3H), 1.04-1.50 (m, 6H), 1.56-1.84 (m, 5H), 2.15 (s, 3H), 2.24 (s, 3H), 2.41 (s, 3H), 2.61 (s, 3H), 7.30-7.43 (m, 3H), 7.49-7.60 (m, 2H)

$^{13}$C-NMR (CDCl$_3$, δ ppm): −3.47, 14.15, 14.50, 17.73, 17.79, 24.90, 26.73, 27.73, 28.06, 28.13, 28.24, 127.83, 129.54, 134.90, 135.31, 139.69, 141.89, 142.81, 144.45, 144.71

Mass Spectrum (EI-MS, m/z): 394 (M$^+$-Cy) (Cy: cyclohexyl)

Example 4

Synthesis of [1-methyl(n-octadecyl)phenyl silyl-2,3,4,5-tetramethylcyclopentadienyl]titanium trichloride (Hereinafter, Referred to as "Complex 4")

Synthesis of 1-methyl(n-octadecyl)phenylsilyl-2,3,4,5-tetramethylcyclopentadiene Under a nitrogen atmosphere, sodium hydride dispersed in mineral oil was washed with hexane to remove the mineral oil. Thereafter, the resultant sodium hydride (0.82 g, 34.09 mmol as pure sodium hydride) and tetrahydrofuran (39 mL) were mixed. This mixture was heated to 50° C. and aniline (0.21 g, 2.27 mmol) was added and stirred at 50° C. for 2.5 hours. To this, a solution of 1,2,3,4-tetramethylcyclopenta-1,3-diene (3.06 g, 25.00 mmol) dissolved in tetrahydrofuran (10 mL) was added dropwise and stirred at 50° C. for 2.5 hours, and then was cooled to 0° C. To this solution, a solution of chloromethyl(n-octadecyl)phenylsilane (9.30 g, 22.73 mmol) dissolved in toluene (10 mL) was added dropwise and stirred at room temperature overnight. The resultant mixture was added dropwise at 0° C. to a 10% aqueous sodium carbonate solution (50 ml). Toluene (70 mL) was added to separate an organic phase, and the organic phase was washed with water (70 mL) twice, and further washed with saturated brine (50 mL). After dried over sodium sulfate, the organic phase was filtrated. The solvent was removed under reduced pressure. Purification was performed by silica gel column chromatography to obtain 1-methyl(n-octadecyl)phenylsilyl-2,3,4,5-tetramethylcyclopentadiene (8.65 g, yield 76.9%).

$^1$H-NMR (CDCl$_3$, δ ppm): 0.13 (s, 3H), 0.88 (t, J=6.9 Hz, 3H), 1.17-1.32 (m, 34H), 1.67 (s, 3H), 1.71 (s, 3H), 1.73 (s, 3H), 1.79 (s, 3H), 3.10 (s, 1H), 7.28-7.38 (m, 3H), 7.40-7.47 (m, 2H)

Mass Spectrum (EI-MS, m/z): 494 (M$^+$)

Synthesis of Complex 4

Under a nitrogen atmosphere, to a toluene solution (49 mL) of 1-methyl(n-octadecyl)phenylsilyl-2,3,4,5-tetramethylcyclopentadiene (1.98 g, 4.00 mmol) and triethylamine (2.02 g, 20.00 mmol), a 1.65 M hexane solution of n-butyllithium (2.67 mL, 4.40 mmol) was added dropwise at −78° C. After the mixture was gradually warmed to room temperature, stirring was performed at room temperature for 3 hours. The resultant mixture was cooled to −78° C. and a solution of titanium tetrachloride (0.83 g, 4.40 mmol) dissolved in toluene (4 mL) was added dropwise at the same temperature. After the mixture was gradually warmed to room temperature, stirring was performed at room temperature overnight. After completion of the reaction, the solvent was removed under reduced pressure. Thereafter, the residue, to which heptane was added, was filtrated to remove insoluble materials. The solvent was removed under reduced pressure. The resultant residue was cooled to −78° C. and washed with pentane. Hexamethyldisiloxane was added and cooled to −20° C. The resultant solid was filtrated and washed with a small amount of hexamethyldisiloxane, and then, dried under reduced pressure to obtain complex 4 (0.30 g, yield 11.7%) as an orange solid.

$^1$H-NMR (CDCl$_3$, δ ppm): 0.76 (s, 3H), 0.88 (t, J=6.8 Hz, 3H), 1.15-1.37 (m, 34H), 2.27 (s, 3H), 2.28 (s, 3H), 2.36 (s, 3H), 2.46 (s, 3H), 7.29-7.40 (m, 3H), 7.43-7.52 (m, 2H)

$^{13}$C-NMR (CDCl$_3$, δ ppm): −2.56, 14.15, 14.34, 15.21, 17.74, 17.84, 22.72, 23.72, 29.25, 29.39, 29.56, 29.68, 29.72, 31.95, 33.56, 128.03, 129.55, 134.48, 136.31, 139.46, 141.94, 142.46, 144.63, 144.92

Mass Spectrum (EI-MS, m/z): 393 (M$^+$-C$_{18}$H$_{37}$)

Example 5

Synthesis of [1-dimethylphenylsilyl-2,3,4,5-tetramethylcyclopentadienyl]titanium trichloride (Hereinafter, Referred to as "Complex 5")

Synthesis of 1-dimethylphenylsilyl-2,3,4,5-tetramethylcyclopentadiene

Under a nitrogen atmosphere, sodium hydride (0.80 g, 33.47 mmol in terms of pure sodium hydride) dispersed in mineral oil and tetrahydrofuran (30 mL) were mixed. This mixture was heated to 50° C. and aniline (0.21 g, 2.23 mmol) was added and stirred at 50° C. for one hour. To this, a solution of 1,2,3,4-tetramethylcyclopenta-1,3-diene (3.00 g, 24.55 mmol) dissolved in tetrahydrofuran (8 mL) was added dropwise and stirred at 50° C. for 2 hours, and then was cooled to 0° C. To this solution, a solution of chlorodimethylphenylsilane (3.81 g, 22.32 mmol) dissolved in toluene (8 mL) was added dropwise and stirred at 35° C. The resultant mixture was added dropwise at 0° C. to a mixed solution of a 10% sodium hydrogen carbonate (19 mL) and a 10% sodium carbonate (19 mL). Toluene (19 mL) was added to separate an organic phase, and the organic phase was dried over sodium sulfate and filtrated. The solvent was removed under reduced pressure and purification was performed by silica gel column chromatography to obtain 1-dimethylphenylsilyl-2,3,4,5-tetramethylcyclopentadiene (4.08 g, yield 71.3%).

Synthesis of Complex 5

Under a nitrogen atmosphere, to a toluene solution (27 mL) of 1-dimethylphenylsilyl-2,3,4,5-tetramethylcyclopentadiene (1.36 g, 5.30 mmol) and triethylamine (2.68 g, 26.50 mmol), a 1.65 M hexane solution of n-butyllithium (3.85 mL, 6.36 mmol) was added dropwise at −78° C. After the mixture was gradually warmed to room temperature, stirring was performed at 35° C. for 2 hours. The resultant mixture was cooled to −78° C. and a solution of titanium tetrachloride (1.11 g, 5.83 mmol) dissolved in toluene (6 mL) was added dropwise at the same temperature. After the mixture was warmed, the mixture was stirred at room temperature for 1.5 hours. After the completion of the reaction, the solvent was removed under reduced pressure. Thereafter, the residue, to which heptane was added, was filtrated to remove insoluble materials. The solvent was removed under reduced pressure. Pentane was added and the resultant solid was filtrated and washed with a small amount of pentane, and then, dried under reduced pressure to obtain complex 5 (0.11 g, yield 4.9%) as an orange solid.

$^1$H-NMR (CDCl$_3$, δ ppm): 0.77 (s, 6H), 2.33 (s, 6H), 2.40 (s, 6H), 7.31-7.47 (m, 5H)

$^{13}$C-NMR (CDCl$_3$, δ ppm): 0.20, 14.19, 17.65, 128.08, 129.57, 133.96, 137.38, 138.66, 142.17, 144.90

Mass Spectrum (EI-MS, m/z): 408 (M$^+$)

Example 6

Synthesis of [1-dimethyl(3,5-dimethylphenyl)silyl-2,3,4,5-tetramethylcyclopentadienyl]titanium trichloride (Hereinafter, Referred to as "Complex 6")

Synthesis of 1-dimethyl(3,5-dimethylphenyl)silyl-2,3,4,5-tetramethylcyclopentadiene Under a nitrogen atmosphere, sodium hydride dispersed in mineral oil was washed with hexane to remove the mineral oil. Thereafter, the resultant sodium hydride (0.96 g, 40.00 mmol as pure sodium hydride) and tetrahydrofuran (43 mL) were mixed. This mixture was heated to 50° C. and aniline (0.25 g, 2.67 mmol) was added and stirred at 50° C. for 1.5 hours. To this, a solution of 1,2,3,4-tetramethylcyclopenta-1,3-diene (3.42 g, 28.00 mmol) dissolved in tetrahydrofuran (11 mL) was added dropwise and stirred at 50° C. for 2 hours, and then was cooled to 0° C. To this solution, a solution of chlorodimethyl(3,5-dimethylphenyl)silane (5.30 g, 26.67 mmol) dissolved in toluene (11 mL) was added dropwise and stirred at room temperature overnight. The resultant mixture was added dropwise at 0° C. to a 10% aqueous sodium carbonate solution (56 ml). Toluene (80 mL) was added to separate an organic phase, and the organic phase was washed with water (80 mL) twice, and further washed with saturated brine (50 mL). After dried over sodium sulfate, the organic phase was filtrated. The solvent was removed under reduced pressure to obtain 1-dimethyl (3,5-dimethylphenyl)silyl-2,3,4,5-tetramethylcyclopentadiene (6.60 g, yield 87.0%).

$^1$H-NMR (CDCl$_3$, δ ppm): 0.14 (s, 6H), 1.72 (s, 6H), 1.76 (s, 6H), 2.31 (s, 6H), 3.06 (s, 1H), 6.98 (s, 1H), 7.07 (s, 2H)

Mass Spectrum (EI-MS, m/z): 284 (M$^+$)

Synthesis of Complex 6

Under a nitrogen atmosphere, to a toluene solution (53 mL) of 1-dimethyl(3,5-dimethylphenyl)silyl-2,3,4,5-tetramethylcyclopentadiene (1.99 g, 7.00 mmol) and triethylamine (3.54 g, 35.00 mmol), a 1.65 M hexane solution of n-butyllithium (5.09 mL, 8.40 mmol) was added dropwise at −78° C. After the mixture was gradually warmed to room temperature, stirring was performed at room temperature for 3 hours. The resultant mixture was cooled to −78° C. and a solution of titanium tetrachloride (1.46 g, 7.70 mmol) dissolved in toluene (8 mL) was added dropwise at the same temperature. After the temperature was gradually warmed to room temperature, the mixture was stirred at room temperature overnight. After completion of the reaction, the solvent was removed under reduced pressure. Thereafter, the residue, to which heptane was added, was filtrated to remove insoluble materials. The solvent was removed under reduced pressure. Pentane was added and cooled to −20° C. and the resultant solid was filtrate and, washed with a small amount of pentane, and then, dried under reduced pressure to obtain complex 6 (0.49 g, yield 16.0%) as an orange solid.

$^1$H-NMR (CDCl$_3$, δ ppm): 0.74 (s, 6H), 2.30 (s, 6H), 2.33 (s, 6H), 2.41 (s, 6H), 7.02 (s, 1H), 7.06 (s, 2H)

$^{13}$C-NMR (CDCl$_3$, δ ppm): 0.41, 14.38, 17.85, 21.53, 131.51, 131.82, 137.18, 137.54, 139.47, 142.33, 145.10

Mass Spectrum (EI-MS, m/z): 436 (M$^+$)

Example 7

Synthesis of [1-diethylphenylsilyl-2,3,4,5-tetramethylcyclopentadienyl]titanium trichloride (Hereinafter, Referred to as "Complex 7")

Synthesis of 1-diethylphenylsilyl-2,3,4,5-tetramethylcyclopentadiene

Under a nitrogen atmosphere, sodium hydride (0.68 g, 28.45 mmol in terms of pure sodium hydride) dispersed in mineral oil and tetrahydrofuran (30 mL) were mixed. This mixture was heated to 50° C. and aniline (0.18 g, 1.90 mmol) was added and stirred at 50° C. for one hour. To this, a solution of 1,2,3,4-tetramethylcyclopenta-1,3-diene (2.55 g, 20.87 mmol) dissolved in tetrahydrofuran (8 mL) was added dropwise and stirred at 50° C. for 2 hours, and then was cooled to 0° C. To this solution, a solution of chlorodiethylphenylsilane (3.77 g, 18.97 mmol) dissolved in toluene (8 mL) was added dropwise and stirred at 35° C. The resultant mixture was added dropwise at 0° C. to a mixed solution of a 10% sodium hydrogen carbonate (19 mL) and a 10% sodium carbonate (19 mL). Toluene (19 mL) was added to separate an organic phase, and the organic phase was dried over sodium sulfate and filtrated. The solvent was removed under reduced pressure and purification was performed by silica gel column chromatography to obtain 1-diethylphenylsilyl-2,3,4,5-tetramethylcyclopentadiene (2.90 g, yield 53.7%).

$^1$H-NMR (CDCl$_3$, δ ppm): 0.74-0.99 (m, 10H), 1.71 (s, 6H), 1.76 (s, 6H), 3.17 (s, 1H), 7.27-7.32 (m, 3H), 7.40-7.44 (m, 2H)

$^{13}$C-NMR (CDCl$_3$, δ ppm): 2.66, 7.58, 11.10, 14.47, 52.65, 127.27, 128.69, 133.05, 134.15, 135.92, 136.46

Mass Spectrum (EI-MS, m/z): 284 (M$^+$)

Synthesis of Complex 7

Under a nitrogen atmosphere, to a toluene solution (30 mL) of 1-diethylphenylsilyl-2,3,4,5-tetramethylcyclopentadiene (1.38 g, 4.85 mmol) and triethylamine (2.47 g, 24.41 mmol), a 1.65 M hexane solution of n-butyllithium (3.6 mL, 6.01 mmol) was added dropwise at −78° C. After the mixture was gradually warmed to room temperature, stirring was performed at 35° C. for 4 hours. The resultant mixture was cooled to −78° C. and a solution of titanium tetrachloride (1.03 g, 5.41 mmol) dissolved in toluene (5.4 mL) was added dropwise at the same temperature. After the mixture was warmed to room temperature, the mixture was stirred at room temperature overnight. After completion of the reaction, the solvent was removed under reduced pressure. The residue, to which heptane was added, was filtrated to remove insoluble materials. The solvent was removed under reduced pressure. Pentane was added and the resultant solid was filtrated and washed with a small amount of pentane. The solid, to which toluene was added, was filtrated to remove insoluble materials. The solvent was removed under reduced pressure. Pentane was added and the resultant solid was filtrated and washed with a small amount of pentane, and then, concentrated under reduced pressure to obtain complex 7 (0.032 g, yield 1.5%) as an orange solid.

$^1$H-NMR (CDCl$_3$, δ ppm): 0.99 (t, J=7.8 Hz, 6H), 1.29-1.39 (m, 4H), 2.31 (s, 6H), 2.35 (s, 6H), 7.36-7.41 (m, 3H), 7.56-7.60 (m, 2H)

$^{13}$C-NMR (CDCl$_3$, δ ppm): 5.13, 7.71, 14.31, 17.80, 128.00, 129.63, 134.43, 135.17, 139.81, 142.36, 144.61

Mass Spectrum (EI-MS, m/z): 407 (M$^+$-Et)

Example 8

Synthesis of [1-(3,5-di-n-hexylphenyl)dimethylsilyl-2,3,4,5-tetramethylcyclopentadienyl]titanium trichloride (Hereinafter, Referred to as "Complex 8")

Synthesis of 1-(3,5-di-n-hexylphenyl)dimethylsilyl-2,3,4,5-tetramethylcyclopentadiene Under a nitrogen atmosphere, sodium hydride (0.49 g, 20.45 mmol in terms of pure sodium hydride) dispersed in mineral oil was washed with hexane to remove the mineral oil, and then tetrahydrofuran (23 mL) was added thereto. This mixture was heated to 50° C. and aniline (0.13 g, 1.36 mmol) was added and stirred at 50° C. for one hour. To this, a solution of 1,2,3,4-tetramethylcyclopenta-1,3-diene (1.83 g, 15.00 mmol) dissolved in tetrahydrofuran (6 mL) was added dropwise at 50° C. for 3 hours and a half, and then was cooled to 0° C. To this solution, a solution of chloro(3,5-di-n-hexylphenyl)dimethylsilane (4.62 g, 13.64 mmol) dissolved in toluene (6 mL) was added dropwise and stirred at room temperature for 4 hours. The resultant mixture was added dropwise at 0° C. to 10% aqueous solution of sodium carbonate (50 mL). Toluene (50 mL) was added to separate an organic phase, and the organic phase was washed twice with water (50 mL) and further washed with saturated brine (50 mL). The organic phase was dried over sodium sulfate and then filtrated and concentrated by removing the solvent under reduced pressure. Purification was performed by silica gel column chromatography to obtain 1-(3,5-di-n-hexylphenyl)dimethylsilyl-2,3,4,5-tetramethylcyclopentadiene (3.53 g, yield 60.9%).

$^1$H-NMR (CDCl$_3$, δ ppm): 0.19 (s, 6H), 0.90 (t, J=6.9 Hz, 6H), 1.23-1.44 (m, 12H), 1.53-1.68 (m, 4H), 1.74 (s, 6H), 1.78 (s, 6H), 2.59 (t, J=7.4 Hz, 4H), 3.08 (s, 1H), 6.98 (s, 1H), 7.08 (s, 2H)

Mass Spectrum (EI-MS, m/z): 424 (M$^+$)

Synthesis of Complex 8

Under a nitrogen atmosphere, to a toluene solution (44 mL) of 1-(3,5-di-n-hexylphenyl)dimethylsilyl-2,3,4,5-tetramethylcyclopentadiene (1.91 g, 4.50 mmol) and triethylamine (2.28 g, 22.50 mmol), a 1.65 M hexane solution of n-butyllithium (3.27 mL, 5.40 mmol) was added dropwise at −78° C. After the mixture was gradually warmed to room temperature, stirring was performed at room temperature for 6 hours. The resultant mixture was cooled to −78° C. and a solution (5 mL) of titanium tetrachloride (0.94 g, 4.95 mmol) dissolved in toluene was added dropwise at the same temperature. After the mixture was gradually warmed to room temperature, the mixture was stirred at room temperature overnight. After the reaction, the solvent was concentrated under reduced pressure, and then, heptane was added to the residue and filtered to remove insoluble materials. The solvent was removed from the filtrate under reduced pressure and complex 8 (0.73 g) was obtained as red oil.
$^1$H-NMR (CDCl$_3$, δ ppm): 0.74 (s, 6H), 0.82-0.93 (m, 6H), 1.21-1.38 (m, 12H), 1.48-1.67 (m, 4H), 2.32 (s, 6H), 2.38 (s, 6H), 2.49-2.61 (m, 4H), 6.95 (s, 1H), 7.06 (s, 2H)
Mass Spectrum (EI-MS, m/z): (576 M$^+$)

Example 9

Synthesis of [1-triphenylsilyl-2,3,4,5-tetramethylcyclopentadienyl]titanium trichloride (Hereinafter, Referred to as "Complex 9")

Synthesis of 1-triphenylsilyl-2,3,4,5-tetramethylcyclopentadiene

Under a nitrogen atmosphere, sodium hydride dispersed in mineral oil was washed with hexane to remove the mineral oil. Thereafter, the resultant sodium hydride (0.54 g, 22.32 mmol as pure sodium hydride) and tetrahydrofuran (35 mL) were mixed. This mixture was heated to 50° C. and aniline (0.14 g, 1.49 mmol) was added and stirred at 50° C. for one hour. To this, a solution of 1,2,3,4-tetramethylcyclopenta-1,3-diene (2.00 g, 16.37 mmol) dissolved in tetrahydrofuran (9 mL) was added dropwise and stirred at 50° C. for 2 hours, and then was cooled to 20° C. To this solution, a solution of chlorotriphenylsilane (4.39 g, 14.88 mmol) dissolved in toluene (9 mL) was added dropwise and stirred at 35° C. overnight. The resultant mixture was added dropwise at 0° C. to a mixed solution of a 10% sodium hydrogen carbonate (22 mL) and a 10% sodium carbonate (22 mL). Toluene (22 mL) was added to separate an organic phase. After dried over sodium sulfate, the organic phase was filtrated. The solvent was removed under reduced pressure to obtain 1-triphenylsilyl-2,3,4,5-tetramethylcyclopentadiene (3.76 g, yield 66.3%).
$^1$H-NMR (CDCl$_3$, δ ppm): 1.55 (s, 6H), 1.57 (s, 6H), 3.77 (s, 1H), 7.27-7.42 (m, 9H), 7.54-7.63 (m, 6H)
Mass Spectrum (EI-MS, m/z): 380 (M$^+$)

Synthesis of Complex 9

Under a nitrogen atmosphere, to a toluene solution (28 mL) of 1-triphenylsilyl-2,3,4,5-tetramethylcyclopentadiene (1.42 g, 4.45 mmol) and triethylamine (2.25 g, 22.24 mmol), a 1.55 M hexane solution of n-butyllithium (3.44 mL, 5.34 mmol) was added dropwise at −78° C. After the mixture was gradually warmed to room temperature, stirring was performed at 35° C. for 3 hours. The resultant mixture was cooled to −78° C. and a solution of titanium tetrachloride (0.93 g, 4.89 mmol) dissolved in toluene (5 mL) was added dropwise at the same temperature. After the mixture was warmed and the internal temperature was set to 35° C., stirring was performed at the same temperature for one hour. After completion of the reaction, the solvent was removed under reduced pressure. The residue, to which heptane was added, was filtrated to remove insoluble materials. The solvent was removed under reduced pressure. Pentane was added and the resultant solid was filtrated and washed with a small amount of pentane, and then, dried under reduced pressure to obtain complex 9 (0.07 g, yield 3.1%) as an orange solid. Furthermore, to the insoluble materials removed by adding heptane, toluene was added and filtrated to further remove insoluble matter in toluene. The solvent was removed from the filtrate under reduced pressure. Pentane was added and the resultant solid was filtrate and, washed with a small amount of pentane, and then, dried under reduced pressure to obtain complex 9 (0.34 g, yield 14.5%) as an orange solid.
$^1$H-NMR (CDCl$_3$, δ ppm): 2.05 (s, 6H), 2.36 (s, 6H), 7.32-7.49 (m, 9H), 7.59-7.65 (m, 6H)
$^{13}$C-NMR (CDCl$_3$, δ ppm): 14.48, 17.76, 127.96, 130.07, 132.99, 136.93, 142.35, 146.04
Mass Spectrum (EI-MS, m/z): 532 (M$^+$)

Example 10

Synthesis of [1-tri(4-n-butylphenyl)silyl-2,3,4,5-tetramethylcyclopentadienyl]titanium trichloride (Hereinafter, Referred to as "Complex 10")

Synthesis of 1-tri(4-n-butylphenyl)silyl-2,3,4,5-tetramethylcyclopentadiene

Under a nitrogen atmosphere, sodium hydride (0.83 g, 34.48 mmol in terms of pure sodium hydride) dispersed in mineral oil and tetrahydrofuran (85 mL) were mixed. This mixture was heated to 50° C. and aniline (0.21 g, 2.30 mmol) was added, and then, stirred at 50° C. for one hour. To this, a solution of 1,2,3,4-tetramethylcyclopenta-1,3-diene (3.09 g, 25.28 mmol) dissolved in tetrahydrofuran (21 mL) was added dropwise and stirred at 50° C. for 2 hours, and then was cooled to 0° C. To this solution, a solution of chlorotri(4-n-butylphenyl)silane (10.65 g, 22.99 mmol) dissolved in toluene (21 mL) was added dropwise and stirred at 35° C. The resultant mixture was added dropwise at 0° C. to a mixed solution of a 10% sodium hydrogen carbonate (53 mL) and a 10% sodium carbonate (53 mL). Toluene (53 mL) was added to separate an organic phase, and the organic phase was dried over sodium sulfate and filtrated. The solvent was removed under reduced pressure. Purification was performed by silica gel column chromatography to obtain 1-tri(4-n-butylphenyl)silyl-2,3,4,5-tetramethylcyclopentadiene (6.42 g, yield 50.9%).
$^1$H-NMR (CDCl$_3$, δ ppm): 0.92 (t, J=7.3 Hz, 9H), 1.15-1.43 (m, 6H), 1.50-1.67 (m, 6H), 1.52 (s, 6H), 1.57 (s, 6H), 2.54-2.65 (m, 6H), 3.71 (s, 1H), 7.12 (d, J=8.0 Hz, 6H), 7.47 (d, J=8.0 Hz, 6H)
$^{13}$C-NMR (CDCl$_3$, δ ppm): 11.00, 13.96, 14.79, 22.40, 33.43, 35.65, 51.57, 127.48, 127.67, 131.26, 135.24, 135.69, 143.80
Mass Spectrum (EI-MS, m/z): 548 (M$^+$)

Synthesis of Complex 10

Under a nitrogen atmosphere, to a toluene solution (60 mL) of 1-tri(4-n-butylphenyl)silyl-2,3,4,5-tetramethylcyclopentadiene (2.98 g, 5.43 mmol) and triethylamine (2.75 g, 27.13 mmol), a 1.67 M hexane solution of n-butyllithium (3.90 mL, 6.51 mmol) was added dropwise at −78° C. After the mixture was gradually warmed to room temperature, stirring was performed at 35° C. for 5.5 hours. The resultant mixture was cooled to −78° C. and a solution of titanium tetrachloride (1.13 g, 5.97 mmol) dissolved in toluene (6 mL) was added dropwise at the same temperature. After the mixture was warmed again to room temperature, stirring was performed at room temperature overnight. After completion of the reaction, the solvent was removed under reduced pressure. The residue, to which heptane was added, was filtrated to remove insoluble materials. The solvent was removed under reduced pressure. Hexamethyldisiloxane was added and cooled to −20° C. The resultant solid was filtrated and washed with a small amount of pentane, and then, dried under reduced pressure to obtain complex (0.19 g, yield 5.0%) as an orange solid.

$^1$H-NMR (CDCl$_3$, δ ppm): 0.92 (t, J=7.3 Hz, 9H), 1.29-1.42 (m, 6H), 1.55-1.66 (m, 6H), 2.03 (s, 6H), 2.35 (s, 6H), 2.62 (t, J=7.6 Hz, 6H), 7.18 (d, J=8.0 Hz, 6H), 7.51 (d, J=8.0 Hz, 6H)

$^{13}$C-NMR (CDCl$_3$, δ ppm): 13.96, 14.46, 17.72, 22.40, 33.32, 35.66, 128.02, 129.96, 136.53, 136.89, 142.28, 144.81, 146.22

Mass Spectrum (EI-MS, m/z): 700 (M$^+$)

Example 11

Synthesis of [1-tris(3,5-dimethylphenyl)silyl-2,3,4,5-tetramethylcyclopentadienyl]titanium trichloride (Hereinafter, Referred to as "Complex 11")

Synthesis of 1-tris(3,5-dimethylphenyl)silyl-2,3,4,5-tetramethylcyclopentadiene

Under a nitrogen atmosphere, sodium hydride (0.49 g, 20.45 mmol in terms of pure sodium hydride) dispersed in mineral oil and tetrahydrofuran (23 mL) were mixed. This mixture was heated to 50° C. and aniline (0.13 g, 1.36 mmol) was added and stirred at 50° C. for one hour. To this, a solution of 1,2,3,4-tetramethylcyclopenta-1,3-diene (1.83 g, 15.00 mmol) dissolved in tetrahydrofuran (6 mL) was added dropwise and stirred at 50° C. for 3.5 hours, and then was cooled to 0° C. To this solution, a solution of chlorotris(3,5-dimethylphenyl)silane (5.17 g, 13.64 mmol) dissolved in toluene (6 mL) was added dropwise and stirred at room temperature for 3 hours, and thereafter, stirred at 50° C. for 22 hours. The resultant mixture was added dropwise at 0° C. to 10% aqueous sodium carbonate solution (40 mL). Toluene was added to separate an organic phase, and the organic phase was washed with water (50 mL) twice and further washed with saturated brine (50 mL). The organic phase was dried over sodium sulfate and filtrated. The solvent was removed under reduced pressure. After purification was performed by silica gel column chromatography, hexane of 50° C. was added to the resultant solid, and filtrated to remove insoluble materials. The solvent was removed under reduced pressure. The resultant solid was washed with a small amount of hexane and then dried under reduced pressure to obtain 1-tris(3,5-dimethylphenyl)silyl-2,3,4,5-tetramethylcyclopentadiene (1.49 g, yield 23.4%).

$^1$H-NMR (CDCl$_3$, δ ppm): 1.54 (s, 6H), 1.60 (s, 6H), 2.27 (s, 18H), 3.73 (s, 1H), 6.98 (s, 3H), 7.17 (s, 6H)

Mass Spectrum (EI-MS, m/z): 464 (M$^+$)

Synthesis of Complex 11

Under a nitrogen atmosphere, to a toluene solution (20 mL) of 1-tris(3,5-dimethylphenyl)silyl-2,3,4,5-tetramethylcyclopentadiene (0.93 g, 2.00 mmol) and triethylamine (1.01 g, 10.00 mmol), a 1.67 M hexane solution of n-butyllithium (1.32 mL, 2.20 mmol) was added dropwise at −78° C. After the mixture was gradually warmed to room temperature, stirring was performed at room temperature for 5 hours. The resultant mixture was cooled to −78° C. and a solution of titanium tetrachloride (0.42 g, 2.20 mmol) dissolved in toluene (2 mL) was added dropwise at the same temperature. After the mixture was gradually warmed to room temperature, stirring was performed at room temperature overnight. After completion of the reaction, the solvent was removed under reduced pressure. Thereafter, the residue, to which heptane was added, was filtrated to remove insoluble materials. The solvent was removed under reduced pressure. Furthermore, to the resultant residue, diethyl ether was added and filtrated to remove insoluble materials. The solvent was removed from the filtrate under reduced pressure. Pentane was added and cooled to −20° C. The resultant solid substance was filtrated and washed with a small amount of pentane, and then dried under reduced pressure to obtain complex 11 (0.03 g, yield 2.7%) as an orange solid.

$^1$H-NMR (CDCl$_3$, δ ppm): 2.03 (s, 6H), 2.27 (s, 18H), 2.36 (s, 6H), 7.06 (s, 3H), 7.20 (s, 6H)

$^{13}$C-NMR (CDCl$_3$, δ ppm): 14.52, 17.83, 21.41, 131.63, 132.93, 134.60, 137.03, 142.26, 146.34

Mass Spectrum (EI-MS, m/z): 616 (M$^+$)

Example 12

Synthesis of [1-dimethyl(4-methoxyphenyl)silyl-2,3,4,5-tetramethylcyclopentadienyl]titanium trichloride (Hereinafter, Referred to as "Complex 12")

Synthesis of 1-dimethyl(4-methoxyphenyl)silyl-2,3,4,5-tetramethylcyclopentadiene Under a nitrogen atmosphere, sodium hydride dispersed in mineral oil was washed with hexane to remove the mineral oil. Thereafter, the resultant sodium hydride (0.96 g, 40.00 mmol as pure sodium hydride) and tetrahydrofuran (43 mL) were mixed. This mixture was heated to 50° C. and aniline (0.25 g, 2.67 mmol) was added and stirred at 50° C. for 2.5 hours. To this, a solution of 1,2,3,4-tetramethylcyclopenta-1,3-diene (3.42 g, 28.00 mmol) dissolved in tetrahydrofuran (11 mL) was added dropwise and stirred at 50° C. for 2.5 hours, and then was cooled to 0° C. To this solution, a solution of chlorodimethyl(4-methoxyphenyl)silane (5.35 g, 26.67 mmol) dissolved in toluene (11 mL) was added dropwise and stirred at room temperature overnight. The resultant mixture was added dropwise at 0° C. to a 10% aqueous sodium carbonate solution (56 ml). Toluene (80 mL) was added to separate an organic phase, and the organic phase was washed with water (80 mL) twice, and further washed with saturated brine (50 mL). After dried over sodium sulfate, the organic phase was filtrated. The solvent was removed under reduced pressure to obtain 1-dimethyl(4-methoxyphenyl)silyl-2,3,4,5-tetramethylcyclopentadiene (7.30 g, yield 95.5%).

$^1$H-NMR (CDCl$_3$, δ ppm): 0.18 (s, 6H), 1.75 (s, 6H), 1.77 (s, 6H), 3.06 (s, 1H), 3.83 (s, 3H), 6.90 (d, J=8.6 Hz, 2H), 7.39 (d, J=8.7 Hz, 2H)

Mass Spectrum (EI-MS, m/z): 286 (M$^+$)

Synthesis of Complex 12

Under a nitrogen atmosphere, to a toluene solution (48 mL) of 1-dimethyl(4-methoxyphenyl)silyl-2,3,4,5-tetramethylcyclopentadiene (2.01 g, 7.00 mmol) and triethylamine (3.54 g, 35.00 mmol), a 1.65 M hexane solution of n-butyllithium (5.09 mL, 8.40 mmol) was added dropwise at −78° C. After the mixture was gradually warmed to room temperature, stirring was performed at room temperature for 2 hours. The resultant mixture was cooled to −78° C. and a solution of titanium tetrachloride (1.46 g, 7.70 mmol) dissolved in toluene (8 mL) was added dropwise at the same temperature. After the mixture was gradually warmed to room temperature, stirring was performed at room temperature overnight. After completion of the reaction, the solvent was removed under reduced pressure. Thereafter, the residue, to which heptane was added, was filtrated to remove insoluble materials. The solvent was removed under reduced pressure. Pentane was added and the resultant solid was filtrated and washed with a small amount of pentane, and then, dried under reduced pressure to obtain complex 12 (0.48 g, yield 15.6%) as an orange solid.

$^1$H-NMR (CDCl$_3$, δ ppm): 0.73 (s, 6H), 2.32 (s, 6H), 2.39 (s, 6H), 3.81 (s, 3H), 6.90 (d, J=8.7 Hz, 2H), 7.39 (d, J=8.7 Hz, 2H)

$^{13}$C-NMR (CDCl$_3$, δ ppm): 0.50, 14.35, 17.81, 55.20, 114.00, 128.16, 135.71, 139.59, 142.33, 145.04, 160.98

Mass Spectrum (EI-MS, m/z): 438 (M$^+$)

Example 13

Synthesis of [1-benzyldiphenylsilyl-2,3,4,5-tetramethylcyclopentadienyl]titanium trichloride (Hereinafter, Referred to as "Complex 13")

Synthesis of 1-benzyldiphenylsilyl-2,3,4,5-tetramethylcyclopentadiene

Under a nitrogen atmosphere, sodium hydride (0.51 g, 21.20 mmol in terms of pure sodium hydride) dispersed in mineral oil and tetrahydrofuran (35 mL) were mixed. This mixture was heated to 50° C. and aniline (0.13 g, 1.41 mmol) was added and stirred at 50° C. for one hour. To this, a solution of 1,2,3,4-tetramethylcyclopenta-1,3-diene (1.90 g, 15.55 mmol) dissolved in tetrahydrofuran (9 mL) was added dropwise and stirred at 50° C. for 2 hours, and then was cooled to 0° C. To this solution, a solution of benzylchlorodiphenylsilane (4.37 g, 14.13 mmol) dissolved in toluene (9 mL) was added dropwise and stirred at 35° C. The resultant mixture was added dropwise at 0° C. to a mixed solution of a 10% sodium hydrogen carbonate (22 mL) and a 10% sodium carbonate (22 mL). Toluene (22 mL) was added to separate an organic phase, and the organic phase was dried over sodium sulfate and filtrated. The solvent was removed under reduced pressure. Purification was performed by silica gel column chromatography to obtain 1-benzyldiphenylsilyl-2,3,4,5-tetramethylcyclopentadiene (2.59 g, yield 46.4%).

$^1$H-NMR (CDCl$_3$, δ ppm): 1.53 (s, 6H), 1.76 (s, 6H), 2.73 (s, 2H), 3.54 (s, 1H), 6.72-6.79 (m, 2H), 6.95-7.02 (m, 3H), 7.17-7.40 (m, 10H)

Mass Spectrum (EI-MS, m/z): 394 (M$^+$)

Synthesis of Complex 13

Under a nitrogen atmosphere, to a toluene solution (26 mL) of 1-benzyldiphenylsilyl-2,3,4,5-tetramethylcyclopentadiene (1.28 g, 3.24 mmol) and triethylamine (1.64 g, 16.21 mmol), a 1.67 M hexane solution of n-butyllithium (2.33 mL, 3.89 mmol) was added dropwise at −78° C. After the mixture was gradually warmed to room temperature, stirring was performed at 35° C. for 3.5 hours. The resultant mixture was cooled to −78° C. and a solution of titanium tetrachloride (0.68 g, 3.57 mmol) dissolved in toluene (4 mL) was added dropwise at the same temperature. After the mixture was warmed to room temperature, the mixture was stirred at room temperature overnight. After completion of the reaction, the solvent was removed under reduced pressure. Thereafter, the residue, to which heptane was added, was filtrated to remove insoluble materials. The solvent was removed under reduced pressure. Pentane was added and the resultant solid was filtrated and washed with a small amount of pentane, and then, dried under reduced pressure to obtain complex 13 (47.9 mg, yield 2.7%) as an orange solid.

$^1$H-NMR (CDCl$_3$, δ ppm): 2.20 (s, 6H), 2.37 (s, 6H), 3.28 (s, 2H), 6.88-6.94 (m, 2H), 7.03-7.08 (m, 3H), 7.24-7.44 (m, 10H)

$^{13}$C-NMR (CDCl$_3$, δ ppm): 14.44, 17.80, 24.38, 124.85, 127.86, 128.09, 129.53, 130.05, 132.63, 136.47, 136.65, 137.49, 142.49, 145.41

Mass Spectrum (EI-MS, m/z): 455 (M$^+$-Bn)

Example 14

Synthesis of [9-dimethylphenyl silyl-octahydrofluorenyl]titanium trichloride (Hereinafter, Referred to as "Complex 14")

Synthesis of 9-dimethylphenylsilyl-octahydrofluorene

Under a nitrogen atmosphere, octahydrofluorenyllithium (1.50 g, 8.32 mmol) and tetrahydrofuran (30 mL) were mixed. This mixture was cooled to −30° C. To this solution, a solution of chlorodimethylphenylsilane (1.56 g, 9.16 mmol) dissolved in toluene (8 mL) was added dropwise and stirred at room temperature. The resultant mixture was added dropwise at 0° C. to a mixed solution of a 10% sodium hydrogen carbonate (8 mL) and a 10% sodium carbonate (8 mL). Toluene (8 mL) was added to separate an organic phase, and the organic phase was dried over sodium sulfate and filtrated. Thereafter, the solvent was removed under reduced pressure and purification was performed by silica gel column chromatography to obtain 9-dimethylphenylsilyl-octahydrofluorene (1.75 g, yield 67.9%).

$^1$H-NMR (CDCl$_3$, δ ppm): 0.22 (s, 6H), 1.41-1.58 (m, 4H), 1.60-1.80 (m, 4H), 2.08 (br s, 4H), 2.16 (br s, 4H), 3.00 (s, 1H), 7.28-7.38 (m, 3H), 7.43-7.51 (m, 2H)

Mass Spectrum (EI-MS, m/z): 308 (M$^+$)

Synthesis of Complex 14

Under a nitrogen atmosphere, to a toluene solution (33 mL) of (9-dimethylphenylsilyl-octahydrofluorene) (1.66 g, 5.38 mmol) and triethylamine (2.72 g, 26.88 mmol), a 1.67 M hexane solution of n-butyllithium (3.86 mL, 6.45 mmol) was added dropwise at −78° C. After the mixture was gradually warmed to room temperature, stirring was performed at 35° C. for 3.5 hours. The resultant mixture was cooled to −78° C. and a solution of titanium tetrachloride (1.12 g, 5.91 mmol) dissolved in toluene (6 mL) was added dropwise at the same temperature. After the mixture was warmed again, the mixture was stirred at room temperature overnight. After completion of the reaction, the solvent was removed under reduced pressure. Thereafter, the residue, to which heptane was added, was filtrated to remove insoluble materials. The solvent was removed under reduced pressure. Pentane was added and the resultant solid was filtrated and washed with a small amount of pentane, and then, dried under reduced pressure to obtain complex 14 (0.17 g, yield 6.7%) as an orange solid. Furthermore, to the insoluble materials removed by adding heptane described above toluene was added and filtrated to further remove toluene-insoluble materials. The solvent was removed under reduced pressure. Pentane was added and the resultant solid was filtrated and washed with a small amount of pentane, and then, dried under reduced pressure to obtain complex 14 (0.40 g, yield 16.3%) as an orange solid.

$^1$H-NMR (CDCl$_3$, δ ppm): 0.73 (s, 6H), 1.56-1.77 (m, 4H), 1.82-2.00 (m, 4H), 2.49-2.67 (m, 4H), 3.08-3.22 (m, 2H), 3.45 (dt, J=17.1, 6.0 Hz, 2H), 7.30-7.40 (m, 3H), 7.40-7.46 (m, 2H)

$^{13}$C-NMR (CDCl$_3$, δ ppm): −0.33, 21.47, 22.46, 25.35, 29.09, 128.05, 129.56, 134.01, 137.17, 137.88, 144.01, 147.11

Mass Spectrum (EI-MS, m/z): 460 (M$^+$)

Example 15

Synthesis of [1-dimethylphenylsilyl-indenyl]titanium trichloride (Hereinafter, Referred to as "Complex 15")

Synthesis of 1-dimethylphenylsilylindene

Under a nitrogen atmosphere, to a tetrahydrofuran solution (34 mL) of indene (1.85 g, 15.93 mmol), a 1.67 M hexane solution (10 mL, 16.7 mmol) of n-butyllithium was added dropwise at −78° C. After the mixture was gradually warmed to room temperature, stirring was performed at room temperature for 2 hours. The resultant mixture was added dropwise to a mixed solution of a 10% sodium hydrogen carbonate (17 mL) and a 10% sodium carbonate (17 mL) at 0° C. Toluene (17 mL) was added to separate an organic phase, and the organic phase was dried over sodium sulfate and filtrated. The solvent was removed under reduced pressure and purification was performed by silica gel column chromatography to obtain 1-dimethylphenylsilylindene (3.07 g, yield 76.9%).

Synthesis of (1-dimethylphenylsilylindenyl)lithium

Under a nitrogen atmosphere, to a hexane solution (30 mL) of 1-dimethylphenylsilylindene (1.30 g, 5.19 mmol), a 1.67 M hexane solution (3.7 mL, 6.18 mmol) of n-butyllithium was added dropwise at −78° C. After the mixture was gradually warmed to room temperature, stirring was performed at room temperature for 2 hours. After the completion of the reaction, filtration and washing with hexane were performed to obtain (1-dimethylphenylsilylindenyl)lithium (1.17 g, yield 88%).

Synthesis of 1,3-bis(dimethylphenylsilyl)indene

Under a nitrogen atmosphere, to a tetrahydrofuran solution (20 mL) of (1-dimethylphenylsilylindenyl)lithium (0.96 g, 3.75 mmol), a solution of chlorodimethylphenylsilane (0.73 g, 4.25 mmol) dissolved in tetrahydrofuran (5 mL) was added dropwise at −78° C. After the mixture was warmed, stirring was performed at room temperature for 4 hours and thereafter stirring was performed at 35° C. The resultant mixture was added dropwise at 0° C. to a mixed solution of a 10% sodium hydrogen carbonate (15 mL) and a 10% sodium carbonate (15 mL). Toluene (20 mL) was added to separate an organic phase, and the organic phase was dried over sodium sulfate and filtrated. The solvent was removed under reduced pressure and purification was performed by silica gel column chromatography to obtain 1,3-bis(dimethylphenylsilyl)indene (0.65 g, yield 45.1%).

Synthesis of complex 15

Under a nitrogen atmosphere, to a dichloromethane solution (8 mL) of titanium tetrachloride (0.34 g, 1.79 mmol), a dichloromethane solution (8 mL) of 1,3-bis(dimethylphenylsilyl)indene (0.65 g, 1.69 mmol) was added dropwise at room temperature, and thereafter, stirred at room temperature for 17 days. After the completion of the reaction, the solvent was removed under reduced pressure. Thereafter, to the residue, pentane was added at −20° C. to obtain a solid. The resultant solid was washed with a small amount of pentane and dried under reduced pressure to obtain complex 15 (0.25 g, yield 37.0%) as a red brown solid.

$^1$H-NMR (CDCl$_3$, δ ppm): 0.83 (s, 3H), 0.83 (s, 3H), 7.26-7.28 (m, 1H), 7.36-7.55 (m, 8H), 7.73-7.76 (m, 1H), 7.81-7.84 (m, 1H)

$^{13}$C-NMR (CDCl$_3$, δ ppm): −1.93, −1.44, 120.20, 126.75, 128.18, 128.67, 129.54, 129.58, 129.92, 130.14, 133.65, 134.13, 134.86, 135.27, 135.97

Mass Spectrum (EI-MS, m/z): 402 (M$^+$)

Example 16

Synthesis of [1-dimethyl(2,4,6-trimethylphenyl)silyl-2,3,4,5-tetramethylcyclopentadienyl]titanium trichloride (Hereinafter, Referred to as "Complex 16")

Synthesis of 1-dimethyl(2,4,6-trimethylphenyl)silyl-2,3,4,5-tetramethylcyclopentadiene Under a nitrogen atmosphere, sodium hydride dispersed in mineral oil was washed with hexane to remove the mineral oil. Thereafter, the resultant sodium hydride (0.82 g, 34.09 mmol in terms of pure sodium hydride) and tetrahydrofuran (39 mL) were mixed. This mixture was heated to 50° C. and aniline (0.21 g, 2.27 mmol) was added and stirred at 50° C. for 2 hours. To this, a solution of 1,2,3,4-tetramethylcyclopenta-1,3-diene (3.06 g, 25.00 mmol) dissolved in tetrahydrofuran (10 mL) was added dropwise and stirred at 50° C. for 2 hours, and then was cooled to 0° C. To this solution, a solution of chlorodimethyl(2,4,6-trimethylphenyl)silane (4.84 g, 22.73 mmol) dissolved in toluene (10 mL) was added dropwise and stirred at room temperature overnight. The resultant mixture was added dropwise at 0° C. to a 10% aqueous sodium carbonate solution (50 ml). Toluene (70 mL) was added to separate an organic phase, and the organic phase was washed with water (70 mL) twice and further washed with saturated brine (50 mL). After dried over sodium sulfate, the organic phase was filtrated. The solvent was removed under reduced pressure to obtain 1-dimethyl(2,4,6-trimethylphenyl)silyl-2,3,4,5-tetramethylcyclopentadiene (5.93 g, yield 87.3%).

$^1$H-NMR (CDCl$_3$, δ ppm): 0.20 (s, 6H), 1.69 (s, 6H), 1.81 (s, 6H), 2.26 (s, 3H), 2.41 (s, 6H), 3.28 (s, 1H), 6.81 (s, 2H)

Mass Spectrum (EI-MS, m/z): 298 (M$^+$)

Synthesis of Complex 16

Under a nitrogen atmosphere, to a toluene solution (32 mL) of 1-dimethyl(2,4,6-trimethylphenyl)silyl-2,3,4,5-tetramethylcyclopentadiene (1.49 g, 5.00 mmol) and triethylamine (2.53 g, 25.00 mmol), a 1.65 M hexane solution of n-butyllithium (3.33 mL, 5.50 mmol) was added dropwise at −78° C. After the mixture was gradually warmed to room temperature, stirring was performed at room temperature for 4 hours. The resultant mixture was cooled to −78° C. and a solution of titanium tetrachloride (1.04 g, 5.50 mmol) dissolved in toluene (6 mL) was added dropwise. After the mixture was gradually warmed to room temperature, stirring was performed at room temperature overnight. After the completion of the reaction, the solvent was removed under reduced pressure. The residue, to which heptane was added, was filtrated to remove insoluble materials. The solvent was removed under reduced pressure. Pentane was added and cooled to −20° C. The resultant solid was filtrated and washed with a small amount of pentane, and then, dried under reduced pressure to obtain complex 16 (0.21 g, yield 9.2%) as an orange solid.

$^1$H-NMR (CDCl$_3$, δ ppm): 0.83 (s, 6H), 2.21 (s, 6H), 2.24 (s, 3H), 2.32 (s, 6H), 2.36 (s, 6H), 6.78 (s, 2H)

$^{13}$C-NMR (CDCl$_3$, δ ppm): 4.90, 14.29, 17.75, 20.90, 24.63, 129.58, 130.67, 139.43, 142.35, 143.70, 144.10, 144.67

Mass Spectrum (EI-MS, m/z): 450 (M$^+$)

Example 17

Synthesis of [1-dimethylphenylsilyl-2-methyltetrahydroindenyl]titanium trichloride (Hereinafter, Referred to as "Complex 17")

Synthesis of (2-methyltetrahydroindenyl)lithium

Under a nitrogen atmosphere, 3,3a,4,5,6,7-hexahydro-2 (2H)-indenone (3.00 g, 22.04 mmol) and tetrahydrofuran (30 mL) were mixed. This mixture was cooled to −78° C. and a 1.07 M diethyl ether solution (34.72 mL, 37.15 mmol) of methyllithium was added dropwise and stirred at room temperature. The resultant mixture was added dropwise 0° C. to a saturated aqueous ammonium chloride solution. Toluene was added to separate an oil phase, and the organic phase was dried over sodium sulfate and filtrated. The solvent was removed under reduced pressure. To the resultant mixture, tetrahydrofuran (30 mL) was added. This mixture was cooled to 0° C. and a 3% aqueous hydrochloric acid solution (9 mL) was added and stirred at room temperature for 2 hours. Toluene and water were added to separate an organic phase, and the organic phase was washed with a saturated aqueous sodium chloride solution. The organic phase was dried over magnesium sulfate, and then filtrated. The solvent was removed under reduced pressure. To the resultant mixture, hexane (60 mL) was added. This mixture was cooled to −78° C., a 1.67 M hexane solution (15.2 mL, 25.36 mmol) of n-butyllithium was added dropwise. After the mixture was gradually warmed to room temperature, stirring was performed at room temperature for 2 hours. The solvent was removed by filtration and the resultant solid substance was washed with hexane to obtain (2-methyltetrahydroindenyl)lithium (2.10 g, yield 68%).

Synthesis of 1-dimethylphenylsilyl-2-methyltetrahydroindene

Under a nitrogen atmosphere, (2-methyltetrahydroindenyl)lithium (1.50 g, 10.70 mmol) and tetrahydrofuran (25 mL) were mixed. This mixture was cooled to −78° C. To this solution, a solution of chlorodimethylphenylsilane (2.19 g, 12.84 mmol) dissolved in tetrahydrofuran (5 mL) was added dropwise and stirred at room temperature for 2 hours. To the resultant mixture, a mixed solution of a 10% sodium hydrogen carbonate (10 mL) and a 10% sodium carbonate (10 mL) was added dropwise at 0° C. Toluene (10 mL) was added to separate an organic phase, and the organic phase was dried over sodium sulfate and filtrated. The solvent was removed under reduced pressure and purification was performed by silica gel column chromatography to obtain 1-dimethylphenylsilyl-2-methyltetrahydroindene (1.94 g, yield 67.5%).

$^1$H-NMR (CDCl$_3$, δ ppm): 0.22 (s, 3H), 0.23 (s, 3H), 1.46-1.72 (m, 4H), 1.81 (s, 3H), 2.07 (br, 2H), 2.24 (br, 2H), 3.11 (s, 1H), 5.97 (s, 1H), 7.31-7.38 (m, 3H), 7.46-7.54 (m, 2H)

$^{13}$C-NMR (CDCl$_3$, δ ppm): −4.05, −4.05, 16.93, 23.29, 23.73, 24.54, 26.63, 53.36, 127.57, 128.94, 129.16, 133.67, 137.38, 137.44, 138.56, 141.85

Mass Spectrum (EI-MS, m/z): 268 (M$^+$)

Synthesis of Complex 17

Under a nitrogen atmosphere, to a toluene solution (30 mL) of 1-dimethylphenylsilyl-2-methyltetrahydroindene (1.50 g, 5.59 mmol) and triethylamine (2.83 g, 27.95 mmol), a 1.67 M hexane solution of n-butyllithium (4.02 mL, 6.71 mmol) was added dropwise at −78° C. After the mixture was gradually warmed to room temperature, stirring was performed at 35° C. for 3 hours. The resultant mixture was cooled to −78° C. and a solution of titanium tetrachloride (1.17 g, 6.15 mmol) dissolved in toluene (6 mL) was added dropwise at the same temperature. The mixture was warmed and stirring was performed at room temperature overnight. After completion of the reaction, the solvent was removed under reduced pressure. Thereafter, the residue, to which heptane was added, was filtrated to remove insoluble materials. The solvent was removed under reduced pressure. Pentane was added and the resultant solid was filtrated and washed with a small amount of pentane, and then, dried under reduced pressure to obtain complex 17 (0.17 g, yield 7.0%) as an orange solid.

$^1$H-NMR (CDCl$_3$, δ ppm): 0.73 (s, 6H), 1.60-1.74 (m, 2H), 1.77-1.93 (m, 2H), 2.49 (s, 3H), 2.54-2.79 (m, 2H), 3.17-3.41 (m, 2H), 7.33-7.47 (m, 5H)

$^{13}$C-NMR (CDCl$_3$, δ ppm): −0.34, −0.32, 20.22, 21.54, 22.38, 26.96, 28.54, 128.10, 128.35, 129.66, 133.99, 136.97, 137.71, 144.95, 147.06, 148.14

Mass Spectrum (EI-MS, m/z): 405 (M$^+$-Me)

Example 18

Synthesis of [1-dimethyl(1-naphthyl)silyl-2,3,4,5-tetramethylcyclopentadienyl]titanium trichloride (Hereinafter, Referred to as "Complex 18")

Synthesis of 1-dimethyl(1-naphthyl)silyl-2,3,4,5-tetramethylcyclopentadiene

Under a nitrogen atmosphere, sodium hydride dispersed in mineral oil was washed with hexane to remove the mineral oil. Thereafter, the resultant sodium hydride (0.66 g, 27.27 mmol in terms of pure sodium hydride) and tetrahydrofuran (31 mL) were mixed. This mixture was heated to 50° C. and aniline (0.17 g, 1.82 mmol) was added and stirred at 50° C. for one hour. To this, a solution of 1,2,3,4-tetramethylcyclopenta-1,3-diene (2.44 g, 20.00 mmol) dissolved in tetrahydrofuran (8 mL) was added dropwise and stirred at 50° C. for 2.5 hours, and then was cooled to 0° C. To this solution, a solution of chlorodimethyl(1-naphthyl)silane (4.01 g, 18.18 mmol) dissolved in toluene (8 mL) was added dropwise and stirred at room temperature overnight. The resultant mixture was added dropwise at 0° C. to a 10% aqueous sodium carbonate solution (40 ml). Toluene (50 mL) was added to separate an organic phase, and the organic phase was washed with water (50 mL) twice and further washed with saturated brine (50 mL). The organic phase was dried over sodium sulfate and filtrated. The solvent was removed under reduced pressure and purification was performed by silica gel column chromatography to obtain 1-dimethyl(1-naphthyl)silyl-2,3,4,5-tetramethylcyclopentadiene (3.24 g, yield 58.2%).

$^1$H-NMR (CDCl$_3$, δ ppm): 0.34 (s, 6H), 1.66 (s, 6H), 1.81 (s, 6H), 3.46 (s, 1H), 7.40-7.66 (m, 4H), 7.82-7.95 (m, 2H), 8.24 (d, J=7.9 Hz, 1H)

Mass Spectrum (EI-MS, m/z): 306 (M$^+$)

Synthesis of Complex 18

Under a nitrogen atmosphere, to a toluene solution (31 mL) of 1-dimethyl(1-naphthyl)silyl-2,3,4,5-tetramethylcyclopentadiene (1.38 g, 4.50 mmol) and triethylamine (2.28 g, 22.50 mmol), a 1.65 M hexane solution of n-butyllithium (3.00 mL, 4.95 mmol) was added dropwise at −78° C. After the mixture was gradually warmed to room temperature, stirring was performed at room temperature for 4.5 hours. The resultant mixture was cooled to −78° C., and a solution of titanium tetrachloride (0.94 g, 4.95 mmol) dissolved in toluene (5 mL) was added dropwise at the same temperature. After the mixture was gradually warmed to room temperature, stirring was performed at room temperature overnight. After the completion of the reaction, the solvent was removed under reduced pressure. Thereafter, the residue, to which heptane was added, was filtrated to remove insoluble materials. The solvent was removed from the filtrate under reduced pressure. Pentane was added and the resultant solid was filtrated and washed with a small amount of pentane, and then, dried under reduced pressure to obtain complex 18 (0.57 g, yield 27.7%) as an orange solid.

$^1$H-NMR (CDCl$_3$, δ ppm): 0.94 (s, 6H), 2.31 (s, 6H), 2.40 (s, 6H), 7.30-7.53 (m, 3H), 7.62-7.77 (m, 2H), 7.88 (t, J=8.2 Hz, 2H)

$^{13}$C-NMR (CDCl$_3$, δ ppm): 1.43, 14.23, 17.72, 125.31, 125.49, 125.80, 127.34, 129.34, 130.57, 133.46, 134.21, 135.36, 136.46, 139.92, 142.31, 144.49

Mass Spectrum (EI-MS, m/z): 458 (M$^+$)

Example 19

Synthesis of [1-(3,5-bis(trifluoromethyl)phenyl) dimethylsilyl-2,3,4,5-tetramethylcyclopentadienyl] titanium trichloride (Hereinafter, Referred to as "Complex 19")

Synthesis of 1-(3,5-bis(trifluoromethyl)phenyl)dimethylsilyl-2,3,4,5-tetramethylcyclopentadiene Under a nitrogen atmosphere, sodium hydride dispersed in mineral oil was washed with hexane to remove the mineral oil. Thereafter, the resultant sodium hydride (0.47 g, 19.50 mmol in terms of pure sodium hydride) and tetrahydrofuran (22 mL) were mixed. This mixture was heated to 50° C. and aniline (0.14 g, 1.50 mmol) was added and stirred at 50° C. for 2 hours. To this, a solution of 1,2,3,4-tetramethylcyclopenta-1,3-diene (1.83 g, 15.00 mmol) dissolved in tetrahydrofuran (7 mL) was added dropwise and stirred at 50° C. for 4.5 hours, was cooled to room temperature, and then was added dropwise to a solution of (3,5-bis (trifluoromethyl)phenyl)dimethylsilane (4.60 g, 15.00 mmol) dissolved in toluene (22 mL) that had been cooled to 0° C. and stirred at room temperature overnight. The resultant mixture was added dropwise at 0° C. to a 10% aqueous sodium carbonate solution (30 ml). Toluene (50 mL) was added to separate an organic phase, and the organic phase was washed with water (50 mL) twice and further washed with saturated brine (50 mL). The organic phase was dried over sodium sulfate and filtrated. The solvent was removed under reduced pressure and purification was performed by silica gel column chromatography to obtain 1-(3,5-bis(trifluoromethyl)phenyl)dimethylsilyl-2,3,4,5-tetramethylcyclopentadiene (3.20 g, yield 54.3%).

$^1$H-NMR (CDCl$_3$, δ ppm): 0.15 (s, 6H), 1.40 (s, 6H), 1.57 (s, 6H), 2.82 (s, 1H), 7.49 (s, 2H), 7.57 (s, 1H)

Mass Spectrum (EI-MS, m/z): 392 (M$^+$)

Synthesis of Complex 19

Under a nitrogen atmosphere, to a toluene solution (35 mL) of 1-(3,5-bis(trifluoromethyl)phenyl)dimethylsilyl-2,3, 4,5-tetramethylcyclopentadiene (1.37 g, 3.50 mmol) and triethylamine (1.77 g, 17.50 mmol), a 1.65 M hexane solution of n-butyllithium (2.33 mL, 3.85 mmol) was added dropwise at −78° C. After the mixture was gradually warmed to room temperature, stirring was performed at room temperature for 5 hours. The resultant mixture was cooled to −78° C. and a solution of titanium tetrachloride (0.73 g, 3.85 mmol) dissolved in toluene (4 mL) was added dropwise at the same temperature. After the mixture was gradually warmed to room temperature, stirring was performed at room temperature overnight. After the completion of the reaction, the solvent was removed under reduced pressure. Thereafter, the residue, to which heptane was added, was filtrated to remove insoluble materials. The solvent was removed under reduced pressure. Pentane was added and cooled to −20° C. The resultant solid was filtrated and washed with a small amount of pentane, and then, dried under reduced pressure to obtain complex 19 (0.13 g, yield 6.8%) as an orange solid.

$^1$H-NMR (CDCl$_3$, δ ppm): 0.83 (s, 6H), 2.35 (s, 6H), 2.38 (s, 6H), 7.88 (s, 3H)

Mass Spectrum (EI-MS, m/z): 544 (M$^+$)

Example 20

Synthesis of [3-methyl-1-dimethylphenylsilylcyclopentadienyl]titanium trichloride (Hereinafter, Referred to as "Complex 20")

Synthesis of 1-dimethylphenylsilyl-methylcyclopentadiene

Under a nitrogen atmosphere, to a tetrahydrofuran solution (30 mL) of methylcyclopentadienyllithium (1.50 g, 17.43 mmol), a solution of dimethylphenylsilyl chloride (3.27 g, 19.17 mmol) dissolved in toluene (16 mL) was added dropwise at −30° C. The mixture was heated to room temperature and stirred overnight. The resultant mixture was added dropwise to a mixed solution of a 10% sodium hydrogen carbonate (16 mL) and a 10% sodium carbonate (16 mL) at 0° C. Toluene (16 mL) was added to separate an organic phase, and the organic phase was dried over sodium sulfate and then filtrated. The solvent was removed under reduced pressure to obtain 1-dimethylphenylsilyl-methylcyclopentadiene (3.47 g, yield 92.8%) as a mixture of regioisomers.

$^1$H-NMR (CDCl$_3$, δ ppm)(major isomer): 0.17 (br s, 6H), 2.03 (s, 3H), 3.46 (s, 1H), 6.07 (s, 1H), 6.42 (s, 2H), 7.32-7.40 (m, 3H), 7.51-7.57 (m, 2H)

Mass Spectrum (EI-MS, m/z): 214 (M$^+$)

Synthesis of 1-dimethylphenylsilyl-methylcyclopentadienyllithium

Under a nitrogen atmosphere, to a hexane solution (52 mL) of 1-dimethylphenylsilyl-methylcyclopentadiene (2.58 g, 12.02 mmol), a 1.67 M hexane solution of n-butyllithium (8.64 mL, 14.43 mmol) was added dropwise at 0° C. After the mixture was gradually warmed to room temperature, stirring was performed at 40° C. Diethyl ether was added and the resultant white solid was filtrated and washed with a small amount of pentane, and then, dried under reduced pressure to obtain 1-dimethylphenylsilyl-methylcyclopentadienyllithium (2.31 g, yield 86.1%) as a white solid.

Synthesis of 3-methyl-1,1-bis(dimethylphenylsilyl)cyclopentadiene

Under a nitrogen atmosphere, a tetrahydrofuran solution (26 mL) of 1-dimethylphenylsilyl-methylcyclopentadienyllithium (1.30 g, 5.90 mmol), a solution of dimethylphenylsilyl chloride (1.11 g, 6.49 mmol) dissolved in toluene (5 mL) was added dropwise at −30° C. The mixture was heated to room temperature and stirring was performed overnight. The resultant mixture was added dropwise at 0° C. to a mixed solution of a 10% sodium hydrogen carbonate (13 mL) and a 10% sodium carbonate (13 mL). Toluene (13 mL) was added to separate an organic phase, and the organic phase was dried over sodium sulfate and then filtrated. The solvent was removed under reduced pressure and purification was performed by silica gel column chromatography to obtain 3-methyl-1,1-bis(dimethylphenylsilyl)cyclopentadiene (0.72 g, yield 35.0%).

$^1$H-NMR (CDCl$_3$, δ ppm): −0.10 (s, 6H), −0.09 (s, 6H), 2.02 (s, 3H), 6.25 (s, 1H), 6.48 (d, J=4.6 Hz, 1H), 6.56 (d, J=4.6 Hz, 1H), 7.25-7.37 (m, 6H), 7.38-7.45 (m, 4H)

Mass Spectrum (EI-MS, m/z): 348 (M$^+$)

Synthesis Complex 20

Under a nitrogen atmosphere, to a toluene solution (15 mL) of 3-methyl-1,1-bis(dimethylphenylsilyl)cyclopentadiene (0.72 g, 2.05 mmol), a solution of titanium tetrachloride (0.39 g, 2.05 mmol) dissolved in toluene (4 mL) was added dropwise at −30° C. The mixture was warmed to room temperature and stirring was performed overnight. After the completion of the reaction, the solvent was removed under reduced pressure and then pentane was added. The supernatant was removed at −20° C. This operation was repeated four times. The resultant residue was dried under reduced pressure to obtain complex 20 (0.39 g, yield 51.4%) as a brown oil.

$^1$H-NMR (CDCl$_3$, δ ppm): 0.67 (s, 3H), 0.67 (s, 3H), 2.47 (s, 3H), 6.87-6.91 (m, 1H), 7.01-7.05 (m, 1H), 7.13-7.16 (m, 1H), 7.34-7.43 (m, 3H), 7.48-7.54 (m, 2H)

$^{13}$C-NMR (CDCl$_3$, δ ppm): −2.46, −2.29, 17.35, 127.72, 128.11, 129.49, 129.83, 129.87, 133.91, 136.03, 141.84, 143.62

Mass Spectrum (EI-MS, m/z): 366 (M$^+$)

Example 21

Synthesis of [1-dimethylphenylsilyl-2,3,5-trimethylcyclopentadienyl]titanium trichloride (Hereinafter, Referred to as "Complex 21")

Synthesis of 1-dimethylphenylsilyl-2,3,5-trimethylcyclopentadiene

Under a nitrogen atmosphere, (1,2,4-trimethylcyclopentadienyl)lithium (2.10 g, 18.40 mmol) and tetrahydrofuran (90 mL) were mixed. This mixture was cooled to −78° C. To this solution, a solution of chlorodimethylphenylsilane (1.89 g, 11.04 mmol) dissolved in tetrahydrofuran (10 mL) was added dropwise and stirred at room temperature for 2 hours. The resultant mixture was added dropwise at 0° C. to a mixed solution of a 10% sodium hydrogen carbonate and a 10% sodium carbonate. Toluene was added to separate an organic phase, and the organic phase was dried over sodium sulfate and filtrated. The solvent was removed under reduced pressure and purification was performed by silica gel column chromatography to obtain 1-dimethylphenylsilyl-2,3,5-trimethylcyclopentadiene (0.99 g, yield 37%).

$^1$H-NMR (CDCl$_3$, δ ppm): 0.20 (s, 3H), 0.23 (s, 3H), 1.72 (s, 3H), 1.79 (s, 3H), 1.81 (s, 3H), 3.17 (s, 1H), 5.97 (s, 1H), 7.34-7.37 (m, 3H), 7.49-7.57 (m, 2H)

Mass Spectrum (EI-MS, m/z): 242 (M$^+$)

Synthesis of Complex 21

Under a nitrogen atmosphere, to a toluene solution (20 mL) of 1-dimethylphenylsilyl-2,3,5-trimethylcyclopentadiene (0.98 g, 4.04 mmol) and triethylamine (2.05 g, 20.22 mmol), a 1.65 M hexane solution of n-butyllithium (2.9 mL, 4.85 mmol) was added dropwise at −78° C. After the mixture was gradually warmed to room temperature, stirring was performed at 35° C. for 4 hours. The resultant mixture was cooled to −78° C., and a solution of titanium tetrachloride (0.84 g, 4.45 mmol) dissolved in toluene (4.5 mL) was added dropwise at the same temperature. The mixture was warmed and stirring was performed at room temperature overnight. After the completion of the reaction, the solvent was removed under reduced pressure. Thereafter, the residue, to which heptane was added, was filtrated to remove insoluble materials. The solvent was removed under reduced pressure. Pentane was added and the resultant solid was filtrated and washed with a small amount of pentane. To the solid substance, toluene was added and filtrated to remove insoluble materials. The solvent was removed under reduced pressure. Pentane was added and the resultant solid was filtrated and washed with a small amount of pentane and then concentrated under reduced pressure to obtain complex 21 (0.037 g, yield 2.3%) as an orange solid.

$^1$H-NMR (CDCl$_3$, δ ppm): 0.74 (s, 3H), 0.75 (s, 3H), 2.33 (s, 3H), 2.36 (s, 3H), 2.47 (s, 3H), 6.75 (s, 1H), 7.33-7.47 (m, 5H)

Mass Spectrum (EI-MS, m/z): 394 (M$^+$)

Example 22

Synthesis of [1-(9-anthryl)dimethylsilyl-2,3,4,5-tetramethylcyclopentadienyl]titanium trichloride (Hereinafter, Referred to as "Complex 22")

Synthesis of 1-(9-anthryl)dimethylsilyl-2,3,4,5-tetramethylcyclopentadiene

Under a nitrogen atmosphere, sodium hydride dispersed in mineral oil was washed with hexane to remove the mineral oil. Thereafter, the resultant sodium hydride (0.82 g, 34.09 mmol in terms of pure sodium hydride) and tetrahydrofuran (39 mL) were mixed. This mixture was heated to 50° C. and aniline (0.21 g, 2.27 mmol) was added and stirred at 50° C. for one hour. To this, a solution of 1,2,3,4-tetramethylcyclopenta-1,3-diene (3.06 g, 25.00 mmol) dissolved in tetrahydrofuran (10 mL) was added dropwise and stirred at 50° C. for 4 hours, and then was cooled to 0° C. To this solution, a solution of (9-anthryl)chlorodimethylsilane (6.16 g, 22.73 mmol) dissolved in toluene (10 mL) was added dropwise and stirred at room temperature overnight. The resultant mixture was added dropwise at 0° C. to a 10% aqueous sodium carbonate solution (50 ml). Toluene (70 mL) was added to separate an organic phase, and the organic phase was washed with water (80 mL) twice and further washed with saturated brine (50 mL). The organic phase was dried over sodium sulfate and filtrated. The solvent was removed under reduced pressure and purification was performed by silica gel column chromatography to obtain 1-(9-anthryl)dimethylsilyl-2,3,4,5-tetramethylcyclopentadiene (4.41 g, yield 54.4%).

$^1$H-NMR (CDCl$_3$, δ ppm): 0.49 (s, 6H), 1.68 (s, 6H), 1.88 (s, 6H), 3.68 (s, 1H), 7.41-7.53 (m, 4H), 7.98-8.07 (m, 2H), 8.34-8.43 (m, 2H), 8.49 (s, 1H)

Mass Spectrum (EI-MS, m/z): 356 (M$^+$)

Synthesis of Complex 22

Under a nitrogen atmosphere, to a toluene solution (31 mL) of 1-(9-anthryl)dimethylsilyl-2,3,4,5-tetramethylcyclopentadiene (1.43 g, 4.00 mmol) and triethylamine (2.02 g, 20.00 mmol), a 1.65 M hexane solution of n-butyllithium (2.67 mL, 4.40 mmol) was added dropwise at −78° C. After the mixture was gradually warmed to room temperature, stirring was performed at room temperature for 8 hours. The resultant mixture was cooled to −78° C., and a solution of titanium tetrachloride (0.83 g, 4.40 mmol) dissolved in toluene (4 mL) was added dropwise at the same temperature. After the mixture was gradually warmed to room temperature, stirring was performed at room temperature overnight. After the completion of the reaction, the solvent was removed under reduced pressure. Thereafter, the residue, to which heptane was added, was filtrated to remove insoluble materials. The solvent was removed under reduced pressure. Pentane was added and the resultant solid substance was filtrated and washed with a small amount of pentane, and then, dried under reduced pressure to obtain complex 22 (0.087 g, yield 4.3%) as an orange solid.

$^1$H-NMR (CDCl$_3$, δ ppm): 1.10 (s, 6H), 2.29 (s, 6H), 2.33 (s, 6H), 7.30-7.48 (m, 4H), 8.01 (d, J=8.6 Hz, 2H), 8.21 (d, J=9.1 Hz, 2H), 8.51 (s, 1H)

Mass Spectrum (EI-MS, m/z): 508 (M$^+$)

Example 23

Synthesis of [1-(cyclotetramethylene)phenylsilyl-2, 3,4,5-tetramethylcyclopentadienyl]titanium trichloride (Hereinafter, Referred to as "Complex 23")

Synthesis of 1-(cyclotetramethylene)phenylsilyl-2,3, 4,5-tetramethylcyclopentadiene Under a nitrogen atmosphere, sodium hydride dispersed in mineral oil was washed with hexane to remove the mineral oil. Thereafter, the resultant sodium hydride (0.82 g, 34.09 mmol in terms of pure sodium hydride) and tetrahydrofuran (39 mL) were mixed. This mixture was heated to 50° C. and aniline (0.21 g, 2.27 mmol) was added and stirred at 50° C. for one hour. To this, a solution of 1,2,3,4-tetramethylcyclopenta-1,3-diene (3.06 g, 25.00 mmol) dissolved in tetrahydrofuran (10 mL) was added dropwise and stirred at 50° C. for 3 hours, and then was cooled to 0° C. To this solution, a solution of chloro(cyclotetramethylene)phenylsilane (4.47 g, 22.73 mmol) dissolved in toluene (10 mL) was added dropwise and stirred at room temperature for 5 hours. The resultant mixture was added dropwise at 0° C. to a 10% aqueous sodium carbonate solution (50 ml). Toluene (70 mL) was added to separate an organic phase, and the organic phase was washed with water (70 mL) twice and further washed with saturated brine (50 mL). The organic phase was dried over sodium sulfate and filtrated. The solvent was removed under reduced pressure and purification was performed by silica gel column chromatography to obtain 1-(cyclotetramethylene)phenylsilyl-2,3,4,5-tetramethylcyclopentadiene (4.35 g, yield 67.8%).

$^1$H-NMR (CDCl$_3$, δ ppm): 0.87-0.98 (m, 4H), 1.55-1.68 (m, 4H), 1.58 (s, 6H), 1.91 (s, 6H), 3.11 (s, 1H), 7.16-7.33 (m, 5H)

Mass Spectrum (EI-MS, m/z): 282 (M$^+$)

Synthesis of Complex 23

Under a nitrogen atmosphere, to a toluene solution (31 mL) of 1-(cyclotetramethylene)phenylsilyl-2,3,4,5-tetramethylcyclopentadiene (1.41 g, 5.00 mmol) and triethylamine (2.53 g, 25.00 mmol), a 1.67 M hexane solution of n-butyllithium (3.29 mL, 5.50 mmol) was added dropwise at −78° C. After the mixture was gradually warmed to room temperature, stirring was performed at room temperature for 6 hours. The resultant mixture was cooled to −78° C. and a solution of titanium tetrachloride (1.04 g, 5.50 mmol) dissolved in toluene (6 mL) was added dropwise at the same temperature. After the mixture was gradually warmed to room temperature, stirring was performed at room temperature overnight. After the completion of the reaction, the solvent was removed under reduced pressure. Thereafter, the residue, to which heptane was added, was filtrated to remove insoluble materials. The solvent was removed to concentrate the filtrate under reduced pressure. Furthermore, to the resultant residue, diethyl ether was added and filtrated to remove insoluble materials. The solvent was removed to concentrate the filtrate under reduced pressure. Pentane was added and the resultant solid was filtrated and washed with a small amount of pentane, and then, dried under reduced pressure to obtain complex 23 (0.13 g, yield 6.1%) as an orange solid.

$^1$H-NMR (CDCl$_3$, δ ppm): 1.18-1.35 (m, 2H), 1.49-1.68 (m, 2H), 1.69-1.99 (m, 4H), 2.36 (s, 6H), 2.50 (s, 6H), 7.28-7.40 (m, 5H)

$^{13}$C-NMR (CDCl$_3$, δ ppm): 13.25, 14.26, 17.36, 26.85, 128.14, 129.49, 133.93, 137.08, 138.26, 142.19, 144.70

Mass Spectrum (EI-MS, m/z): 434 (M$^+$)

Example 24

Synthesis of [1-methyldi(4-methylphenyl)silyl-2,3, 4,5-tetramethylcyclopentadienyl]titanium trichloride (Hereinafter, Referred to as "Complex 24")

Synthesis of 1-methyldi(4-methylphenyl)silyl-2,3,4, 5-tetramethylcyclopentadiene Under a nitrogen atmosphere, sodium hydride (0.98 g, 40.95 mmol in terms of pure sodium hydride) dispersed in mineral oil and tetrahydrofuran (57 mL) were mixed. This mixture was heated to 50° C. and aniline (0.25 g, 2.73 mmol) was added and stirred at 50° C. for one hour. To this, a solution of 1,2,3,4-tetramethylcyclopenta-1,3-diene (3.67 g, 30.03 mmol) dissolved in tetrahydrofuran (14 mL) was added dropwise and stirred at 50° C. for 2 hours, and then was cooled to 0° C. To this solution, a solution of chloromethyldi(4-methylphenyl)silane (7.12 g, 27.30 mmol) dissolved in toluene (14 mL) was added dropwise and stirred at 35° C. The resultant mixture was added dropwise at 0° C. to a mixed solution of a 10% sodium hydrogen carbonate (36 mL) and a 10% sodium carbonate (36 mL). Toluene (36 mL)

was added to separate an organic phase, and the organic phase was dried over sodium sulfate and filtrated. The solvent was removed under reduced pressure and purification was performed by silica gel column chromatography to obtain 1-methyldi(4-methylphenyl)silyl-2,3,4,5-tetramethylcyclopentadiene (3.74 g, yield 39.5%).

$^1$H-NMR (CDCl$_3$, δ ppm): 0.30 (s, 3H), 1.55 (s, 6H), 1.73 (s, 6H), 2.33 (s, 6H), 3.40 (s, 1H), 7.13 (d, J=8.0 Hz, 4H), 7.39 (d, J=8.0 Hz, 4H)

$^{13}$C-NMR (CDCl$_3$, δ ppm): −6.69, 11.10, 14.49, 21.47, 53.03, 128.37, 128.62, 133.23, 134.56, 135.27, 138.77

Mass Spectrum (EI-MS, m/z): 346 (M$^+$)

Synthesis of Complex 24

Under a nitrogen atmosphere, to a toluene solution (60 mL) of 1-methyldi(4-methylphenyl)silyl-2,3,4,5-tetramethylcyclopentadiene (3.00 g, 8.66 mmol) and triethylamine (4.38 g, 43.32 mmol), a 1.67 M hexane solution of n-butyllithium (6.23 mL, 10.40 mmol) was added dropwise at −78° C. After the mixture was gradually warmed to room temperature, stirring was performed at room temperature for 5 hours. The resultant mixture was cooled to −78° C. and a solution of titanium tetrachloride (1.81 g, 9.53 mmol) dissolved in toluene (10 mL) was added dropwise at the same temperature. After the mixture was gradually warmed to room temperature and the mixture was stirred at room temperature overnight. After the completion of the reaction, the solvent was removed under reduced pressure. Thereafter, the residue, to which heptane was added, was filtrated to remove insoluble materials. The solvent was removed under reduced pressure. Pentane was added and the resultant solid was filtrated and washed with a small amount of pentane, and then, dried under reduced pressure to obtain complex 24 (1.24 g, yield 28.6%) as an orange solid.

$^1$H-NMR (CDCl$_3$, δ ppm): 1.06 (s, 3H), 2.13 (s, 6H), 2.33 (s, 6H), 2.36 (s, 6H), 7.17 (d, J=7.9 Hz, 4H), 7.34 (d, J=7.9 Hz, 4H)

$^{13}$C-NMR (CDCl$_3$, δ ppm): −0.86, 14.26, 17.72, 21.55, 128.92, 131.62, 135.39, 138.30, 139.84, 142.31, 145.33

Mass Spectrum (EI-MS, m/z): 498 (M$^+$)

Example 25

Synthesis of [1-methylbis(3,5-dimethylphenyl)silyl-2,3,4,5-tetramethylcyclopentadienyl]titanium trichloride (Hereinafter, Referred to as "Complex 25")

Synthesis of 1-methylbis(3,5-dimethylphenyl)silyl-2,3,4,5-tetramethylcyclopentadiene Under a nitrogen atmosphere, sodium hydride dispersed in mineral oil was washed with hexane to remove the mineral oil. Thereafter, the resultant sodium hydride (0.66 g, 27.27 mmol in terms of pure sodium hydride) and tetrahydrofuran (31 mL) were mixed. This mixture was heated to 50° C. and aniline (0.17 g, 1.82 mmol) was added and stirred at 50° C. for one hour. To this, a solution of 1,2,3,4-tetramethylcyclopenta-1,3-diene (2.44 g, 20.00 mmol) dissolved in tetrahydrofuran (8 mL) was added dropwise and stirred at 50° C. for 2.5 hours, and then was cooled to 0° C. To this solution, a solution of chloromethylbis(3,5-dimethylphenyl)silane (5.25 g, 18.18 mmol) dissolved in toluene (8 mL) was added dropwise and stirred at room temperature for 5 hours. The resultant mixture was added dropwise at 0° C. to a 10% aqueous sodium carbonate solution (50 ml). Toluene (50 mL) was added to separate an organic phase, and the organic phase was washed with water (50 mL) twice and further washed with saturated brine (50 mL). The organic phase was dried over sodium sulfate and filtrated. The solvent was removed under reduced pressure and purification was performed by silica gel column chromatography to obtain 1-methylbis(3,5-dimethylphenyl)silyl-2,3,4,5-tetramethylcyclopentadiene (5.08 g, yield 74.6%).

$^1$H-NMR (CDCl$_3$, δ ppm): 0.30 (s, 3H), 1.54 (s, 6H), 1.74 (s, 6H), 2.29 (s, 12H), 3.40 (s, 1H), 6.97 (s, 2H), 7.10 (s, 4H)

Mass Spectrum (EI-MS, m/z): 374 (M$^+$)

Synthesis of Complex 25

Under a nitrogen atmosphere, to a toluene solution (39 mL) of 1-methylbis(3,5-dimethylphenyl)silyl-2,3,4,5-tetramethylcyclopentadiene (1.87 g, 5.00 mmol) and triethylamine (2.53 g, 25.00 mmol), a 1.65 M hexane solution of n-butyllithium (3.64 mL, 6.00 mmol) was added dropwise at −78° C. After the mixture was gradually warmed to room temperature, stirring was performed at 40° C. for 6 hours. The resultant mixture was cooled to −78° C., and a solution of titanium tetrachloride (1.04 g, 5.50 mmol) dissolved in toluene (6 mL) was added dropwise at the same temperature. After the mixture was gradually warmed to room temperature, stirring was performed at room temperature overnight. After the completion of the reaction, the solvent was removed under reduced pressure. Thereafter, the residue, to which heptane was added, was filtrated to remove insoluble materials. The solvent was removed under reduced pressure. Pentane was added and the resultant solid was filtrated and washed with a small amount of pentane, and then, dried under reduced pressure to obtain complex 25 (0.34 g, yield 12.9%) as an orange solid.

$^1$H-NMR (CDCl$_3$, δ ppm): 1.06 (s, 3H), 2.13 (s, 6H), 2.28 (s, 12H), 2.34 (s, 6H), 7.06 (s, 6H)

$^{13}$C-NMR (CDCl$_3$, δ ppm): −0.76, 14.32, 17.76, 21.39, 131.61, 133.04, 134.85, 137.29, 138.77, 142.28, 145.27

Mass Spectrum (EI-MS, m/z): 526 (M$^+$)

Example 26

Synthesis of [3-tert-butyl-1-dimethylphenylsilylcyclopentadienyl]titanium trichloride (Hereinafter, Referred to as "Complex 26")

Synthesis of 1-dimethylphenylsilyl-tert-butylcyclopentadiene

Under a nitrogen atmosphere, to a tetrahydrofuran solution (30 mL) of tert-butylcyclopentadienyllithium (1.50 g, 11.71 mmol), a solution of dimethylphenylsilyl chloride (2.20 g, 12.88 mmol) dissolved in toluene (11 mL) was added dropwise at −30° C. After the mixture was warmed to room temperature, stirring was performed overnight. The resultant mixture was added dropwise at 0° C. to a mixed solution of a 10% sodium hydrogen carbonate (11 mL) and a 10% sodium carbonate (11 mL). Toluene (11 mL) was added to separate an organic phase, and the organic phase was dried over sodium sulfate and filtrated. The solvent was removed under reduced pressure to obtain 1-dimethylphenylsilyl-tert-butylcyclopentadiene (2.84 g, yield 94.8%) as a mixture of regioisomers.

$^1$H-NMR (CDCl$_3$, δ ppm) (major isomer): 0.17 (s, 6H), 1.14 (s, 9H), 3.45 (s, 1H), 6.05 (s, 1H), 6.45 (d, J=4.8 Hz, 1H), 6.61 (d, J=4.8 Hz, 1H), 7.31-7.41 (m, 3H), 7.48-7.56 (m, 2H)

Mass Spectrum (EI-MS, m/z): 256 (M$^+$)

Synthesis of 1-dimethylphenylsilyl-tert-butylcyclopentadienyllithium

Under a nitrogen atmosphere, to a hexane solution (38 mL) of 1-dimethylphenylsilyl-tert-butylcyclopentadiene (1.92 g, 7.50 mmol), a 1.67 M hexane solution of n-butyllithium (5.39 mL, 9.00 mmol) was added dropwise at 0° C. After the mixture was gradually warmed to room temperature, stirring was performed at 40° C. Diethyl ether was added to obtain a white solid, which was filtrated and washed with a small amount of pentane, and then, dried under reduced pressure to obtain 1-dimethylphenylsilyl-tert-butylcyclopentadienyllithium (0.28 g, yield 14.3%) as a white solid.

Synthesis of 3-tert-butyl-1,1-bis(dimethylphenylsilyl)cyclopentadiene

Under a nitrogen atmosphere, to a tetrahydrofuran solution (34 mL) of 1-dimethylphenylsilyl-tert-butylcyclopentadienyllithium (1.68 g, 6.40 mmol), a solution of dimethylphenylsilyl chloride (1.20 g, 7.04 mmol) dissolved in toluene (6 mL) was added dropwise at −30° C. After the mixture was warmed to room temperature, stirring was performed overnight. The resultant mixture was added dropwise at 0° C. to a mixed solution of a 10% sodium hydrogen carbonate (17 mL) and a 10% sodium carbonate (17 mL). Toluene (17 mL) was added to separate an organic phase, and the organic phase was dried over sodium sulfate and filtrated. The solvent was removed under reduced pressure and purification was performed by silica gel column chromatography to obtain 3-tert-butyl-1,1-bis(dimethylphenylsilyl)cyclopentadiene (0.64 g, yield 25.7%).

$^1$H-NMR (CDCl$_3$, δ ppm): −0.07 (s, 6H), −0.07 (s, 6H), 1.01 (s, 9H), 6.16 (dd, J=2.5, 1.6 Hz, 1H), 6.51 (dd, J=4.6, 2.5 Hz, 1H), 6.56 (dd, J=4.6, 1.6 Hz, 1H), 7.17-7.27 (m, 6H), 7.27-7.36 (m, 4H)

Mass Spectrum (EI-MS, m/z): 348 (M$^+$)

Synthesis of Complex 26

Under a nitrogen atmosphere, to a toluene solution (15 mL) of 3-tert-butyl-1,1-bis(dimethylphenylsilyl)cyclopentadiene (0.64 g, 1.65 mmol), a solution of titanium tetrachloride (0.31 g, 1.65 mmol) dissolved in toluene (4 mL) was added dropwise at −30° C. The mixed solution was heated to room temperature and stirring was performed for 3 weeks. After the completion of the reaction, the solvent was removed under reduced pressure to obtain complex 26 (0.30 g, yield 44.5%) as an orange solid substance.

$^1$H-NMR (CDCl$_3$, δ ppm): 0.65 (s, 3H), 0.70 (s, 3H), 1.37 (s, 9H), 7.05 (dd, J=3.1, 2.0 Hz, 1H), 7.07 (dd, J=3.1, 2.3 Hz, 1H), 7.21 (dd, J=2.3, 2.1 Hz, 1H), 7.33-7.44 (m, 3H), 7.46-7.53 (m, 2H)

$^{13}$C-NMR (CDCl$_3$, δ ppm): −2.40, −1.80, 30.89, 34.56, 123.69, 127.01, 128.11, 129.18, 129.80, 133.97, 136.27, 142.45, 160.05

Mass Spectrum (EI-MS, m/z): 408 (M$^+$)

Example 27

Synthesis of [1-n-butylmethylphenyl silyl-2,3,4,5-tetramethylcyclopentadienyl]zirconium trichloride (Hereinafter, Referred to as "Complex 27")

Under a nitrogen atmosphere, to a toluene solution (22 mL) of 1-n-butylmethylphenylsilyl-2,3,4,5-tetramethylcyclopentadiene (1.11 g, 3.73 mmol) and triethylamine (1.89 g, 18.64 mmol), a 1.67 M hexane solution of n-butyllithium (2.68 mL, 4.47 mmol) was added dropwise at −78° C. After the mixture was gradually warmed to room temperature, stirring was performed at 35° C. for 3 hours. The resultant mixture was added dropwise to a suspension of zirconium tetrachloride (0.96 g, 4.10 mmol) in toluene (4 mL) at −78° C. The resultant mixture was heated to room temperature and stirred overnight. After the completion of the reaction, the solvent was removed under reduced pressure. Thereafter, the residue, to which heptane was added, was filtrated to remove insoluble materials. The solvent was removed under reduced pressure. Pentane was added and cooled to −20° C. The resultant solid was filtrated and washed with a small amount of pentane, and then, dried under reduced pressure to obtain complex 27 (0.56 g, yield 27.4%) as a pale yellow solid. The resultant complex contained 0.5 molecules of triethylamine per molecule.

$^1$H-NMR (CDCl$_3$, δ ppm): 0.71 (s, 3H), 0.86 (t, J=7.1 Hz, 3H), 1.02 (t, J=7.2 Hz, NEt$_3$), 1.14-1.42 (m, 6H), 2.07 (s, 3H), 2.09 (s, 3H), 2.13 (s, 3H), 2.30 (s, 3H), 2.64 (q, J=7.2 Hz, NEt$_3$), 7.26-7.34 (m, 3H), 7.37-7.44 (m, 2H)

$^{13}$C-NMR (CD$_2$Cl$_2$, δ ppm): −2.39, 10.38, 13.26, 13.36, 13.95, 15.94, 16.67, 16.88, 26.58, 27.05, 45.67, 128.05, 129.24, 134.73, 137.94; Cp ring carbons observed as broad signals around 135.15, 135.67 and 139.01.

Mass Spectrum (EI-MS, m/z): 435 (M$^+$-Bu)

Example 28

Synthesis of [1-dimethylphenylsilyl-2,3,4,5-tetramethylcyclopentadienyl]hafnium trichloride (Hereinafter, Referred to as "Complex 28")

Under a nitrogen atmosphere, to a toluene solution (27 mL) of 1-dimethylphenylsilyl-2,3,4,5-tetramethylcyclopentadiene (1.36 g, 5.30 mmol) and triethylamine (2.68 g, 26.50 mmol), a 1.67 M hexane solution of n-butyllithium (3.81 mL, 6.36 mmol) was added dropwise at −78° C. After the mixture was gradually warmed to room temperature, stirring was performed at 35° C. for 5.5 hours. The resultant mixture was added dropwise to a suspension of hafnium tetrachloride (1.87 g, 5.83 mmol) in toluene (10 mL) at −78° C. The mixture was warmed and stirring was performed at room temperature overnight. After the completion of the reaction, the solvent was removed under reduced pressure. Thereafter, the residue, to which heptane was added, was filtrated to remove insoluble materials. The solvent was removed to concentrate the filtrate under reduced pressure. Pentane was added and the resultant solid was filtrated and washed with a small amount of pentane, and then, dried under reduced pressure to obtain complex 28 (0.48 g, yield 16.8%) as a pale yellow solid. The solvent was further removed under reduced pressure. The resultant solid was filtrated and washed with a small amount of pentane, and then, dried under reduced pressure to obtain complex 28 (0.38 g, yield 13.3%) as a pale yellow solid. To the insoluble materials removed by adding heptane, toluene was added and filtrated to further remove toluene-insoluble materials. The solvent was removed under reduced pressure. Pentane was added and the resultant solid was filtrated and washed with a small amount of pentane, and then, dried under reduced pressure to obtain complex 28 (0.42 g, yield 14.8%) as a pale yellow solid.

$^1$H-NMR (CD$_2$Cl$_2$, δ ppm): 0.68 (s, 6H), 2.27 (s, 6H), 2.33 (s, 6H), 7.29-7.39 (m, 3H), 7.42-7.48 (m, 2H)

$^{13}$C-NMR (CD$_2$Cl$_2$, δ ppm): 0.47, 12.41, 15.72, 124.69, 128.34, 129.76, 133.69, 134.34, 135.58, 138.40

Mass Spectrum (EI-MS, m/z): 540 (M$^+$)

Example 29

Synthesis of [1-triphenylsilyl-2,3,4,5-tetramethylcyclopentadienyl]trimethyltitanium (Hereinafter, Referred to as "Complex 29")

Under a nitrogen atmosphere, to a diethyl ether solution (15 mL) of [1-triphenylsilyl-2,3,4,5-tetramethylcyclopentadienyl]titanium trichloride (0.30 g, 0.57 mmol), a 0.93 M diethyl ether solution of methylmagnesium iodide (1.91 mL, 1.78 mmol) was added dropwise at −78° C. The mixture was gradually warmed to 0° C. while stirring. After the completion of the reaction, the solvent was removed under reduced pressure. Thereafter, to the residue, hexane was added and filtrated to remove insoluble materials. The solvent was removed under reduced pressure. The resultant solid was dried under reduced pressure to obtain complex 29 (0.23 g, yield 86.3%) as a pale yellow solid.

$^1$H-NMR (CD$_2$Cl$_2$, δ ppm): 0.95 (s, 9H), 1.62 (s, 6H), 1.95 (s, 6H), 7.27-7.43 (m, 9H), 7.50-7.60 (m, 6H)

$^{13}$C-NMR (CD$_2$Cl$_2$, δ ppm): 12.47, 15.47, 63.59, 116.34, 128.00, 129.76, 130.58, 135.78, 136.33, 137.13

Mass Spectrum (EI-MS, m/z): 472 (M$^+$)

Example 30

Synthesis of [1-tris(3,5-dimethylphenyl)silyl-2,3,4,5-tetramethylcyclopentadienyl]trimethyltitanium (Hereinafter, Referred to as "Complex 30")

Under a nitrogen atmosphere, to a diethyl ether solution (5 mL) of [1-tris(3,5-dimethylphenyl)silyl-2,3,4,5-tetramethylcyclopentadienyl]titanium trichloride (87.0 mg, 0.14 mmol), a 3.00 M tetrahydrofuran solution of methylmagnesium chloride (0.23 mL, 0.70 mmol) was added dropwise at −20° C. The mixture was gradually warmed to room temperature while stirring. After the completion of the reaction, the solvent was removed under reduced pressure. Thereafter, to the residue, hexane was added and filtrated to remove insoluble materials. The solvent was removed under reduced pressure. The resultant solid was dried under reduced pressure to obtain complex 30 (57.3 mg, yield 73.1%) as a pale yellow solid.

$^1$H-NMR (CD$_2$C$_2$, δ ppm): 0.95 (s, 9H), 1.60 (s, 6H), 1.95 (s, 6H), 2.26 (s, 18H), 7.02 (s, 3H), 7.11 (s, 6H)

$^{13}$C-NMR (CD$_2$Cl$_2$, δ ppm): 12.47, 15.53, 21.47, 63.32, 117.74, 129.08, 130.62, 131.25, 134.77, 135.68, 137.15

Example 31

Synthesis of [1-triphenylsilyl-2,3,4,5-tetramethylcyclopentadienyl]titanium triphenoxide (Hereinafter, Referred to as "Complex 31")

Under a nitrogen atmosphere, to a toluene solution (10 mL) of lithium phenoxide (0.34 g, 3.37 mmol), a toluene solution (10 mL) of (1-triphenylsilyl-2,3,4,5-tetramethylcyclopentadienyl)titanium trichloride (0.50 g, 0.94 mmol) was added dropwise at −30° C. The mixture was gradually warmed to room temperature while stirring. After the completion of the reaction at room temperature for 20 hours, additional lithium phenoxide (0.10 g, 1.00 mmol) was added and a small amount of tetrahydrofuran was added. After the solvent was removed under reduced pressure, hexane was added to the residue and filtrated to remove insoluble materials. The solvent was removed under reduced pressure and recrystallization was performed from toluene/pentane at −20° C. to obtain complex 31 (0.47 g, yield 71.2%) as a yellow solid.

$^1$H-NMR (CDCl$_3$, δ ppm): 1.87 (s, 6H), 2.14 (s, 6H), 6.59 (d, J=7.4 Hz, 6H), 6.80 (t, J=7.4 Hz, 3H), 7.08 (t, J=7.4 Hz, 6H), 7.26 (t, J=7.4 Hz, 6H), 7.37 (t, J=7.4 Hz, 3H), 7.61 (d, J=7.4 Hz, 6H)

$^{13}$C-NMR (CDCl$_3$, δ ppm): 12.06, 15.23, 118.88, 120.09, 120.68, 127.77, 128.97, 129.39, 131.92, 134.83, 136.71, 137.38, 164.90

Mass Spectrum (EI-MS, m/z): 706 (M$^+$)

Example 32

Synthesis of [1-triphenylsilyl-2,3,4,5-tetramethylcyclopentadienyl]titanium triethoxide (Hereinafter, Referred to as "Complex 32")

Under a nitrogen atmosphere, to a tetrahydrofuran solution (5 mL) of magnesium diethoxide (74.7 mg, 0.65 mmol), a tetrahydrofuran solution (5 mL) of (1-triphenylsilyl-2,3,4,5-tetramethylcyclopentadienyl)titanium trichloride (193.6 mg, 0.36 mmol) was added dropwise at −30° C. and gradually heated to room temperature while stirring. After the completion of the reaction at room temperature for 18 hours, additional magnesium diethoxide (32.0 mg, 0.28 mmol) was added. After the solvent was removed under reduced pressure, heptane was added to the residue and filtrated to remove insoluble materials. The solvent was removed under reduced pressure. Pentane was added and filtrated at −20° C. to remove insoluble materials. The solvent was removed under reduced pressure to obtain complex 32 (152.6 mg, yield 74.8%) as yellow oil. The resultant complex 32 was crystallized by standing at −20° C.

$^1$H-NMR (CD$_2$Cl$_2$, δ ppm): 1.12 (t, J=6.9 Hz, 9H), 1.66 (s, 6H), 1.99 (s, 6H), 4.22 (q, J=6.9 Hz, 6H), 7.28-7.41 (m, 9H), 7.64-7.70 (m, 6H)

$^{13}$C-NMR (CDCl$_3$, δ ppm): 11.43, 14.60, 20.02, 70.04, 112.53, 127.13, 127.81, 129.38, 132.06, 136.51, 137.07

Mass Spectrum (EI-MS, m/z): 562 (M$^+$)

Example 33

Synthesis of Complex 29

A reaction is performed in the same manner as in Example 29 except that a 1.12 M diethyl ether solution (1.83 mL, 2.05 mmol) of methyllithium is used instead of the 0.93 M diethyl ether solution (1.91 mL, 1.78 mmol) of methylmagnesium iodide to obtain complex 29.

Example 34

Synthesis of [1-triphenylsilyl-2,3,4,5-tetramethylcyclopentadienyl]methyltitanium dichloride Under a nitrogen atmosphere, to a diethyl ether solution (15 mL) of [1-triphenylsilyl-2,3,4,5-tetramethylcyclopentadienyl]titanium trichloride (0.30 g, 0.57 mmol), a 0.93 M diethyl ether solution of methylmagnesium iodide (0.63 mL, 0.59 mmol) is added dropwise at −78° C. The temperature is gradually increased to 0° C. while stirring to obtain [1-triphenylsilyl-2,3,4,5-tetramethylcyclopentadienyl]methyltitanium dichloride.

Example 35

Synthesis of [1-triphenylsilyl-2,3,4,5-tetramethylcyclopentadienyl]dimethyltitanium chloride Under a nitrogen atmosphere, to a diethyl ether solution (15 mL) of [1-triphenylsilyl-2,3,4,5-tetramethylcyclopentadienyl]titanium trichloride (0.30 g, 0.57 mmol), a 0.93 M diethyl ether solution of methylmagnesium iodide (1.26 mL, 1.18 mmol) is added dropwise at −78° C. The temperature is gradually increased to 0° C. while stirring to obtain [1-triphenylsilyl-2,3,4,5-tetramethylcyclopentadienyl]dimethyltitanium chloride.

Example 36

Synthesis of [1-triphenylsilyl-2,3,4,5-tetramethylcyclopentadienyl]tribenzyltitanium Under a nitrogen atmosphere, to a tetrahydrofuran solution (15 mL) of [1-triphenylsilyl-2,3,4,5-tetramethylcyclopentadienyl]titanium trichloride (0.30 g, 0.57 mmol), a 0.96 M tetrahydrofuran solution of benzylmagnesium chloride (1.85 mL, 1.80 mmol) is added dropwise at −78° C. The temperature is gradually increased to 0° C. while stirring to obtain [1-triphenylsilyl-2,3,4,5-tetramethylcyclopentadienyl]tribenzyltitanium.

Example 37

Synthesis of Complex 31

A reaction is performed in the same manner as in Example 30 except that 3.00 M tetrahydrofuran solution (0.94 mL, 2.82 mmol) of methylmagnesium chloride and phenoxy magnesium chloride (0.43 g, 2.82 mmol) generated from phenol (0.27 g, 2.82 mmol) are used instead of the toluene solution of lithium phenoxide (0.34 g, 3.37 mmol) to obtain complex 31.

Example 38

Synthesis of [1-triphenylsilyl-2,3,4,5-tetramethylcyclopentadienyl]dichlorotitanium phenoxide Under a nitrogen atmosphere, to a tetrahydrofuran solution (10 mL) of lithium phenoxide (0.11 g, 1.12 mmol), a tetrahydrofuran solution (10 mL) of [1-triphenylsilyl-2,3,4,5-tetramethylcyclopentadienyl]titanium trichloride (0.50 g, 0.94 mmol) is added dropwise at −30° C. The temperature is gradually increased to 0° C. while stirring to obtain [1-triphenylsilyl-2,3,4,5-tetramethylcyclopentadienyl]dichlorotitanium phenoxide.

Example 39

Synthesis of [1-triphenylsilyl-2,3,4,5-tetramethylcyclopentadienyl]chlorotitanium diphenoxide Under a nitrogen atmosphere, to a tetrahydrofuran solution (10 mL) of lithium phenoxide (0.22 g, 2.24 mmol), a tetrahydrofuran solution (10 mL) of [1-triphenylsilyl-2,3,4,5-tetramethylcyclopentadienyl]titanium trichloride (0.50 g, 0.94 mmol) is added dropwise at −30° C. The temperature is gradually increased to 0° C. while stirring to obtain [1-triphenylsilyl-2,3,4,5-tetramethylcyclopentadienyl]chlorotitanium diphenoxide.

Example 40

Synthesis of [1-triphenylsilyl-2,3,4,5-tetramethylcyclopentadienyl]titanium trimethoxide A reaction is performed in the same manner as in Example 31 except that a 1.57 M hexane solution (0.36 mL, 1.08 mmol) of n-butyllithium and lithium methoxide (4.1 mg, 1.08 mmol) generated from methanol (3.5 mg, 1.08 mmol) are used instead of the tetrahydrofuran solution of magnesium diethoxide (74.7 mg, 0.65 mmol) to obtain [1-triphenylsilyl-2,3,4,5-tetramethylcyclopentadienyl]titanium trimethoxide.

<Production of 1-Hexene>

(1) Activity of 1-Hexene

Analysis was made using gas chromatography (Shimadzu GC-2010, DB-1 column).

(2) Synthesis of Publicly-Known Transition Metal Complex

[1-(1-methyl-1-phenylethyl)-cyclopentadienyl]titanium trichloride (hereinafter, referred to as "complex 33") was synthesized in accordance with a well known method (J. Organomet. Chem. 1999, 592, pp 84-94.). [1-(1-methyl-1-(3,5-dimethylphenyl)ethyl)-3-trimethylsilylcyclopentadienyl]titanium trichloride (hereinafter, referred to as "complex 34") was synthesized in accordance with a well known method (Organometallics 2002, 21, pp 5122-5135.).

Example 41

An autoclave (0.4 liter) equipped with a stirrer was dried under reduced pressure, purged with argon and then evacuated. After toluene (90 ml) was supplied and the interior temperature of the system was increased to 40° C., a hexane solution (0.41 mL) of methylaluminoxane having a methylaluminoxane (PMAO-s manufactured by Tosoh Finechem Corp.) concentration of 2.45 mmol/mL was supplied. Then, ethylene was introduced so as to obtain the partial pressure of 0.5 MPa to stabilize the system. To the system, 1.0 ml of a toluene solution (1 μmol/ml) of complex 1 was supplied. A reaction was performed at 40° C. for 30 minutes while continuously supplying ethylene gas so as to maintain the whole pressure at a constant value. Thereafter, ethylene was purged and the content of the autoclave was deashed with ethanol-hydrochloric acid and then filtrated. 1-hexene was obtained at an activity of $4.01 \times 10^6$ g/mol-complex h and a polymer was obtained at an activity of $0.52 \times 10^6$ g/mol-complex h.

The results are shown in Table 1.

Example 42

An autoclave (0.4 liter) equipped with a stirrer was dried under reduced pressure, purged with argon and then evacuated. After toluene (90 ml) was supplied and the interior temperature of the system was increased to 80° C., a hexane solution (0.41 mL) of methylaluminoxane having an methylaluminoxane (PMAO-s manufactured by Tosoh Finechem Corp.) concentration of 2.45 mmol/mL was supplied. Then, ethylene was introduced so as to obtain the partial pressure of 0.5 MPa to stabilize the system. To the system, 1.0 ml of a toluene solution (1 μmol/ml) of complex 1 was supplied. A reaction was performed at 80° C. for 30 minutes while continuously supplying ethylene gas so as to maintain the whole pressure at a constant value during the reaction. Thereafter, ethylene was purged and the content of the autoclave was deashed with ethanol-hydrochloric acid and then filtrated. 1-hexene was obtained at an activity of $1.65 \times 10^6$ g/mol-complex h and a polymer was obtained at an activity of $0.14 \times 10^6$ g/mol-complex h.

The results are shown in Table 1.

Example 43

An autoclave (0.4 liter) equipped with a stirrer was dried under reduced pressure, purged with argon and then evacuated. After toluene (90 ml) was supplied and the interior temperature of the system was increased to 80° C., 0.73 g of a toluene solution (TMAO-s manufactured by Tosoh Finechem Corp.) of methylaluminoxane having an Al concentration of 9.2 wt % (3.4 mmol/g) was supplied. Then, ethylene was introduced so as to obtain the partial pressure of 0.5 MPa to stabilize the system. To the system, 1.0 ml of a toluene solution (1 µmol/ml) of complex 1 was supplied. A reaction was performed at 80° C. for 30 minutes while continuously supplying ethylene gas so as to maintain the whole pressure at a constant value during the reaction. Thereafter, ethylene was purged and the content of the autoclave was deashed with ethanol-hydrochloric acid and then filtrated. 1-hexene was obtained at an activity of $1.96 \times 10^6$ g/mol-complex h and a polymer was obtained at an activity of $0.06 \times 10^6$ g/mol-complex h.

Example 44

The same operation was performed as in Example 43 except that complex 2 was used instead of complex C0484. As a result, 1-hexene was obtained at an activity of $2.10 \times 10^6$ g/mol-complex h and a polymer was obtained at an activity of $0.1 \times 10^6$ g/mol-complex h.

The results are shown in Table 1.

Example 45

The same operation was performed as in Example 43 except that complex 9 was used instead of complex 1. As a result, 1-hexene was obtained at an activity of $1.28 \times 10^6$ g/mol-complex h and a polymer was obtained at an activity of $0.02 \times 10^6$ g/mol-complex h.

The results are shown in Table 1.

Example 46

The same operation was performed as in Example 43 except that complex 5 was used instead of complex 1. As a result, 1-hexene was obtained at an activity of $1.09 \times 10^6$ g/mol-complex h and a polymer was obtained at an activity of $0.02 \times 10^6$ g/mol-complex h.

The results are shown in Table 1.

Example 47

The same operation was performed as in Example 43 except that complex 3 was used instead of complex 1. As a result, 1-hexene was obtained at an activity of $1.21 \times 10^6$ g/mol-complex h and a polymer was obtained at an activity of $0.06 \times 10^6$ g/mol-complex h.

The results are shown in Table 1.

Example 48

The same operation was performed as in Example 43 except that complex 6 was used instead of complex 1. As a result, 1-hexene was obtained at an activity of $1.09 \times 10^6$ g/mol-complex h and a polymer was obtained at an activity of $0.12 \times 10^6$ g/mol-complex h.

The results are shown in Table 1.

Example 49

The same operation was performed as in Example 43 except that complex 7 was used instead of complex 1. As a result, 1-hexene was obtained at an activity of $1.43 \times 10^6$ g/mol-complex h and a polymer was obtained at an activity of $0.07 \times 10^6$ g/mol-complex h.

The results are shown in Table 1.

Example 50

The same operation was performed as in Example 43 except that complex 4 was used instead of complex 1. As a result, 1-hexene was obtained at an activity of $1.15 \times 10^6$ g/mol-complex h and a polymer was obtained at an activity of $0.03 \times 10^6$ g/mol-complex h.

The results are shown in Table 1.

Example 51

The same operation was performed as in Example 43 except that complex 11 was used instead of complex 1. As a result, 1-hexene was obtained at an activity of $3.71 \times 10^6$ g/mol-complex h and a polymer was obtained at an activity of $0.01 \times 10^6$ g/mol-complex h.

The results are shown in Table 1.

Example 52

The same operation was performed as in Example 43 except that complex 21 was used instead of complex 1. As a result, 1-hexene was obtained at an activity of $0.91 \times 10^6$ g/mol-complex h and a polymer was obtained at an activity of $0.04 \times 10^6$ g/mol-complex h.

The results are shown in Table 1.

Example 53

An autoclave (0.4 liter) equipped with a stirrer was dried under reduced pressure, purged with argon and then evacuated. After toluene (90 ml) was supplied, the interior temperature of the system was increased to 80° C. Then, a toluene solution (0.4 mL) of triisobutylaluminum (TIBA) having a concentration of 1.0 mmol/mL was supplied to the autoclave. Then, ethylene was introduced so as to obtain the partial pressure of 0.5 MPa to stabilize the system. To the system, 1.0 ml of a toluene solution (1 µmol/ml) of complex 9 was supplied. Subsequently, 3 mL of a toluene solution (1 µmol/ml) of triphenylmethyltetrakis(pentafluorophenyl)borate (TB) was supplied. A reaction was performed at 80° C. for 30 minutes while continuously supplying ethylene gas so as to maintain the whole pressure at a constant value during the reaction. Thereafter, ethylene was purged and the content of the autoclave was deashed with ethanol-hydrochloric acid and then filtrated. 1-hexene was obtained at an activity of $1.20 \times 10^6$ g/mol-complex h and a polymer was obtained at an activity of $0.62 \times 10^6$ g/mol-complex h.

The results are shown in Table 1.

Example 54

The same operation was performed as in Example 53 except that N,N-dimethylaniliniumtetrakis(pentafluorophenyl)borate (AB) was used instead of triphenylmethyltetrakis(pentafluorophenyl)borate (TB). As a result, 1-hexene was obtained at an activity of $1.65 \times 10^6$ g/mol-complex h and a polymer was obtained at an activity of $0.32 \times 10^6$ g/mol-complex h.
The results are shown in Table 1.

Example 55

The same operation was performed as in Example 53 except that complex 11 was used instead of complex 9. As a result, 1-hexene was obtained at an activity of $3.43 \times 10^6$ g/mol-complex h and a polymer was obtained at an activity of $0.10 \times 10^6$ g/mol-complex h.
The results are shown in Table 1.

Example 56

The same operation was performed as in Example 54 except that complex 11 was used instead of complex 9. As a result, 1-hexene was obtained at an activity of $4.75 \times 10^6$ g/mol-complex h and a polymer was obtained at an activity of $0.12 \times 10^6$ g/mol-complex h.
The results are shown in Table 1.

Example 57

The same operation was performed as in Example 43 except that complex 23 was used instead of complex 1. As a result, 1-hexene was obtained at an activity of $0.77 \times 10^6$ g/mol-complex h and a polymer was obtained at an activity of $0.03 \times 10^6$ g/mol-complex h.
The results are shown in Table 1.

Example 58

The same operation was performed as in Example 43 except that complex 24 was used instead of complex 1. As a result, 1-hexene was obtained at an activity of $1.61 \times 10^6$ g/mol-complex h and a polymer was obtained at an activity of $0.05 \times 10^6$ g/mol-complex h.
The results are shown in Table 1.

Example 59

An autoclave (0.4 liter) equipped with a stirrer was dried under reduced pressure, purged with argon and then evacuated. After toluene (90 ml) was supplied and the interior temperature of the system was increased to 80° C., 0.73 g of a toluene solution of methylaluminoxane (TMAO-s manufactured by Tosoh Finechem Corp.) having an Al concentration of 9.2 wt % (3.4 mmol/g) was supplied. Then, ethylene was introduced so as to obtain the partial pressure of 2.0 MPa to stabilize the system. To the system, 1.0 ml of a toluene solution (1 µmol/ml) of complex 11 was supplied. A reaction was performed at 80° C. for 30 minutes while continuously supplying ethylene gas so as to maintain the whole pressure at a constant value during the reaction. Thereafter, ethylene was purged and the content of the autoclave was deashed with ethanol-hydrochloric acid and then filtrated. 1-hexene was obtained at an activity of $11.46 \times 10^6$ g/mol-complex h and a polymer was obtained at an activity of $0.40 \times 10^6$ g/mol-complex h.

Comparative Example 1

The same operation was performed as in Example 43 except that complex 34 was used instead of complex 1. As a result, 1-hexene was obtained at an activity of $0.58 \times 10^6$ g/mol-complex h and a polymer was obtained at an activity of $0.09 \times 10^6$ g/mol-complex h.
The results are shown in Table 1.

Comparative Example 2

An autoclave (0.4 liter) equipped with a stirrer was dried under reduced pressure, purged with argon and then evacuated. After toluene (90 ml) was supplied and the interior temperature of the system was increased to 80° C., a 1.22 mL of a hexane solution of methylaluminoxane having a methylaluminoxane (PMAO-s manufactured by Tosoh Finechem Corp.) concentration of 2.45 mmol/mL was supplied. Then, ethylene was introduced so as to obtain the partial pressure of 0.5 MPa to stabilize the system. To the system, 1.0 ml of a toluene solution (1 µmol/ml) of complex 33 was supplied. A reaction was performed at 80° C. for 30 minutes while continuously supplying ethylene gas so as to maintain the whole pressure at a constant value during the reaction. Thereafter, ethylene was purged and the content of the autoclave was deashed with ethanol-hydrochloric acid and then filtrated. 1-hexene was obtained at an activity of $0.06 \times 10^6$ g/mol-complex h and a polymer was obtained at an activity of $0.01 \times 10^6$ g/mol-complex h.
The results are shown in Table 1.

TABLE 1

| | Complex | Aluminum compound Type | Aluminum compound Amount (mmol) | Borate compound Type | Borate compound Amount (µmol) | Temperature (° C.) | C'6 activity (t/mol complex h*) | PE activity (t/mol complex h*) |
|---|---|---|---|---|---|---|---|---|
| Example 41 | 1 | PMAO | 1.0 | — | — | 40 | 4.01 | 0.52 |
| Example 42 | 1 | PMAO | 1.0 | — | — | 80 | 1.65 | 0.14 |
| Example 43 | 1 | TMAO | 2.5 | — | — | 80 | 1.96 | 0.06 |
| Example 44 | 2 | TMAO | 2.5 | — | — | 80 | 2.10 | 0.10 |
| Example 45 | 9 | TMAO | 2.5 | — | — | 80 | 1.28 | 0.02 |
| Example 46 | 5 | TMAO | 2.5 | — | — | 80 | 1.09 | 0.02 |
| Example 47 | 3 | TMAO | 2.5 | — | — | 80 | 1.21 | 0.06 |
| Example 48 | 6 | TMAO | 2.5 | — | — | 80 | 1.09 | 0.12 |
| Example 49 | 7 | TMAO | 2.5 | — | — | 80 | 1.43 | 0.07 |
| Example 50 | 4 | TMAO | 2.5 | — | — | 80 | 1.15 | 0.03 |
| Example 51 | 11 | TMAO | 2.5 | — | — | 80 | 3.71 | 0.01 |
| Example 52 | 21 | TMAO | 2.5 | — | — | 80 | 0.91 | 0.04 |
| Example 53 | 9 | TIBA | 0.4 | TB | 3 | 80 | 1.20 | 0.62 |
| Example 54 | 9 | TIBA | 0.4 | AB | 3 | 80 | 1.65 | 0.32 |

TABLE 1-continued

|  | Complex | Aluminum compound Type | Amount (mmol) | Borate compound Type | Amount (μmol) | Temperature (° C.) | C'6 activity (t/mol complex h*) | PE activity (t/mol complex h*) |
|---|---|---|---|---|---|---|---|---|
| Example 55 | 11 | TIBA | 0.4 | TB | 3 | 80 | 3.43 | 0.10 |
| Example 56 | 11 | TIBA | 0.4 | AB | 3 | 80 | 4.75 | 0.12 |
| Example 57 | 23 | TMAO | 2.5 | — | — | 80 | 0.77 | 0.03 |
| Example 58 | 24 | TMAO | 2.5 | — | — | 80 | 1.61 | 0.05 |
| Example 59** | 11 | TMAO | 2.5 | — | — | 80 | 11.5 | 0.40 |
| Comparative Example 1 | 34 | TMAO | 2.5 | — | — | 80 | 0.58 | 0.09 |
| Comparative Example 2 | 33 | PMAO | 3 | — | — | 80 | 0.06 | 0.01 |

*t = $10^6$ g
**The ethylene pressure was set at 2.0 MPa in Example 59 only.

<Production of Ethylenic Polymer>

(1) Molecular Weight and Molecular Weight Distribution (Mw/Mn)

Measurement was performed using Rapid GPC (manufactured by Symyx) in the following conditions.

| | |
|---|---|
| Liquid feeding apparatus: | (LC pump) manufactured by Gilson Model 305 (pump head 25.SC) |
| Column: | PLgel Mixed-B 10 μm Manufactured by Polymer Laboratories (PL) 7.5 mm in diameter × 300 mm |
| Mobile phase: | o-Dichlorobenzene |
| Dissolving solvent: | 1,2,4-trichlorobenzene |
| Flow rate: | 2 ml/minute |
| Column temperature: | 160° C. |
| Calibration curve: | PL Standard product, polystyrene (PS) 8 samples (Standard PS molecular weight) 5,000, 10,050, 28,500, 65,500 185,400, 483,000, 1,013,000, 3,390,000 |

(2) Melting Point (Unit: ° C.)

Using a differential scanning calorimeter (DSC 6200R manufactured by Seiko Instruments Inc.), the melting point of a polymer was measured in the following conditions. The melting point was obtained from the thermogram of the second temperature increase.

[Conditions] 20° C. (20° C./minute)→200° C. (10 minute hold) (−20° C./minute)→−100° C. (10 minute hold) (20° C./minute)→200° C. (10 minute hold)

(3) Number of Butyl Branches

The number of butyl branches in the resultant polymer was obtained from infrared absorption spectrum. Note that measurement and calculation were performed using characteristic absorption due to hexene in accordance with the method described in a literature (Characterization of Polyethylene by Infrared Absorption Spectrum written by Takayama and Usami, et al.). The number of butyl branches was indicated in terms of the number of branches per 1000 carbon atoms (Me/1000 C).

(4) Synthesis of Publicly-Known Transition Metal Complex

Dimethylsilylene(tetramethylcyclopentadienyl)(3-tert-butyl-5-methyl-2-phenoxy)titanium dichloride (hereinafter, referred to as "complex 35") was synthesized in accordance with a publicly known method (JP 9-87313 A).

Dimethylsilylene(tert-butylamido)(tetramethylcyclopentadienyl)titanium dichloride (hereinafter, referred to as "complex 36") was synthesized in accordance with a publicly known method (JP 2535249B).

Isopropylidenebis(indenyl)hafnium dichloride (hereinafter, referred to as "complex 37") was synthesized in accordance with a publicly known method (Organometallics (1997), 16 (4), pp 713).

rac-Dimethylsilylenebis[2-ethyl-4-(2-fluoro-4-biphenylyl)-4H-azulenyl]hafnium dichloride (hereinafter, referred to as "complex 38") was synthesized in accordance with a publicly known method (WO2009/019919).

Diphenylmethylene(cyclopentadienyl)(fluorenyl)zirconium dichloride (hereinafter, referred to as "complex 39") was synthesized in accordance with a publicly known method (JP 3154999B).

1,2-Ethylenebis(indenyl)zirconium diphenoxide (hereinafter, referred to as "complex 40") was synthesized in accordance with a publicly known method (JP 2003-12682 A).

2-[N-(2,6-diisopropylphenylamide)-o-isopropylphenylmethyl]-6-(2-$\eta^1$-naphthyl)-pyridylhafnium dimethyl (hereinafter, referred to as "complex 41") was synthesized in accordance with a publicly known method (JP 2006-525314 A).

1,2-Ethylenebis(indenyl)zirconium dichloride (hereinafter, referred to as "complex 42") was synthesized in accordance with a publicly well known method (Organometallics (1995), 14 (1), 5).

Isopropylidene(cyclopentadienyl)(3-tert-butyl-5-methyl-2-phenoxy)titanium dichloride (hereinafter, referred to as "complex 43") was synthesized in accordance with a publicly known method (JP 9-87313 A).

Dimethylsilylene(indenyl)(3-tert-butyl-5-methyl-2-phenoxy)titanium dichloride (hereinafter, referred to as "complex 44") was synthesized in accordance with a publicly known method (JP 9-87313 A).

Isopropylidene(3-tert-butyl-5-methylcyclopentadienyl)(3,6-di-tert-butylfluorenyl)zirconium dichloride (hereinafter, referred to as "complex 45") was synthesized in accordance with a publicly known method (WO2001/027124).

Dimethylsilylene(fluorenyl)(3-tert-butyl-5-methyl-2-phenoxy)titanium dichloride (hereinafter, referred to as "complex 46") was synthesized in accordance with a publicly known method (Macromolecules 2010, 43, pp 2299-2306).

Example 60

In an autoclave, toluene (3.7 ml) was placed under a nitrogen atmosphere. The interior temperature was increased to 70° C., and ethylene was pressurized to 0.60 MPa to stabilize the system. Then, a toluene solution (400 μL) of methylaluminoxane (TMAO manufactured by Tosoh Finechem Corp.) having a concentration of 0.25 mmol/mL was supplied to the autoclave. Then, to the autoclave, a toluene solution (900 μL) of 0.005 μmol of [1-(n-butylmethylphenylsilyl)-2,3,4,5-tetramethylcyclopentadienyl]titanium trichloride (complex 1) and 0.095 μmol of dimethylsilylene (tetramethylcyclopentadienyl)(3-tert-butyl-5-methyl-2-phenoxy)titanium dichloride (complex 35) was supplied to initiate the polymerization. The polymerization was performed at 70° C. for 7 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $21.9 \times 10^6$ g/mol-complex h.

The physical properties of the resultant polymer were measured. Mw was $4.0 \times 10^5$, Mw/Mn was 1.8, the melting point was 118.3° C. and the number of butyl branches was 6.

The results are shown in Table 2.

Example 61

In an autoclave, toluene (3.7 ml) was placed under a nitrogen atmosphere. The interior temperature was increased to 70° C., and ethylene was pressurized to 0.60 MPa to stabilize the system. Then, a toluene solution (400 μL) of methylaluminoxane (TMAO manufactured by Tosoh Finechem Corp.) having a concentration of 0.25 mmol/mL was supplied to the autoclave. Then, to the autoclave, a toluene solution (900 μL) of 0.005 μmol of [1-(n-butylmethylphenylsilyl)-2,3,4,5-tetramethylcyclopentadinyl]titanium trichloride (complex 1) and 0.095 μmol of dimethylsilylene (tert-butylamido)(tetramethylcyclopentadienyl)titanium dichloride (complex 36) was supplied to initiate the polymerization. The polymerization was performed at 70° C. for 6 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $25.7 \times 10^6$ g/mol-complex h.

The physical properties of the resultant polymer were measured. Mw was $9.4 \times 10^5$, Mw/Mn was 1.7, the melting point was 121.4° C. and the number of butyl branches was 4.

The results are shown in Table 2.

Example 62

In an autoclave, toluene (3.7 ml) was placed under a nitrogen atmosphere. The interior temperature was increased to 70° C. and ethylene was pressurized to 0.60 MPa to stabilize the system. Then, a toluene solution (400 μL) of methylaluminoxane (TMAO manufactured by Tosoh Finechem Corp.) having a concentration of 0.25 mmol/mL was supplied to the autoclave. Then, to the autoclave, a toluene solution (900 μL) of 0.01 μmol of [1-(n-butylmethylphenylsilyl)-2,3,4,5-tetramethylcyclopentadinyl]titanium trichloride (complex 1) and 0.09 μmol of dimethylsilylene(tert-butylamido)(tetramethylcyclopentadienyl)titanium dichloride (complex 36) was supplied to initiate the polymerization. The polymerization was performed at 70° C. for 9 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $19.3 \times 10^6$ g/mol-complex h.

The physical properties of the resultant polymer were measured. Mw was $1.1 \times 10^6$, Mw/Mn was 1.7, the melting point was 118.8° C. and the number of butyl branches per 1000 carbon atoms was 11.

The results are shown in Table 2.

Example 63

In an autoclave, toluene (3.7 ml) was placed under a nitrogen atmosphere. The interior temperature was increased to 70° C., and ethylene was pressurized to 0.60 MPa to stabilize the system. Then, a toluene solution (400 μL) of methylaluminoxane (TMAO manufactured by Tosoh Finechem Corp.) having a concentration of 0.25 mmol/mL was supplied to the autoclave. Then, to the autoclave, a toluene solution (900 μL) of 0.005 μmol of [1-(methyldiphenylsilyl)-2,3,4,5-tetramethylcyclopentadienyl]titanium trichloride (complex 2) and 0.095 μmol of isopropylidene(bisindenyl)hafnium dichloride (complex 37) was supplied to initiate the polymerization. The polymerization was performed at 70° C. for 8 minutes. During the polymerization, ethylene gas was supplied so as to maintain the whole pressure of the autoclave at a constant value. After completion of the polymerization, ethylene within the autoclave was purged and the volatile component therein was removed by distillation under reduced pressure to obtain a polymer. The activity was $19.7 \times 10^6$ g/mol-complex h.

The physical properties of the resultant polymer were measured. Mw was $1.1 \times 10^6$, Mw/Mn was 1.8, the melting point was 122.7° C. and the number of butyl branches was 3.

The results are shown in Table 2.

Example 64

In an autoclave, toluene (3.7 ml) was placed under a nitrogen atmosphere. The interior temperature was increased to 70° C., and ethylene was pressurized to 0.60 MPa to stabilize the system. Then, a toluene solution (400 μL) of methylaluminoxane (TMAO manufactured by Tosoh Finechem Corp.) having a concentration of 0.25 mmol/mL was supplied to the autoclave. Then, to the autoclave, a toluene solution (900 μL) of 0.01 μmol of [1-(methyldiphenylsilyl)-2,3,4,5-tetramethylcyclopentadienyl]titanium trichloride (complex 2) and 0.09 μmol of isopropylidene(bisindenyl) hafnium dichloride (complex 37) was supplied to initiate the polymerization. The polymerization was performed at 70° C. for 13 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $9.8 \times 10^6$ g/mol-complex h.

The physical properties of the resultant polymer were measured. Mw was $1.3 \times 10^6$, Mw/Mn was 1.7, the melting point was 118.3° C. and the number of butyl branches was 8.

The results are shown in Table 2.

Example 65

In an autoclave, toluene (3.7 ml) was placed under a nitrogen atmosphere. The interior temperature was increased to 70° C., and ethylene was pressurized to 0.60 MPa to stabilize the system. Then, a toluene solution (400 μL) of methylaluminoxane (TMAO manufactured by Tosoh Finechem Corp.) having a concentration of 0.25 mmol/mL was supplied to the autoclave. Then, to the autoclave, a toluene solution (900 μL) of 0.005 μmol of [1-(methyldiphenylsilyl)-2,3,4,5-tetramethylcyclopentadienyl]titanium trichloride (complex 2) and 0.095 μmol of rac-dimethylsilylenebis[2-ethyl-4-(2-fluoro-4-biphenylyl)-4H-azulenyl]hafnium dichloride (complex 38) was supplied to initiate the polymerization. The polymerization was performed at 70° C. for 36 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $3.1 \times 10^6$ g/mol-complex h.

As the physical properties of the resultant polymer were measured. Mw was $6.1 \times 10^5$, Mw/Mn was 2.3, the melting point was 121.9° C. and the number of butyl branches was 3.

The results are shown in Table 2.

Example 66

In an autoclave, toluene (3.7 ml) was placed under a nitrogen atmosphere. The interior temperature was increased to 70° C., and ethylene was pressurized to 0.60 MPa to stabilize the system. Then, a toluene solution (400 μL) of methylaluminoxane (TMAO manufactured by Tosoh Finechem Corp.) having a concentration of 0.25 mmol/mL was supplied to the autoclave. Then, to the autoclave, a toluene solution (900 μL) of 0.01 μmol of [1-(methyldiphenylsilyl)-2,3,4,5-tetramethylcyclopentadienyl]titanium trichloride (complex 2) and 0.09 μmol of rac-dimethylsilylenebis[2-ethyl-4-(2-fluoro-4-biphenylyl)-4H-azulenyl]hafnium dichloride (complex 38) was supplied to initiate the polymerization. The polymerization was performed at 70° C. for 40 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $2.5 \times 10^6$ g/mol-complex h.

The physical properties of the resultant polymer were measured. Mw was $7.8 \times 10^5$, Mw/Mn was 2.6, the melting point was 119.6° C. and the number of butyl branches was 8.

The results are shown in Table 2.

Example 67

In an autoclave, toluene (3.7 ml) was placed under a nitrogen atmosphere. The interior temperature was increased to 70° C., and ethylene was pressurized to 0.60 MPa to stabilize the system. Then, a toluene solution (400 μL) of methylaluminoxane (TMAO manufactured by Tosoh Finechem Corp.) having a concentration of 0.25 mmol/mL was supplied to the autoclave. Then, to the autoclave, a toluene solution (900 μL) of 0.01 μmol of [1-(methyldiphenylsilyl)-2,3,4,5-tetramethylcyclopentadienyl]titanium trichloride (complex 2) and 0.09 μmol of diphenylmethylene(cyclopentadienyl)(fluorenyl)zirconium dichloride (complex 39) was supplied to initiate the polymerization. The polymerization was performed at 70° C. for 4 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $47.0 \times 10^6$ g/mol-complex h.

The physical properties of the resultant polymer were measured, Mw was $5.9 \times 10^5$, Mw/Mn was 1.8, the melting point was 125.2° C. and the number of butyl branches was 2.

The results are shown in Table 2.

Example 68

In an autoclave, toluene (3.7 ml) was placed under a nitrogen atmosphere. The interior temperature was increased to 70° C., and ethylene was pressurized to 0.60 MPa to stabilize the system. Then, a toluene solution (400 μL) of methylaluminoxane (TMAO manufactured by Tosoh Finechem Corp.) having a concentration of 0.25 mmol/mL was supplied to the autoclave. Then, to the autoclave, a toluene solution (900 μL) of 0.01 μmol of [1-(triphenylsilyl)-2,3,4,5-tetramethylcyclopentadienyl]titanium trichloride (complex 9) and 0.09 μmol of ethylene(bisindenyl)zirconium diphenoxide (complex 40) was supplied to initiate the polymerization. The polymerization was performed at 70° C. for 2 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $121.2 \times 10^6$ g/mol-complex h.

As the physical properties of the resultant polymer were measured Mw was $2.1 \times 10^5$, Mw/Mn was 1.8, the melting point was 129.7° C. and the number of butyl branches was 5.

The results are shown in Table 2.

Example 69

In an autoclave, toluene (3.7 ml) was placed under a nitrogen atmosphere. The interior temperature was increased to 70° C., and ethylene was pressurized to 0.60 MPa to stabilize the system. Then, a toluene solution (400 μL) of methylaluminoxane (TMAO manufactured by Tosoh Finechem Corp.) having a concentration of 0.25 mmol/mL was supplied to the autoclave. Then, to the autoclave, a toluene solution (900 μL) of 0.01 μmol of [1-(triphenylsilyl)-2,3,4, 5-tetramethylcyclopentadienyl]titanium trichloride (complex 9) and 0.09 μmol of 2-[N-(2,6-diisopropylphenylamide)-o-methylphenylmethyl]-6-(2-η-1-naphthyl)
pyridylhafnium dimethyl (complex 41) was supplied to initiate the polymerization. The polymerization was performed at 70° C. for 2 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $95.1 \times 10^6$ g/mol-complex h.

The physical properties of the resultant polymer were measured Mw was $3.0 \times 10^4$, Mw/Mn was 1.4, the melting point was 126.2° C. and the number of butyl branches per 1000 carbon atoms was 9.

The results are shown in Table 2.

Comparative Example 3

In an autoclave, toluene (3.7 ml) was placed under a nitrogen atmosphere. The interior temperature was increased to 70° C., and ethylene was pressurized to 0.60 MPa to stabilize the system. Then, a toluene solution (400 μL) of methylaluminoxane (TMAO manufactured by Tosoh Finechem Corp.) having a concentration of 0.25 mmol/mL was supplied to the autoclave. Then, to the autoclave, a toluene solution (900 µL) of 0.01 µmol of [1-(1-methyl-1-phenylethyl)-cyclopentadienyl]titanium trichloride (complex 33) and 0.09 µmol of dimethylsilylene(tert-butylamido)(tetramethylcyclopentadienyl)titanium dichloride (complex 36) was supplied to initiate the polymerization. The polymerization was performed at 70° C. for 8 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was 21.1×10$^6$ g/mol-complex h.

The physical properties of the resultant polymer were measured. The melting point was 132.4° C.

The results are shown in Table 2.

Comparative Example 4

In an autoclave, toluene (3.7 ml) was placed under a nitrogen atmosphere. The interior temperature was increased to 70° C., and ethylene was pressurized to 0.60 MPa to stabilize the system. Then, a toluene solution (400 µL) of methylaluminoxane (TMAO manufactured by Tosoh Finechem Corp.) having a concentration of 0.25 mmol/mL was supplied to the autoclave. Then, to the autoclave, a toluene Example 70

In an autoclave, 1-hexene (0.02 ml) and toluene (3.7 ml) were placed under a nitrogen atmosphere. The interior temperature was increased to 70° C., and ethylene was pressurized to 0.60 MPa to stabilize the system. Then, a toluene solution (400 µL) of methylaluminoxane (TMAO manufactured by Tosoh Finechem Corp.) having a concentration of 0.25 mmol/mL was supplied to the autoclave. Then, to the autoclave, a toluene solution (900 µL) of 0.005 µmol of [1-(n-butylmethylphenylsilyl)-2,3,4,5-tetramethylcyclopentadienyl]titanium trichloride (complex 1) and 0.095 µmol of dimethylsilylene(tetramethylcyclopentadienyl)(3-tert-butyl-5-methyl-2-phenoxy)titanium dichloride (complex 35) was supplied to initiate the polymerization. The polymerization was performed at 70° C. for 8 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was 15.9×10$^6$ g/mol-complex h.

The physical properties of the resultant polymer were measured, Mw was 2.7×10$^5$, Mw/Mn was 2.3, the melting point was 105.7° C. and the number of butyl branches was 18.

The results are shown in Table 2.

TABLE 2

|  | Time min | cocat* | polym. cat.** | trim. cat.*** | trim. cat. mol % | Tm(° C.) | Me/1000C | act t/molh**** | Mw | Mw/Mn |
|---|---|---|---|---|---|---|---|---|---|---|
| Example 60 | 7 | TMAO(tol) | 35 | 1 | 5 | 118.3 | 6 | 21.9 | 400000 | 1.8 |
| Example 61 | 6 | TMAO(tol) | 36 | 1 | 5 | 121.4 | 4 | 25.7 | 940000 | 1.7 |
| Example 62 | 9 | TMAO(tol) | 36 | 1 | 10 | 118.8 | 11 | 19.3 | 1100000 | 1.7 |
| Example 63 | 8 | TMAO(tol) | 37 | 2 | 5 | 122.7 | 3 | 19.7 | 1100000 | 1.8 |
| Example 64 | 13 | TMAO(tol) | 37 | 2 | 10 | 118.3 | 8 | 9.8 | 1300000 | 1.7 |
| Example 65 | 36 | TMAO(tol) | 38 | 2 | 5 | 121.9 | 3 | 3.1 | 610000 | 2.3 |
| Example 66 | 40 | TMAO(tol) | 38 | 2 | 10 | 119.6 | 8 | 2.5 | 780000 | 2.6 |
| Example 67 | 4 | TMAO(tol) | 39 | 2 | 10 | 125.2 | 2 | 47.0 | 590000 | 1.8 |
| Example 68 | 2 | TMAO(tol) | 40 | 9 | 10 | 129.7 | 5 | 121.2 | 210000 | 1.8 |
| Example 69 | 2 | TMAO(tol) | 41 | 9 | 10 | 126.2 | 9 | 95.1 | 30000 | 1.4 |
| Example 70 | 8 | TMAO(tol) | 35 | 1 | 5 | 105.7 | 18 | 15.9 | 270000 | 2.3 |
| Comparative Example 3 | 8 | TMAO(tol) | 36 | 33 | 10 | 132.4 | — | 21.1 | — | — |
| Comparative Example 4 | 6 | TMAO(tol) | 42 | 33 | 10 | 132.8 | — | 34.4 | — | — |

*co cat = activating co-catalytic component
**polym. cat. = catalytic component for polymerization
***trim. cat. = catalytic component for trimerization
****t = 10$^6$g solution (900 µL) of 0.01 µmol of [1-(1-methyl-1-phenylethyl)-cyclopentadienyl]titanium trichloride (complex 33) and 0.09 µmol of ethylene(bisindenyl)zirconium dichloride (complex 42) was supplied to initiate the polymerization. The polymerization was performed at 70° C. for 6 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was 34.4×10$^6$ g/mol-complex h.

The physical properties of the resultant polymer were measured. The melting point was 132.8° C.

The results are shown in Table 2.

Example 71

In an autoclave, toluene (3.64 ml) was placed under a nitrogen atmosphere. The interior temperature was increased to 70° C., and ethylene was pressurized to 0.60 MPa to stabilize the system. Then, a toluene solution (160 µL) of triisobutylaluminum (TIBA) having a concentration of 0.25 mmol/mL was supplied to the autoclave. Then, to the autoclave, a toluene solution (900 µL) of 0.005 µmol of [1-(n-butylmethylphenylsilyl)-2,3,4,5-tetramethylcyclopentadienyl]titanium trichloride (complex 1) and 0.095 µmol of dimethylsilylene(tetramethylcyclopentadienyl)(3-tert-butyl-5-methyl-2-phenoxy)titanium dichloride (complex 35) and a toluene solution (300 µL) of N,N-dimethylanilinium tetrakis (pentafluorophenyl)borate (AB) having a concentration of 0.001 mmol/mL were supplied to initiate the polymerization. The polymerization was performed at 70° C. for 3 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $63.5 \times 10^6$ g/mol-complex h.

The physical properties of the resultant polymer were measured. Mw was $3.4 \times 10^5$, Mw/Mn was 1.7, the melting point was 128.1° C. and the number of butyl branches was 2.

The results are shown in Table 3.

Example 72

In an autoclave, toluene (3.64 ml) was placed under a nitrogen atmosphere. The interior temperature was increased to 70° C., and ethylene was pressurized to 0.60 MPa to stabilize the system. Then, a toluene solution (160 µL) of triisobutylaluminum (TIBA) having a concentration of 0.25 mmol/mL was supplied to the autoclave. Then, to the autoclave, a toluene solution (900 µL) of 0.01 µmol of [1-(n-butylmethylphenylsilyl)-2,3,4,5-tetramethylcyclopentadienyl]titanium trichloride (complex 1) and 0.09 µmol of dimethylsilylene(tetramethylcyclopentadienyl)(3-tert-butyl-5-methyl-2-phenoxy)titanium dichloride (complex 35) and a toluene solution (300 µL) of N,N-dimethylanilinium tetrakis (pentafluorophenyl)borate (AB) having a concentration of 0.001 mmol/mL were supplied to initiate the polymerization. The polymerization was performed at 70° C. for 3 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $45.8 \times 10^6$ g/mol-complex h.

The physical properties of the resultant polymer were measured. Mw was $3.8 \times 10^5$, Mw/Mn was 1.9, the melting point was 122.1° C. and the number of butyl branches was 5.

The results are shown in Table 3.

Example 73

In an autoclave, toluene (3.64 ml) was placed under a nitrogen atmosphere. The interior temperature was increased to 70° C., and ethylene was pressurized to 0.60 MPa to stabilize the system. Then, a toluene solution (160 µL) of triisobutylaluminum (TIBA) having a concentration of 0.25 mmol/mL was supplied to the autoclave. Then, to the autoclave, a toluene solution (900 µL) of 0.005 µmol of [1-(n-butylmethylphenylsilyl)-2,3,4,5-tetramethylcyclopentadienyl]titanium trichloride (complex 1) and 0.095 µmol of isopropylidene(cyclopentadienyl)(3-tert-butyl-5-methyl-2-phenoxy)titanium dichloride (complex 43) and a toluene solution (300 µL) of N,N-dimethylanilinium tetrakis(pentafluorophenyl)borate (AB) having a concentration of 0.001 mmol/mL were supplied to initiate the polymerization. The polymerization was performed at 70° C. for 2 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $69.0 \times 10^6$ g/mol-complex h.

The physical properties of the resultant polymer were measured, Mw was $1.2 \times 10^5$, Mw/Mn was 1.5, the melting point was 121.6° C. and the number of butyl branches was 9.

The results are shown in Table 3.

Example 74

In an autoclave, toluene (3.64 ml) was placed under a nitrogen atmosphere. The interior temperature was increased to 70° C., and ethylene was pressurized to 0.60 MPa to stabilize the system. Then, a toluene solution (160 µL) of triisobutylaluminum (TIBA) having a concentration of 0.25 mmol/mL was supplied to the autoclave. Then, to the autoclave, a toluene solution (900 µL) of 0.01 µmol of [1-(n-butylmethylphenylsilyl)-2,3,4,5-tetramethylcyclopentadienyl]titanium trichloride (complex 1) and 0.09 µmol of isopropylidene(cyclopentadienyl)(3-tert-butyl-5-methyl-2-phenoxy)titanium dichloride (complex 43) and a toluene solution (300 µL) of N,N-dimethylanilinium tetrakis(pentafluorophenyl)borate (AB) having a concentration of 0.001 mmol/mL were supplied to initiate the polymerization. The polymerization was performed at 70° C. for 2 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $72.4 \times 10^6$ g/mol-complex h.

The physical properties of the resultant polymer were measured. Mw was $7.9 \times 10^4$, Mw/Mn was 1.5, the melting point was 120.2° C. and the number of butyl branches was 20.

The results are shown in Table 3.

Example 75

In an autoclave, toluene (3.64 ml) was placed under a nitrogen atmosphere. The interior temperature was increased to 70° C., and ethylene was pressurized to 0.60 MPa to stabilize the system. Then, a toluene solution (160 µL) of triisobutylaluminum (TIBA) having a concentration of 0.25 mmol/mL was supplied to the autoclave. Then, to the autoclave, a toluene solution (900 µL) of 0.005 µmol of [1-(n-butylmethylphenylsilyl)-2,3,4,5-tetramethylcyclopentadienyl]titanium trichloride (complex 1) and 0.095 µmol of dimethylsilylene(indenyl)(3-tert-butyl-5-methyl-2-phenoxy)titanium dichloride (complex 44) and a toluene solution (300 µL) of N,N-dimethylanilinium tetrakis(pentafluorophenyl)borate (AB) having a concentration of 0.001 mmol/mL were supplied to initiate the polymerization. The polymerization was performed at 70° C. for 3 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $54.0 \times 10^6$ g/mol-complex h.

The physical properties of the resultant polymer were measured. Mw was $1.8 \times 10^5$, Mw/Mn was 1.5, the melting point was 118.7° C. and the number of butyl branches was 7.

The results are shown in Table 3.

Example 76

In an autoclave, toluene (3.64 ml) was placed under a nitrogen atmosphere. The interior temperature was increased to 70° C., and ethylene was pressurized to 0.60 MPa to stabilize the system. Then, a toluene solution (160 µL) of triisobutylaluminum (TIBA) having a concentration of 0.25 mmol/mL was supplied to the autoclave. Then, to the autoclave, a toluene solution (900 µL) of 0.005 µmol of [1-(n-butylmethylphenylsilyl)-2,3,4,5-tetramethylcyclopentadienyl]titanium trichloride (complex 1) and 0.095 µmol of dimethylsilylene(fluorenyl)(3-tert-butyl-5-methyl-2-phenoxy)titanium dichloride (complex 46) and a toluene solution (300 µL) of N,N-dimethylanilinium tetrakis(pentafluorophenyl)borate (AB) having a concentration of 0.001 mmol/mL were supplied to initiate the polymerization. The polymerization was performed at 70° C. for 2 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $82.5 \times 10^6$ g/mol-complex h.

The physical properties of the resultant polymer were measured. Mw was $2.5 \times 10^5$, Mw/Mn was 1.6, the melting point was 128.4° C. and the number of butyl branches was 2.

The results are shown in Table 3.

Example 77

In an autoclave, toluene (3.64 ml) was placed under a nitrogen atmosphere. The interior temperature was increased to 70° C., and ethylene was pressurized to 0.60 MPa to stabilize the system. Then, a toluene solution (160 µL) of triisobutylaluminum (TIBA) having a concentration of 0.25 mmol/mL was supplied to the autoclave. Then, to the autoclave, a toluene solution (900 µL) of 0.01 µmol of [1-(n-butylmethylphenylsilyl)-2,3,4,5-tetramethylcyclopentadienyl]titanium trichloride (complex 1) and 0.09 µmol of dimethylsilylene(tert-butylamido)(tetramethylcyclopentadienyl)titanium dichloride (complex 36) and a toluene solution (300 µL) of N,N-dimethylanilinium tetrakis(pentafluorophenyl)borate (AB) having a concentration of 0.001 mmol/mL were supplied to initiate the polymerization. The polymerization was performed at 70° C. for 8 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $17.4 \times 10^6$ g/mol-complex h.

The physical properties of the resultant polymer were measured. Mw was $7.1 \times 10^5$, Mw/Mn was 2.4, the melting point was 123.9° C. and the number of butyl branches was 8.

The results are shown in Table 3.

Example 78

In an autoclave, toluene (3.64 ml) was placed under a nitrogen atmosphere. The interior temperature was increased to 70° C., and ethylene was pressurized to 0.60 MPa to stabilize the system. Then, a toluene solution (160 µL) of triisobutylaluminum (TIBA) having a concentration of 0.25 mmol/mL was supplied to the autoclave. Then, to the autoclave, a toluene solution (900 µL) of 0.01 µmol of [1-(methyldiphenylsilyl)-2,3,4,5-tetramethylcyclopentadienyl]titanium trichloride (complex 2) and 0.09 µmol of rac-dimethylsilylenebis[2-ethyl-4-(2-fluoro-4-biphenylyl)-4H-azulenyl]hafnium dichloride (complex 38) and a toluene solution (300 µL) of triphenylmethyltetrakis(pentafluorophenyl)borate (TB) having a concentration of 0.001 mmol/mL were supplied to initiate the polymerization. The polymerization was performed at 70° C. for 60 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $6.0 \times 10^5$ g/mol-complex h.

The physical properties of the resultant polymer were measured. Mw was $5.6 \times 10^5$, Mw/Mn was 2.5, the melting point was 128.6° C. and the number of butyl branches was 5.

The results are shown in Table 3.

Example 79

In an autoclave, toluene (3.64 ml) was placed under a nitrogen atmosphere. The interior temperature was increased to 70° C., and ethylene was pressurized to 0.60 MPa to stabilize the system. Then, a toluene solution (160 µL) of triisobutylaluminum (TIBA) having a concentration of 0.25 mmol/mL was supplied the autoclave. Then, to the autoclave, a toluene solution (900 µL) of 0.01 µmol of [1-(methyldiphenylsilyl)-2,3,4,5-tetramethylcyclopentadienyl] titanium trichloride (complex 2) and 0.09 µmol of isopropylidene (3-tert-butyl-5-methylcyclopentadienyl)(3,6-di-tert-butylfluorenyl)zirconium dichloride (complex 45) and a toluene solution (300 µL) of triphenylmethyltetrakis (pentafluorophenyl)borate (TB) having a concentration of 0.001 mmol/mL were supplied to initiate the polymerization. The polymerization was performed at 70° C. for 3 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was $42.1 \times 10^6$ g/mol-complex h.

The physical properties of the resultant polymer were measured. Mw was $3.5 \times 10^5$, Mw/Mn was 1.8, the melting point was 129.3° C. and the number of butyl branches was 3.

The results are shown in Table 3.

Comparative Example 5

In an autoclave, toluene (3.64 ml) was placed under a nitrogen atmosphere. The interior temperature was increased to 70° C., and ethylene was pressurized to 0.60 MPa to stabilize the system. Then, a toluene solution (160 µL) of triisobutylaluminum (TIBA) having a concentration of 0.25 mmol/mL was supplied to the autoclave. Then, to the autoclave, a toluene solution (900 µL) of 0.01 µmol of [1-(1-methyl-1-phenylethyl)-cyclopentadienyl]titanium trichloride (complex 33) and 0.09 µmol of dimethylsilylene (tert-butylamido)(tetramethylcyclopentadienyl)titanium dichloride (complex 36) and a toluene solution (300 µL) of N,N-dimethylanilinium tetrakis(pentafluorophenyl)borate (AB) having a concentration of 0.001 mmol/mL were supplied to initiate the polymerization. The polymerization was performed at 70° C. for 6 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was 23.1×10⁶ g/mol-complex h.

The physical properties of the resultant polymer were measured. The melting point was 134.5° C.
The results are shown in Table 3.

Comparative Example 6

In an autoclave, toluene (3.64 ml) was placed under a nitrogen atmosphere. The interior temperature was increased to 70° C., and ethylene was pressurized to 0.60 MPa to stabilize the system. Then, a toluene solution (160 µL) of triisobutylaluminum (TIBA) having a concentration of 0.25 mmol/mL was supplied to the autoclave. Then, to the autoclave, a toluene solution (900 µL) of 0.01 µmol of [1-(1-methyl-1-phenylethyl)-cyclopentadienyl]titanium trichloride (complex 33) and 0.09 µmol of dimethylsilylene(tert-butylamido)(tetramethylcyclopentadienyl)titanium dichloride (complex 36) and a toluene solution (300 µL) of tetramethylcyclopentadienyl]titanium trichloride (complex 1) and 0.09 µmol of dimethylsilylene(tert-butylamido)(tetramethylcyclopentadienyl)titanium dichloride (complex 36) and a toluene solution (300 µL) of triphenylmethyltetrakis(pentafluorophenyl)borate (TB) having a concentration of 0.001 mmol/mL were supplied to initiate the polymerization. The polymerization was performed at 70° C. for 6 minutes. During the polymerization, ethylene gas was supplied so as to maintain the whole pressure of the autoclave at a constant value. After the completion of the polymerization, ethylene within the autoclave was purged and the a volatile component therein was removed by distillation under reduced pressure to obtain a polymer. The activity was 19.8×10⁶ g/mol-complex h.

The physical properties of the resultant polymer were measured. Mw was 3.8×10⁵, Mw/Mn was 2.2, the melting point was 117.8° C. and the number of butyl branches was 10.

The results are shown in Table 3.

TABLE 3

| | Time min | cocat* | polym. cat** | trim. cat.*** | trim. cat mol % | Tm(° C.) | Me/1000C | act t/molh**** | Mw | Mw/Mn |
|---|---|---|---|---|---|---|---|---|---|---|
| Example 71 | 3 | TIBA/AB | 35 | 1 | 5 | 128.1 | 2 | 63.5 | 340000 | 1.7 |
| Example 72 | 3 | TIBA/AB | 35 | 1 | 10 | 122.1 | 5 | 45.8 | 380000 | 1.9 |
| Example 73 | 2 | TIBA/AB | 43 | 1 | 5 | 121.6 | 9 | 69.0 | 120000 | 1.5 |
| Example 74 | 2 | TIBA/AB | 43 | 1 | 10 | 120.2 | 20 | 72.4 | 79000 | 1.5 |
| Example 75 | 3 | TIBA/AB | 44 | 1 | 5 | 118.7 | 7 | 54.0 | 180000 | 1.5 |
| Example 76 | 2 | TIBA/AB | 46 | 1 | 5 | 128.4 | 2 | 82.5 | 250000 | 1.6 |
| Example 77 | 8 | TIBA/AB | 36 | 1 | 10 | 123.9 | 8 | 17.4 | 710000 | 2.4 |
| Example 78 | 60 | TIBA/TB | 38 | 2 | 10 | 128.6 | 5 | 0.6 | 560000 | 2.5 |
| Example 79 | 3 | TIBA/TB | 45 | 2 | 10 | 129.3 | 3 | 42.1 | 350000 | 1.8 |
| Example 80 | 6 | TIBA/AB | 36 | 1 | 10 | 117.8 | 10 | 19.8 | 380000 | 2.2 |
| Comparative Example 5 | 6 | TIBA/AB | 36 | 33 | 10 | 134.5 | — | 23.1 | — | — |
| Comparative Example 6 | 2 | TIBA/TB | 36 | 33 | 10 | 134.8 | — | 63.0 | — | — |

*co cat = activating co-catalytic component
**polym. cat. = catalytic component for polymerization
***trim. cat. = catalytic component for trimerization
****t = 10⁶g triphenylmethyltetrakis(pentafluorophenyl)borate (TB) having a concentration of 0.001 mmol/mL were supplied to initiate the polymerization. The polymerization was performed at 70° C. for 2 minutes. During the polymerization, ethylene gas was supplied so as to maintain the whole pressure of the autoclave at a constant value. After the completion of the polymerization, ethylene within the autoclave was purged and the volatile component therein was removed by distillation under reduced pressure to obtain a polymer. The activity was 63.0×10⁶ g/mol-complex h.

The physical properties of the resultant polymer were measured. The melting point was 134.8° C.
The results are shown in Table 3.

Example 80

In an autoclave, 1-hexene (0.02 ml) and toluene (3.62 ml) were placed under a nitrogen atmosphere. The interior temperature was increased to 70° C., and ethylene was pressurized to 0.60 MPa to stabilize the system. Then, a toluene solution (160 µL) of triisobutylaluminum (TIBA) having a concentration of 0.25 mmol/mL was supplied to the autoclave. Then, to the autoclave, a toluene solution (900 µL) of 0.01 µmol of [1-(n-butylmethylphenylsilyl)-2,3,4,5-

Example 81

In an autoclave, toluene (3.68 ml) was placed under a nitrogen atmosphere. The interior temperature of the system was increased to 80° C., and ethylene was pressurized to 0.50 MPa to stabilize the system. Then, a toluene solution (160 µL) of triisobutylaluminum having the concentration of 0.10 mmol/mL was supplied the autoclave. Then, 40 µL of toluene solution of [1-tris(3,5-dimethylphenyl)silyl-2,3,4,5-tetramethylcyclopentadienyl]trimethyltitanium (complex 30) having the concentration of 0.001 mmol/mL and 120 µL of toluene solution of N,N-dimethylanilinium tetrakis(pentafluorophenyl)borate having the concentration of 0.001 mmol/mL were supplied to the autoclave to initiate reaction. The reaction was performed at 80° C. for 36 minutes. During the reaction, ethylene gas was supplied so as to maintain the total pressure in the autoclave at a constant value. Thereafter, the ethylene was purged and the supernatant solution of the content of the autoclave was taken and GC-analyzed and the volatile component therein was removed by distillation under reduced pressure to obtain a polymer. The results are shown in Table 4 and the time-dependent change of the ethylene absorption is shown in FIG. 1. The ethylene absorption is presented in terms of the cumulative value of the pressure needed for elevating the pressure to the target pressure when the pressure was dropped by the ethylene absorption in the reaction in psi unit.

Example 82

Figure 2:
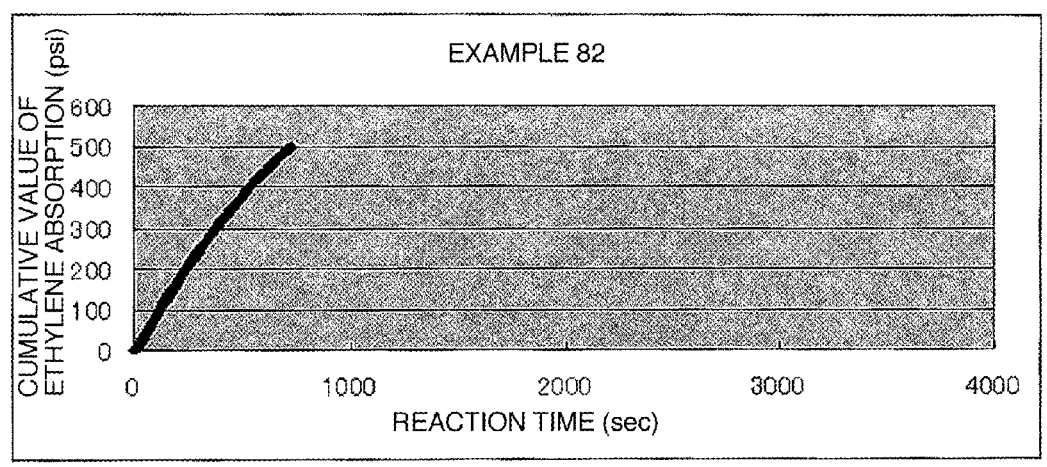
FIG. 2 graphically represents the time-dependent change of ethylene absorption in an embodiment of the present invention.

The operation was carried out in the same manner as in Example 81 except that the ethylene pressure was changed from 0.50 MPa to 0.80 MPa and that the reaction time was 12 min. The results are shown in Table 4, and the time-dependent change of the ethylene absorption is shown in FIG. 2.

Example 83

Figure 3:
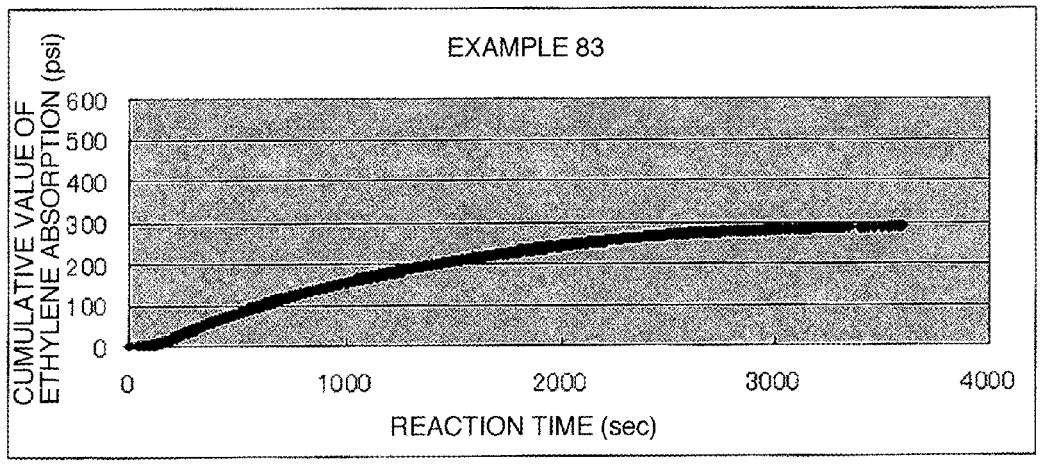
FIG. 3 graphically represents the time-dependent change of ethylene absorption in an embodiment of the present invention.

The operation was carried out in the same manner as in Example 81 except that complex 11 is used instead of complex 30 and that the reaction time was 60 min. The results are shown in Table 4 and the time-dependent change of the ethylene absorption is shown in FIG. 3.

TABLE 4

|  | complex | temp (° C.) | ethylene (MPa) | Final conv.* (psi) | time (min) | polymer g | act.(polymer) t/molh** | 1-hexene GC area % vs solvent (toluene) |
|---|---|---|---|---|---|---|---|---|
| Example 81 | 30 | 80 | 0.5 | 500 | 36 | 0.004 | 0.2 | 12.2 |
| Example 82 | 30 | 80 | 0.8 | 501 | 12 | 0.002 | 0.3 | 14.3 |
| Example 83 | 11 | 80 | 0.5 | 289 | 60 | 0.001 | 0.0 | 8.8 |

Evaluation Condition: TIBA/Complex/AB = 400/1/3
*presented in terms of the cumulative value of the pressure needed for elevating the pressure to the target pressure when the pressure was dropped by the ethylene absorption in the reaction in psi unit.
**t = $10^6$ g

Example 84

Figure 4:
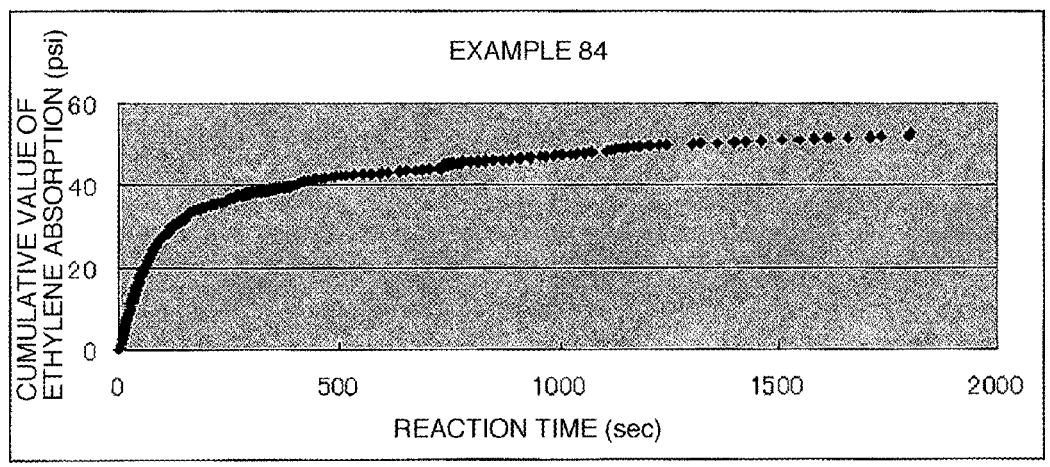
FIG. 4 graphically represents the time-dependent change of ethylene absorption in an embodiment of the present invention.

In an autoclave, toluene (3.8 ml) was placed under a nitrogen atmosphere. The interior temperature of the system was increased to 80° C., and ethylene was pressurized to 0.50 MPa to stabilize the system. Then, a toluene solution (160 μL) of methylaluminoxane (manufactured by Tosoh Finechem Corporation, TMAO) having the concentration of 0.25 mmol/mL was supplied to the autoclave. Then, 40 μL of toluene solution of [1-triphenylsilyl-2,3,4,5-tetramethyl-cyclopentadienyl]trimethyltitanium (complex 29) having the concentration of 0.001 mmol/mL was supplied to initiate reaction. The reaction was performed at 80° C. for 30 minutes. During the reaction, ethylene gas was supplied so as to maintain the total pressure in the autoclave at a constant value. Thereafter, the ethylene was purged and the supernatant solution of the content of the autoclave was taken and GC-analyzed, and the volatile component therein was removed by distillation under reduced pressure to obtain a polymer. The results are shown in Table and the time-dependent change of the ethylene absorption is shown in FIG. 4.

Example 85

Figure 5:
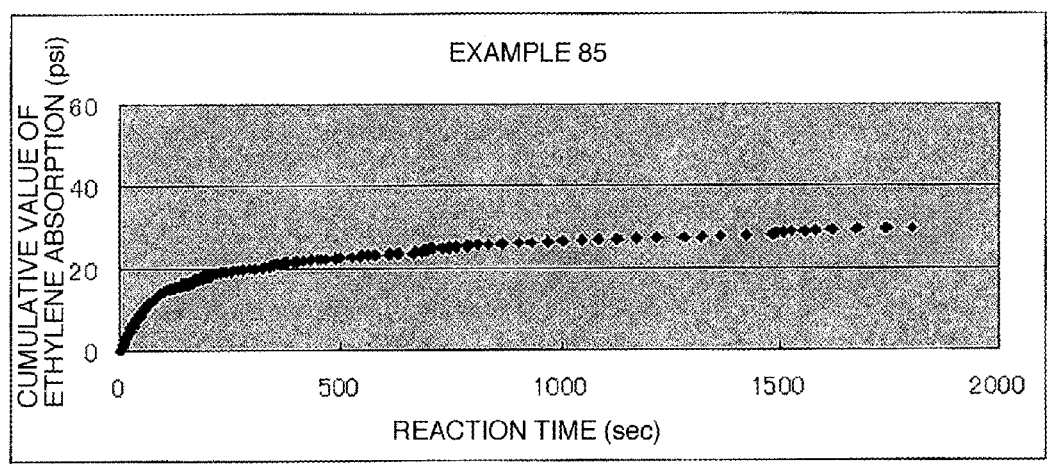
FIG. 5 graphically represents the time-dependent change of ethylene absorption in an embodiment of the present invention.

The operation was carried out in the same manner as in Example 84 except that complex 9 is used instead of complex 29. The results are shown in Table 5 and the time-dependent change of the ethylene absorption is shown in FIG. 5.

TABLE 5

|  | complex | temp (° C.) | ethylene (MPa) | Final conv.* (psi) | time (min) | polymer g | act.(polymer) t/molh** | 1-hexene GC area % vs solvent (toluene) |
|---|---|---|---|---|---|---|---|---|
| Example 84 | 29 | 80 | 0.5 | 53 | 30 | 0.005 | 0.3 | 1.8 |
| Example 85 | 9 | 80 | 0.5 | 30 | 30 | 0.013 | 0.7 | 0.7 |

Evaluation Condition: TMAO/Complex = 1000/1
*presented in terms of the cumulative value of the pressure needed for elevating the pressure to the target pressure when the pressure was dropped by the ethylene absorption in the reaction in psi unit.
**t = $10^6$ g

INDUSTRIAL APPLICABILITY

The present invention has high industrial applicability as providing a transition metal complex that serves as a catalytic component capable of efficiently and highly selectively producing 1-hexene through the trimerization reaction of ethylene even under high temperature conditions and also providing a process for economically producing an ethylenic polymer having a butyl branch by polymerizing ethylene even under high temperature conditions.

The invention claimed is:

1. A process for producing 1-hexene using a trimerization catalyst obtained by bringing a transition metal complex into contact with an activating co-catalytic component, wherein the transition metal complex is represented by general formula (1):

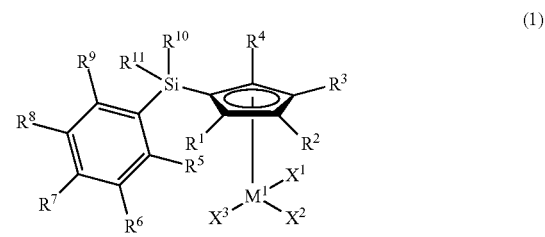

(1)

wherein
M$^1$ represents a transition metal atom of Group 4 of the Periodic Table of the Elements; R$^1$, R$^2$, R$^3$ and R$^4$ each independently represent
a hydrogen atom, a halogen atom,
an alkyl group having 1 to 20 carbon atoms optionally having a halogen atom as a substituent,
an alkoxy group having 1 to 20 carbon atoms optionally having a halogen atom as a substituent,
an aryl group having 6 to 20 carbon atoms optionally having a halogen atom as a substituent, an aryloxy group having 6 to 20 carbon atoms optionally having a halogen atom as a substituent, an aralkyl group having 7 to 20 carbon atoms optionally having a halogen atom as a substituent, an aralkyloxy group having 7 to 20 carbon atoms optionally having a halogen atom as a substituent, a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20, and at least one of $R^1$, $R^2$, $R^3$ and $R^4$ is a halogen atom, the alkyl group, the alkoxy group, the aryl group, the aryloxy group, the aralkyl group, the aralkyloxy group, the substituted silyl group or the disubstituted amino group;

$R^5$ and $R^9$ each independently represent a hydrogen atom, a halogen atom, an alkyl group having 1 to 20 carbon atoms optionally having a halogen atom as a substituent, an aryl group having 6 to 20 carbon atoms optionally having a halogen atom as a substituent, or an aralkyl group having 7 to 20 carbon atoms optionally having a halogen atom as a substituent;

$R^6$, $R^7$ and $R^8$ each independently represent a hydrogen atom, a halogen atom, an alkyl group having 1 to 20 carbon atoms optionally having a halogen atom as a substituent, an aryl group having 6 to 20 carbon atoms optionally having a halogen atom as a substituent, or an aralkyl group having 7 to 20 carbon atoms optionally having a halogen atom as a substituent;

$R^{10}$ and $R^{11}$ each independently represent an aryl group having 6 to 20 carbon atoms optionally having a halogen atom as a substituent, $X^1$, $X^2$ and $X^3$ each independently represent a hydrogen atom, a halogen atom, an alkyl group having 1 to 20 carbon atoms optionally having a halogen atom as a substituent, an alkoxy group having 1 to 20 carbon atoms optionally having a halogen atom as a substituent, an aryl group having 6 to 20 carbon atoms optionally having a halogen atom as a substituent, an aryloxy group having 6 to 20 carbon atoms optionally having a halogen atom as a substituent, an aralkyl group having 7 to 20 carbon atoms optionally having a halogen atom as a substituent, an aralkyloxy group having 7 to 20 carbon atoms optionally having a halogen atom as a substituent, a substituted silyl group represented by —Si($R^{12}$)$_3$, wherein the three $R^{12}$ groups each independently represent a hydrogen atom, a hydrocarbyl group or a halogenated hydrocarbyl group, and the total number of the carbon atoms in the three $R^{12}$ groups is 1 to 20, or a disubstituted amino group represented by —N($R^{13}$)$_2$, wherein the two $R^{13}$ groups each independently represent a hydrocarbyl group or a halogenated hydrocarbyl group, and the total number of the carbon atoms in the two $R^{13}$ groups is 2 to 20;

of $R^1$, $R^2$, $R^3$ and $R^4$, two groups bonded to two adjacent carbon atoms are optionally bonded to each other to form a ring together with the two carbon atoms to which the two groups are bonded;

of $R^5$, $R^6$, $R^7$, $R^8$ and $R^9$, two groups bonded to two adjacent carbon atoms are optionally bonded to each other to form a ring together with the two carbon atoms to which the two groups are bonded; and $R^{10}$ and $R^{11}$ are optionally bonded to each other to form a ring together with the silicon atom to which $R^{10}$ and $R^{11}$ are bonded.

2. The process according to claim 1, wherein $M^1$ in the general formula (1) is a titanium atom.

3. The process according to claim 1, wherein each of $R^1$, $R^2$, $R^3$ and $R^4$ in the general formula (1) is a methyl group.

4. The process according to claim 1, wherein in the general formula (1), $R^{10}$ and $R^{11}$ are the same.

5. The process according to claim 1, wherein in the general formula (1), $R^6$ and $R^8$ are each an alkyl group having 1 to 20 carbon atoms optionally having a halogen atom as a substituent or an aryl group having 6 to 20 carbon atoms optionally having a halogen atom as a substituent.

6. The process according to claim 1, wherein in the general formula (1), at least one of $R^6$ or $R^8$ is an alkyl group having 1 to 20 carbon atoms optionally having a halogen atom as a substituent or an aryl group having 6 to 20 carbon atoms optionally having a halogen atom as a substituent.

* * * * *